(12) United States Patent
Wu et al.

(10) Patent No.: US 8,771,685 B2
(45) Date of Patent: Jul. 8, 2014

(54) ANTI-BV8 ANTIBODIES AND USES THEREOF

(75) Inventors: Xiumin Wu, South San Francisco, CA (US); Yan Wu, South San Francisco, CA (US); Lanlan Yu, South San Francisco, CA (US); Napoleone Ferrara, South San Francisco, CA (US); Wei-Ching Liang, South San Francisco, CA (US); Yu-Ju G. Meng, South San Francisco, CA (US); Janet Tien, South San Francisco, CA (US)

(73) Assignee: F. Hoffmann-La Roche AG, Basel (CH)

( * ) Notice: Subject to any disclaimer, the term of this patent is extended or adjusted under 35 U.S.C. 154(b) by 430 days.

(21) Appl. No.: 12/975,784

(22) Filed: Dec. 22, 2010

(65) Prior Publication Data

US 2012/0014941 A1  Jan. 19, 2012

Related U.S. Application Data

(60) Provisional application No. 61/284,743, filed on Dec. 23, 2009, provisional application No. 61/414,052, filed on Nov. 16, 2010.

(51) Int. Cl.
*A61K 39/395* (2006.01)

(52) U.S. Cl.
USPC .................................. 424/130.1; 530/387.1

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 3,896,111 A | 7/1975 | Kupchan et al. |
| 3,940,475 A | 2/1976 | Gross |
| 4,137,230 A | 1/1979 | Hashimoto et al. |
| 4,151,042 A | 4/1979 | Higashide et al. |
| 4,248,870 A | 2/1981 | Miyashita et al. |
| 4,256,746 A | 3/1981 | Miyashita et al. |
| 4,260,608 A | 4/1981 | Miyashita et al. |
| 4,265,814 A | 5/1981 | Hashimoto et al. |
| 4,294,757 A | 10/1981 | Asai et al. |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,315,929 A | 2/1982 | Freedman et al. |
| 4,317,821 A | 3/1982 | Miyashita et al. |
| 4,322,348 A | 3/1982 | Asai et al. |
| 4,331,598 A | 5/1982 | Hasegawa et al. |
| RE30,985 E | 6/1982 | Cartaya |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,419,446 A | 12/1983 | Howley et al. |
| 4,424,219 A | 1/1984 | Hashimoto et al. |
| 4,450,254 A | 5/1984 | Isley et al. |
| 4,560,655 A | 12/1985 | Baker et al. |
| 4,601,978 A | 7/1986 | Karin et al. |
| 4,657,866 A | 4/1987 | Kumar et al. |
| 4,676,980 A | 6/1987 | Segal et al. |
| 4,737,456 A | 4/1988 | Weng et al. |
| 4,767,704 A | 8/1988 | Cleveland et al. |
| 4,816,567 A | 3/1989 | Cabilly et al. |
| 4,892,538 A | 1/1990 | Aebischer et al. |
| 4,927,762 A | 5/1990 | Darfler et al. |
| 4,965,199 A | 10/1990 | Capon et al. |
| 4,970,198 A | 11/1990 | Lee et al. |
| 4,975,278 A | 12/1990 | Senter et al. |
| 5,004,697 A | 4/1991 | Pardridge et al. |
| 5,053,394 A | 10/1991 | Ellestad et al. |
| 5,079,233 A | 1/1992 | Lee et al. |
| 5,112,596 A | 5/1992 | Malfroy-Camine et al. |
| 5,122,469 A | 6/1992 | Mather et al. |
| 5,208,020 A | 5/1993 | Chari et al. |
| 5,264,365 A | 11/1993 | Georgiou et al. |
| 5,268,164 A | 12/1993 | Kozarich et al. |
| 5,283,187 A | 2/1994 | Aebischer et al. |
| 5,445,934 A | 8/1995 | Fodor et al. |
| 5,500,362 A | 3/1996 | Robinson et al. |
| 5,506,206 A | 4/1996 | Kozarich et al. |
| 5,508,192 A | 4/1996 | Georgiou et al. |
| 5,545,806 A | 8/1996 | Lonberg et al. |
| 5,545,807 A | 8/1996 | Surani et al. |
| 5,569,825 A | 10/1996 | Lonberg et al. |
| 5,571,894 A | 11/1996 | Wels et al. |
| 5,585,089 A | 12/1996 | Queen et al. |
| 5,587,458 A | 12/1996 | King et al. |
| 5,606,040 A | 2/1997 | Gahren et al. |
| 5,624,821 A | 4/1997 | Winter et al. |
| 5,625,126 A | 4/1997 | Lonberg et al. |
| 5,633,425 A | 5/1997 | Lonberg et al. |
| 5,635,483 A | 6/1997 | Pettit et al. |
| 5,639,635 A | 6/1997 | Joly et al. |
| 5,648,260 A | 7/1997 | Winter et al. |
| 5,661,016 A | 8/1997 | Lonberg et al. |
| 5,663,149 A | 9/1997 | Pettit et al. |
| 5,686,416 A | 11/1997 | Kozarich et al. |

(Continued)

FOREIGN PATENT DOCUMENTS

| | | |
|---|---|---|
| EP | 03089 | 7/1979 |
| EP | 0 425 235 | 9/1996 |

(Continued)

OTHER PUBLICATIONS

Rudikoff et al. Proc Natl Acad Sci USA 1982 vol. 79 p. 1979.*

(Continued)

*Primary Examiner* — Laura B Goddard
*Assistant Examiner* — Meera Natarajan
(74) *Attorney, Agent, or Firm* — Jones Day

(57) ABSTRACT

The present invention concerns antibodies to Bv8 and the uses of same.

6 Claims, 58 Drawing Sheets

(56) References Cited

U.S. PATENT DOCUMENTS

| | | |
|---|---|---|
| 5,693,762 A | 12/1997 | Queen et al. |
| 5,700,637 A | 12/1997 | Southern et al. |
| 5,712,374 A | 1/1998 | Kuntsmann et al. |
| 5,714,586 A | 2/1998 | Kunstmann et al. |
| 5,731,168 A | 3/1998 | Carter et al. |
| 5,739,116 A | 4/1998 | Hamann et al. |
| 5,767,285 A | 6/1998 | Hamann et al. |
| 5,770,701 A | 6/1998 | Mcgahren et al. |
| 5,770,710 A | 6/1998 | Mcgahren et al. |
| 5,773,001 A | 6/1998 | Hamann et al. |
| 5,780,588 A | 7/1998 | Pettit et al. |
| 5,807,522 A | 9/1998 | Shalon et al. |
| 5,821,337 A | 10/1998 | Carter et al. |
| 5,869,046 A | 2/1999 | Presta et al. |
| 5,877,296 A | 3/1999 | Hamann et al. |
| 6,004,940 A | 12/1999 | Marasco et al. |
| 6,054,297 A | 4/2000 | Carter et al. |
| 6,075,181 A | 6/2000 | Kucherlapati et al. |
| 6,150,584 A | 11/2000 | Kucherlapati et al. |
| 6,194,551 B1 | 2/2001 | Idusogie et al. |
| 6,248,516 B1 | 6/2001 | Winter et al. |
| 6,329,173 B1 | 12/2001 | Marasco et al. |
| 6,582,959 B2 | 6/2003 | Kim et al. |
| 6,602,684 B1 | 8/2003 | Umana et al. |
| 6,703,019 B1 | 3/2004 | Malfroy-Camine et al. |
| 6,703,020 B1 | 3/2004 | Thorpe et al. |
| 6,737,056 B1 | 5/2004 | Presta et al. |
| 6,884,879 B1 | 4/2005 | Baca et al. |
| 6,982,321 B2 | 1/2006 | Winter et al. |
| 7,060,269 B1 | 6/2006 | Baca et al. |
| 7,087,409 B2 | 8/2006 | Barbas et al. |
| 2002/0025313 A1 | 2/2002 | Micklus et al. |
| 2002/0038086 A1 | 3/2002 | Hynynen et al. |
| 2002/0065259 A1 | 5/2002 | Schatzberg et al. |
| 2002/0164328 A1 | 11/2002 | Shinkawa et al. |
| 2003/0055006 A1 | 3/2003 | Siemeister et al. |
| 2003/0073713 A1 | 4/2003 | Schoenhard |
| 2003/0083299 A1 | 5/2003 | Ferguson |
| 2003/0104402 A1 | 6/2003 | Zauderer et al. |
| 2003/0115614 A1 | 6/2003 | Kanda et al. |
| 2003/0129186 A1 | 7/2003 | Beliveau et al. |
| 2003/0157108 A1 | 8/2003 | Presta |
| 2003/0162695 A1 | 8/2003 | Schatzberg et al. |
| 2003/0190317 A1 | 10/2003 | Baca et al. |
| 2003/0203409 A1 | 10/2003 | Kim |
| 2003/0206899 A1 | 11/2003 | Ferrara et al. |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0131692 A1 | 7/2004 | Kreuter et al. |
| 2004/0132140 A1 | 7/2004 | Satoh et al. |
| 2004/0204354 A1 | 10/2004 | Nelson et al. |
| 2005/0014934 A1 | 1/2005 | Hinton et al. |
| 2005/0089473 A1 | 4/2005 | Black et al. |
| 2005/0112126 A1 | 5/2005 | Baca et al. |
| 2005/0123546 A1 | 6/2005 | Umana et al. |
| 2005/0124533 A1 | 6/2005 | Schatzberg et al. |
| 2005/0169933 A1 | 8/2005 | Steeves et al. |
| 2005/0186208 A1 | 8/2005 | Fyfe et al. |
| 2005/0238649 A1 | 10/2005 | Doronina et al. |
| 2006/0009360 A1 | 1/2006 | Pifer et al. |
| 2006/0280747 A1 | 12/2006 | Fuh et al. |
| 2007/0020267 A1 | 1/2007 | Fuh et al. |
| 2007/0141065 A1 | 6/2007 | Fuh et al. |
| 2007/0178552 A1 | 8/2007 | Arathoon et al. |
| 2010/0098730 A1 | 4/2010 | Lowman et al. |

FOREIGN PATENT DOCUMENTS

| | | |
|---|---|---|
| EP | 404 097 | 9/1996 |
| EP | 0 666 868 | 6/2006 |
| WO | WO 87/00195 | 1/1987 |
| WO | WO 89/06692 | 7/1989 |
| WO | WO 90/03430 | 4/1990 |
| WO | WO 91/00360 | 1/1991 |
| WO | WO 91/10741 | 7/1991 |
| WO | WO 92/00373 | 1/1992 |
| WO | WO 92/09690 | 12/1992 |
| WO | WO 93/06213 | 4/1993 |
| WO | WO 93/08829 | 5/1993 |
| WO | WO 93/11161 | 6/1993 |
| WO | WO 93/16185 | 8/1993 |
| WO | WO 93/21232 | 10/1993 |
| WO | WO 93/25673 | 12/1993 |
| WO | WO 94/04690 | 3/1994 |
| WO | WO 94/10202 | 5/1994 |
| WO | WO 94/11026 | 5/1994 |
| WO | WO 94/29351 | 12/1994 |
| WO | WO 95/27062 | 10/1995 |
| WO | WO 96/07321 | 3/1996 |
| WO | WO 96/27011 | 9/1996 |
| WO | WO 96/30046 | 10/1996 |
| WO | WO 96/33735 | 10/1996 |
| WO | WO 96/34096 | 10/1996 |
| WO | WO 97/30087 | 8/1997 |
| WO | WO 98/24893 | 6/1998 |
| WO | WO 98/45332 | 10/1998 |
| WO | WO 98/50431 | 11/1998 |
| WO | WO 98/58964 | 12/1998 |
| WO | WO 99/22764 | 5/1999 |
| WO | WO 99/51642 | 10/1999 |
| WO | WO 00/42072 | 7/2000 |
| WO | WO 00/61739 | 10/2000 |
| WO | WO 01/29246 | 4/2001 |
| WO | WO 01/75166 | 10/2001 |
| WO | WO 02/31140 | 4/2002 |
| WO | WO 02/088172 | 11/2002 |
| WO | WO 03/011878 | 2/2003 |
| WO | WO 03/020892 | 3/2003 |
| WO | WO 03/077945 | 9/2003 |
| WO | WO 03/084570 | 10/2003 |
| WO | WO 03/085107 | 10/2003 |
| WO | WO 03/085119 | 10/2003 |
| WO | WO 2004/056312 | 7/2004 |
| WO | WO 2004/092219 | 10/2004 |
| WO | WO 2005/012359 | 2/2005 |
| WO | WO 2005/035586 | 4/2005 |
| WO | WO 2005/035778 | 4/2005 |
| WO | WO 2005/044853 | 5/2005 |
| WO | WO 2005/053742 | 6/2005 |
| WO | WO 2007/033140 | 3/2007 |
| WO | WO 2008/047242 | 4/2008 |
| WO | WO 2009/039337 | 3/2009 |
| WO | WO 2009/073160 | 6/2009 |

OTHER PUBLICATIONS

MacCallum et al. J. Mol. Biol. (1996) 262, 732-745.*
Pascalis et al. The Journal of Immunology (2002) 169, 3076-3084.*
Casset et al. BBRC 2003, 307:198-205.*
Vajdos et al. J. Mol. Biol. (2002) 320, 415-428.*
Chen et al. J. Mol. Bio. (1999) 293, 865-881.*
Wu et al. J. Mol. Biol. (1999) 294, 151-162.*
Padlan et al. PNAS 1989, 86:5938-5942.*
Lamminmaki et al. JBC 2001, 276:36687-36694.*
Abrahmséen et al., Analysis of signals for secretion in the staphylococcal protein A gene. EMBO J. Dec. 30, 1985;4(13B):3901-6.
Adamis et al., Inhibition of vascular endothelial growth factor prevents retinal ischemia-associated iris neovascularization in a nonhuman primate. Arch. Ophthalmol. Jan. 1996;114(1):66-71.
Anderson WF. Human gene therapy. Science, May 8, 1992;256(5058):808-13.
Arié et al., Chaperone function of FkpA, a heat shock prolyl isomerase, in the periplasm of *Escherichia coli*. Mol Microbiol. Jan. 2001;39(1):199-2.
Bai et al., Structure-activity studies with chiral isomers and with segments of the antimitotic marine peptide dolastatin 10. Biochem Pharmacol. Oct. 15, 1990;40(8):1859-64.
Baldwin et al., Monoclonal antibodies in cancer treatment. Lancet. Mar. 15, 1986;1(8481):603-5.

(56) References Cited

OTHER PUBLICATIONS

Barbas et al., Assembly of combinatorial antibody libraries on phage surfaces: the gene III site. Proc Natl Acad Sci U S A. Sep. 15, 1991;88(18):7978-82.

Barbas et al., Semisynthetic combinatorial antibody libraries: a chemical solution to the diversity problem. Proc Natl Acad Sci U S A. May 15, 1992;89(10):4457-61.

Barnes et al., Methods for growth of cultured cells in serum-free medium. Anal Biochem. Mar. 1, 1980;102(2):255-70.

Bass et al., Hormone phage: an enrichment method for variant proteins with altered binding properties. Proteins. 1990;8(4):309-14.

Berkman et al., Expression of the vascular permeability factor/vascular endothelial growth factor gene in nervous system neopslasms. J Clin. Invest. Jan. 1993;91(1):153-9.

Bobo et al., Convection-enhanced delivery of macromolecules in the brain. Proc Natl Acad Sci US A. Mar. 15, 1991;91(6):2076-80.

Boerner et al., Production of antigen-specific human monoclonal antibodies from in vitro-primed human splenocytes. J Immunol. Jul. 1, 1991;147(1):86-95.

Borgström et al., Complete inhibition of angiogenesis and growth of microtumors by anti-vascular endothelial growth factor neutralizing antibody: novel concepts of angiostatic therapy from intravital videomicroscopy. Cancer Res. Sep. 1, 1996;56(17):4032-9.

Bothmann et al., The periplasmic *Escherichia coli* peptidylprolyl cis,trans-isomerase FkpA. I. Increased functional expression of antibody fragments with and without cis-prolines. J Biol Chem. Jun. 2, 2000;275(22):17100-5.

Brennan et al., Preparation of bispecific antibodies by chemical recombination of monoclonal immunotlobulin G1 fragments. Science. Jul. 5, 1985;229(4708):81-3.

Brown et al., Expression of vascular permeability factor (vascular endothelial growth factor) and its receptors in adenocarcinomas of the tastrointestinal tract. Cancer Res. Oct. 1, 1993;53(19):4727-35.

Brown et al., Expression of vascular permeability factor (vascular endothelial growth factor) and its in breast cancer. Hum Pathol. Jan. 1995;26(1):86-91.

Brüggemann et al., Designer mice: the production of human antibody repertoires in transgenic animals. Year Immunol. 1993;7:33-40.

Brüggemann et al., Comparison of the effector functions of human immunoglobulins using a matched set of chimeric antibodies. J Exp Med. Nov. 1, 1987;166(5):1351-61.

Capel et al., Heterogeneity of human IgG Fc receptors. Immunomethods. Feb. 1994;4(1):25-34.

Carlsson et al., Protein thiolation and reversible protein-protein conjugation, N-Succinimidyl 3-(2-pyridyldithio)propionate, a new heterobifunctional reagent. Biochem J. Sep. 1, 1978;173(3):723-3.

Carmeliet et al, Angiogenesis in cancer and other diseases. Nature. Sep. 14, 2000;407(6801):249-57.

Carter et al., High level *Escherichia coli* expression and production of a bivalent humanized antibody fragment. Biotechnology (N Y). Feb. 1992;10(2):163-7.

Carter et al., Humanization of an anti-p185HER2 antibody for human cancer therapy. Proc Natl Acad Sci U S A. May 15, 1992;89(10):4285-9.

Chari et al., Immunoconjugates containing novel maytansinoids: promising anticancer drugs. Cancer Res. Jan. 1, 1992;52(1):127-31.

Chen et al., Chaperone activity of DsbC. J Biol Chem. Jul. 9, 1999;274(28):19601-5.

Chen et al., Selection and analysis of an optimized anti-VEGF antibody: crystal structure of an affinity-matured Fab in complex with antigen. J Mol Biol. Nov. 5, 1999;293(4):865-81.

Chen et al., Selective killing of transformed cells by cyclin/cyclin-dependent kinase 2 antagonists. Proc Natl Acad Sci U S A. Apr. 13, 1999;96(8):4325-9.

Cheng et al., Prokineticin 2 transmits the behavioural circadian rhythm of the suprachiasmatic nucleus. Nature. May 23, 2002;417(6887):405-10.

Cheung et al., Making and reading microarrays. Nat Genet. Jan. 1999;21(1 Suppl):5-9.

Chothia et al., Canonical structures for the hypervariable regions of immunoglobulins. J Mol Biol, Aug. 20, 1987;196(4):901-17.

Clackson et al., Making antibody fragments using phage display libraries. Nature. Aug. 15, 1991;352(6336):624-8.

Clynes et al., Fc receptors are required in passive and active immunity to melanoma. Proc Natl Acad Sci U S A. Jan. 20, 1998;95(2):652-6.

Coussens et al., Inflammation and cancer. Nature. Dec. 19-26, 2002;420(6917):860-7.

Cragg et al., Complement-mediated lysis by anti-CD20 mAb correlates with segregation into lipid rafts. Blood. Feb. 1, 2003;101(3):1045-52.

Cragg et al., Antibody specificity controls in vivo effector mechanisms of anti-CD20 reagents. Blood. Apr. 1, 2004;103(7):2738-43.

Cunningham et al., High-resolution epitope mapping of hGH-receptor interactions by alanine-scanning mutagenesis. Science. Jun. 2, 1989;244(4908):1081-5.

Daëron M. Fc receptor biology. Annu Rev Immunol. 1997;15:203-34.

David and Reisfeld, Protein iodination with solid state lactoperoxidase. Biochemistry. Feb. 26, 1974;13(5):1014-21.

de Haas et al., Fc gamma receptors of phagocytes. J Lab Clin Med. Oct. 1995; 26(4):330-41.

Doronina et al., Development of potent monoclonal antibody auristatin conjugates for cancer therapy. Nat Biotechnol, Jul. 2003;21(7):778-84.

Dorsch et al, PK1/EG-VEGF induces monocyte differentiation and activation, J Leukoc Biol. Aug. 2005,78(2):426-34.

Duncan et al., The binding site for C1q on IgG. Nature. Apr. 21, 1988;332(6166):738-40.

Dvorak et al., Vascular permeability factor/vascular endothelial growth factor, microvascular hyperpermeability, and angiogenesis. Am J Pathol. May 1995;146(5):1029-39.

Embleton et al., In-cell PCR from mRNA: amplifying and linking the rearranged immunoglobulin heavy and light chain V-genes within single cells. Nucleic Acids Res. Aug. 11, 1992;20(15):3831-7.

Engels et al., Agnew. Chem, Int. Ed. Engl. 28:716-743, 1989.

Fellouse et al., Synthetic antibodies from a four-amino-acid code: a dominant role for tyrosine in antigen recognition. Proc Natl Acad Sci U S A. Aug. 24, 2004;101(34):12467-72.

Ferrara et al., Discovery and development of bevacizumab, an anti-VEGF antibody for treating cancer. Nat Rev Drug Discov. May 2004;3(5):391-400.

Ferrara et al., Clinical applications of angiogenic growth factors and their inhibitors. Nat Med. Dec. 1999;5(12):1359-64.

Ferrara et al., The biology of vascular endothelial growth factor. Endocr Rev. Feb. 1997;18 11:4-25.

Fishwild et al., High-avidity human IgG kappa monoclonal antibodies from a novel strain of minilocus transgenic mice. Nat.Biotechnol. Jul. 1996;14(7):845-51.

Folkman et al., Angiogenesis. J Biol Chem. Jun. 5, 1992;267(16):10931-4.

Folkman J., Angiogenesis in cancer, vascular, rheumatoid and other disease. Nat. Med. Jan. 1999;1(1):27-31.

Gallop et al., Applications of combinatorial technologies to drug discovery. 1. Background and peptide combinatorial libraries. J Med Chem. Apr. 1994 29;37(9):1233-51.

Garner A., "Vascular diseases", In *Pathobiology of Ocular Disease. A Dynamic Approach*, Garner A., Klintworth GK, eds., 2$^{nd}$ Ed. Marcel Dekker, NY, 1994, pp. 1625-1710.

Gazzano-Santoro et al., A non-radioactive complement-dependent cytotoxicity assay for anti-CD20 monoclonal antibody. J. Immunol Methods. Mar. 28, 1997;202(2):163-71.

Geoghegan et al., Site-directed conjugation of nonpeptide groups to peptides and proteins via periodate oxidation of a 2-amino alcohol Applicaton to modificaton at N-terminal serine. Bioconjug Chem. Mar.-Apr. 1992;3(2):138-46.

Ghetie et al., FcRn: the MHC class I-related receptor that is more than an IgG transporter. Immunol Today. Dec. 1997;18(12):592-8.

Ghetie et al., Increasing the serum persistence of an IgG fragment by random mutagenesis. Nat. Biotechnol. Jul. 1997;15(7):637-40.

Gill et al., Direct brain infusion of glial cell line-derived neurotrophic factor in Parkinson disease. Nat Med. May 2003;9(5):589-95.

(56) References Cited

OTHER PUBLICATIONS

Graham et al., Characteristics of a human cell line transformed by DNA from human adenovirus type 5. J Gen Virol. Jul. 1977;36(1):59-74.
Gram et al., In vitro selection and affinity maturation of antibodies from a naive combinatorial immunoulobulin library. Proc Natl Acad Sci U S A, Apr. 15, 1992;89(8):3576-80.
Griffiths et al., Human anti-self antibodies with high specificity from phage display libraries. EMBO J. Feb. 1993;12(2):725-34.
Gruber et al., Efficient tumor cell lysis mediated by a bispecific single chain antibody expressed in Escherichia coli. J Immunol. Jun. 1, 1994;152(11):5368-74.
Guss et al., Structure of the IgG-binding regions of streptococcal protein G. EMBO J. Jul. 5, 1986(7):1567-75.
Guyer et al., Immunoglobulin binding by mouse intestinal epithelial cell receptors. J Immunol. Aug. 1976;117(2):587-93.
Ham et al., Media and growth requirements. Methods Enzymol. 1979;58:44-93.
Hamers-Casterman et al., Naturally occurring antibodies devoid of light chains. Nature. Jun. 3, 1993;363(6428):446-8.
Hara et al., Overproduction of penicillin-binding protein 7 suppresses thermosensitive growth defect at low osmolarity due to an spr mutation of Escherichia coli. Microb Drug Resist. 1996 Spring;2(1):63-72.
Harris WJ. Production of humanized monoclonal antibodies for in vivo imaging and therapy. Biochem Soc Trans. Nov. 1995;23(4):1035-8.
Hawkins et al., Selection of phage antibodies by binding affinity. Mimicking affinity maturation. J Mol Biol. Aug. 5, 1992;226(3):889-96.
Hellström et al., Strong antitumor activities of IgG3 antibodies to a human melanoma-associated ganglioside. Proc Natl Acad Sci U S A. Mar. 1985;82(5):1499-502.
Hellström et al., Antitumor effects of L6, an IgG2a antibody that reacts with most human carcinomas. Proc Natl Acad Sci U S A. Sep. 1986;83(18):7059-63.
Hinman et al., Preparation and characterization of monoclonal antibody conjugates of the calicheamicins: a novel and potent family of antitumor antibiotics. Cancer Res. Jul. 15, 1993;53(14):3336-42.
Hinton et al., Engineered human IgG antibodies with longer serum half-lives in primates. J Biol Chem. Feb. 20, 2004;279(8):6213-6.
Hogrefe et al., A bacteriophage lambda vector for the cloning and expression of immunoglobulin Fab fragments on the surface of filamentous phage. Gene. Jun. 15, 1993;128(1):119-26.
Holliger et al., "Diabodies": small bivalent and bispecific antibody fragments. Proc Natl Acad Sci U S A. Jul. 15, 1993;90(14):6444-8.
Hongo et al., Development and characterization of murine monoclonal antibodies to the latency-associated peptide of transforming growth factor beta 1. Hybridoma. Jun. 1995;14(3):253-60.
Hoogenboom et al., Multi-subunit proteins on the surface of filamentous phage: methodologies for displaying antibody (Fab) heavy and light chains. Nucleic Acids Res. Aug. 11, 1991;19(15):4133-7.
Hoogenboom et al., By-passing immunisation. Human antibodies from synthetic repertoires of germline VH gene segments rearranged in vitro. J Mol. Biol. Sep. 20, 1992;227(2):381-8.
Horak et al., Angiogenesis, assessed by platelet/endothelial cell adhesion molecule antibodies, as indicator of node metastases and survival in breast cancer. Lancet. Nov. 7, 1992:340(8828):1120-4.
Houck et al., The vascular endothelial growth factor family: identification of a fourth molecular species and characterization of alternative splicing of RNA. Mol Endocrinol. Dec. 1991;5(12):1806-14.
Hudson et al., Engineered antibodies. Nat Med. Jan. 2003;9(1):129-34.
Hunter et al., Nature, 144:945, 1962.
Hurle et al., Protein engineering techniques for antibody humanization. Curr Opin Biotechnol. Aug. 1994;5(4):428-33.
Idusogie et al., Mapping of the C1q binding site on rituxan, a chimeric antibody with a human IgG1 Fc. J Immunol. Apr. 15, 2000;164(8):4178-84.

Jakobovits et al., Analysis of homozygous mutant chimeric mice: deletion of the immunoglobulin heavy-chain joining region blocks B-cell development and antibody production. Proc Natl Acad Sci U S A. Mar. 15, 1993;90(6):2551-5.
Jakobovits et al., Germ-line transmission and expression of a human-derived yeast artificial chromosome. Nature. Mar. 18, 1993;362(6417):255-8.
Jones et al., Replacing the complementarity-determining regions in a human antibody with those from a mouse. Nature. May 29-Jun. 4, 1986;321(6069):522-5.
Jones et al., Rapid PCR-cloning of full-length mouse immunoglobulin variable regions. Biotechnology (NY). Jan. 1991;9(1):88-9.
Kam et al., Carbon nanotubes as multifunctional biological transporters and near-infrared agents for selective cancer cell destruction. Proc Natl Acad Sci U S A. Aug. 16, 2005;102(33):11600-5.
Kanda et al., Comparison of cell lines for stable production of fucose-negative antibodies with enhanced ADCC. Biotechnol Bioeng. Jul. 5, 2006;94(4):680-8.
Kim et al., Inhibition of vascular endothelial growth factor-induced angiogenesis suppresses tumour growth in vivo. Nature. Apr. 29, 1993;362(6423):841-4.
Klagsbrun et al., Regulators of angiogenesis. Annu Rev Physiol. 1991;53:217-39.
Köhler et al., Continuous cultures of fused cells secreting antibody of predefined specificity. Nature. Aug. 7, 1975;256(5517):495-7.
Kontermann RE. Intrabodies as therapeutic agents. Methods. Oct. 2004;34(2):163-70.
Kostelny et al., Formation of a bispecific antibody by the use of leucine zippers. J Immunol. Mar. 1, 1992;148(5):1547-53.
Kozbor et al., A human hybrid myeloma for production of human monoclonal antibodies. J Immunol. Dec. 1984;133(6):3001-5.
Lambert JM. Drug-conjugated monoclonal antibodies for the treatment of cancer. Curr Opin Pharrnacol. Oct. 2005;5(5):543-9.
Lechner et al., Characterization of strand displacement synthesis catalyzed by bacteriophage T7 DNA polymerase. J Biol Chem. Sep. 25, 1983;258(18):11174-84.
LeCouter et al., Identification of an angiogenic mitogen selective for endocrine gland endothelium. Nature. Aug. 30, 2001,412(6850).877-84.
LeCouter et al., The endocrine-gland-derived VEGF homologue Bv8 promotes angiogenesis in the testis: Localization of Bv8 recestors to endothelial cells. Proc Natl Acad Sci U S A, Mar. 4, 2003;100(5). 2685-90.
LeCouter et al., Bv8 and endocrine gland-derived vascular endothelial growth factor stimulate hematopoiesis and hematopoietic cell mobilization. Proc Natl Acad Sci U S A. Nov. 30, 2004;101(48):16813-8.
Lee et al., Bivalent antibody phage display mimics natural immunoglobulin. J Immunol Methods. Jan. 2004;284(1-2):119-32.
Lee et al., High-affinity human antibodies from phage-displayed synthetic Fab libraries with a single framework scaffold. J Mol Biol. Jul. 23, 2004;340(5):1073-93.
Leong et al., *Appl. Immunohistochem*. 4(31:201, 1996.
Leung et al., Vascular endothelial growth factor is a secreted angiogenic mitogen. Science. Dec. 8, 1989;246(4935):1306-9.
Leung et al., Technique, 1:11-15, 1989.
Li et al., Identification of two prokineticin cDNAs: recombinant proteins potently contract gastrointestinal smooth muscle. Mol Pharmacol. Apr. 2001;59(4):692-8.
Li et al., Human antibodies for immunotherapy development generated via a human B cell hybridoma technology. Proc Natl Acad Sci U S A. Mar. 7, 2006;103(10):3557-62.
Liang et al., Cross-species vascular endothelial growth factor (VEGF)-blocking antibodies completely inhibit the growth of human tumor xenografts and measure the contribution of stromal VEGF. J Biol Chem. Jan. 13, 2006;281(2):951-61.
Lin et al., Identification and molecular characterization of two closely related G protein-coupled receptors activated by prokineticins/endocrine gland vascular endothelial growth factor. J Biol Chem. May 31, 2002;277(22):19276-80.

(56) References Cited

OTHER PUBLICATIONS

Lindmark et al., Binding of immunoglobulins to protein A and immunoglobulin levels in mammalian sera. J Immunol Methods. Aug. 12, 1983;62(1):1-13.
Liu et al., Eradication of large colon tumor xenografts by targeted delivery of maytansinoids. Proc Natl Acad Sci U S A. Aug. 6, 1996;93(16):8618-23.
Lockhart et al., Expression monitoring by hybridization to high-density oligonucleotide arrays. Nat Biotechnol. Dec. 1996;14(13):1675-80.
Lode et al., Targeted therapy with a novel enediyne antibiotic calicheamicin theta(I)1 effectively suppresses growth and dissemination of liver metastases in a syngeneic model of murine neuroblastoma. Cancer Res. Jul. 15, 1998;58(14):2925-8.
Lonberg et al., Antigen-specific human antibodies from mice comprising four distinct genetic modifications. Nature. Apr. 28, 1994;368(6474):856-9.
Lonberg et al., Human antibodies from transgenic mice. Int Rev Immunol. 1995;13(1):65-93.
Maccharni et al. Relation of neovscularisation to metastasis of non-small-cell lung cancer Lancet. Jul. 18, 1992;340(8812):145-6.
Mandler et al., Immunoconjugates of geldanamycin and anti-HER2 monoclonal antibodies: antiproliferative activity on human breast carcinoma cell lines. J Nat Cancer Inst. Oct. 4, 2000;92(19):1573-81.
Mandler et al., Modifications in synthesis strategy improve the yield and efficacy of geldanamycin-herceptin immunoconjugates. Bioconjug Chem. Jul.-Aug. 2002;13(4):786-91.
Mandler et al., Synthesis and evaluation of antiproliferative activity of a geldanamycin-Herceptin immunoconjugate. Bioorg Med Chem Lett. May 15, 2000;10(10):1025-8.
Marasco et al., Design, intracellular expression, and activity of a human anti-human immunodeficiency virus type 1 gp120 single-chain antibody. Proc Natl Acad Sci U S A. Aug. 15, 1993;90(16):7889-93.
Marasco WA. lntrabodies: turning the humoral immune system outside in for intracellular immunization. Gene Ther. Jan. 1997;4(1):11-5.
Marks et al., By-passing immunization. Human antibodies from V-gene libraries displayed on phage. J Mol Biol. Dec. 5, 1991;222(3):581-97.
Marks et al., By-passing immunization: building high affinity human antibodies by chain shuffling. Biotechnology (N Y). Jul. 1992;10(7):779-83.
Masuda et al., Isolation and identification of EG-VEGF/prokineticins as cognate ligands for two orphan G-protein-coupled receptors. Biochem Biophys Res Commun. Apr. 26, 2002;293(1):396-402.
Mather et al., Culture of testicular cells in hormone-supplemented serum-free medium. Ann N Y Acad Sci. 1982;383:44-68.
Mather JP. Establishment and characterization of two distinct mouse testicular epithelial cell lines. Biol Reprod. Aug. 1980;23(1):243-52.
Matsuda et al., Structure and physical map of 64 variable segments in the 3'0.8-megabase region of the human immunoglobulin heavy-chain locus. Nat Genet. Jan. 1993;3(1):88-94.
Matsumoto et al., Abnormal development of the olfactory bulb and reproductive system in mice lacking prokineticin receptor PKR2. Proc Natl Acad Sci U S A. Mar. 14, 2006;103(111:4140-5.
Mattern et al., Association of vascular endothelial growth factor expression with intratumoral microvessel density and tumour cell proliferation in human epidermoid lung carcinoma. Br J Cancer. Apr. 1996;73(7):931-4.
Melnyk et al., Vascular endothelial growth factor promotes tumor dissemination by a mechanism distinct from its effect on primary tumor growth. Cancer Res. Feb. 15, 1996;56(4):921-4.
Milstein et al., Hybrid hybridomas and their use in immunohistochemistry. Nature. Oct. 6-12, 1983;305(5934):537-40.
Mollay et al., Bv8, a small protein from frog skin and its homologue from snake venom induce hyperalgesia in rats. Eur J Pharmacol. Jun. 18, 1999;374(2):189-96.

Morimoto et al., Single-step purification of F(ab')2 fragments of mouse monoclonal antibodies (immunoglobulins G1) by hydrophobic interaction high performance liquid chromatography using TSKgel Phenyl-5PW. J Biochem Biophys Methods. Mar. 1992;24(1-2):107-17.
Morrison et al., Chimeric human antibody molecules: mouse antigen-binding domains with human constant region domains. Proc. Nati Acad Sci U S A, Nov. 1984;81(21):6851-5.
Morrison SL. Immunology. Success in specification. Nature. Apr. 28, 1994;368(6474):812-3.
Munson et al., Ligand: a versatile computerized approach for characterization of ligand-bindin systems. Anal Biochem. Sep. 1, 1980;107(1):220-39.
Murakami et al. "Cell cycle regulation, oncogenes, and antineoplastic drugs"., Mendelsohn and Isreal, eds., Chp. 1 of *The Molecular Basis of Cancer*, W.B. Saunders, Philedelphia, 1995, p. 13.
Neuberger M. Generating high-avidity human Mabs in mice. Nat Biotechnol. Jul. 1996; 4(7):826.
Nicolaou et al., Angew. Chem, Intl. Ed. Engl., 33:183-6, 1994.
Nygren H. Conjugation of horseradish peroxidase to Fab fragments with different homobifunctional and heterobifunctional cross-linking reagents. A comparative study. J Histochem Cytochem. May 1982;30(5):407-12.
Okazaki et al., Fucose depletion from human IgG1 oligosaccharide enhances binding enthalpy and association rate between IgG1 and FcgammaRIIIa. J. Mol Biol. Mar. 5, 2004;336(5):1239-49.
Orlandi et al., Cloning immunoglobulin variable domains for expression by the polymerase chain reaction. Proc Natl Acad Sci U S A. May 1989;86(10):3833-7.
Orum et al., Efficient method for constructing comprehensive murine Fab antibody libraries displayed on phage. Nucleic Acids Res. Sep. 25, 1993;21(19):4491-8.
Pain et al., Preparation of protein A-peroxidase monoconjugate using a heterobifunctional reagent, and its use in enzyme immunoassays. J Immunol. Methods. 1981;40(2):219-30.
Papanastassiou et al., The potential for efficacy of the modified (ICP 34.5(-31)) herpes simplex virus HSV1716 following intratumoural injection into human malignant glioma: a proof of principle study. Gene Ther. Mar. 2002;9(6):398-406.
Payne G. Progress in immunoconjugate cancer therapeutics. Cancer Cell. Mar. 2003;3(3):207-12.
Petkova et al., Enhanced half-life of genetically engineered human IgG1 antibodies in a humanized FcRn mouse model: potential application in humorally mediated autoimmune disease. Int Immunol. Dec. 2006;18(12):1759-69.
Pettit et al., Specific activities of dolastatin 10 and peptide derivatives against *Cryptococcus neoformans*. Antimicrob Agents Chemother. Nov. 1998;42(11):2961-5.
Pettit et al., J. Chem. Soc. Perkin. Trans. 1 5:859-863, 1996.
Pettit et al., Synthesis, 719-725, 1996.
Plückthun A. Mono- and bivalent antibody fragments produced in *Escherichia coli*: engineering, foldingand antigen binding. Immunol Rev. Dec. 1992;130:151-88.
Popkov et al., Human/mouse cross-reactive anti-VEGF receptor 2 recombinant antibodies selected from an immune b9 allotype rabbit antibody library. J Immunol Methods. May 2004;288(1-2):149-64.
Presta et al., Humanization of an antibody directed against IgE. J Immunol. Sep. 1, 1993;15(5):2623-32.
Presta et al., Humanization of an anti-vascular endothelial growth factor monoclonal antibody for the therapy of solid tumors and other disorders. Cancer Res. Oct. 15, 1997;57(201:4593-9.
Presta LG. Antibody engineering, Curr Opin Biotechnol. Aug. 1992:301:394-8.
Proba et al,. Functional antibody single-chain fragments from the cytoplasm of *Escherichia coli*: influence of thioredoxin reductase (TrxB). Gene. Jul. 4, 1995;159(2):203-7.
Ramm et al., The periplasmic *Escherichia coli* peptidylprolyl cis,trans-isomerase FkpA. If. lsomerase-independent chaperone activity in vitro. J Biol Chem. Jun. 2, 2000;275(22):17106-13.
Ravetch et al., Fc receptors. Annu Rev Immunol. 1991;9:457-92.
Riechmann et al., Reshaping human antibodies for therapy. Nature. Mar. 24, 1988;332(6162):323-7.

(56) References Cited

OTHER PUBLICATIONS

Ripka et al., Two Chinese hamster ovary glycosylation mutants affected in the conversion of GDP-mannose to GDP-fucose. Arch Biochem Biophys. Sep. 1986;249(2):533-45.
Rowland et al., Drug localisation and growth inhibition studies of vindesine-monoclonal anti-CEA conjugates in a human tumour xenograft. Cancer Immunol Immunother. 1986;21(3):183-7.
Sastry et al., Cloning of the immunological repertoire in *Escherichia coli* for generation of monoclonal catalytic antibodies: construction of a heavy chain variable region-specific cDNA library. Proc Natl Acad Sci U S A. Aug. 1989;86(15):5728-32.
Sato Y. Molecular diagnosis of tumor angiogenesis and anti-angiogenic cancer therapy. Int Clin Oncol. Aug. 2003;8(4):200-6.
Shalaby et al., Development of humanized bispecific antibodies reactive with cytotoxic lymphocytes and tumor cells overexpressing the HER2 protooncogene. J Exp Med. Jan. 1, 1992;175(1):217-25.
Sheriff et al., Redefining the minimal antigen-binding fragment. Nat Struct Biol. Sep. 1996;3(9):733-6.
Shields et al., High resolution mapping of the binding site on human IgG1 for Fc gamma RI, Fc gamma RII, Fc gamma RIII, and FcRn and design of IgG1 variants with improved binding to the Fc gamma R. J Biol Chem. Mar. 2, 2001;276(9):6591-604.
Shojaei et al., Bv8 regulates myeloid-cell-dependent tumour angiogenesis. Nature. Dec. 6, 2007;450(7171):825-31.
Sidhu et al., Phage display for selection of novel binding peptides. Methods Enzymol. 2000;328:333-63.
Sidhu et al., Phage-displayed antibody libraries of synthetic heavy chain complementarity determining regions. J Mol Biol. Apr. 23, 2004;338(2):299-310.
Siebenlist et al., *E. coli* RNA polymerase interacts homologously with two different promoters. Cell. Jun. 1980;20(2):269-81.
Simmons et al., Expression of full-length immunoglobulins in *Escherichia coli*: rapid and efficient production of aglycosylated antibodies. J Immunol Methods. May 1, 2002;263(1-2):133-47.
Sims et al., A humanized CD18 antibody can block function without cell destruction. J Immunol. Aug. 15, 1993;151(4):2296-308.
Skerra A. Bacterial expression of immunoglobulin fragments. Curr Opin Immunol. Apr. 1993;5(2):256-62.
Springer and Niculescu-Duvaz, Antibody-directed enzyme prodrug therapy (ADEPT): a review. Adv Drug Deliv Rev. Jul. 7, 1997;26(2-3):151-172.
Streit et al., Angiogenesis, lymphangiogenesis, and melanoma metastasis. Oncogene, May 19, 2003:22(20):3172-9.
Suresh et al., Bispecific monoclonal antibodies from hybrid hybridomas. Methods Enzymol. 1986;121:210-28.
Syrigos et al., Antibody directed enzyme prodrug therapy (ADEPT): a review of the experimental and clinical considerations. Anticancer Res. Jan.-Feb. 1999;19(1A):605-13.
Thorpe, Antibody Carriers of Cytotoxic Agents in Cancer Therapy: A Review. In *Monoclonal Antibodies '84: Biological and Clinical Applications* (A. Pinchera et al. Eds.), pp. 475-506.
Tomlinson et al., The repertoire of human germline VH sequences reveals about fifty groups of VH segments with different hypervariable loops. J Mol Biol. Oct. 5, 1992;227(3):776-98.
Tonini et al., Molecular basis of angiogenesis and cancer. Oncogene. Sep. 29, 2003;22(42):6549-56.
Traunecker et al., Bispecific single chain molecules (Janusins) target cytotoxic lymphocytes on HIV infected cells. EMBO J. Dec. 1991;10(12):3655-9.
Tutt et al., Trispecific F(ab')3 derivatives that use cooperative signaling via the TCR/CD3 complex and CD2 to activate and redirect resting cytotoxic T cells. J Immunol. Jul. 1, 1991;147(1):60-9.
van Dijk et al., Human antibodies as next generation therapeutics. Curr Opin Chem Biol. Aug. 2001; 5(4):368-74.
Vaswani et al., Humanized antibodies as potential therapeutic drugs. Ann Allergy Asthma Immunol. Aug. 1998;81(2):105-15.
Verhoeyen et al., Reshaping human antibodies: grafting an antilysozyme activity. Science. Mar. 25, 1988;239(4847):1534-6.
Vitetta et al., Redesigning nature's poisons to create anti-tumor reagents. Science. Nov. 20, 1987;238(4830):1098-104.
Ward et al., Binding activities of a repertoire of single immunoglobulin variable domains secreted from *Escherichia coli*. Nature. Oct. 12, 1989;341(6242):544-6.
Warren et al., Regulation by vascular endothelial growth factor of human colon cancer tumorigenesis in a mouse model of experimental liver metastasis. J Clin Invest. Apr. 1995;95(4):1789-97.
Waterhouse et al., Combinatorial infection and in vivo recombination: a strategy for making large phage antibody repertoires. Nucleic Acids Res. May 11, 1993;21(9):2265-6.
Wechselberger et al., The mammalian homologues of frog Bv8 are mainly expressed in spermatocytes. FEBS Lett. Nov. 26, 1999;462(1-2):177-81.
Weidner et al., Tumor angiogenesis and metastasis—correlation in invasive breast carcinoma. N Engl J Med. Jan. 3, 1991;324(1):1-8.
Weissman et al., Four cases of keratoconus and posterior polymorphous corneal dystrophy. Optom Vis Sci. Apr. 1989;66(4):243-6.
Williams et al., Cloning and sequencing of human immunoglobulin V lambda gene segments. Eur J Immunol. Jul. 1993;23(7):1456-61.
Winter et al. Making antibodies by phage display technology. Annu Rev Immunol. 1994;12:433-55.
Wiseman et al., Phase I/II 90Y-Zexalin (yttrium-90 ibritumomab tiuxetan, IDEC-Y2B8) radioimmunotherapy dosimetry results in relapsed or refractory non-Hoddcin's lymphoma, Eur J Nucl Med., Jul. 2000;27(7):766-77.
Witzig et al., Randomized controlled trial of yttrium-90-labeled ibritumomab tiuxetan radioimmunotherapy versus rituximab immunotherapy for patients with relapsed or refractory low-grade, follicular, or transformed B-cell non-Hodgkin's lymphoma. J. Clin Oncol. May 15, 2002;20(10):2453-63.
Witzig et al., Treatment with ibritumomab tiuxetan radioimmunotherapy in patients with rituximab-refractory follicular non-Hodgkin's lymphoma. J Clin Oncol. Aug. 1, 2002;20(15):3262-9.
Woyke et al., In vitro activities and postantifungal effects of the potent dolastatin 10 derivative auristatin PHE. Antimicrob Agents Chemother. Dec. 2001;45(12):3580-4.
Wright et al., Effect of glycosylation on antibody function: implications for genetic engineering. Trends Biotechnol. Jan. 1997;15(1):26-32.
Wu et al., Arming antibodies: prospects and challenges for immunoconjugates. Nat Biotechnol. Sep. 2005;23(9):1137-46.
Xu et al., Diversity in the CDR3 region of V(H) is sufficient for most antibody specificities. Immunity. Jul. 2000;13(1):37-45.
Yamane-Ohnuki et al., Establishment of FUT8 knockout Chinese hamster ovary cells: an ideal host cell line for producing completely defucosylated antibodies with enhanced antibody-dependent cellular cytotoxicity. Biotechnol Bioeng. Sep. 5, 2004;87(5):614-22.
Yaniv M. Enhancing elements for activation of eukaryotic promoters. Nature. May 6, 1982;297(5861):17-8.
Zhu et al., Remodeling domain interfaces to enhance heterodimer formation. Protein Sci. Apr. 1997;6(4):781-8.
Written Opinion and International Search Report for PCT Application No. PCT/US2010/061760 (WO 2011/079185) dated May 20, 2011.

\* cited by examiner

| Antibody | L1 | | | | | | | | | | | | | | | SEQ ID NO. |
|---|---|---|---|---|---|---|---|---|---|---|---|---|---|---|---|---|
| | 24 | 25 | 26 | 27 | A | B | C | D | 28 | 29 | 30 | 31 | 32 | 33 | 34 | |
| 2G9 Chimeric | K | A | S | Q | S | V | D | Y | D | G | D | S | Y | M | N | 49 |
| h2G9.K4G1.Polish | K | A | S | Q | S | V | D | Y | S | G | D | S | Y | M | N | 55 |
| h2G9.K4G1.v19 | K | A | S | Q | S | V | D | Y | S | G | D | S | Y | M | N | 61 |
| h2G9.K4G1.v25 | K | A | S | Q | S | V | D | Y | S | G | D | S | Y | M | N | 67 |
| h2G9.K4G1.v27 | K | A | S | Q | S | V | D | Y | Y | G | D | S | Y | M | N | 73 |
| h2G9.K4G1.v37 | K | A | S | Q | S | V | D | Y | S | G | D | S | Y | M | N | 79 |
| h2G9.K4G1.v52 | K | A | S | Q | S | L | I | Y | G | A | D | S | Y | M | N | 85 |
| h2G9.K4G1.v55 | K | A | S | Q | S | L | D | Y | Y | H | Y | S | Y | M | N | 91 |
| h2G9.K4G1.v63 | K | A | S | Q | S | V | D | Y | Y | G | D | S | Y | M | N | 97 |
| h2G9.K4G1.v64 | K | A | S | Q | S | V | D | Y | Y | G | D | S | Y | M | N | 103 |
| h2G9.K4G1.v65 | K | A | S | Q | S | V | D | Y | S | G | D | S | Y | M | N | 109 |
| h2G9.K4G1.v67 | K | A | S | Q | S | L | D | Y | W | V | D | S | Y | M | N | 115 |
| h2G9.K4G1.v73 | K | A | S | Q | S | V | D | Y | S | G | D | S | Y | M | N | 121 |
| h2G9.K4G1.v75 | K | A | S | Q | S | V | D | Y | S | G | D | S | Y | M | N | 127 |
| h2G9.K4G1.v77 | K | A | S | Q | S | V | D | Y | G | G | D | S | Y | M | N | 133 |
| h2G9.K4G1.v80 | K | A | S | Q | S | V | D | Y | F | A | E | S | Y | M | N | 139 |
| h2G9.K4G1.v92 | K | A | S | Q | S | V | D | Y | S | G | D | S | Y | M | N | 145 |
| h2G9.K4G1.v19H/v55L | K | A | S | Q | S | L | D | Y | Y | H | Y | S | Y | M | N | 151 |
| | | | | | | | | | | | | | | | | |
| 2B9 Chimeric | S | A | S | S | -- | -- | -- | -- | -- | S | V | F | Y | M | H | 157 |
| h2B9.v1 | S | A | S | S | -- | -- | -- | -- | -- | S | V | F | Y | M | H | 163 |
| h2B9.v10 | S | A | S | S | -- | -- | -- | -- | -- | S | V | F | Y | M | H | 169 |
| h2B9.v23 | S | A | S | S | -- | -- | -- | -- | -- | S | V | F | Y | M | H | 175 |
| h2B9.v37 | S | A | S | S | -- | -- | -- | -- | -- | P | V | F | Y | M | H | 181 |
| h2B9.v56 | S | A | S | S | -- | -- | -- | -- | -- | S | V | F | Y | M | H | 187 |
| h2B9.v76 | S | A | S | S | -- | -- | -- | -- | -- | S | V | F | Y | M | H | 193 |
| | | | | | | | | | | | | | | | | |
| 3F1 Chimeric | E | A | S | Q | S | V | D | Y | D | D | D | S | Y | M | N | 199 |
| h3F1.v1 | E | A | S | Q | S | V | D | Y | D | D | D | S | Y | M | N | 205 |
| | | | | | | | | | | | | | | | | |
| 2D3 Chimeric | K | S | S | E | -- | -- | -- | -- | Y | V | S | N | A | L | S | 211 |

*FIG. 1A*

| Antibody | L2 | | | | | | | SEQ ID NO. |
|---|---|---|---|---|---|---|---|---|
| | 50 | 51 | 52 | 53 | 54 | 55 | 56 | |
| 2G9 Chimeric | A | A | S | N | L | E | S | 50 |
| h2G9.K4G1.Polish | A | A | S | N | L | E | S | 56 |
| h2G9.K4G1.v19 | A | A | S | N | L | E | S | 62 |
| h2G9.K4G1.v25 | A | A | S | N | L | E | S | 68 |
| h2G9.K4G1.v27 | A | A | S | N | L | E | S | 74 |
| h2G9.K4G1.v37 | A | A | S | N | L | E | S | 80 |
| h2G9.K4G1.v52 | A | A | S | N | R | E | T | 86 |
| h2G9.K4G1.v55 | A | A | S | N | R | E | S | 92 |
| h2G9.K4G1.v63 | A | A | S | N | L | E | T | 98 |
| h2G9.K4G1.v64 | A | A | S | N | R | E | S | 104 |
| h2G9.K4G1.v65 | A | A | S | N | L | E | S | 110 |
| h2G9.K4G1.v67 | A | A | S | N | R | E | T | 116 |
| h2G9.K4G1.v73 | A | A | S | N | L | E | S | 122 |
| h2G9.K4G1.v75 | A | A | S | N | L | E | S | 128 |
| h2G9.K4G1.v77 | A | A | S | N | R | E | T | 134 |
| h2G9.K4G1.v80 | A | A | S | Y | R | E | S | 140 |
| h2G9.K4G1.v92 | A | A | S | N | L | E | S | 146 |
| h2G9.K4G1.v19H/v55L | A | A | S | N | R | E | S | 152 |
| | | | | | | | | |
| 2B9 Chimeric | D | T | S | K | L | A | S | 158 |
| h2B9.v1 | D | T | S | K | L | A | S | 164 |
| h2B9.v10 | D | T | S | K | L | A | S | 170 |
| h2B9.v23 | D | T | S | K | L | A | S | 176 |
| h2B9.v37 | D | T | S | N | L | A | S | 182 |
| h2B9.v56 | D | T | S | K | L | A | S | 188 |
| h2B9.v76 | D | T | S | K | L | A | S | 194 |
| | | | | | | | | |
| 3F1 Chimeric | A | T | S | N | L | A | S | 200 |
| h3F1.v1 | A | T | S | N | L | A | S | 206 |
| | | | | | | | | |
| 2D3 Chimeric | G | T | N | K | L | E | D | 212 |

FIG. 1B

| Antibody | L3 | | | | | | | | | SEQ ID NO. |
|---|---|---|---|---|---|---|---|---|---|---|
| | 89 | 90 | 91 | 92 | 93 | 94 | 95 | 96 | 97 | |
| 2G9 Chimeric | Q | Q | I | N | E | D | P | F | T | 51 |
| h2G9.K4G1.Polish | Q | Q | I | N | E | D | P | F | T | 57 |
| h2G9.K4G1.v19 | Q | Q | I | N | E | D | P | F | T | 63 |
| h2G9.K4G1.v25 | Q | Q | I | N | E | D | P | F | T | 69 |
| h2G9.K4G1.v27 | Q | Q | I | N | E | D | P | F | T | 75 |
| h2G9.K4G1.v37 | Q | Q | I | N | E | D | P | F | T | 81 |
| h2G9.K4G1.v52 | Q | Q | I | N | E | D | P | F | T | 87 |
| h2G9.K4G1.v55 | Q | Q | I | N | E | D | P | F | T | 93 |
| h2G9.K4G1.v63 | Q | Q | I | N | E | D | P | F | T | 99 |
| h2G9.K4G1.v64 | Q | Q | I | N | E | D | P | F | T | 105 |
| h2G9.K4G1.v65 | Q | Q | I | N | E | D | P | F | T | 111 |
| h2G9.K4G1.v67 | Q | Q | I | N | E | D | P | F | T | 117 |
| h2G9.K4G1.v73 | Q | Q | I | N | E | D | P | F | T | 123 |
| h2G9.K4G1.v75 | Q | Q | I | N | E | D | P | F | T | 129 |
| h2G9.K4G1.v77 | Q | Q | I | N | E | D | P | F | T | 135 |
| h2G9.K4G1.v80 | Q | Q | I | N | E | D | P | F | T | 141 |
| h2G9.K4G1.v92 | Q | Q | I | N | E | D | P | F | T | 147 |
| h2G9.K4G1.v19H/v55L | Q | Q | I | N | E | D | P | F | T | 153 |
| | | | | | | | | | | |
| 2B9 Chimeric | Q | Q | W | S | S | D | P | L | T | 159 |
| h2B9.v1 | Q | Q | W | S | S | D | P | L | T | 165 |
| h2B9.v10 | Q | Q | W | S | F | D | P | I | T | 171 |
| h2B9.v23 | Q | Q | W | S | W | E | P | L | T | 177 |
| h2B9.v37 | Q | Q | W | S | Y | E | P | L | T | 183 |
| h2B9.v56 | Q | Q | W | S | S | D | P | L | T | 189 |
| h2B9.v76 | Q | Q | W | S | Y | D | P | M | T | 195 |
| | | | | | | | | | | |
| 3F1 Chimeric | Q | Q | S | N | E | D | P | F | T | 201 |
| h3F1.v1 | Q | Q | S | N | E | D | P | F | T | 207 |
| | | | | | | | | | | |
| 2D3 Chimeric | Q | Q | G | Y | D | I | P | -- | T | 213 |

*FIG. 1C*

| Antibody | H1 | | | | | | | | | | | SEQ ID NO. |
|---|---|---|---|---|---|---|---|---|---|---|---|---|
| | 26 | 27 | 28 | 29 | 30 | 31 | 32 | 33 | 34 | 35 | A | B | |
| 2G9 Chimeric | G | Y | S | F | T | D | Y | D | M | H | -- | -- | 52 |
| h2G9.K4G1.Polish | G | Y | S | F | T | D | Y | D | M | H | -- | -- | 58 |
| h2G9.K4G1.v19 | G | Y | S | L | T | N | Y | D | M | H | -- | -- | 64 |
| h2G9.K4G1.v25 | G | Y | S | L | F | H | Y | D | M | H | -- | -- | 70 |
| h2G9.K4G1.v27 | G | Y | S | F | T | D | Y | D | M | H | -- | -- | 76 |
| h2G9.K4G1.v37 | G | Y | S | F | T | H | Y | D | M | H | -- | -- | 82 |
| h2G9.K4G1.v52 | G | Y | S | F | T | D | Y | D | M | H | -- | -- | 88 |
| h2G9.K4G1.v55 | G | Y | S | F | T | D | Y | D | M | H | -- | -- | 94 |
| h2G9.K4G1.v63 | G | Y | S | F | T | D | Y | D | M | H | -- | -- | 100 |
| h2G9.K4G1.v64 | G | Y | S | F | T | D | Y | D | M | H | -- | -- | 106 |
| h2G9.K4G1.v65 | G | Y | T | F | M | H | Y | D | M | H | -- | -- | 112 |
| h2G9.K4G1.v67 | G | Y | S | F | T | D | Y | D | M | H | -- | -- | 118 |
| h2G9.K4G1.v73 | G | Y | S | F | T | H | Y | D | M | H | -- | -- | 124 |
| h2G9.K4G1.v75 | G | Y | T | F | P | I | Y | D | M | H | -- | -- | 130 |
| h2G9.K4G1.v77 | G | Y | T | F | T | E | Y | D | M | H | -- | -- | 136 |
| h2G9.K4G1.v80 | G | Y | S | F | T | D | Y | D | M | H | -- | -- | 142 |
| h2G9.K4G1.v92 | G | Y | S | F | V | H | Y | D | M | H | -- | -- | 148 |
| h2G9.K4G1.v19H/v55L | G | Y | S | L | T | N | Y | D | M | H | -- | -- | 154 |
| | | | | | | | | | | | | | |
| 2B9 Chimeric | G | F | L | L | S | T | S | G | M | G | V | S | 160 |
| h2B9.v1 | G | F | L | L | S | T | S | G | M | G | V | S | 166 |
| h2B9.v10 | G | F | L | L | S | T | S | G | M | G | V | S | 172 |
| h2B9.v23 | G | F | L | L | S | T | S | G | M | G | V | S | 178 |
| h2B9.v37 | G | F | L | L | S | T | S | G | M | G | V | S | 184 |
| h2B9.v56 | G | F | Y | I | S | T | P | G | M | G | V | S | 190 |
| h2B9.v76 | G | F | L | L | S | T | S | G | M | G | V | S | 196 |
| | | | | | | | | | | | | | |
| 3F1 Chimeric | G | Y | T | F | T | N | S | W | M | N | -- | -- | 202 |
| h3F1.v1 | G | Y | T | F | T | N | S | W | M | N | -- | -- | 208 |
| | | | | | | | | | | | | | |
| 2D3 Chimeric | G | F | T | F | S | D | Y | F | M | G | -- | -- | 214 |

*FIG. 1D*

| Antibody | H2 | | | | | | | | | | | | | | | | | SEQ ID NO. |
|---|---|---|---|---|---|---|---|---|---|---|---|---|---|---|---|---|---|---|
| | 50 | 51 | 52 | A | 53 | 54 | 55 | 56 | 57 | 58 | 59 | 60 | 61 | 62 | 63 | 64 | 65 | |
| 2G9 Chimeric | Y | I | S | C | Y | N | G | A | T | T | Y | N | Q | K | F | K | G | 53 |
| h2G9.K4G1.Polish | Y | I | S | S | Y | S | G | A | T | T | Y | N | Q | K | F | K | G | 59 |
| h2G9.K4G1.v19 | Y | I | H | S | Y | S | G | S | T | L | Y | N | Q | K | F | K | G | 65 |
| h2G9.K4G1.v25 | Y | I | S | T | Y | T | G | S | T | T | Y | N | Q | K | F | K | G | 71 |
| h2G9.K4G1.v27 | Y | I | S | S | Y | S | G | A | T | T | Y | N | Q | K | F | K | G | 77 |
| h2G9.K4G1.v37 | Y | I | S | T | Y | A | G | E | T | Y | Y | N | Q | K | F | K | G | 83 |
| h2G9.K4G1.v52 | Y | I | S | S | Y | S | G | A | T | T | Y | N | Q | K | F | K | G | 89 |
| h2G9.K4G1.v55 | Y | I | S | S | Y | S | G | A | T | T | Y | N | Q | K | F | K | G | 95 |
| h2G9.K4G1.v63 | Y | I | S | S | Y | S | G | A | T | T | Y | N | Q | K | F | K | G | 101 |
| h2G9.K4G1.v64 | Y | I | S | S | Y | S | G | A | T | T | Y | N | Q | K | F | K | G | 107 |
| h2G9.K4G1.v65 | Y | I | S | S | Y | T | G | S | T | T | Y | N | Q | K | F | K | G | 113 |
| h2G9.K4G1.v67 | Y | I | S | S | Y | S | G | A | T | T | Y | N | Q | K | F | K | G | 119 |
| h2G9.K4G1.v73 | Y | I | S | S | Y | L | G | A | T | I | Y | N | Q | K | F | K | G | 125 |
| h2G9.K4G1.v75 | Y | I | S | S | Y | S | G | A | T | T | Y | N | Q | K | F | K | G | 131 |
| h2G9.K4G1.v77 | Y | I | T | T | Y | S | G | A | T | T | Y | N | Q | K | F | K | G | 137 |
| h2G9.K4G1.v80 | Y | I | S | S | Y | S | G | A | T | T | Y | N | Q | K | F | K | G | 143 |
| h2G9.K4G1.v92 | Y | I | S | S | Y | S | G | A | T | S | Y | N | Q | K | F | K | G | 149 |
| h2G9.K4G1.v19H/v55L | Y | I | H | S | Y | S | G | S | T | L | Y | N | Q | K | F | K | G | 155 |
| 2B9 Chimeric | H | I | Y | -- | W | D | D | D | T | R | Y | N | P | S | L | K | S | 161 |
| h2B9.v1 | H | I | Y | -- | W | D | D | D | T | R | Y | N | P | S | L | K | S | 167 |
| h2B9.v10 | H | I | Y | -- | W | D | D | D | T | R | Y | N | P | S | L | K | S | 173 |
| h2B9.v23 | H | I | Y | -- | W | D | D | D | T | R | Y | N | P | S | L | K | S | 179 |
| h2B9.v37 | H | I | Y | -- | W | D | D | D | T | R | Y | N | P | S | L | K | S | 185 |
| h2B9.v56 | H | I | Y | -- | W | D | D | D | T | R | Y | N | P | S | L | K | S | 191 |
| h2B9.v76 | H | I | Y | -- | W | D | D | D | T | R | Y | N | P | S | L | K | S | 197 |
| 3F1 Chimeric | R | I | D | P | S | D | S | E | T | H | Y | N | Q | K | F | K | D | 203 |
| h3F1.v1 | R | I | D | P | S | D | S | E | T | H | Y | N | Q | K | F | K | D | 209 |

| Antibody | H2 | | | | | | | | | | | | | | | | | | SEQ ID No. |
|---|---|---|---|---|---|---|---|---|---|---|---|---|---|---|---|---|---|---|---|
| | 50 | 51 | 52 | A | B | C | 53 | 54 | 55 | 56 | 57 | 58 | 59 | 60 | 61 | 62 | 63 | 64 | 65 | |
| 2D3 Chimeric | G | I | D | T | K | S | Y | N | Y | A | T | Y | Y | S | G | S | V | K | G | 215 |

*FIG. 1E*

| Antibody | H3 | | | | | | | | | | | SEQ ID NO. |
|---|---|---|---|---|---|---|---|---|---|---|---|---|
| | 95 | 96 | 97 | 98 | 99 | 100 | A | B | C | D | 101 | 102 | |
| 2G9 Chimeric | D | G | N | Y | G | E | A | Y | A | M | D | Y | 54 |
| h2G9.K4G1.Polish | D | S | N | Y | G | E | A | Y | A | M | D | Y | 60 |
| h2G9.K4G1.v19 | D | S | N | Y | G | E | A | Y | A | M | D | Y | 66 |
| h2G9.K4G1.v25 | D | S | N | Y | G | E | A | Y | A | M | D | Y | 72 |
| h2G9.K4G1.v27 | D | S | N | Y | G | E | A | Y | A | M | D | Y | 78 |
| h2G9.K4G1.v37 | D | S | N | Y | G | E | A | Y | A | M | D | Y | 84 |
| h2G9.K4G1.v52 | D | S | N | Y | G | E | A | Y | A | M | D | Y | 90 |
| h2G9.K4G1.v55 | D | S | N | Y | G | E | A | Y | A | M | D | Y | 96 |
| h2G9.K4G1.v63 | D | S | N | Y | G | E | A | Y | A | M | D | Y | 102 |
| h2G9.K4G1.v64 | D | S | N | Y | G | E | A | Y | A | M | D | Y | 108 |
| h2G9.K4G1.v65 | D | S | N | Y | G | E | A | Y | A | M | D | Y | 114 |
| h2G9.K4G1.v67 | D | S | N | Y | G | E | A | Y | A | M | D | Y | 120 |
| h2G9.K4G1.v73 | D | S | N | Y | G | E | A | Y | A | M | D | Y | 126 |
| h2G9.K4G1.v75 | D | S | N | Y | G | E | A | Y | A | M | D | Y | 132 |
| h2G9.K4G1.v77 | D | S | N | Y | G | E | A | Y | A | M | D | Y | 138 |
| h2G9.K4G1.v80 | D | S | N | Y | G | E | A | Y | A | M | D | Y | 144 |
| h2G9.K4G1.v92 | D | S | N | Y | G | E | A | Y | A | M | D | Y | 150 |
| h2G9.K4G1.v19H/v55L | D | S | N | Y | G | E | A | Y | A | M | D | Y | 156 |
| | | | | | | | | | | | | | |
| 2B9 Chimeric | R | D | H | G | Y | Y | W | -- | -- | F | T | Y | 162 |
| h2B9.v1 | R | D | H | G | Y | Y | W | -- | -- | F | T | Y | 168 |
| h2B9.v10 | R | D | H | G | Y | Y | W | -- | -- | F | D | Y | 174 |
| h2B9.v23 | R | D | H | G | Y | Y | W | -- | -- | F | D | Y | 180 |
| h2B9.v37 | R | D | H | G | Y | Y | W | -- | -- | F | D | Y | 186 |
| h2B9.v56 | R | D | H | G | Y | Y | W | -- | -- | F | D | Y | 192 |
| h2B9.v76 | R | D | H | G | Y | Y | W | -- | -- | F | D | Y | 198 |
| | | | | | | | | | | | | | |
| 3F1 Chimeric | D | S | S | Y | D | G | F | Y | A | M | D | Y | 204 |
| h3F1.v1 | D | S | S | Y | D | G | F | Y | A | M | D | Y | 210 |
| | | | | | | | | | | | | | |
| 2D3 Chimeric | N | Y | G | N | Y | G | A | -- | -- | F | D | S | 216 |

*FIG. 1F*

DIVMTQSPDSLAVSLGERATINC -L1- WYQQKPGQPPKLLIY -L2-
└─ ─ ─ ─→ GVPDRFSGSGSGTDFTLTISSLQAEDVAVYYC -L3- FGQGTKVEIKR (SEQ ID NO:240)

EVQLVQSGAEVKKPGASVKVSCKAS -H1- WVRQAPGQGLEWIG -H2-
└─ ─ ─ ─→ RVTITVDKSTSTAYLELSSLRSEDTAVYYCAR -H3- WGQGTLVTVSS (SEQ ID NO:241)

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C | D | E | F | 28 | 29 | 30 | 31 | 32 | 33 | 34 | 35 | 36 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | Kabat - CDR L1 | | | | | | | | | | |
| | | | | | | | | | | | | | | | | | | | | | | | | | | | | | | | | Chothia - CDR L1 | | | | | | | | | |
| | | | | | | | | | | | | | | | | | | | | | | | | | | | | | | | | | | Contact - CDR L1 | | | | | | | |
| huKIV | D | I | V | M | T | Q | S | P | D | S | L | A | V | S | L | G | E | R | A | T | I | N | C | K | S | S | Q | S | V | L | Y | S | S | N | N | K | N | Y | L | A | W | Y |
| mouse/chimeric 2G9 | D | I | V | M | T | Q | S | P | A | S | L | A | V | S | L | G | Q | R | A | T | I | S | C | K | A | S | Q | S | V | D | Y | D | - | - | - | G | D | S | Y | M | N | W | Y |
| h2G9.K4.Polish | D | I | V | M | T | Q | S | P | D | S | L | A | V | S | L | G | E | R | A | T | I | N | C | K | A | S | Q | S | V | D | Y | D | - | - | - | S | G | D | S | Y | M | N | W | Y |
| h2G9.K4.v19 | D | I | V | M | T | Q | S | P | D | S | L | A | V | S | L | G | E | R | A | T | I | N | C | K | A | S | Q | S | L | I | Y | D | - | - | - | G | A | D | S | Y | M | N | W | Y |
| h2G9.K4.v52 | D | I | V | M | T | Q | S | P | D | S | L | A | V | S | L | G | E | R | A | T | I | N | C | K | A | S | Q | S | L | L | D | Y | - | - | - | S | Y | H | Y | Y | M | N | W | Y |
| h2G9.K4.v55 | D | I | V | M | T | Q | S | P | D | S | L | A | V | S | L | G | E | R | A | T | I | N | C | K | A | S | Q | S | V | D | Y | - | - | - | S | G | D | Y | Y | M | N | W | Y |
| h2G9.K4.v73 | D | I | V | M | T | Q | S | P | D | S | L | A | V | S | L | G | E | R | A | T | I | N | C | K | A | S | Q | S | L | D | Y | - | - | - | S | Y | H | Y | Y | M | N | W | Y |
| h2G9.K4.v19H/v55L | * | * | * | * | * | * | * | * | * | * | * | * | * | * | * | * | * | * | * | * | * | * | * | * | * | * | * | * | * | * | * | * | * | * | * | * | * | * | * | * | * | * | * |

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | A | B | 36 | 37 | 38 | 39 | 40 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| humI | E | V | Q | L | V | Q | S | G | A | E | V | K | K | P | G | A | S | V | K | V | S | C | K | A | S | G | Y | T | F | T | S | Y | Y | I | H | - | - | W | V | R | Q | A |
| mouse/chimeric 2G9 | E | V | Q | L | Q | Q | S | G | P | E | V | V | T | P | G | A | S | V | I | V | S | C | K | A | S | G | Y | S | F | T | D | Y | Y | M | H | - | - | W | V | K | Q | S |
| h2G9.G1.Polish | E | V | Q | L | V | Q | S | G | A | E | V | V | K | P | G | A | S | V | K | V | S | C | K | A | S | G | Y | S | F | T | D | Y | Y | M | H | - | - | W | V | R | Q | A |
| h2G9.G1.v19 | E | V | Q | L | V | Q | S | G | A | E | V | K | K | P | G | A | S | V | K | V | S | C | K | A | S | G | Y | S | F | T | D | Y | Y | M | H | - | - | W | V | R | Q | A |
| h2G9.G1.v52 | E | V | Q | L | V | Q | S | G | A | E | V | K | K | P | G | A | S | V | K | V | S | C | K | A | S | G | Y | S | F | L | N | Y | D | M | H | - | - | W | V | R | Q | A |
| h2G9.G1.v55 | E | V | Q | L | V | Q | S | G | A | E | V | K | K | P | G | A | S | V | K | V | S | C | K | A | S | G | Y | S | F | T | D | Y | D | M | H | - | - | W | V | R | Q | A |
| h2G9.G1.v73 | E | V | Q | L | V | Q | S | G | A | E | V | K | K | P | G | A | S | V | K | V | S | C | K | A | S | G | Y | S | F | T | H | Y | D | M | H | - | - | W | V | R | Q | A |
| h2G9.K4.v19H/v55L | E | V | Q | L | V | Q | S | G | A | E | V | K | K | P | G | A | S | V | K | V | S | C | K | A | S | G | Y | S | F | L | N | Y | D | M | H | - | - | W | V | R | Q | A |
| | * | | | | | | | | | | | | | | | | | | | | | * | | | | | | | | | | | | | | | | * | | | * | |

Chothia - CDR H1
Kabat - CDR H1
Contact - CDR H1

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C | D | 28 | 29 | 30 | 31 | 32 | 33 | 34 | 35 | 36 |
|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | | | | | Kabat - CDR L1 | | | | |
| | | | | | | | | | | | | | | | | | | | | | | | | | | | | | | | | | | | Chothia - CDR L1 | | | | |
| | | | | | | | | | | | | | | | | | | | | | | | | | | | | | | | | | | | | Contact - CDR L1 | | | |
| huKI | D | I | Q | M | T | Q | S | P | S | S | L | S | A | S | V | G | D | R | V | T | I | T | C | R | A | S | Q | - | - | - | - | S | I | S | N | Y | L | A | W | Y |
| m2B9 | D | I | H | V | L | T | Q | S | P | A | I | M | S | A | S | P | G | E | K | V | T | M | T | C | S | A | S | - | - | - | - | S | S | V | F | Y | M | H | W | Y |
| Chimeric 2B9 | D | I | H | V | L | T | Q | S | P | A | I | M | S | A | S | P | G | E | K | V | T | M | T | C | S | A | S | - | - | - | - | S | S | V | F | Y | M | H | W | Y |
| h2B9.v76a | D | I | Q | M | T | Q | S | P | S | S | L | S | A | S | V | G | D | R | V | T | I | T | C | S | A | S | - | - | - | - | S | S | V | F | Y | M | H | W | Y |
| | * | | | | | | | | | | | | | | | | | | | | | | | | * | * | * | | | | | * | * | * | * | * | * | * | | |

| Kabat# | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 |
|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | Kabat - CDR L2 | | | | | | | | | | | | | | | | | | | | | | | |
| | | | | | | | | | | | | | | | | | Chothia - CDR L2 | | | | | | | | | | | | | | | | | | | | | | | |
| | | | | | | | | | | | Contact - CDR L2 | | | | | | | | | | | | | | | | | | | | | | | | | | | | | |
| huKI | Q | Q | K | P | G | K | A | P | K | L | L | I | Y | A | A | S | S | L | E | S | G | V | P | S | R | F | S | G | S | G | S | G | T | D | F | T | L | T | I | S |
| m2B9 | L | Q | K | S | G | E | S | P | K | L | W | I | Y | Y | D | T | S | K | L | A | S | G | V | P | A | R | F | S | G | S | G | S | G | T | D | F | S | L | T | I |
| Chimeric 2B9 | L | Q | K | S | G | E | S | P | K | L | W | I | Y | Y | D | T | S | K | L | A | S | G | V | P | A | R | F | S | G | S | G | S | G | T | D | F | S | L | T | I |
| h2B9.v76a | Q | Q | K | P | G | K | A | P | K | L | L | I | Y | Y | D | T | S | K | L | A | S | G | V | P | S | R | F | S | G | S | G | S | G | T | D | F | T | L | T | I |
| | | | | * | | * | * | | | | * | | | * | * | * | | * | | | | | | | * | | | | | | | | | | | | * | | | |

| Kabat# | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | Kabat - CDR L3 | | | | | | | | | | | | | | | | | | | | | | | | | | |
| | | | | | | | | | | | | | | Chothia - CDR L3 | | | | | | | | | | | | | | | | | | | | | | | | | | |
| | | | | | | | | | | | | | | Contact - CDR L3 | | | | | | | | | | | | | | | | | | | | | | | | | | |
| huKI | S | L | Q | P | E | D | F | A | T | Y | Y | C | Q | Q | Y | N | S | L | P | W | T | F | G | Q | G | T | K | V | E | I | K | R | | | | | SEQ ID NO:17 | | | |
| m2B9 | N | M | E | A | E | D | A | A | T | Y | Y | C | Q | Q | W | S | S | D | P | L | T | F | G | A | G | T | K | V | E | I | K | R | | | | | SEQ ID NO:19 | | | |
| Chimeric 2B9 | N | M | E | A | E | D | A | A | T | Y | Y | C | Q | Q | W | S | S | D | P | L | T | F | G | A | G | T | K | V | E | I | K | R | | | | | SEQ ID NO:21 | | | |
| h2B9.v76a | S | L | Q | P | E | D | F | A | T | Y | Y | C | Q | Q | W | S | Y | D | P | M | T | F | G | Q | G | T | K | V | E | I | K | R | | | | | SEQ ID NO:23 | | | |
| | * | * | * | * | | | * | | | | | | | | * | * | * | * | | * | | | | * | | | | | | | | | | | | | | | | |

☐ Highlight framework difference between mouse 2B9 and human consensus Kappa I (24)
⋮☐⋮ Highlight CDR difference between mouse 2B9 and humanized 2B9 variants

Figure 4B:
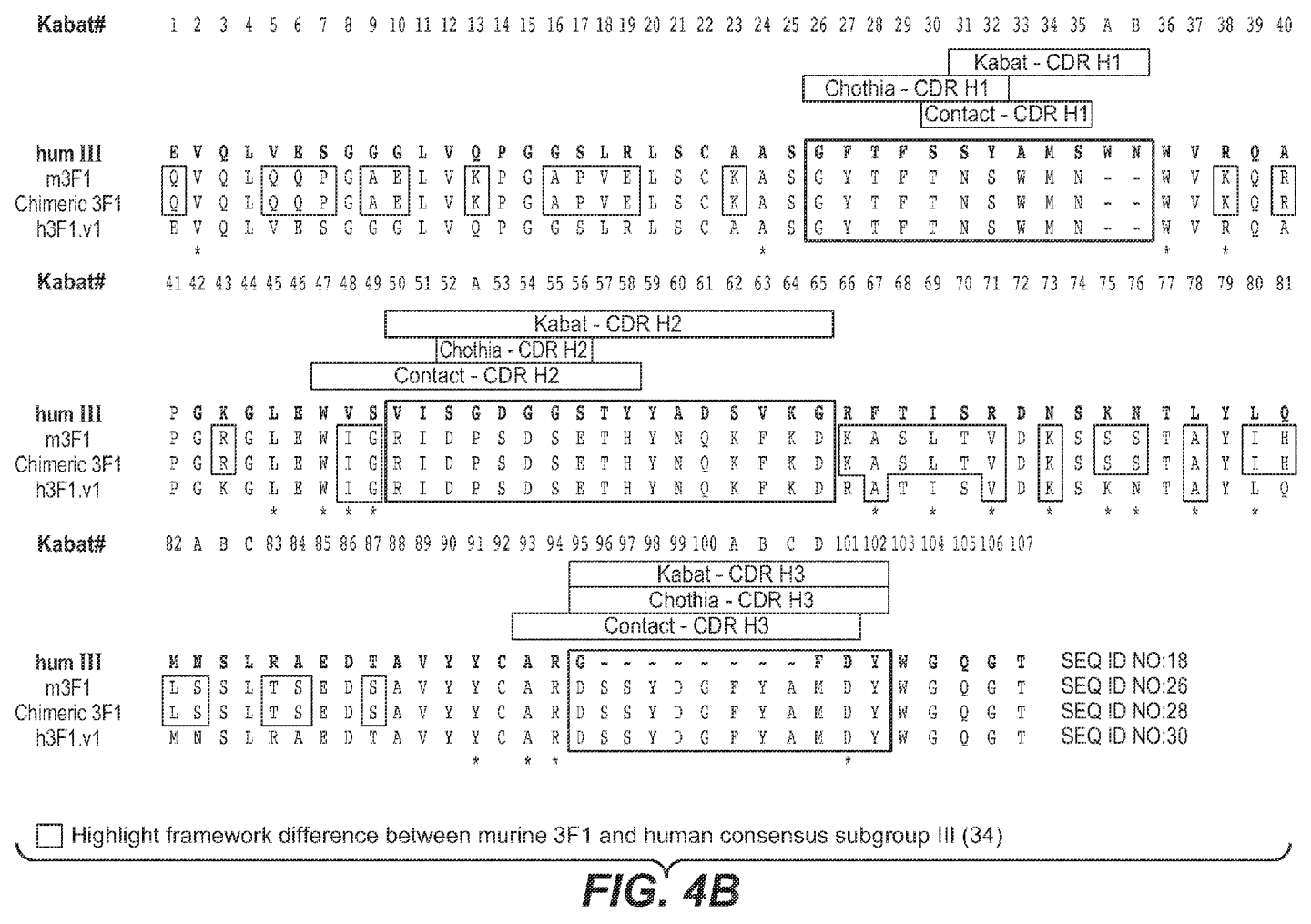

Alignment of murine 3F1, chimeric 3F1, humanized 3F1.v1 heavy chain variable region sequences with human consensus subgroup III framework.

| | SEQ ID |
|---|---|
| m3F1 | SEQ ID NO:18 |
| Chimeric 3F1 | SEQ ID NO:26 |
| h3F1.v1 | SEQ ID NO:28 |
| hum III | SEQ ID NO:30 |

☐ Highlight framework difference between murine 3F1 and human consensus subgroup III (34)

| Kabat# | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C | D | 28 | 29 | 30 | 31 | 32 | 33 | 34 | 35 | 36 |

Kabat - CDR L1
Chothia - CDR L1
Contact - CDR L1 huKI: D I Q M T Q S P S S L S A S V G D R V T I T C R A S Q — — — S I S S Y L A W Y
Hamster 2D3: D I Q M T Q T P S S L S V S L G D R V S I H C K S S E — — — Y V S N A L S W Y
Chimeric 2D3: D I Q M Q E I P S S L S V S L G D R V S I S C K C S E — — — Y V S N A L S W Y

FIG. 5A

Highlight framework difference between hamster 2D3 and human consensus Kappa I (21)

SEQ ID NO:17
SEQ ID NO:31
SEQ ID NO:33

FIG. 5B

Sequence alignment of hamster 2D3, chimeric 2D3, and human consensus subgroup III heavy chain variable regions with Kabat numbering. CDR H1, H2, and H3 regions are indicated per Kabat, Chothia, and Contact definitions.

| | |
|---|---|
| hum III | SEQ ID NO:18 |
| Hamster 2D3 | SEQ ID NO:32 |
| Chimeric 2D3 | SEQ ID NO:34 |

☐ Highlight framework difference between hamster 2D3 and human consensus subgroup III (17)

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C | D | 28 | 29 | 30 | 31 | 32 | 33 | 34 | 35 | 36 |
|---|---|---|---|---|---|---|---|---|---|---|---|---|---|---|---|---|---|---|---|---|---|---|---|---|---|---|---|---|---|---|---|---|---|---|---|---|---|---|---|---|
| huKI | D | I | Q | M | T | Q | S | P | S | S | L | S | A | S | V | G | D | R | V | T | I | T | C | R | A | S | Q | - | - | - | - | S | I | S | N | Y | L | A | W | Y |
| mouse/Chimeric 2B9 | D | V | H | Q | T | Q | S | P | A | I | M | S | A | S | P | G | E | K | V | T | M | T | C | S | A | S | S | - | - | - | - | S | V | F | Y | M | H | W | Y |
| h2B9.v1 | D | I | Q | M | T | Q | S | P | S | S | L | S | A | S | V | G | D | R | V | T | I | T | C | S | A | S | S | - | - | - | - | S | V | F | Y | M | H | W | Y |
| h2B9.v10 | D | I | Q | M | T | Q | S | P | S | S | L | S | A | S | V | G | D | R | V | T | I | T | C | S | A | S | S | - | - | - | - | S | V | F | Y | M | H | W | Y |
| h2B9.v23 | D | I | Q | M | T | Q | S | P | S | S | L | S | A | S | V | G | D | R | V | T | I | T | C | S | A | S | S | - | - | - | - | S | V | F | Y | M | H | W | Y |
| h2B9.v37 | D | I | Q | M | T | Q | S | P | S | S | L | S | A | S | V | G | D | R | V | T | I | T | C | S | A | S | S | - | - | - | - | S | V | F | Y | M | H | W | Y |
| h2B9.v56 | D | I | Q | M | T | Q | S | P | S | S | L | S | A | S | V | G | D | R | V | T | I | T | C | S | A | S | S | - | - | - | - | S | V | F | Y | M | H | W | Y |
| h2B9.v76 | D | I | Q | M | T | Q | S | P | S | S | L | S | A | S | V | G | D | R | V | T | I | T | C | S | A | S | S | - | - | - | - | S | V | F | Y | M | H | W | Y |

Chothia - CDR L1 (positions 24-34)
Kabat - CDR L1 (positions 24-36)
Contact - CDR L1 (positions 27-36)

| Kabat# | | 37 38 39 40 41 42 43 44 45 46 47 48 49 50 51 52 53 54 55 56 57 58 59 60 61 62 63 64 65 66 67 68 69 70 71 72 73 74 75 76 |
|---|---|---|
| | | Kabat - CDR L2 |
| | | Chothia - CDR L2 |
| | | Contact - CDR L2 |
| huKI | | Q Q K P G K A P K L L I Y A A S S L E S G V P S R F S G S G S G T D F T L T I S |
| mouse/chimeric 2B9 | | Q Q K P G S S P K L L I W T A S S L E S G V P A R F S G S G S G T S Y S L T I S  SEQ ID NO:17 |
| h2B9.v1 | | Q Q K P G K A P K L L I W T A S S L E S G V P S R F S G S G S G T D F T L T I S  SEQ ID NO:35 |
| h2B9.v10 | | Q Q K P G K A P K L L I W T A S S L E S G V P S R F S G S G S G T D F T L T I S  SEQ ID NO:37 |
| h2B9.v23 | | Q Q K P G K A P K L L I W T A S S L E S G V P S R F S G S G S G T D F T L T I S  SEQ ID NO:39 |
| h2B9.v37 | | Q Q K P G K A P K L L I W T A S S L E S G V P S R F S G S G S G T D F T L T I S  SEQ ID NO:41 |
| h2B9.v56 | | Q Q K P G K A P K L L I W T N S S K L A S G V P S R F S G S G S G T D F T L T I S  SEQ ID NO:43 |
| h2B9.v76 | | Q Q K P G K A P K L L I W T A S S L A S G V P S R F S G S G S G T D F T L T I S  SEQ ID NO:45 |
| | | Q Q K P G K A P K L L I W T A S S L A S G V P S R F S G S G S G T D F T L T I S  SEQ ID NO:47 |
| | | *   * *         *       *                           * * *        |

| Kabat# | | 77 78 79 80 81 82 83 84 85 86 87 88 89 90 91 92 93 94 95 96 97 98 99 100 101 102 103 104 105 106 107 108 |
|---|---|---|
| | | Kabat - CDR L3 |
| | | Chothia - CDR L3 |
| | | Contact - CDR L3 |
| huKI | | S L Q P E D F A T Y Y C Q Q Y N S L P W T F G Q G T K V E I K R |
| mouse/chimeric 2B9 | | N M E A E D A A T Y Y C Q Q S S S F D P L T F G A G T K V E I K R  SEQ ID NO:17 |
| h2B9.v1 | | S L Q P E D F A T Y Y C Q Q S S W E P L T F G Q G T K V E I K R  SEQ ID NO:35 |
| h2B9.v10 | | S L Q P E D F A T Y Y C Q Q S S S F D P L T F G Q G T K V E I K R  SEQ ID NO:37 |
| h2B9.v23 | | S L Q P E D F A T Y Y C Q Q W S S Y E P L T F G Q G T K V E I K R  SEQ ID NO:39 |
| h2B9.v37 | | S L Q P E D F A T Y Y C Q Q S S S D P L T F G Q G T K V E I K R  SEQ ID NO:41 |
| h2B9.v56 | | S L Q P E D F A T Y Y C Q Q N W S V E P L T F G Q G T K V E I K R  SEQ ID NO:43 |
| h2B9.v76 | | S L Q P E D F A T Y Y C Q Q N S L P M T F G Q G T K V E I K R  SEQ ID NO:45 |
| | | *   *           *                       *                |

☐ Highlight framework difference between mouse/humanized 2B9 and human consensus Kappa I
☐ Highlight CDR difference between mouse 2B9 and humanized 2B9 variants

| Kabat# | 1 2 3 4 5 6 7 8 9 10 11 12 13 14 15 16 17 18 19 20 21 22 23 24 25 | 26 27 28 29 30 31 32 33 34 35 A B 36 37 38 39 40 |
|---|---|---|
| | | Chothia - CDR H1 / Kabat - CDR H1 / Contact - CDR H1 |
| hum III | E V Q L V E S G G G L V Q P G G S L R L S C A A S | G F T F S S Y A M S W V R Q A |
| mouse/chimeric 2B9 | [Q] V [I] L [K] E S G [P] G I L Q P [S] [T] [I] C [T] [F] [S] | G F [L] [I] T S G M G V W [I] R Q [P] |
| h2B9.v1 | E V Q L V E S G G G L V Q P G G S L R L S C A A S | G F L L T S G M G V S W V R Q A |
| h2B9.v10 | E V Q L V E S G G G L V Q P G G S L R L S C A A S | G F L L T S G M G V S W V R Q A |
| h2B9.v23 | E V Q L V E S G G G L V Q P G G S L R L S C A A S | G F L L T S G M G V S W V R Q A |
| h2B9.v37 | E V Q L V E S G G G L V Q P G G S L R L S C A A S | G F L L S G M G V S W V R Q A |
| h2B9.v56 | E V Q L V E S G G G L V Q P G G S L R L S C A A S | G F [V/I] L T [D] G M G V S W V R Q A |
| h2B9.v76 | E V Q L V E S G G G L V Q P G G S L R L S C A A S | G F L L S G M G V S W V R Q A |
| | * * * * * * * * * * * * * * * * * * * * * * * * * | * * * * * * * * * * * * * * * * |

| FIG. 7A |
| FIG. 7B |

FIG. 7A

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C | D | E | F | 28 | 29 | 30 | 31 | 32 | 33 | 34 | 35 | 36 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | | | | Kabat – CDR L1 | | | | | | | | |
| | | | | | | | | | | | | | | | | | | | | | | | | | | | | | | | | | | Chothia – CDR L1 | | | | | | | | |
| | | | | | | | | | | | | | | | | | | | | | | | | | | | | | | | | | | | | | | Contact – CDR L1 | | | | |
| huKI | D | I | Q | M | T | Q | S | P | S | S | L | S | A | S | V | G | D | R | V | T | I | T | C | R | A | S | Q | - | - | - | - | - | - | S | I | S | N | Y | L | A | W | Y |
| m2G9 | D | I | V | L | T | Q | S | P | A | S | L | A | V | S | L | G | Q | R | A | T | I | S | C | K | A | S | Q | S | V | D | Y | - | - | D | G | D | S | Y | M | N | W | Y |
| h2G9.K1 | D | I | Q | M | T | Q | S | P | S | S | L | S | A | S | V | G | D | R | V | T | I | T | C | K | A | S | Q | S | V | D | Y | - | - | D | G | D | S | Y | M | N | W | Y |
| huKIV | D | I | V | M | T | Q | S | P | D | S | L | A | V | S | L | G | E | R | A | T | I | N | C | K | S | S | Q | S | V | L | Y | S | S | N | N | K | N | Y | L | A | W | Y |
| m2G9 | D | I | V | L | T | Q | S | P | A | S | L | A | V | S | L | G | Q | R | A | T | I | S | C | K | A | S | Q | S | V | D | Y | - | - | D | G | D | S | Y | M | N | W | Y |
| h2G9.K4 | D | I | V | M | T | Q | S | P | D | S | L | A | V | S | L | G | E | R | A | T | I | N | C | K | A | S | Q | S | V | D | Y | - | - | D | G | D | S | Y | M | N | W | Y |
| | * | | | | | | | | | | | | | | | | | | | | | | | | | | | | | | | | | | | | | | | | | * |

| FIG. 8A |
|---------|
| FIG. 8B |

FIG. 8A

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | A | B | 36 | 37 | 38 | 39 | 40 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | | | | | | | | | | | | |
| humI | E | V | Q | L | V | Q | S | G | A | E | V | K | K | P | G | A | S | V | K | V | S | C | K | A | S | G | Y | T | F | T | S | Y | Y | I | H | - | - | W | V | R | Q | A |
| m2G9 | E | V | Q | L | Q | Q | S | G | P | E | V | V | K | T | G | A | S | V | K | I | S | C | K | A | S | G | Y | S | F | T | D | Y | N | M | H | - | - | W | V | K | Q | S |
| h2G9.G1 | E | V | Q | L | V | Q | S | G | A | E | V | K | K | P | G | A | S | V | K | V | S | C | K | A | S | G | Y | S | F | T | D | Y | N | M | H | - | - | W | V | R | Q | A |
| humIII | E | V | Q | L | V | E | S | G | G | G | L | V | Q | P | G | G | S | L | R | L | S | C | A | A | S | G | F | T | F | S | S | Y | A | M | S | N | W | V | R | Q | A |
| m2G9 | E | V | Q | L | Q | Q | S | G | P | E | V | V | K | T | G | A | S | V | K | I | S | C | K | A | S | G | Y | S | F | T | D | Y | N | M | H | - | - | W | V | K | Q | S |
| h2G9.G3 | E | V | Q | L | V | E | S | G | G | G | L | V | Q | P | G | G | S | L | R | L | S | C | A | A | S | G | Y | S | F | T | D | Y | N | M | H | - | - | W | V | R | Q | A |
| | * | | | | | | | | | | | | | | | | | | | | | | | | | | | | | | | | | | | | | * | | | | |

Chothia - CDR H1: positions 26-32
Kabat - CDR H1: positions 31-35B
Contact - CDR H1: positions 30-35B

FIG. 8B

L1/L2 Soft Library

CDR-L1 / CDR-L2

| ID | 24 | 25 | 26 | 27 | A | B | C | D | 28 | 29 | 30 | 31 | 32 | 33 | 34 | 50 | 51 | 52 | 53 | 54 | 55 | 56 |
|---|---|---|---|---|---|---|---|---|---|---|---|---|---|---|---|---|---|---|---|---|---|---|
| h2G9.K4G1.Polish | K | A | S | Q | S | V | D | Y | S | G | D | S | Y | M | N | A | A | S | N | L | E | S |
| h2G9.K4G1.v27 | K | A | S | Q | S | V | D | Y | Y | G | D | S | Y | M | N | A | A | S | N | L | E | S |
| h2G9.K4G1.v52 | K | A | S | Q | S | L | I | Y | G | A | D | S | Y | M | N | A | A | S | N | R | E | T |
| h2G9.K4G1.v55 | K | A | S | Q | S | L | D | Y | Y | H | Y | S | Y | M | N | A | A | S | N | R | E | S |
| h2G9.K4G1.v63 | K | A | S | Q | S | V | D | Y | Y | G | D | S | Y | M | N | A | A | S | N | L | E | T |
| h2G9.K4G1.v64 | K | A | S | Q | S | V | D | Y | Y | G | D | S | Y | M | N | A | A | S | N | R | E | S |
| h2G9.K4G1.v67 | K | A | S | Q | S | L | D | Y | W | V | D | S | Y | M | N | A | A | S | N | R | E | T |
| h2G9.K4G1.v77 | K | A | S | Q | S | V | D | Y | G | G | D | S | Y | M | N | A | A | S | N | R | E | T |
| h2G9.K4G1.v80 | K | A | S | Q | S | V | D | Y | F | A | E | S | Y | M | N | A | A | S | Y | R | E | S |

L1/L2 Soft Library

CDR-L3

| ID | 89 | 90 | 91 | 92 | 93 | 94 | 95 | 96 | 97 |
|---|---|---|---|---|---|---|---|---|---|
| h2G9.K4G1.Polish | Q | Q | I | N | E | D | P | F | T |
| h2G9.K4G1.v27 | Q | Q | I | N | E | D | P | F | T |
| h2G9.K4G1.v52 | Q | Q | I | N | E | D | P | F | T |
| h2G9.K4G1.v55 | Q | Q | I | N | E | D | P | F | T |
| h2G9.K4G1.v63 | Q | Q | I | N | E | D | P | F | T |
| h2G9.K4G1.v64 | Q | Q | I | N | E | D | P | F | T |
| h2G9.K4G1.v67 | Q | Q | I | N | E | D | P | F | T |
| h2G9.K4G1.v77 | Q | Q | I | N | E | D | P | F | T |
| h2G9.K4G1.v80 | Q | Q | I | N | E | D | P | F | T |

*FIG. 9*

H1/H2 Soft Library

| ID | CDR-H1 | | | | | | | | | | CDR-H2 | | | | | | | | | | | | | | |
|---|---|---|---|---|---|---|---|---|---|---|---|---|---|---|---|---|---|---|---|---|---|---|---|---|---|
| | 26 | 27 | 28 | 29 | 30 | 31 | 32 | 33 | 34 | 35 | 50 | 51 | 52 | 53 | 54 | 55 | 56 | 57 | 58 | 59 | 60 | 61 | 62 | 63 | 64 | 65 |
| h2G9.K4G1.Polish | G | Y | S | F | T | D | Y | D | M | H | Y | I | S | Y | S | G | A | T | T | Y | N | Q | K | F | K | G |
| h2G9.K4G1.v19 | G | Y | S | L | T | N | Y | D | M | H | Y | I | H | Y | T | G | S | T | L | Y | N | Q | K | F | K | G |
| h2G9.K4G1.v25 | G | Y | S | L | F | H | Y | D | M | H | Y | I | S | Y | A | G | S | T | T | Y | N | Q | K | F | K | G |
| h2G9.K4G1.v37 | G | Y | S | F | T | H | Y | D | M | H | Y | I | S | Y | T | G | E | T | S | Y | N | Q | K | F | K | G |
| h2G9.K4G1.v65 | G | Y | T | F | M | H | Y | D | M | H | Y | I | S | Y | L | G | S | T | T | Y | N | Q | K | F | K | G |
| h2G9.K4G1.v73 | G | Y | S | F | T | H | Y | D | M | H | Y | I | S | Y | L | G | A | T | I | Y | N | Q | K | F | K | G |
| h2G9.K4G1.v75 | G | Y | T | F | P | — | Y | D | M | H | Y | I | S | Y | S | G | A | T | T | Y | N | Q | K | F | K | G |
| h2G9.K4G1.v77 | G | Y | T | F | T | E | Y | D | M | H | Y | I | T | Y | S | G | A | T | T | Y | N | Q | K | F | K | G |
| h2G9.K4G1.v92 | G | Y | S | F | V | H | Y | D | M | H | Y | I | S | Y | S | G | A | T | S | Y | N | Q | K | F | K | G |

H1/H2 Soft Library

| ID | CDR-H3 | | | | | | | | | |
|---|---|---|---|---|---|---|---|---|---|---|
| | 95 | 96 | 97 | 98 | 99 | 100 | A | B | C | D | 101 | 102 |
| h2G9.K4G1.Polish | D | S | N | Y | G | E | A | Y | A | M | D | Y |
| h2G9.K4G1.v19 | D | S | N | Y | G | E | A | Y | A | M | D | Y |
| h2G9.K4G1.v25 | D | S | N | Y | G | E | A | Y | A | M | D | Y |
| h2G9.K4G1.v37 | D | S | N | Y | G | E | A | Y | A | M | D | Y |
| h2G9.K4G1.v65 | D | S | N | Y | G | E | A | Y | A | M | D | Y |
| h2G9.K4G1.v73 | D | S | N | Y | G | E | A | Y | A | M | D | Y |
| h2G9.K4G1.v75 | D | S | N | Y | G | E | A | Y | A | M | D | Y |
| h2G9.K4G1.v77 | D | S | N | Y | G | E | A | Y | A | M | D | Y |
| h2G9.K4G1.v92 | D | S | N | Y | G | E | A | Y | A | M | D | Y |

| Analytes | Human Bv8 (N=3) | | |
|---|---|---|---|
| | $k_{on}(10^5 M^{-1}S^{-1})$ | $k_{off}(10^{-4}S^{-1})$ | $K_D(nM)$ |
| h2G9.K4G1.Polish | 4.75 ± 0.45 | 6.89 ± 1.13 | 1.44 ± 0.11 |
| h2G9.K4G1.v19 | 4.71 ± 0.21 | 0.38 ± 0.02 | 0.08 ± 0.01 |
| h2G9.K4G1.v52 | 4.43 ± 0.49 | 1.19 ± 0.32 | 0.27 ± 0.04 |
| h2G9.K4G1.v55 | 4.84 ± 0.29 | 1.36 ± 0.06 | 0.28 ± 0.01 |
| h2G9.K4G1.v73 | 3.52 ± 0.21 | 0.50 ± 0.01 | 0.14 ± 0.01 |

FIG. 19

| Humanized anti-BV8 clones | Human Bv8 | | | Cyno Bv8 | | |
|---|---|---|---|---|---|---|
| | $k_{on}(10^5 M^{-1}S^{-1})$ | $k_{off}(10^{-4}S^{-1})$ | $K_D(nM)$ | $k_{on}(10^5 M^{-1}S^{-1})$ | $k_{off}(10^{-4}S^{-1})$ | $K_D(nM)$ |
| V19 Fab | 3.59 | 0.16 | 0.04 | 2.67 | 0.28 | 0.10 |
| V55 Fab | 3.96 | 0.72 | 0.18 | 3.1 | 1.29 | 0.42 |

| Humanized anti-BV8 clones | Human Bv8 | | | Cyno Bv8 | | |
|---|---|---|---|---|---|---|
| | $k_{on}(10^5 M^{-1}S^{-1})$ | $k_{off}(10^{-4}S^{-1})$ | $K_D(nM)$ | $k_{on}(10^5 M^{-1}S^{-1})$ | $k_{off}(10^{-4}S^{-1})$ | $K_D(nM)$ |
| V19 IgG | 7.60 | ≥ 0.05 * | ≥ 0.007 * | 5.01 | ≥ 0.05 * | ≥ 0.009 * |
| V55 IgG | 9.5 | ≥ 0.05 * | ≥ 0.005 * | 7.8 | ≥ 0.05 * | ≥ 0.006 * |

* The off-rate constant observed for 30 min at 25°C was at or near the detection limit of the instrument (BIAcore 3000); therefore, the reported $K_{off}$ and $K_D$ are upper limits.

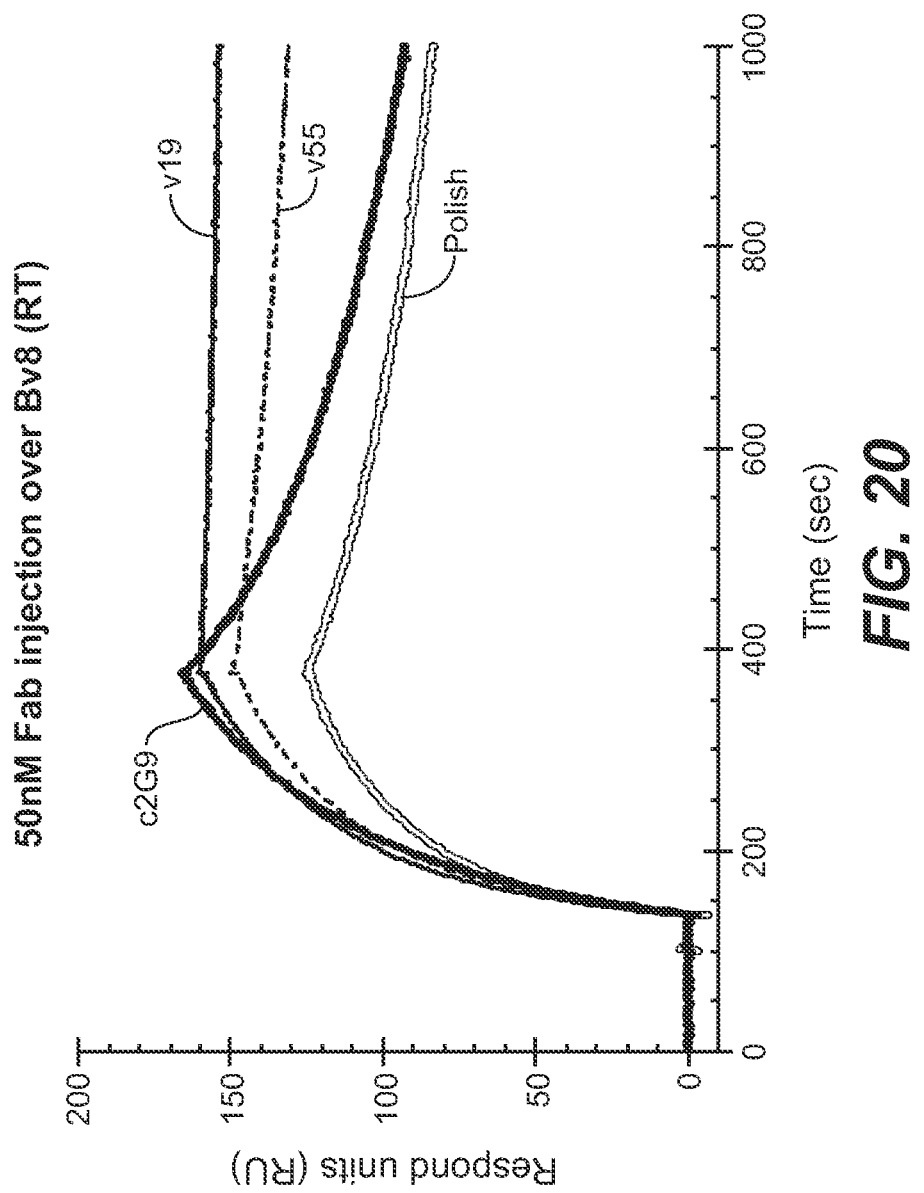

FIG. 21

2G9 Variants IgG BIAcore Analysis

| Humanized anti-BV8 clones | Human Bv8 | | | Cyno Bv8 | | |
|---|---|---|---|---|---|---|
| | $k_{on}(10^5 M^{-1}S^{-1})$ | $k_{off}(10^{-4}S^{-1})$ | $K_D(nM)$ | $k_{on}(10^5 M^{-1}S^{-1})$ | $k_{off}(10^{-4}S^{-1})$ | $K_D(nM)$ |
| Chimeric 2G9 | 7.58 | 0.18 | 0.02 | 6.46 | 0.25 | 0.04 |
| h2G9.K4G1.Polish | 5.28 | 0.12 | 0.02 | 4.54 | 0.15 | 0.03 |
| h2G9.K4G1.V19 | 7.60 | ≥0.05 * | ≥0.007 * | 5.01 | ≥0.05 * | ≥0.009 * |
| h2G9.K4G1.V55 | 9.45 | ≥0.05 * | ≥0.005 * | 7.75 | ≥0.05 * | ≥0.006 * |

* The off-rate constant observed for 30 min at 25°C was at or near the detection limit of the instrument (BIAcore 3000); therefore, the reported $K_{off}$ and $K_D$ are upper limits.

SEQUENCE LISTING

```
<160> NUMBER OF SEQ ID NOS: 241

<210> SEQ ID NO 1
<211> LENGTH: 114
<212> TYPE: PRT
<213> ORGANISM: Artificial sequence
<220> FEATURE:
<223> OTHER INFORMATION: sequence is synthesized

<400> SEQUENCE: 1

Asp Ile Val Met Thr Gln Ser Pro Asp Ser Leu Ala Val Ser Leu
 1               5                  10                  15

Gly Glu Arg Ala Thr Ile Asn Cys Lys Ser Ser Gln Ser Val Leu
                20                  25                  30

Tyr Ser Ser Asn Asn Lys Asn Tyr Leu Ala Trp Tyr Gln Gln Lys
                35                  40                  45

Pro Gly Gln Pro Pro Lys Leu Leu Ile Tyr Trp Ala Ser Thr Arg
                50                  55                  60

Glu Ser Gly Val Pro Asp Arg Phe Ser Gly Ser Gly Ser Gly Thr
                65                  70                  75

Asp Phe Thr Leu Thr Ile Ser Ser Leu Gln Ala Glu Asp Val Ala
                80                  85                  90

Val Tyr Tyr Cys Gln Gln Tyr Tyr Ser Thr Pro Phe Thr Phe Gly
                95                 100                 105

Gln Gly Thr Lys Val Glu Ile Lys Arg
               110

<210> SEQ ID NO 2
<211> LENGTH: 113
<212> TYPE: PRT
<213> ORGANISM: Artificial sequence
<220> FEATURE:
<223> OTHER INFORMATION: sequence is synthesized

<400> SEQUENCE: 2

Glu Val Gln Leu Val Gln Ser Gly Ala Glu Val Lys Lys Pro Gly
 1               5                  10                  15

Ala Ser Val Lys Val Ser Cys Lys Ala Ser Gly Tyr Thr Phe Thr
                20                  25                  30

Ser Tyr Tyr Ile His Trp Val Arg Gln Ala Pro Gly Gln Gly Leu
                35                  40                  45

Glu Trp Ile Gly Trp Ile Asn Pro Gly Ser Gly Asn Thr Asn Tyr
                50                  55                  60

Ala Gln Lys Phe Gln Gly Arg Val Thr Ile Thr Arg Asp Thr Ser
                65                  70                  75
```

```
Thr Ser Thr Ala Tyr Leu Glu Leu Ser Ser Leu Arg Ser Glu Asp
                80                  85                  90

Thr Ala Val Tyr Tyr Cys Ala Arg Gly Phe Asp Tyr Trp Gly Gln
                95                 100                 105

Gly Thr Leu Val Thr Val Ser Ser
                110
```

<210> SEQ ID NO 3
<211> LENGTH: 112
<212> TYPE: PRT
<213> ORGANISM: Artificial sequence
<220> FEATURE:
<223> OTHER INFORMATION: sequence is synthesized

<400> SEQUENCE: 3

```
Asp Ile Val Leu Thr Gln Ser Pro Ala Ser Leu Ala Val Ser Leu
 1               5                  10                  15

Gly Gln Arg Ala Thr Ile Ser Cys Lys Ala Ser Gln Ser Val Asp
                20                  25                  30

Tyr Asp Gly Asp Ser Tyr Met Asn Trp Tyr Gln Gln Lys Pro Gly
                35                  40                  45

Gln Pro Pro Lys Leu Leu Ile Tyr Ala Ala Ser Asn Leu Glu Ser
                50                  55                  60

Gly Ile Pro Ala Arg Phe Ser Gly Ser Gly Ser Gly Thr Asp Phe
                65                  70                  75

Thr Leu Asn Ile His Pro Val Glu Glu Asp Ala Ala Thr Tyr
                80                  85                  90

Tyr Cys Gln Gln Ile Asn Glu Asp Pro Phe Thr Phe Gly Gln Gly
                95                 100                 105

Thr Lys Val Glu Ile Lys Arg
                110
```

<210> SEQ ID NO 4
<211> LENGTH: 121
<212> TYPE: PRT
<213> ORGANISM: Artificial sequence
<220> FEATURE:
<223> OTHER INFORMATION: sequence is synthesized

<400> SEQUENCE: 4

```
Glu Val Gln Leu Gln Gln Ser Gly Pro Glu Val Val Lys Thr Gly
 1               5                  10                  15

Ala Ser Val Lys Ile Ser Cys Lys Ala Ser Gly Tyr Ser Phe Thr
                20                  25                  30

Asp Tyr Asp Met His Trp Val Lys Gln Ser Gln Gly Lys Ser Leu
                35                  40                  45

Glu Trp Ile Gly Tyr Ile Ser Cys Tyr Asn Gly Ala Thr Thr Tyr
                50                  55                  60

Asn Gln Lys Phe Lys Gly Lys Ala Thr Phe Thr Val Asp Lys Ser
                65                  70                  75

Ser Thr Thr Ala Tyr Met Gln Phe Asn Ser Leu Thr Ser Glu Asp
                80                  85                  90

Ser Ala Val Tyr Tyr Cys Ala Arg Asp Gly Asn Tyr Gly Glu Ala
                95                 100                 105

Tyr Ala Met Asp Tyr Trp Gly Gln Gly Thr Ser Leu Thr Val Ser
                110                 115                 120

Ser
```

<210> SEQ ID NO 5
<211> LENGTH: 112
<212> TYPE: PRT
<213> ORGANISM: Artificial sequence
<220> FEATURE:
<223> OTHER INFORMATION: sequence is synthesized

<400> SEQUENCE: 5

Asp Ile Val Met Thr Gln Ser Pro Asp Ser Leu Ala Val Ser Leu
1               5                   10                  15

Gly Glu Arg Ala Thr Ile Asn Cys Lys Ala Ser Gln Ser Val Asp
            20                  25                  30

Tyr Ser Gly Asp Ser Tyr Met Asn Trp Tyr Gln Gln Lys Pro Gly
        35                  40                  45

Gln Pro Pro Lys Leu Leu Ile Tyr Ala Ala Ser Asn Leu Glu Ser
    50                  55                  60

Gly Val Pro Asp Arg Phe Ser Gly Ser Gly Ser Gly Thr Asp Phe
65                  70                  75

Thr Leu Thr Ile Ser Ser Leu Gln Ala Glu Asp Val Ala Val Tyr
                80                  85                  90

Tyr Cys Gln Gln Ile Asn Glu Asp Pro Phe Thr Phe Gly Gln Gly
            95                  100                 105

Thr Lys Val Glu Ile Lys Arg
            110

<210> SEQ ID NO 6
<211> LENGTH: 121
<212> TYPE: PRT
<213> ORGANISM: Artificial sequence
<220> FEATURE:
<223> OTHER INFORMATION: sequence is synthesized

<400> SEQUENCE: 6

Glu Val Gln Leu Val Gln Ser Gly Ala Glu Val Lys Lys Pro Gly
1               5                   10                  15

Ala Ser Val Lys Val Ser Cys Lys Ala Ser Gly Tyr Ser Phe Thr
            20                  25                  30

Asp Tyr Asp Met His Trp Val Arg Gln Ala Pro Gly Gln Gly Leu
        35                  40                  45

Glu Trp Ile Gly Tyr Ile Ser Ser Tyr Ser Gly Ala Thr Thr Tyr
    50                  55                  60

Asn Gln Lys Phe Lys Gly Arg Val Thr Ile Thr Val Asp Lys Ser
65                  70                  75

Thr Ser Thr Ala Tyr Leu Glu Leu Ser Ser Leu Arg Ser Glu Asp
                80                  85                  90

Thr Ala Val Tyr Tyr Cys Ala Arg Asp Ser Asn Tyr Gly Glu Ala
            95                  100                 105

Tyr Ala Met Asp Tyr Trp Gly Gln Gly Thr Leu Val Thr Val Ser
        110                 115                 120

Ser

<210> SEQ ID NO 7
<211> LENGTH: 112
<212> TYPE: PRT
<213> ORGANISM: Artificial sequence
<220> FEATURE:
<223> OTHER INFORMATION: sequence is synthesized

<400> SEQUENCE: 7

```
Asp Ile Val Met Thr Gln Ser Pro Asp Ser Leu Ala Val Ser Leu
  1               5                  10                  15

Gly Glu Arg Ala Thr Ile Asn Cys Lys Ala Ser Gln Ser Val Asp
                 20                  25                  30

Tyr Ser Gly Asp Ser Tyr Met Asn Trp Tyr Gln Gln Lys Pro Gly
                 35                  40                  45

Gln Pro Pro Lys Leu Leu Ile Tyr Ala Ala Ser Asn Leu Glu Ser
                 50                  55                  60

Gly Val Pro Asp Arg Phe Ser Gly Ser Gly Ser Gly Thr Asp Phe
                 65                  70                  75

Thr Leu Thr Ile Ser Ser Leu Gln Ala Glu Asp Val Ala Val Tyr
                 80                  85                  90

Tyr Cys Gln Gln Ile Asn Glu Asp Pro Phe Thr Phe Gly Gln Gly
                 95                 100                 105

Thr Lys Val Glu Ile Lys Arg
                110
```

<210> SEQ ID NO 8
<211> LENGTH: 121
<212> TYPE: PRT
<213> ORGANISM: Artificial sequence
<220> FEATURE:
<223> OTHER INFORMATION: sequence is synthesized

<400> SEQUENCE: 8

```
Glu Val Gln Leu Val Gln Ser Gly Ala Glu Val Lys Lys Pro Gly
  1               5                  10                  15

Ala Ser Val Lys Val Ser Cys Lys Ala Ser Gly Tyr Ser Leu Thr
                 20                  25                  30

Asn Tyr Asp Met His Trp Val Arg Gln Ala Pro Gly Gln Gly Leu
                 35                  40                  45

Glu Trp Ile Gly Tyr Ile His Ser Tyr Ser Gly Ser Thr Leu Tyr
                 50                  55                  60

Asn Gln Lys Phe Lys Gly Arg Val Thr Ile Thr Val Asp Lys Ser
                 65                  70                  75

Thr Ser Thr Ala Tyr Leu Glu Leu Ser Ser Leu Arg Ser Glu Asp
                 80                  85                  90

Thr Ala Val Tyr Tyr Cys Ala Arg Asp Ser Asn Tyr Gly Glu Ala
                 95                 100                 105

Tyr Ala Met Asp Tyr Trp Gly Gln Gly Thr Leu Val Thr Val Ser
                110                 115                 120

Ser
```

<210> SEQ ID NO 9
<211> LENGTH: 112
<212> TYPE: PRT
<213> ORGANISM: Artificial sequence
<220> FEATURE:
<223> OTHER INFORMATION: sequence is synthesized

<400> SEQUENCE: 9

```
Asp Ile Val Met Thr Gln Ser Pro Asp Ser Leu Ala Val Ser Leu
  1               5                  10                  15

Gly Glu Arg Ala Thr Ile Asn Cys Lys Ala Ser Gln Ser Leu Ile
                 20                  25                  30

Tyr Gly Ala Asp Ser Tyr Met Asn Trp Tyr Gln Gln Lys Pro Gly
                 35                  40                  45
```

```
Gln Pro Pro Lys Leu Leu Ile Tyr Ala Ala Ser Asn Arg Glu Thr
                50                  55                  60

Gly Val Pro Asp Arg Phe Ser Gly Ser Gly Ser Gly Thr Asp Phe
            65                  70                  75

Thr Leu Thr Ile Ser Ser Leu Gln Ala Glu Asp Val Ala Val Tyr
            80                  85                  90

Tyr Cys Gln Gln Ile Asn Glu Asp Pro Phe Thr Phe Gly Gln Gly
            95                 100                 105

Thr Lys Val Glu Ile Lys Arg
               110
```

<210> SEQ ID NO 10
<211> LENGTH: 121
<212> TYPE: PRT
<213> ORGANISM: Artificial sequence
<220> FEATURE:
<223> OTHER INFORMATION: sequence is synthesized

<400> SEQUENCE: 10

```
Glu Val Gln Leu Val Gln Ser Gly Ala Glu Val Lys Lys Pro Gly
 1               5                  10                  15

Ala Ser Val Lys Val Ser Cys Lys Ala Ser Gly Tyr Ser Phe Thr
            20                  25                  30

Asp Tyr Asp Met His Trp Val Arg Gln Ala Pro Gly Gln Gly Leu
            35                  40                  45

Glu Trp Ile Gly Tyr Ile Ser Ser Tyr Ser Gly Ala Thr Thr Tyr
            50                  55                  60

Asn Gln Lys Phe Lys Gly Arg Val Thr Ile Thr Val Asp Lys Ser
            65                  70                  75

Thr Ser Thr Ala Tyr Leu Glu Leu Ser Ser Leu Arg Ser Glu Asp
            80                  85                  90

Thr Ala Val Tyr Tyr Cys Ala Arg Asp Ser Asn Tyr Gly Glu Ala
            95                 100                 105

Tyr Ala Met Asp Tyr Trp Gly Gln Gly Thr Leu Val Thr Val Ser
           110                 115                 120

Ser
```

<210> SEQ ID NO 11
<211> LENGTH: 112
<212> TYPE: PRT
<213> ORGANISM: Artificial sequence
<220> FEATURE:
<223> OTHER INFORMATION: sequence is synthesized

<400> SEQUENCE: 11

```
Asp Ile Val Met Thr Gln Ser Pro Asp Ser Leu Ala Val Ser Leu
 1               5                  10                  15

Gly Glu Arg Ala Thr Ile Asn Cys Lys Ala Ser Gln Ser Leu Asp
            20                  25                  30

Tyr Tyr His Tyr Ser Tyr Met Asn Trp Tyr Gln Gln Lys Pro Gly
            35                  40                  45

Gln Pro Pro Lys Leu Leu Ile Tyr Ala Ala Ser Asn Arg Glu Ser
            50                  55                  60

Gly Val Pro Asp Arg Phe Ser Gly Ser Gly Ser Gly Thr Asp Phe
            65                  70                  75

Thr Leu Thr Ile Ser Ser Leu Gln Ala Glu Asp Val Ala Val Tyr
            80                  85                  90
```

```
Tyr Cys Gln Gln Ile Asn Glu Asp Pro Phe Thr Phe Gly Gln Gly
                95                 100                 105

Thr Lys Val Glu Ile Lys Arg
            110

<210> SEQ ID NO 12
<211> LENGTH: 121
<212> TYPE: PRT
<213> ORGANISM: Artificial sequence
<220> FEATURE:
<223> OTHER INFORMATION: sequence is synthesized

<400> SEQUENCE: 12

Glu Val Gln Leu Val Gln Ser Gly Ala Glu Val Lys Lys Pro Gly
  1               5                  10                  15

Ala Ser Val Lys Val Ser Cys Lys Ala Ser Gly Tyr Ser Phe Thr
                 20                  25                  30

Asp Tyr Asp Met His Trp Val Arg Gln Ala Pro Gly Gln Gly Leu
             35                  40                  45

Glu Trp Ile Gly Tyr Ile Ser Ser Tyr Ser Gly Ala Thr Thr Tyr
         50                  55                  60

Asn Gln Lys Phe Lys Gly Arg Val Thr Ile Thr Val Asp Lys Ser
             65                  70                  75

Thr Ser Thr Ala Tyr Leu Glu Leu Ser Ser Leu Arg Ser Glu Asp
             80                  85                  90

Thr Ala Val Tyr Tyr Cys Ala Arg Asp Ser Asn Tyr Gly Glu Ala
             95                 100                 105

Tyr Ala Met Asp Tyr Trp Gly Gln Gly Thr Leu Val Thr Val Ser
            110                 115                 120

Ser

<210> SEQ ID NO 13
<211> LENGTH: 112
<212> TYPE: PRT
<213> ORGANISM: Artificial sequence
<220> FEATURE:
<223> OTHER INFORMATION: sequence is synthesized

<400> SEQUENCE: 13

Asp Ile Val Met Thr Gln Ser Pro Asp Ser Leu Ala Val Ser Leu
  1               5                  10                  15

Gly Glu Arg Ala Thr Ile Asn Cys Lys Ala Ser Gln Ser Val Asp
                 20                  25                  30

Tyr Ser Gly Asp Ser Tyr Met Asn Trp Tyr Gln Gln Lys Pro Gly
             35                  40                  45

Gln Pro Pro Lys Leu Leu Ile Tyr Ala Ala Ser Asn Leu Glu Ser
             50                  55                  60

Gly Val Pro Asp Arg Phe Ser Gly Ser Gly Ser Gly Thr Asp Phe
             65                  70                  75

Thr Leu Thr Ile Ser Ser Leu Gln Ala Glu Asp Val Ala Val Tyr
             80                  85                  90

Tyr Cys Gln Gln Ile Asn Glu Asp Pro Phe Thr Phe Gly Gln Gly
                 95                 100                 105

Thr Lys Val Glu Ile Lys Arg
            110

<210> SEQ ID NO 14
```

<211> LENGTH: 121
<212> TYPE: PRT
<213> ORGANISM: Artificial sequence
<220> FEATURE:
<223> OTHER INFORMATION: sequence is synthesized

<400> SEQUENCE: 14

Glu Val Gln Leu Val Gln Ser Gly Ala Glu Val Lys Lys Pro Gly
 1               5                  10                  15

Ala Ser Val Lys Val Ser Cys Lys Ala Ser Gly Tyr Ser Phe Thr
                20                  25                  30

His Tyr Asp Met His Trp Val Arg Gln Ala Pro Gly Gln Gly Leu
            35                  40                  45

Glu Trp Ile Gly Tyr Ile Ser Ser Tyr Leu Gly Ala Thr Ile Tyr
        50                  55                  60

Asn Gln Lys Phe Lys Gly Arg Val Thr Ile Thr Val Asp Lys Ser
    65                  70                  75

Thr Ser Thr Ala Tyr Leu Glu Leu Ser Ser Leu Arg Ser Glu Asp
80                  85                  90

Thr Ala Val Tyr Tyr Cys Ala Arg Asp Ser Asn Tyr Gly Glu Ala
            95                 100                 105

Tyr Ala Met Asp Tyr Trp Gly Gln Gly Thr Leu Val Thr Val Ser
            110                 115                 120

Ser

<210> SEQ ID NO 15
<211> LENGTH: 112
<212> TYPE: PRT
<213> ORGANISM: Artificial sequence
<220> FEATURE:
<223> OTHER INFORMATION: sequence is synthesized

<400> SEQUENCE: 15

Asp Ile Val Met Thr Gln Ser Pro Asp Ser Leu Ala Val Ser Leu
 1               5                  10                  15

Gly Glu Arg Ala Thr Ile Asn Cys Lys Ala Ser Gln Ser Leu Asp
                20                  25                  30

Tyr Tyr His Tyr Ser Tyr Met Asn Trp Tyr Gln Gln Lys Pro Gly
            35                  40                  45

Gln Pro Pro Lys Leu Leu Ile Tyr Ala Ala Ser Asn Arg Glu Ser
        50                  55                  60

Gly Val Pro Asp Arg Phe Ser Gly Ser Gly Ser Gly Thr Asp Phe
    65                  70                  75

Thr Leu Thr Ile Ser Ser Leu Gln Ala Glu Asp Val Ala Val Tyr
80                  85                  90

Tyr Cys Gln Gln Ile Asn Glu Asp Pro Phe Thr Phe Gly Gln Gly
            95                 100                 105

Thr Lys Val Glu Ile Lys Arg
            110

<210> SEQ ID NO 16
<211> LENGTH: 121
<212> TYPE: PRT
<213> ORGANISM: Artificial sequence
<220> FEATURE:
<223> OTHER INFORMATION: sequence is synthesized

<400> SEQUENCE: 16

Glu Val Gln Leu Val Gln Ser Gly Ala Glu Val Lys Lys Pro Gly

```
   1               5                  10                  15
Ala Ser Val Lys Val Ser Cys Lys Ala Ser Gly Tyr Ser Leu Thr
                20                  25                  30

Asn Tyr Asp Met His Trp Val Arg Gln Ala Pro Gly Gln Gly Leu
                35                  40                  45

Glu Trp Ile Gly Tyr Ile His Ser Tyr Ser Gly Ser Thr Leu Tyr
                50                  55                  60

Asn Gln Lys Phe Lys Gly Arg Val Thr Ile Thr Val Asp Lys Ser
                65                  70                  75

Thr Ser Thr Ala Tyr Leu Glu Leu Ser Ser Leu Arg Ser Glu Asp
                80                  85                  90

Thr Ala Val Tyr Tyr Cys Ala Arg Asp Ser Asn Tyr Gly Glu Ala
                95                  100                 105

Tyr Ala Met Asp Tyr Trp Gly Gln Gly Thr Leu Val Thr Val Ser
                110                 115                 120

Ser
```

```
<210> SEQ ID NO 17
<211> LENGTH: 108
<212> TYPE: PRT
<213> ORGANISM: Artificial sequence
<220> FEATURE:
<223> OTHER INFORMATION: sequence is synthesized

<400> SEQUENCE: 17

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Ser Ile Ser
                20                  25                  30

Asn Tyr Leu Ala Trp Tyr Gln Gln Lys Pro Gly Lys Ala Pro Lys
                35                  40                  45

Leu Leu Ile Tyr Ala Ala Ser Ser Leu Glu Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Tyr Asn Ser Leu Pro Trp Thr Phe Gly Gln Gly Thr Lys Val Glu
                95                  100                 105

Ile Lys Arg
```

```
<210> SEQ ID NO 18
<211> LENGTH: 109
<212> TYPE: PRT
<213> ORGANISM: Artificial sequence
<220> FEATURE:
<223> OTHER INFORMATION: sequence is synthesized

<400> SEQUENCE: 18

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Ser
                20                  25                  30

Ser Tyr Ala Met Ser Trp Asn Trp Val Arg Gln Ala Pro Gly Lys
                35                  40                  45

Gly Leu Glu Trp Val Ser Val Ile Ser Gly Asp Gly Gly Ser Thr
                50                  55                  60
```

```
Tyr Tyr Ala Asp Ser Val Lys Gly Arg Phe Thr Ile Ser Arg Asp
                65                  70                  75

Asn Ser Lys Asn Thr Leu Tyr Leu Gln Met Asn Ser Leu Arg Ala
            80                  85                  90

Glu Asp Thr Ala Val Tyr Tyr Cys Ala Arg Gly Phe Asp Tyr Trp
        95                 100                 105

Gly Gln Gly Thr

<210> SEQ ID NO 19
<211> LENGTH: 107
<212> TYPE: PRT
<213> ORGANISM: Artificial sequence
<220> FEATURE:
<223> OTHER INFORMATION: sequence is synthesized

<400> SEQUENCE: 19

Asp Ile Val Leu Thr Gln Ser Pro Ala Ile Met Ser Ala Ser Pro
  1               5                  10                  15

Gly Glu Lys Val Thr Met Thr Cys Ser Ala Ser Ser Ser Val Phe
                 20                  25                  30

Tyr Met His Trp Tyr Gln Gln Lys Ser Gly Thr Ser Pro Lys Thr
                35                  40                  45

Trp Ile Tyr Asp Thr Ser Lys Leu Ala Ser Gly Val Pro Ala Arg
            50                  55                  60

Phe Ser Gly Ser Gly Ser Gly Thr Ser Tyr Ser Leu Thr Ile Ser
65                  70                  75

Asn Met Glu Ala Glu Asp Ala Ala Thr Tyr Tyr Cys Gln Gln Trp
            80                  85                  90

Ser Ser Asp Pro Leu Thr Phe Gly Ala Gly Thr Lys Val Glu Ile
        95                 100                 105

Lys Arg

<210> SEQ ID NO 20
<211> LENGTH: 114
<212> TYPE: PRT
<213> ORGANISM: Artificial sequence
<220> FEATURE:
<223> OTHER INFORMATION: sequence is synthesized

<400> SEQUENCE: 20

Gln Val Thr Leu Lys Glu Ser Gly Pro Gly Ile Leu Gln Pro Ser
  1               5                  10                  15

Gln Thr Leu Ser Leu Thr Cys Ser Phe Ser Gly Phe Leu Leu Ser
                 20                  25                  30

Thr Ser Gly Met Gly Val Ser Trp Ile Arg Gln Pro Ser Gly Lys
                35                  40                  45

Gly Leu Glu Trp Leu Ala His Ile Tyr Trp Asp Asp Asp Thr Arg
            50                  55                  60

Tyr Asn Pro Ser Leu Lys Ser Arg Leu Thr Ile Ser Lys Asp Thr
                65                  70                  75

Ser Ser Asn Gln Val Phe Leu Lys Ile Thr Ser Val Asp Thr Ala
            80                  85                  90

Asp Thr Ala Thr Tyr Tyr Cys Ala Arg Arg Asp His Gly Tyr Tyr
        95                 100                 105

Trp Phe Thr Tyr Trp Gly Gln Gly Thr
                110
```

<210> SEQ ID NO 21
<211> LENGTH: 107
<212> TYPE: PRT
<213> ORGANISM: Artificial sequence
<220> FEATURE:
<223> OTHER INFORMATION: sequence is synthesized

<400> SEQUENCE: 21

Asp Ile Val Leu Thr Gln Ser Pro Ala Ile Met Ser Ala Ser Pro
1               5                   10                  15

Gly Glu Lys Val Thr Met Thr Cys Ser Ala Ser Ser Ser Val Phe
                20                  25                  30

Tyr Met His Trp Tyr Gln Gln Lys Ser Gly Thr Ser Pro Lys Thr
                35                  40                  45

Trp Ile Tyr Asp Thr Ser Lys Leu Ala Ser Gly Val Pro Ala Arg
            50                  55                  60

Phe Ser Gly Ser Gly Ser Gly Thr Ser Tyr Ser Leu Thr Ile Ser
65                  70                  75

Asn Met Glu Ala Glu Asp Ala Ala Thr Tyr Tyr Cys Gln Gln Trp
                80                  85                  90

Ser Ser Asp Pro Leu Thr Phe Gly Ala Gly Thr Lys Val Glu Ile
                95                  100                 105

Lys Arg

<210> SEQ ID NO 22
<211> LENGTH: 114
<212> TYPE: PRT
<213> ORGANISM: Artificial sequence
<220> FEATURE:
<223> OTHER INFORMATION: sequence is synthesized

<400> SEQUENCE: 22

Gln Val Thr Leu Lys Glu Ser Gly Pro Gly Ile Leu Gln Pro Ser
1               5                   10                  15

Gln Thr Leu Ser Leu Thr Cys Ser Phe Ser Gly Phe Leu Leu Ser
                20                  25                  30

Thr Ser Gly Met Gly Val Ser Trp Ile Arg Gln Pro Ser Gly Lys
                35                  40                  45

Gly Leu Glu Trp Leu Ala His Ile Tyr Trp Asp Asp Asp Thr Arg
            50                  55                  60

Tyr Asn Pro Ser Leu Lys Ser Arg Leu Thr Ile Ser Lys Asp Thr
            65                  70                  75

Ser Ser Asn Gln Val Phe Leu Lys Ile Thr Ser Val Asp Thr Ala
                80                  85                  90

Asp Thr Ala Thr Tyr Tyr Cys Ala Arg Arg Asp His Gly Tyr Tyr
                95                  100                 105

Trp Phe Thr Tyr Trp Gly Gln Gly Thr
                110

<210> SEQ ID NO 23
<211> LENGTH: 107
<212> TYPE: PRT
<213> ORGANISM: Artificial sequence
<220> FEATURE:
<223> OTHER INFORMATION: sequence is synthesized

<400> SEQUENCE: 23

Asp Ile Gln Met Thr Gln Ser Pro Ser Ser Leu Ser Ala Ser Val
1               5                   10                  15

-continued

```
Gly Asp Arg Val Thr Ile Thr Cys Ser Ala Ser Ser Ser Val Phe
             20                  25                  30

Tyr Met His Trp Tyr Gln Gln Lys Pro Gly Lys Ala Pro Lys Leu
             35                  40                  45

Leu Ile Tyr Asp Thr Ser Lys Leu Ala Ser Gly Val Pro Ser Arg
             50                  55                  60

Phe Ser Gly Ser Gly Ser Gly Thr Asp Phe Thr Leu Thr Ile Ser
             65                  70                  75

Ser Leu Gln Pro Glu Asp Phe Ala Thr Tyr Tyr Cys Gln Gln Trp
             80                  85                  90

Ser Tyr Asp Pro Met Thr Phe Gly Gln Gly Thr Lys Val Glu Ile
             95                 100                 105

Lys Arg

<210> SEQ ID NO 24
<211> LENGTH: 114
<212> TYPE: PRT
<213> ORGANISM: Artificial sequence
<220> FEATURE:
<223> OTHER INFORMATION: sequence is synthesized

<400> SEQUENCE: 24

Glu Val Gln Leu Val Glu Ser Gly Gly Gly Leu Val Gln Pro Gly
 1               5                  10                  15

Gly Ser Leu Arg Leu Ser Cys Ala Phe Ser Gly Phe Leu Leu Ser
             20                  25                  30

Thr Ser Gly Met Gly Val Ser Trp Val Arg Gln Ala Pro Gly Lys
             35                  40                  45

Gly Leu Glu Trp Leu Ala His Ile Tyr Trp Asp Asp Asp Thr Arg
             50                  55                  60

Tyr Asn Pro Ser Leu Lys Ser Arg Leu Thr Ile Ser Lys Asp Thr
             65                  70                  75

Ser Lys Asn Thr Val Tyr Leu Gln Met Asn Ser Leu Arg Ala Glu
             80                  85                  90

Asp Thr Ala Val Tyr Tyr Cys Ala Arg Arg Asp His Gly Tyr Tyr
             95                 100                 105

Trp Phe Asp Tyr Trp Gly Gln Gly Thr
                110

<210> SEQ ID NO 25
<211> LENGTH: 112
<212> TYPE: PRT
<213> ORGANISM: Artificial sequence
<220> FEATURE:
<223> OTHER INFORMATION: sequence is synthesized

<400> SEQUENCE: 25

Asp Ile Val Leu Thr Gln Ser Pro Ala Ser Leu Ala Val Ser Leu
 1               5                  10                  15

Gly Gln Arg Ala Thr Ile Ser Cys Glu Ala Ser Gln Ser Val Asp
             20                  25                  30

Tyr Asp Asp Asp Ser Tyr Met Asn Trp Tyr Gln Leu Lys Pro Gly
             35                  40                  45

Gln Pro Pro Asn Leu Leu Ile Tyr Ala Thr Ser Asn Leu Ala Ser
             50                  55                  60

Gly Ile Pro Ala Arg Phe Ser Gly Ser Gly Ser Gly Thr Asp Phe
             65                  70                  75
```

```
Thr Leu Asn Ile His Pro Val Glu Glu Asp Val Ala Thr Tyr
             80                  85                  90

Ser Cys Gln Gln Ser Asn Glu Asp Pro Phe Thr Phe Gly Ser Gly
             95                 100                 105

Thr Lys Val Glu Ile Lys Arg
            110

<210> SEQ ID NO 26
<211> LENGTH: 115
<212> TYPE: PRT
<213> ORGANISM: Artificial sequence
<220> FEATURE:
<223> OTHER INFORMATION: sequence is synthesized

<400> SEQUENCE: 26

Gln Val Gln Leu Gln Gln Pro Gly Ala Glu Leu Val Lys Pro Gly
  1               5                  10                  15

Ala Pro Val Glu Leu Ser Cys Lys Ala Ser Gly Tyr Thr Phe Thr
             20                  25                  30

Asn Ser Trp Met Asn Trp Val Lys Gln Arg Pro Gly Arg Gly Leu
             35                  40                  45

Glu Trp Ile Gly Arg Ile Asp Pro Ser Asp Ser Glu Thr His Tyr
             50                  55                  60

Asn Gln Lys Phe Lys Asp Lys Ala Ser Leu Thr Val Asp Lys Ser
             65                  70                  75

Ser Ser Thr Ala Tyr Ile His Leu Ser Ser Leu Thr Ser Glu Asp
             80                  85                  90

Ser Ala Val Tyr Tyr Cys Ala Arg Asp Ser Ser Tyr Asp Gly Phe
             95                 100                 105

Tyr Ala Met Asp Tyr Trp Gly Gln Gly Thr
            110                 115

<210> SEQ ID NO 27
<211> LENGTH: 112
<212> TYPE: PRT
<213> ORGANISM: Artificial sequence
<220> FEATURE:
<223> OTHER INFORMATION: sequence is synthesized

<400> SEQUENCE: 27

Asp Ile Val Leu Thr Gln Ser Pro Ala Ser Leu Ala Val Ser Leu
  1               5                  10                  15

Gly Gln Arg Ala Thr Ile Ser Cys Glu Ala Ser Gln Ser Val Asp
             20                  25                  30

Tyr Asp Asp Asp Ser Tyr Met Asn Trp Tyr Gln Leu Lys Pro Gly
             35                  40                  45

Gln Pro Pro Asn Leu Leu Ile Tyr Ala Thr Ser Asn Leu Ala Ser
             50                  55                  60

Gly Ile Pro Ala Arg Phe Ser Gly Ser Gly Ser Gly Thr Asp Phe
             65                  70                  75

Thr Leu Asn Ile His Pro Val Glu Glu Asp Val Ala Thr Tyr
             80                  85                  90

Ser Cys Gln Gln Ser Asn Glu Asp Pro Phe Thr Phe Gly Ser Gly
             95                 100                 105

Thr Lys Val Glu Ile Lys Arg
            110
```

<210> SEQ ID NO 28
<211> LENGTH: 115
<212> TYPE: PRT
<213> ORGANISM: Artificial sequence
<220> FEATURE:
<223> OTHER INFORMATION: sequence is synthesized

<400> SEQUENCE: 28

```
Gln Val Gln Leu Gln Gln Pro Gly Ala Glu Leu Val Lys Pro Gly
 1               5                  10                  15

Ala Pro Val Glu Leu Ser Cys Lys Ala Ser Gly Tyr Thr Phe Thr
                20                  25                  30

Asn Ser Trp Met Asn Trp Val Lys Gln Arg Pro Gly Arg Gly Leu
                35                  40                  45

Glu Trp Ile Gly Arg Ile Asp Pro Ser Asp Ser Glu Thr His Tyr
            50                  55                  60

Asn Gln Lys Phe Lys Asp Lys Ala Ser Leu Thr Val Asp Lys Ser
        65                  70                  75

Ser Ser Thr Ala Tyr Ile His Leu Ser Ser Leu Thr Ser Glu Asp
                80                  85                  90

Ser Ala Val Tyr Tyr Cys Ala Arg Asp Ser Ser Tyr Asp Gly Phe
                95                 100                 105

Tyr Ala Met Asp Tyr Trp Gly Gln Gly Thr
                110                 115
```

<210> SEQ ID NO 29
<211> LENGTH: 112
<212> TYPE: PRT
<213> ORGANISM: Artificial sequence
<220> FEATURE:
<223> OTHER INFORMATION: sequence is synthesized

<400> SEQUENCE: 29

```
Asp Ile Gln Met Thr Gln Ser Pro Ser Ser Leu Ser Ala Ser Val
 1               5                  10                  15

Gly Asp Arg Val Thr Ile Thr Cys Glu Ala Ser Gln Ser Val Asp
                20                  25                  30

Tyr Asp Asp Asp Ser Tyr Met Asn Trp Tyr Gln Leu Lys Pro Gly
                35                  40                  45

Lys Ala Pro Lys Leu Leu Ile Tyr Ala Thr Ser Asn Leu Ala Ser
                50                  55                  60

Gly Val Pro Ser Arg Phe Ser Gly Ser Gly Ser Gly Thr Asp Phe
                65                  70                  75

Thr Leu Thr Ile Ser Ser Leu Gln Pro Glu Asp Phe Ala Thr Tyr
                80                  85                  90

Ser Cys Gln Gln Ser Asn Glu Asp Pro Phe Thr Phe Gly Gln Gly
                95                 100                 105

Thr Lys Val Glu Ile Lys Arg
                110
```

<210> SEQ ID NO 30
<211> LENGTH: 115
<212> TYPE: PRT
<213> ORGANISM: Artificial sequence
<220> FEATURE:
<223> OTHER INFORMATION: sequence is synthesized

<400> SEQUENCE: 30

```
Glu Val Gln Leu Val Glu Ser Gly Gly Gly Leu Val Gln Pro Gly
 1               5                  10                  15
```

Gly Ser Leu Arg Leu Ser Cys Ala Ala Ser Gly Tyr Thr Phe Thr
            20                  25                  30

Asn Ser Trp Met Asn Trp Val Arg Gln Ala Pro Gly Lys Gly Leu
        35                  40                  45

Glu Trp Ile Gly Arg Ile Asp Pro Ser Asp Ser Glu Thr His Tyr
    50                  55                  60

Asn Gln Lys Phe Lys Asp Arg Ala Thr Ile Ser Val Asp Lys Ser
65                  70                  75

Lys Asn Thr Ala Tyr Leu Gln Met Asn Ser Leu Arg Ala Glu Asp
            80                  85                  90

Thr Ala Val Tyr Tyr Cys Ala Arg Asp Ser Ser Tyr Asp Gly Phe
        95                  100                 105

Tyr Ala Met Asp Tyr Trp Gly Gln Gly Thr
            110                 115

<210> SEQ ID NO 31
<211> LENGTH: 107
<212> TYPE: PRT
<213> ORGANISM: Artificial sequence
<220> FEATURE:
<223> OTHER INFORMATION: sequence is synthesized

<400> SEQUENCE: 31

Asp Ile Gln Met Thr Gln Thr Pro Ser Ser Leu Ser Val Ser Leu
1               5                   10                  15

Gly Asp Arg Val Ser Ile Thr Cys Lys Ser Ser Glu Tyr Val Ser
            20                  25                  30

Asn Ala Leu Ser Trp Tyr Gln Gln Lys Ser Gly Lys Ala Pro Lys
        35                  40                  45

Leu Leu Val Ser Gly Thr Asn Lys Leu Glu Asp Gly Val Pro Ser
    50                  55                  60

Arg Phe Ser Gly Ser Gly Ser Gly Thr Gln Phe Ser Leu Glu Ile
65                  70                  75

Ser Ser Leu Glu Ala Asp Asp Ser Gly Ile Tyr Phe Cys Gln Gln
            80                  85                  90

Gly Tyr Asp Ile Pro Thr Phe Gly Asp Gly Thr Lys Val Glu Ile
        95                  100                 105

Lys Arg

<210> SEQ ID NO 32
<211> LENGTH: 115
<212> TYPE: PRT
<213> ORGANISM: Artificial sequence
<220> FEATURE:
<223> OTHER INFORMATION: sequence is synthesized

<400> SEQUENCE: 32

Glu Val Gln Leu Val Glu Ser Gly Gly Gly Ile Val Lys Pro Ala
1               5                   10                  15

Gly Ser Leu Gln Leu Ser Cys Val Ala Ser Gly Phe Thr Phe Ser
            20                  25                  30

Asp Tyr Phe Met Gly Trp Phe Arg Gln Ala Pro Gly Lys Gly Leu
        35                  40                  45

Glu Trp Val Ala Gly Ile Asp Thr Lys Ser Tyr Asn Tyr Ala Thr
    50                  55                  60

Tyr Tyr Ser Gly Ser Val Lys Gly Arg Phe Thr Ile Ser Arg Asp
65                  70                  75

```
Asp Ser Gln Ser Met Val Tyr Leu Gln Met Asn Asn Leu Arg Thr
                 80                  85                  90

Glu Asp Thr Ala Thr Tyr Tyr Cys Thr Arg Asn Tyr Gly Asn Tyr
             95                 100                 105

Gly Ala Phe Asp Ser Trp Gly Gln Gly Thr
            110                 115

<210> SEQ ID NO 33
<211> LENGTH: 107
<212> TYPE: PRT
<213> ORGANISM: Artificial sequence
<220> FEATURE:
<223> OTHER INFORMATION: sequence is synthesized

<400> SEQUENCE: 33

Asp Ile Gln Met Thr Gln Thr Pro Ser Ser Leu Ser Val Ser Leu
  1               5                  10                  15

Gly Asp Arg Val Ser Ile Thr Cys Lys Ser Ser Glu Tyr Val Ser
                 20                  25                  30

Asn Ala Leu Ser Trp Tyr Gln Gln Lys Ser Gly Lys Ala Pro Lys
                 35                  40                  45

Leu Leu Val Ser Gly Thr Asn Lys Leu Glu Asp Gly Val Pro Ser
                 50                  55                  60

Arg Phe Ser Gly Ser Gly Ser Gly Thr Gln Phe Ser Leu Glu Ile
 65                  70                  75

Ser Ser Leu Glu Ala Asp Asp Ser Gly Ile Tyr Phe Cys Gln Gln
                 80                  85                  90

Gly Tyr Asp Ile Pro Thr Phe Gly Asp Gly Thr Lys Val Glu Ile
                 95                 100                 105

Lys Arg

<210> SEQ ID NO 34
<211> LENGTH: 115
<212> TYPE: PRT
<213> ORGANISM: Artificial sequence
<220> FEATURE:
<223> OTHER INFORMATION: sequence is synthesized

<400> SEQUENCE: 34

Glu Val Gln Leu Val Glu Ser Gly Gly Gly Ile Val Lys Pro Ala
  1               5                  10                  15

Gly Ser Leu Gln Leu Ser Cys Val Ala Ser Gly Phe Thr Phe Ser
                 20                  25                  30

Asp Tyr Phe Met Gly Trp Phe Arg Gln Ala Pro Gly Lys Gly Leu
                 35                  40                  45

Glu Trp Val Ala Gly Ile Asp Thr Lys Ser Tyr Asn Tyr Ala Thr
                 50                  55                  60

Tyr Tyr Ser Gly Ser Val Lys Gly Arg Phe Thr Ile Ser Arg Asp
 65                  70                  75

Asp Ser Gln Ser Met Val Tyr Leu Gln Met Asn Asn Leu Arg Thr
                 80                  85                  90

Glu Asp Thr Ala Thr Tyr Tyr Cys Thr Arg Asn Tyr Gly Asn Tyr
                 95                 100                 105

Gly Ala Phe Asp Ser Trp Gly Gln Gly Thr
            110                 115

<210> SEQ ID NO 35
```

<211> LENGTH: 107
<212> TYPE: PRT
<213> ORGANISM: Artificial sequence
<220> FEATURE:
<223> OTHER INFORMATION: sequence is synthesized

<400> SEQUENCE: 35

```
Asp Ile Val Leu Thr Gln Ser Pro Ala Ile Met Ser Ala Ser Pro
  1               5                  10                  15

Gly Glu Lys Val Thr Met Thr Cys Ser Ala Ser Ser Ser Val Phe
                 20                  25                  30

Tyr Met His Trp Tyr Gln Gln Lys Ser Gly Thr Ser Pro Lys Thr
                 35                  40                  45

Trp Ile Tyr Asp Thr Ser Lys Leu Ala Ser Gly Val Pro Ala Arg
                 50                  55                  60

Phe Ser Gly Ser Gly Ser Gly Thr Ser Tyr Ser Leu Thr Ile Ser
 65                  70                  75

Asn Met Glu Ala Glu Asp Ala Ala Thr Tyr Tyr Cys Gln Gln Trp
                 80                  85                  90

Ser Ser Asp Pro Leu Thr Phe Gly Ala Gly Thr Lys Val Glu Ile
                 95                 100                 105

Lys Arg
```

<210> SEQ ID NO 36
<211> LENGTH: 114
<212> TYPE: PRT
<213> ORGANISM: Artificial sequence
<220> FEATURE:
<223> OTHER INFORMATION: sequence is synthesized

<400> SEQUENCE: 36

```
Gln Val Thr Leu Lys Glu Ser Gly Pro Gly Ile Leu Gln Pro Ser
  1               5                  10                  15

Gln Thr Leu Ser Leu Thr Cys Ser Phe Ser Gly Phe Leu Leu Ser
                 20                  25                  30

Thr Ser Gly Met Gly Val Ser Trp Ile Arg Gln Pro Ser Gly Lys
                 35                  40                  45

Gly Leu Glu Trp Leu Ala His Ile Tyr Trp Asp Asp Asp Thr Arg
                 50                  55                  60

Tyr Asn Pro Ser Leu Lys Ser Arg Leu Thr Ile Ser Lys Asp Thr
                 65                  70                  75

Ser Ser Asn Gln Val Phe Leu Lys Ile Thr Ser Val Asp Thr Ala
                 80                  85                  90

Asp Thr Ala Thr Tyr Tyr Cys Ala Arg Arg Asp His Gly Tyr Tyr
                 95                 100                 105

Trp Phe Thr Tyr Trp Gly Gln Gly Thr
                110
```

<210> SEQ ID NO 37
<211> LENGTH: 107
<212> TYPE: PRT
<213> ORGANISM: Artificial sequence
<220> FEATURE:
<223> OTHER INFORMATION: sequence is synthesized

<400> SEQUENCE: 37

```
Asp Ile Gln Met Thr Gln Ser Pro Ser Ser Leu Ser Ala Ser Val
  1               5                  10                  15

Gly Asp Arg Val Thr Ile Thr Cys Ser Ala Ser Ser Ser Val Phe
```

```
                    20                  25                  30

Tyr Met His Trp Tyr Gln Gln Lys Pro Gly Lys Ala Pro Lys Thr
                35                  40                  45

Trp Ile Tyr Asp Thr Ser Lys Leu Ala Ser Gly Val Pro Ser Arg
                50                  55                  60

Phe Ser Gly Ser Gly Ser Gly Thr Asp Phe Thr Leu Thr Ile Ser
                65                  70                  75

Ser Leu Gln Pro Glu Asp Phe Ala Thr Tyr Tyr Cys Gln Gln Trp
                80                  85                  90

Ser Ser Asp Pro Leu Thr Phe Gly Gln Gly Thr Lys Val Glu Ile
                95                 100                 105

Lys Arg

<210> SEQ ID NO 38
<211> LENGTH: 114
<212> TYPE: PRT
<213> ORGANISM: Artificial sequence
<220> FEATURE:
<223> OTHER INFORMATION: sequence is synthesized

<400> SEQUENCE: 38

Glu Val Gln Leu Val Glu Ser Gly Gly Gly Leu Val Gln Pro Gly
  1               5                  10                  15

Gly Ser Leu Arg Leu Ser Cys Ala Phe Ser Gly Phe Leu Leu Ser
                20                  25                  30

Thr Ser Gly Met Gly Val Ser Trp Val Arg Gln Ala Pro Gly Lys
                35                  40                  45

Gly Leu Glu Trp Leu Ala His Ile Tyr Trp Asp Asp Thr Arg
                50                  55                  60

Tyr Asn Pro Ser Leu Lys Ser Arg Leu Thr Ile Ser Lys Asp Thr
                65                  70                  75

Ser Lys Asn Thr Val Tyr Leu Gln Met Asn Ser Leu Arg Ala Glu
                80                  85                  90

Asp Thr Ala Val Tyr Tyr Cys Ala Arg Arg Asp His Gly Tyr Tyr
                95                 100                 105

Trp Phe Asp Tyr Trp Gly Gln Gly Thr
                110

<210> SEQ ID NO 39
<211> LENGTH: 107
<212> TYPE: PRT
<213> ORGANISM: Artificial sequence
<220> FEATURE:
<223> OTHER INFORMATION: sequence is synthesized

<400> SEQUENCE: 39

Asp Ile Gln Met Thr Gln Ser Pro Ser Ser Leu Ser Ala Ser Val
  1               5                  10                  15

Gly Asp Arg Val Thr Ile Thr Cys Ser Ala Ser Ser Ser Val Phe
                20                  25                  30

Tyr Met His Trp Tyr Gln Gln Lys Pro Gly Lys Ala Pro Lys Thr
                35                  40                  45

Trp Ile Tyr Asp Thr Ser Lys Leu Ala Ser Gly Val Pro Ser Arg
                50                  55                  60

Phe Ser Gly Ser Gly Ser Gly Thr Asp Phe Thr Leu Thr Ile Ser
                65                  70                  75

Ser Leu Gln Pro Glu Asp Phe Ala Thr Tyr Tyr Cys Gln Gln Trp
```

```
                 80                  85                  90

Ser Phe Asp Pro Ile Thr Phe Gly Gln Gly Thr Lys Val Glu Ile
                 95                 100                 105

Lys Arg

<210> SEQ ID NO 40
<211> LENGTH: 114
<212> TYPE: PRT
<213> ORGANISM: Artificial sequence
<220> FEATURE:
<223> OTHER INFORMATION: sequence is synthesized

<400> SEQUENCE: 40

Glu Val Gln Leu Val Glu Ser Gly Gly Gly Leu Val Gln Pro Gly
  1               5                  10                  15

Gly Ser Leu Arg Leu Ser Cys Ala Phe Ser Gly Phe Leu Leu Ser
                 20                  25                  30

Thr Ser Gly Met Gly Val Ser Trp Val Arg Gln Ala Pro Gly Lys
                 35                  40                  45

Gly Leu Glu Trp Leu Ala His Ile Tyr Trp Asp Asp Thr Arg
                 50                  55                  60

Tyr Asn Pro Ser Leu Lys Ser Arg Leu Thr Ile Ser Lys Asp Thr
                 65                  70                  75

Ser Lys Asn Thr Val Tyr Leu Gln Met Asn Ser Leu Arg Ala Glu
                 80                  85                  90

Asp Thr Ala Val Tyr Tyr Cys Ala Arg Arg Asp His Gly Tyr Tyr
                 95                 100                 105

Trp Phe Asp Tyr Trp Gly Gln Gly Thr
                110

<210> SEQ ID NO 41
<211> LENGTH: 107
<212> TYPE: PRT
<213> ORGANISM: Artificial sequence
<220> FEATURE:
<223> OTHER INFORMATION: sequence is synthesized

<400> SEQUENCE: 41

Asp Ile Gln Met Thr Gln Ser Pro Ser Ser Leu Ser Ala Ser Val
  1               5                  10                  15

Gly Asp Arg Val Thr Ile Thr Cys Ser Ala Ser Ser Ser Val Phe
                 20                  25                  30

Tyr Met His Trp Tyr Gln Gln Lys Pro Gly Lys Ala Pro Lys Thr
                 35                  40                  45

Trp Ile Tyr Asp Thr Ser Lys Leu Ala Ser Gly Val Pro Ser Arg
                 50                  55                  60

Phe Ser Gly Ser Gly Ser Gly Thr Asp Phe Thr Leu Thr Ile Ser
                 65                  70                  75

Ser Leu Gln Pro Glu Asp Phe Ala Thr Tyr Tyr Cys Gln Gln Trp
                 80                  85                  90

Ser Trp Glu Pro Leu Thr Phe Gly Gln Gly Thr Lys Val Glu Ile
                 95                 100                 105

Lys Arg

<210> SEQ ID NO 42
<211> LENGTH: 114
<212> TYPE: PRT
<213> ORGANISM: Artificial sequence
```

-continued

```
<220> FEATURE:
<223> OTHER INFORMATION: sequence is synthesized

<400> SEQUENCE: 42

Glu Val Gln Leu Val Glu Ser Gly Gly Gly Leu Val Gln Pro Gly
  1               5                  10                  15

Gly Ser Leu Arg Leu Ser Cys Ala Phe Ser Gly Phe Leu Leu Ser
                 20                  25                  30

Thr Ser Gly Met Gly Val Ser Trp Val Arg Gln Ala Pro Gly Lys
                 35                  40                  45

Gly Leu Glu Trp Leu Ala His Ile Tyr Trp Asp Asp Thr Arg
                 50                  55                  60

Tyr Asn Pro Ser Leu Lys Ser Arg Leu Thr Ile Ser Lys Asp Thr
                 65                  70                  75

Ser Lys Asn Thr Val Tyr Leu Gln Met Asn Ser Leu Arg Ala Glu
                 80                  85                  90

Asp Thr Ala Val Tyr Tyr Cys Ala Arg Arg Asp His Gly Tyr Tyr
                 95                 100                 105

Trp Phe Asp Tyr Trp Gly Gln Gly Thr
                110

<210> SEQ ID NO 43
<211> LENGTH: 107
<212> TYPE: PRT
<213> ORGANISM: Artificial sequence
<220> FEATURE:
<223> OTHER INFORMATION: sequence is synthesized

<400> SEQUENCE: 43

Asp Ile Gln Met Thr Gln Ser Pro Ser Ser Leu Ser Ala Ser Val
  1               5                  10                  15

Gly Asp Arg Val Thr Ile Thr Cys Ser Ala Ser Ser Pro Val Phe
                 20                  25                  30

Tyr Met His Trp Tyr Gln Gln Lys Pro Gly Lys Ala Pro Lys Thr
                 35                  40                  45

Trp Ile Tyr Asp Thr Ser Asn Leu Ala Ser Gly Val Pro Ser Arg
                 50                  55                  60

Phe Ser Gly Ser Gly Ser Gly Thr Asp Phe Thr Leu Thr Ile Ser
                 65                  70                  75

Ser Leu Gln Pro Glu Asp Phe Ala Thr Tyr Tyr Cys Gln Gln Trp
                 80                  85                  90

Ser Tyr Glu Pro Leu Thr Phe Gly Gln Gly Thr Lys Val Glu Ile
                 95                 100                 105

Lys Arg

<210> SEQ ID NO 44
<211> LENGTH: 114
<212> TYPE: PRT
<213> ORGANISM: Artificial sequence
<220> FEATURE:
<223> OTHER INFORMATION: sequence is synthesized

<400> SEQUENCE: 44

Glu Val Gln Leu Val Glu Ser Gly Gly Gly Leu Val Gln Pro Gly
  1               5                  10                  15

Gly Ser Leu Arg Leu Ser Cys Ala Phe Ser Gly Phe Leu Leu Ser
                 20                  25                  30

Thr Ser Gly Met Gly Val Ser Trp Val Arg Gln Ala Pro Gly Lys
```

```
                35                  40                  45

Gly Leu Glu Trp Leu Ala His Ile Tyr Trp Asp Asp Asp Thr Arg
            50                  55                  60

Tyr Asn Pro Ser Leu Lys Ser Arg Leu Thr Ile Ser Lys Asp Thr
        65                  70                  75

Ser Lys Asn Thr Val Tyr Leu Gln Met Asn Ser Leu Arg Ala Glu
    80                  85                  90

Asp Thr Ala Val Tyr Tyr Cys Ala Arg Arg Asp His Gly Tyr Tyr
                95                 100                 105

Trp Phe Asp Tyr Trp Gly Gln Gly Thr
            110

<210> SEQ ID NO 45
<211> LENGTH: 107
<212> TYPE: PRT
<213> ORGANISM: Artificial sequence
<220> FEATURE:
<223> OTHER INFORMATION: sequence is synthesized

<400> SEQUENCE: 45

Asp Ile Gln Met Thr Gln Ser Pro Ser Ser Leu Ser Ala Ser Val
1               5                  10                  15

Gly Asp Arg Val Thr Ile Thr Cys Ser Ala Ser Ser Ser Val Phe
            20                  25                  30

Tyr Met His Trp Tyr Gln Gln Lys Pro Gly Lys Ala Pro Lys Thr
                35                  40                  45

Trp Ile Tyr Asp Thr Ser Lys Leu Ala Ser Gly Val Pro Ser Arg
            50                  55                  60

Phe Ser Gly Ser Gly Ser Gly Thr Asp Phe Thr Leu Thr Ile Ser
        65                  70                  75

Ser Leu Gln Pro Glu Asp Phe Ala Thr Tyr Tyr Cys Gln Gln Trp
    80                  85                  90

Ser Ser Asp Pro Leu Thr Phe Gly Gln Gly Thr Lys Val Glu Ile
                95                 100                 105

Lys Arg

<210> SEQ ID NO 46
<211> LENGTH: 114
<212> TYPE: PRT
<213> ORGANISM: Artificial sequence
<220> FEATURE:
<223> OTHER INFORMATION: sequence is synthesized

<400> SEQUENCE: 46

Glu Val Gln Leu Val Glu Ser Gly Gly Gly Leu Val Gln Pro Gly
1               5                  10                  15

Gly Ser Leu Arg Leu Ser Cys Ala Phe Ser Gly Phe Tyr Ile Ser
            20                  25                  30

Thr Pro Gly Met Gly Val Ser Trp Val Arg Gln Ala Pro Gly Lys
                35                  40                  45

Gly Leu Glu Trp Leu Ala His Ile Tyr Trp Asp Asp Asp Thr Arg
            50                  55                  60

Tyr Asn Pro Ser Leu Lys Ser Arg Leu Thr Ile Ser Lys Asp Thr
        65                  70                  75

Ser Lys Asn Thr Val Tyr Leu Gln Met Asn Ser Leu Arg Ala Glu
    80                  85                  90

Asp Thr Ala Val Tyr Tyr Cys Ala Arg Arg Asp His Gly Tyr Tyr
```

```
                 95                  100                 105
Trp Phe Asp Tyr Trp Gly Gln Gly Thr
                110
```

<210> SEQ ID NO 47
<211> LENGTH: 107
<212> TYPE: PRT
<213> ORGANISM: Artificial sequence
<220> FEATURE:
<223> OTHER INFORMATION: sequence is synthesized

<400> SEQUENCE: 47

```
Asp Ile Gln Met Thr Gln Ser Pro Ser Ser Leu Ser Ala Ser Val
 1               5                  10                  15

Gly Asp Arg Val Thr Ile Thr Cys Ser Ala Ser Ser Ser Val Phe
                20                  25                  30

Tyr Met His Trp Tyr Gln Gln Lys Pro Gly Lys Ala Pro Lys Thr
                35                  40                  45

Trp Ile Tyr Asp Thr Ser Lys Leu Ala Ser Gly Val Pro Ser Arg
                50                  55                  60

Phe Ser Gly Ser Gly Ser Gly Thr Asp Phe Thr Leu Thr Ile Ser
                65                  70                  75

Ser Leu Gln Pro Glu Asp Phe Ala Thr Tyr Tyr Cys Gln Gln Trp
                80                  85                  90

Ser Tyr Asp Pro Met Thr Phe Gly Gln Gly Thr Lys Val Glu Ile
                95                  100                 105

Lys Arg
```

<210> SEQ ID NO 48
<211> LENGTH: 114
<212> TYPE: PRT
<213> ORGANISM: Artificial sequence
<220> FEATURE:
<223> OTHER INFORMATION: sequence is synthesized

<400> SEQUENCE: 48

```
Glu Val Gln Leu Val Glu Ser Gly Gly Gly Leu Val Gln Pro Gly
 1               5                  10                  15

Gly Ser Leu Arg Leu Ser Cys Ala Phe Ser Gly Phe Leu Leu Ser
                20                  25                  30

Thr Ser Gly Met Gly Val Ser Trp Val Arg Gln Ala Pro Gly Lys
                35                  40                  45

Gly Leu Glu Trp Leu Ala His Ile Tyr Trp Asp Asp Asp Thr Arg
                50                  55                  60

Tyr Asn Pro Ser Leu Lys Ser Arg Leu Thr Ile Ser Lys Asp Thr
                65                  70                  75

Ser Lys Asn Thr Val Tyr Leu Gln Met Asn Ser Leu Arg Ala Glu
                80                  85                  90

Asp Thr Ala Val Tyr Tyr Cys Ala Arg Arg Asp His Gly Tyr Tyr
                95                  100                 105

Trp Phe Asp Tyr Trp Gly Gln Gly Thr
                110
```

<210> SEQ ID NO 49
<211> LENGTH: 15
<212> TYPE: PRT
<213> ORGANISM: Artificial sequence
<220> FEATURE:
<223> OTHER INFORMATION: sequence is synthesized

```
<400> SEQUENCE: 49

Lys Ala Ser Gln Ser Val Asp Tyr Asp Gly Asp Ser Tyr Met Asn
 1               5                  10                  15

<210> SEQ ID NO 50
<211> LENGTH: 7
<212> TYPE: PRT
<213> ORGANISM: Artificial sequence
<220> FEATURE:
<223> OTHER INFORMATION: sequence is synthesized

<400> SEQUENCE: 50

Ala Ala Ser Asn Leu Glu Ser
                 5

<210> SEQ ID NO 51
<211> LENGTH: 9
<212> TYPE: PRT
<213> ORGANISM: Artificial sequence
<220> FEATURE:
<223> OTHER INFORMATION: sequence is synthesized

<400> SEQUENCE: 51

Gln Gln Ile Asn Glu Asp Pro Phe Thr
                 5

<210> SEQ ID NO 52
<211> LENGTH: 10
<212> TYPE: PRT
<213> ORGANISM: Artificial sequence
<220> FEATURE:
<223> OTHER INFORMATION: sequence is synthesized

<400> SEQUENCE: 52

Gly Tyr Ser Phe Thr Asp Tyr Asp Met His
                 5                  10

<210> SEQ ID NO 53
<211> LENGTH: 17
<212> TYPE: PRT
<213> ORGANISM: Artificial sequence
<220> FEATURE:
<223> OTHER INFORMATION: sequence is synthesized

<400> SEQUENCE: 53

Tyr Ile Ser Cys Tyr Asn Gly Ala Thr Thr Tyr Asn Gln Lys Phe
 1               5                  10                  15

Lys Gly

<210> SEQ ID NO 54
<211> LENGTH: 12
<212> TYPE: PRT
<213> ORGANISM: Artificial sequence
<220> FEATURE:
<223> OTHER INFORMATION: sequence is synthesized

<400> SEQUENCE: 54

Asp Gly Asn Tyr Gly Glu Ala Tyr Ala Met Asp Tyr
                 5                  10

<210> SEQ ID NO 55
<211> LENGTH: 15
<212> TYPE: PRT
<213> ORGANISM: Artificial sequence
<220> FEATURE:
```

```
<223> OTHER INFORMATION: sequence is synthesized

<400> SEQUENCE: 55

Lys Ala Ser Gln Ser Val Asp Tyr Ser Gly Asp Ser Tyr Met Asn
 1               5                  10                  15

<210> SEQ ID NO 56
<211> LENGTH: 7
<212> TYPE: PRT
<213> ORGANISM: Artificial sequence
<220> FEATURE:
<223> OTHER INFORMATION: sequence is synthesized

<400> SEQUENCE: 56

Ala Ala Ser Asn Leu Glu Ser
                 5

<210> SEQ ID NO 57
<211> LENGTH: 9
<212> TYPE: PRT
<213> ORGANISM: Artificial sequence
<220> FEATURE:
<223> OTHER INFORMATION: sequence is synthesized

<400> SEQUENCE: 57

Gln Gln Ile Asn Glu Asp Pro Phe Thr
                 5

<210> SEQ ID NO 58
<211> LENGTH: 10
<212> TYPE: PRT
<213> ORGANISM: Artificial sequence
<220> FEATURE:
<223> OTHER INFORMATION: sequence is synthesized

<400> SEQUENCE: 58

Gly Tyr Ser Phe Thr Asp Tyr Asp Met His
                 5                  10

<210> SEQ ID NO 59
<211> LENGTH: 17
<212> TYPE: PRT
<213> ORGANISM: Artificial sequence
<220> FEATURE:
<223> OTHER INFORMATION: sequence is synthesized

<400> SEQUENCE: 59

Tyr Ile Ser Ser Tyr Ser Gly Ala Thr Thr Tyr Asn Gln Lys Phe
 1               5                  10                  15

Lys Gly

<210> SEQ ID NO 60
<211> LENGTH: 12
<212> TYPE: PRT
<213> ORGANISM: Artificial sequence
<220> FEATURE:
<223> OTHER INFORMATION: sequence is synthesized

<400> SEQUENCE: 60

Asp Ser Asn Tyr Gly Glu Ala Tyr Ala Met Asp Tyr
                 5                  10

<210> SEQ ID NO 61
<211> LENGTH: 15
<212> TYPE: PRT
<213> ORGANISM: Artificial sequence
```

```
<220> FEATURE:
<223> OTHER INFORMATION: sequence is synthesized

<400> SEQUENCE: 61

Lys Ala Ser Gln Ser Val Asp Tyr Ser Gly Asp Ser Tyr Met Asn
 1               5                  10                  15

<210> SEQ ID NO 62
<211> LENGTH: 7
<212> TYPE: PRT
<213> ORGANISM: Artificial sequence
<220> FEATURE:
<223> OTHER INFORMATION: sequence is synthesized

<400> SEQUENCE: 62

Ala Ala Ser Asn Leu Glu Ser
                5

<210> SEQ ID NO 63
<211> LENGTH: 9
<212> TYPE: PRT
<213> ORGANISM: Artificial sequence
<220> FEATURE:
<223> OTHER INFORMATION: sequence is synthesized

<400> SEQUENCE: 63

Gln Gln Ile Asn Glu Asp Pro Phe Thr
                5

<210> SEQ ID NO 64
<211> LENGTH: 10
<212> TYPE: PRT
<213> ORGANISM: Artificial sequence
<220> FEATURE:
<223> OTHER INFORMATION: sequence is synthesized

<400> SEQUENCE: 64

Gly Tyr Ser Leu Thr Asn Tyr Asp Met His
                5                  10

<210> SEQ ID NO 65
<211> LENGTH: 17
<212> TYPE: PRT
<213> ORGANISM: Artificial sequence
<220> FEATURE:
<223> OTHER INFORMATION: sequence is synthesized

<400> SEQUENCE: 65

Tyr Ile His Ser Tyr Ser Gly Ser Thr Leu Tyr Asn Gln Lys Phe
 1               5                  10                  15

Lys Gly

<210> SEQ ID NO 66
<211> LENGTH: 12
<212> TYPE: PRT
<213> ORGANISM: Artificial sequence
<220> FEATURE:
<223> OTHER INFORMATION: sequence is synthesized

<400> SEQUENCE: 66

Asp Ser Asn Tyr Gly Glu Ala Tyr Ala Met Asp Tyr
                5                  10

<210> SEQ ID NO 67
<211> LENGTH: 15
<212> TYPE: PRT
```

<213> ORGANISM: Artificial sequence
<220> FEATURE:
<223> OTHER INFORMATION: sequence is synthesized

<400> SEQUENCE: 67

Lys Ala Ser Gln Ser Val Asp Tyr Ser Gly Asp Ser Tyr Met Asn
 1               5                  10                  15

<210> SEQ ID NO 68
<211> LENGTH: 7
<212> TYPE: PRT
<213> ORGANISM: Artificial sequence
<220> FEATURE:
<223> OTHER INFORMATION: sequence is synthesized

<400> SEQUENCE: 68

Ala Ala Ser Asn Leu Glu Ser
                 5

<210> SEQ ID NO 69
<211> LENGTH: 9
<212> TYPE: PRT
<213> ORGANISM: Artificial sequence
<220> FEATURE:
<223> OTHER INFORMATION: sequence is synthesized

<400> SEQUENCE: 69

Gln Gln Ile Asn Glu Asp Pro Phe Thr
                 5

<210> SEQ ID NO 70
<211> LENGTH: 10
<212> TYPE: PRT
<213> ORGANISM: Artificial sequence
<220> FEATURE:
<223> OTHER INFORMATION: sequence is synthesized

<400> SEQUENCE: 70

Gly Tyr Ser Leu Phe His Tyr Asp Met His
                 5                  10

<210> SEQ ID NO 71
<211> LENGTH: 17
<212> TYPE: PRT
<213> ORGANISM: Artificial sequence
<220> FEATURE:
<223> OTHER INFORMATION: sequence is synthesized

<400> SEQUENCE: 71

Tyr Ile Ser Thr Tyr Thr Gly Ser Thr Thr Tyr Asn Gln Lys Phe
 1               5                  10                  15

Lys Gly

<210> SEQ ID NO 72
<211> LENGTH: 12
<212> TYPE: PRT
<213> ORGANISM: Artificial sequence
<220> FEATURE:
<223> OTHER INFORMATION: sequence is synthesized

<400> SEQUENCE: 72

Asp Ser Asn Tyr Gly Glu Ala Tyr Ala Met Asp Tyr
                 5                  10

<210> SEQ ID NO 73
<211> LENGTH: 15

```
<212> TYPE: PRT
<213> ORGANISM: Artificial sequence
<220> FEATURE:
<223> OTHER INFORMATION: sequence is synthesized

<400> SEQUENCE: 73

Lys Ala Ser Gln Ser Val Asp Tyr Tyr Gly Asp Ser Tyr Met Asn
 1               5                  10                  15

<210> SEQ ID NO 74
<211> LENGTH: 7
<212> TYPE: PRT
<213> ORGANISM: Artificial sequence
<220> FEATURE:
<223> OTHER INFORMATION: sequence is synthesized

<400> SEQUENCE: 74

Ala Ala Ser Asn Leu Glu Ser
                 5

<210> SEQ ID NO 75
<211> LENGTH: 9
<212> TYPE: PRT
<213> ORGANISM: Artificial sequence
<220> FEATURE:
<223> OTHER INFORMATION: sequence is synthesized

<400> SEQUENCE: 75

Gln Gln Ile Asn Glu Asp Pro Phe Thr
                 5

<210> SEQ ID NO 76
<211> LENGTH: 10
<212> TYPE: PRT
<213> ORGANISM: Artificial sequence
<220> FEATURE:
<223> OTHER INFORMATION: sequence is synthesized

<400> SEQUENCE: 76

Gly Tyr Ser Phe Thr Asp Tyr Asp Met His
                 5                  10

<210> SEQ ID NO 77
<211> LENGTH: 17
<212> TYPE: PRT
<213> ORGANISM: Artificial sequence
<220> FEATURE:
<223> OTHER INFORMATION: sequence is synthesized

<400> SEQUENCE: 77

Tyr Ile Ser Ser Tyr Ser Gly Ala Thr Thr Tyr Asn Gln Lys Phe
 1               5                  10                  15

Lys Gly

<210> SEQ ID NO 78
<211> LENGTH: 12
<212> TYPE: PRT
<213> ORGANISM: Artificial sequence
<220> FEATURE:
<223> OTHER INFORMATION: sequence is synthesized

<400> SEQUENCE: 78

Asp Ser Asn Tyr Gly Glu Ala Tyr Ala Met Asp Tyr
                 5                  10

<210> SEQ ID NO 79
```

```
<211> LENGTH: 15
<212> TYPE: PRT
<213> ORGANISM: Artificial sequence
<220> FEATURE:
<223> OTHER INFORMATION: sequence is synthesized

<400> SEQUENCE: 79

Lys Ala Ser Gln Ser Val Asp Tyr Ser Gly Asp Ser Tyr Met Asn
 1               5                  10                  15

<210> SEQ ID NO 80
<211> LENGTH: 7
<212> TYPE: PRT
<213> ORGANISM: Artificial sequence
<220> FEATURE:
<223> OTHER INFORMATION: sequence is synthesized

<400> SEQUENCE: 80

Ala Ala Ser Asn Leu Glu Ser
                 5

<210> SEQ ID NO 81
<211> LENGTH: 9
<212> TYPE: PRT
<213> ORGANISM: Artificial sequence
<220> FEATURE:
<223> OTHER INFORMATION: sequence is synthesized

<400> SEQUENCE: 81

Gln Gln Ile Asn Glu Asp Pro Phe Thr
                 5

<210> SEQ ID NO 82
<211> LENGTH: 10
<212> TYPE: PRT
<213> ORGANISM: Artificial sequence
<220> FEATURE:
<223> OTHER INFORMATION: sequence is synthesized

<400> SEQUENCE: 82

Gly Tyr Ser Phe Thr His Tyr Asp Met His
                 5                  10

<210> SEQ ID NO 83
<211> LENGTH: 17
<212> TYPE: PRT
<213> ORGANISM: Artificial sequence
<220> FEATURE:
<223> OTHER INFORMATION: sequence is synthesized

<400> SEQUENCE: 83

Tyr Ile Ser Thr Tyr Ala Gly Glu Thr Ser Tyr Asn Gln Lys Phe
 1               5                  10                  15

Lys Gly

<210> SEQ ID NO 84
<211> LENGTH: 12
<212> TYPE: PRT
<213> ORGANISM: Artificial sequence
<220> FEATURE:
<223> OTHER INFORMATION: sequence is synthesized

<400> SEQUENCE: 84

Asp Ser Asn Tyr Gly Glu Ala Tyr Ala Met Asp Tyr
                 5                  10
```

```
<210> SEQ ID NO 85
<211> LENGTH: 15
<212> TYPE: PRT
<213> ORGANISM: Artificial sequence
<220> FEATURE:
<223> OTHER INFORMATION: sequence is synthesized

<400> SEQUENCE: 85

Lys Ala Ser Gln Ser Leu Ile Tyr Gly Ala Asp Ser Tyr Met Asn
  1               5                  10                  15

<210> SEQ ID NO 86
<211> LENGTH: 7
<212> TYPE: PRT
<213> ORGANISM: Artificial sequence
<220> FEATURE:
<223> OTHER INFORMATION: sequence is synthesized

<400> SEQUENCE: 86

Ala Ala Ser Asn Arg Glu Thr
                  5

<210> SEQ ID NO 87
<211> LENGTH: 9
<212> TYPE: PRT
<213> ORGANISM: Artificial sequence
<220> FEATURE:
<223> OTHER INFORMATION: sequence is synthesized

<400> SEQUENCE: 87

Gln Gln Ile Asn Glu Asp Pro Phe Thr
                  5

<210> SEQ ID NO 88
<211> LENGTH: 10
<212> TYPE: PRT
<213> ORGANISM: Artificial sequence
<220> FEATURE:
<223> OTHER INFORMATION: sequence is synthesized

<400> SEQUENCE: 88

Gly Tyr Ser Phe Thr Asp Tyr Asp Met His
                  5                  10

<210> SEQ ID NO 89
<211> LENGTH: 17
<212> TYPE: PRT
<213> ORGANISM: Artificial sequence
<220> FEATURE:
<223> OTHER INFORMATION: sequence is synthesized

<400> SEQUENCE: 89

Tyr Ile Ser Ser Tyr Ser Gly Ala Thr Thr Tyr Asn Gln Lys Phe
  1               5                  10                  15

Lys Gly

<210> SEQ ID NO 90
<211> LENGTH: 12
<212> TYPE: PRT
<213> ORGANISM: Artificial sequence
<220> FEATURE:
<223> OTHER INFORMATION: sequence is synthesized

<400> SEQUENCE: 90

Asp Ser Asn Tyr Gly Glu Ala Tyr Ala Met Asp Tyr
                  5                  10
```

<210> SEQ ID NO 91
<211> LENGTH: 15
<212> TYPE: PRT
<213> ORGANISM: Artificial sequence
<220> FEATURE:
<223> OTHER INFORMATION: sequence is synthesized

<400> SEQUENCE: 91

Lys Ala Ser Gln Ser Leu Asp Tyr Tyr His Tyr Ser Tyr Met Asn
 1               5                  10                  15

<210> SEQ ID NO 92
<211> LENGTH: 7
<212> TYPE: PRT
<213> ORGANISM: Artificial sequence
<220> FEATURE:
<223> OTHER INFORMATION: sequence is synthesized

<400> SEQUENCE: 92

Ala Ala Ser Asn Arg Glu Ser
                 5

<210> SEQ ID NO 93
<211> LENGTH: 9
<212> TYPE: PRT
<213> ORGANISM: Artificial sequence
<220> FEATURE:
<223> OTHER INFORMATION: sequence is synthesized

<400> SEQUENCE: 93

Gln Gln Ile Asn Glu Asp Pro Phe Thr
                 5

<210> SEQ ID NO 94
<211> LENGTH: 10
<212> TYPE: PRT
<213> ORGANISM: Artificial sequence
<220> FEATURE:
<223> OTHER INFORMATION: sequence is synthesized

<400> SEQUENCE: 94

Gly Tyr Ser Phe Thr Asp Tyr Asp Met His
                 5                  10

<210> SEQ ID NO 95
<211> LENGTH: 17
<212> TYPE: PRT
<213> ORGANISM: Artificial sequence
<220> FEATURE:
<223> OTHER INFORMATION: sequence is synthesized

<400> SEQUENCE: 95

Tyr Ile Ser Ser Tyr Ser Gly Ala Thr Thr Tyr Asn Gln Lys Phe
 1               5                  10                  15

Lys Gly

<210> SEQ ID NO 96
<211> LENGTH: 12
<212> TYPE: PRT
<213> ORGANISM: Artificial sequence
<220> FEATURE:
<223> OTHER INFORMATION: sequence is synthesized

<400> SEQUENCE: 96

Asp Ser Asn Tyr Gly Glu Ala Tyr Ala Met Asp Tyr
                 5                  10

<210> SEQ ID NO 97
<211> LENGTH: 15
<212> TYPE: PRT
<213> ORGANISM: Artificial sequence
<220> FEATURE:
<223> OTHER INFORMATION: sequence is synthesized

<400> SEQUENCE: 97

Lys Ala Ser Gln Ser Val Asp Tyr Tyr Gly Asp Ser Tyr Met Asn
 1               5                  10                  15

<210> SEQ ID NO 98
<211> LENGTH: 7
<212> TYPE: PRT
<213> ORGANISM: Artificial sequence
<220> FEATURE:
<223> OTHER INFORMATION: sequence is synthesized

<400> SEQUENCE: 98

Ala Ala Ser Asn Leu Glu Thr
                 5

<210> SEQ ID NO 99
<211> LENGTH: 9
<212> TYPE: PRT
<213> ORGANISM: Artificial sequence
<220> FEATURE:
<223> OTHER INFORMATION: sequence is synthesized

<400> SEQUENCE: 99

Gln Gln Ile Asn Glu Asp Pro Phe Thr
                 5

<210> SEQ ID NO 100
<211> LENGTH: 10
<212> TYPE: PRT
<213> ORGANISM: Artificial sequence
<220> FEATURE:
<223> OTHER INFORMATION: sequence is synthesized

<400> SEQUENCE: 100

Gly Tyr Ser Phe Thr Asp Tyr Asp Met His
                 5                  10

<210> SEQ ID NO 101
<211> LENGTH: 17
<212> TYPE: PRT
<213> ORGANISM: Artificial sequence
<220> FEATURE:
<223> OTHER INFORMATION: sequence is synthesized

<400> SEQUENCE: 101

Tyr Ile Ser Ser Tyr Ser Gly Ala Thr Thr Tyr Asn Gln Lys Phe
 1               5                  10                  15

Lys Gly

<210> SEQ ID NO 102
<211> LENGTH: 12
<212> TYPE: PRT
<213> ORGANISM: Artificial sequence
<220> FEATURE:
<223> OTHER INFORMATION: sequence is synthesized

<400> SEQUENCE: 102

Asp Ser Asn Tyr Gly Glu Ala Tyr Ala Met Asp Tyr

```
                    5                   10

<210> SEQ ID NO 103
<211> LENGTH: 15
<212> TYPE: PRT
<213> ORGANISM: Artificial sequence
<220> FEATURE:
<223> OTHER INFORMATION: sequence is synthesized

<400> SEQUENCE: 103

Lys Ala Ser Gln Ser Val Asp Tyr Tyr Gly Asp Ser Tyr Met Asn
 1               5                  10                  15

<210> SEQ ID NO 104
<211> LENGTH: 7
<212> TYPE: PRT
<213> ORGANISM: Artificial sequence
<220> FEATURE:
<223> OTHER INFORMATION: sequence is synthesized

<400> SEQUENCE: 104

Ala Ala Ser Asn Arg Glu Ser
                  5

<210> SEQ ID NO 105
<211> LENGTH: 9
<212> TYPE: PRT
<213> ORGANISM: Artificial sequence
<220> FEATURE:
<223> OTHER INFORMATION: sequence is synthesized

<400> SEQUENCE: 105

Gln Gln Ile Asn Glu Asp Pro Phe Thr
                  5

<210> SEQ ID NO 106
<211> LENGTH: 10
<212> TYPE: PRT
<213> ORGANISM: Artificial sequence
<220> FEATURE:
<223> OTHER INFORMATION: sequence is synthesized

<400> SEQUENCE: 106

Gly Tyr Ser Phe Thr Asp Tyr Asp Met His
                  5                  10

<210> SEQ ID NO 107
<211> LENGTH: 17
<212> TYPE: PRT
<213> ORGANISM: Artificial sequence
<220> FEATURE:
<223> OTHER INFORMATION: sequence is synthesized

<400> SEQUENCE: 107

Tyr Ile Ser Ser Tyr Ser Gly Ala Thr Thr Tyr Asn Gln Lys Phe
 1               5                  10                  15

Lys Gly

<210> SEQ ID NO 108
<211> LENGTH: 12
<212> TYPE: PRT
<213> ORGANISM: Artificial sequence
<220> FEATURE:
<223> OTHER INFORMATION: sequence is synthesized

<400> SEQUENCE: 108
```

Asp Ser Asn Tyr Gly Glu Ala Tyr Ala Met Asp Tyr
                5                   10

<210> SEQ ID NO 109
<211> LENGTH: 15
<212> TYPE: PRT
<213> ORGANISM: Artificial sequence
<220> FEATURE:
<223> OTHER INFORMATION: sequence is synthesized

<400> SEQUENCE: 109

Lys Ala Ser Gln Ser Val Asp Tyr Ser Gly Asp Ser Tyr Met Asn
 1               5                  10                  15

<210> SEQ ID NO 110
<211> LENGTH: 7
<212> TYPE: PRT
<213> ORGANISM: Artificial sequence
<220> FEATURE:
<223> OTHER INFORMATION: sequence is synthesized

<400> SEQUENCE: 110

Ala Ala Ser Asn Leu Glu Ser
                5

<210> SEQ ID NO 111
<211> LENGTH: 9
<212> TYPE: PRT
<213> ORGANISM: Artificial sequence
<220> FEATURE:
<223> OTHER INFORMATION: sequence is synthesized

<400> SEQUENCE: 111

Gln Gln Ile Asn Glu Asp Pro Phe Thr
                5

<210> SEQ ID NO 112
<211> LENGTH: 10
<212> TYPE: PRT
<213> ORGANISM: Artificial sequence
<220> FEATURE:
<223> OTHER INFORMATION: sequence is synthesized

<400> SEQUENCE: 112

Gly Tyr Thr Phe Met His Tyr Asp Met His
                5                   10

<210> SEQ ID NO 113
<211> LENGTH: 17
<212> TYPE: PRT
<213> ORGANISM: Artificial sequence
<220> FEATURE:
<223> OTHER INFORMATION: sequence is synthesized

<400> SEQUENCE: 113

Tyr Ile Ser Ser Tyr Thr Gly Ser Thr Thr Tyr Asn Gln Lys Phe
 1               5                  10                  15

Lys Gly

<210> SEQ ID NO 114
<211> LENGTH: 12
<212> TYPE: PRT
<213> ORGANISM: Artificial sequence
<220> FEATURE:
<223> OTHER INFORMATION: sequence is synthesized

<400> SEQUENCE: 114

```
Asp Ser Asn Tyr Gly Glu Ala Tyr Ala Met Asp Tyr
            5                   10

<210> SEQ ID NO 115
<211> LENGTH: 15
<212> TYPE: PRT
<213> ORGANISM: Artificial sequence
<220> FEATURE:
<223> OTHER INFORMATION: sequence is synthesized

<400> SEQUENCE: 115

Lys Ala Ser Gln Ser Leu Asp Tyr Trp Val Asp Ser Tyr Met Asn
 1               5                  10                  15

<210> SEQ ID NO 116
<211> LENGTH: 7
<212> TYPE: PRT
<213> ORGANISM: Artificial sequence
<220> FEATURE:
<223> OTHER INFORMATION: sequence is synthesized

<400> SEQUENCE: 116

Ala Ala Ser Asn Arg Glu Thr
                 5

<210> SEQ ID NO 117
<211> LENGTH: 9
<212> TYPE: PRT
<213> ORGANISM: Artificial sequence
<220> FEATURE:
<223> OTHER INFORMATION: sequence is synthesized

<400> SEQUENCE: 117

Gln Gln Ile Asn Glu Asp Pro Phe Thr
                 5

<210> SEQ ID NO 118
<211> LENGTH: 10
<212> TYPE: PRT
<213> ORGANISM: Artificial sequence
<220> FEATURE:
<223> OTHER INFORMATION: sequence is synthesized

<400> SEQUENCE: 118

Gly Tyr Ser Phe Thr Asp Tyr Asp Met His
                 5                  10

<210> SEQ ID NO 119
<211> LENGTH: 17
<212> TYPE: PRT
<213> ORGANISM: Artificial sequence
<220> FEATURE:
<223> OTHER INFORMATION: sequence is synthesized

<400> SEQUENCE: 119

Tyr Ile Ser Ser Tyr Ser Gly Ala Thr Thr Tyr Asn Gln Lys Phe
 1               5                  10                  15

Lys Gly

<210> SEQ ID NO 120
<211> LENGTH: 12
<212> TYPE: PRT
<213> ORGANISM: Artificial sequence
<220> FEATURE:
<223> OTHER INFORMATION: sequence is synthesized
```

```
<400> SEQUENCE: 120

Asp Ser Asn Tyr Gly Glu Ala Tyr Ala Met Asp Tyr
                5                   10

<210> SEQ ID NO 121
<211> LENGTH: 15
<212> TYPE: PRT
<213> ORGANISM: Artificial sequence
<220> FEATURE:
<223> OTHER INFORMATION: sequence is synthesized

<400> SEQUENCE: 121

Lys Ala Ser Gln Ser Val Asp Tyr Ser Gly Asp Ser Tyr Met Asn
1               5                   10                  15

<210> SEQ ID NO 122
<211> LENGTH: 7
<212> TYPE: PRT
<213> ORGANISM: Artificial sequence
<220> FEATURE:
<223> OTHER INFORMATION: sequence is synthesized

<400> SEQUENCE: 122

Ala Ala Ser Asn Leu Glu Ser
                5

<210> SEQ ID NO 123
<211> LENGTH: 9
<212> TYPE: PRT
<213> ORGANISM: Artificial sequence
<220> FEATURE:
<223> OTHER INFORMATION: sequence is synthesized

<400> SEQUENCE: 123

Gln Gln Ile Asn Glu Asp Pro Phe Thr
                5

<210> SEQ ID NO 124
<211> LENGTH: 10
<212> TYPE: PRT
<213> ORGANISM: Artificial sequence
<220> FEATURE:
<223> OTHER INFORMATION: sequence is synthesized

<400> SEQUENCE: 124

Gly Tyr Ser Phe Thr His Tyr Asp Met His
                5                   10

<210> SEQ ID NO 125
<211> LENGTH: 17
<212> TYPE: PRT
<213> ORGANISM: Artificial sequence
<220> FEATURE:
<223> OTHER INFORMATION: sequence is synthesized

<400> SEQUENCE: 125

Tyr Ile Ser Ser Tyr Leu Gly Ala Thr Ile Tyr Asn Gln Lys Phe
1               5                   10                  15

Lys Gly

<210> SEQ ID NO 126
<211> LENGTH: 12
<212> TYPE: PRT
<213> ORGANISM: Artificial sequence
<220> FEATURE:
<223> OTHER INFORMATION: sequence is synthesized
```

<400> SEQUENCE: 126

Asp Ser Asn Tyr Gly Glu Ala Tyr Ala Met Asp Tyr
 1               5                  10

<210> SEQ ID NO 127
<211> LENGTH: 15
<212> TYPE: PRT
<213> ORGANISM: Artificial sequence
<220> FEATURE:
<223> OTHER INFORMATION: sequence is synthesized

<400> SEQUENCE: 127

Lys Ala Ser Gln Ser Val Asp Tyr Ser Gly Asp Ser Tyr Met Asn
 1               5                  10                  15

<210> SEQ ID NO 128
<211> LENGTH: 7
<212> TYPE: PRT
<213> ORGANISM: Artificial sequence
<220> FEATURE:
<223> OTHER INFORMATION: sequence is synthesized

<400> SEQUENCE: 128

Ala Ala Ser Asn Leu Glu Ser
 1               5

<210> SEQ ID NO 129
<211> LENGTH: 9
<212> TYPE: PRT
<213> ORGANISM: Artificial sequence
<220> FEATURE:
<223> OTHER INFORMATION: sequence is synthesized

<400> SEQUENCE: 129

Gln Gln Ile Asn Glu Asp Pro Phe Thr
 1               5

<210> SEQ ID NO 130
<211> LENGTH: 10
<212> TYPE: PRT
<213> ORGANISM: Artificial sequence
<220> FEATURE:
<223> OTHER INFORMATION: sequence is synthesized

<400> SEQUENCE: 130

Gly Tyr Thr Phe Pro Ile Tyr Asp Met His
 1               5                  10

<210> SEQ ID NO 131
<211> LENGTH: 17
<212> TYPE: PRT
<213> ORGANISM: Artificial sequence
<220> FEATURE:
<223> OTHER INFORMATION: sequence is synthesized

<400> SEQUENCE: 131

Tyr Ile Ser Ser Tyr Ser Gly Ala Thr Thr Tyr Asn Gln Lys Phe
 1               5                  10                  15

Lys Gly

<210> SEQ ID NO 132
<211> LENGTH: 12
<212> TYPE: PRT
<213> ORGANISM: Artificial sequence
<220> FEATURE:

<223> OTHER INFORMATION: sequence is synthesized

<400> SEQUENCE: 132

Asp Ser Asn Tyr Gly Glu Ala Tyr Ala Met Asp Tyr
                5                   10

<210> SEQ ID NO 133
<211> LENGTH: 15
<212> TYPE: PRT
<213> ORGANISM: Artificial sequence
<220> FEATURE:
<223> OTHER INFORMATION: sequence is synthesized

<400> SEQUENCE: 133

Lys Ala Ser Gln Ser Val Asp Tyr Gly Gly Asp Ser Tyr Met Asn
 1               5                  10                  15

<210> SEQ ID NO 134
<211> LENGTH: 7
<212> TYPE: PRT
<213> ORGANISM: Artificial sequence
<220> FEATURE:
<223> OTHER INFORMATION: sequence is synthesized

<400> SEQUENCE: 134

Ala Ala Ser Asn Arg Glu Thr
                5

<210> SEQ ID NO 135
<211> LENGTH: 9
<212> TYPE: PRT
<213> ORGANISM: Artificial sequence
<220> FEATURE:
<223> OTHER INFORMATION: sequence is synthesized

<400> SEQUENCE: 135

Gln Gln Ile Asn Glu Asp Pro Phe Thr
                5

<210> SEQ ID NO 136
<211> LENGTH: 10
<212> TYPE: PRT
<213> ORGANISM: Artificial sequence
<220> FEATURE:
<223> OTHER INFORMATION: sequence is synthesized

<400> SEQUENCE: 136

Gly Tyr Thr Phe Thr Glu Tyr Asp Met His
                5                   10

<210> SEQ ID NO 137
<211> LENGTH: 17
<212> TYPE: PRT
<213> ORGANISM: Artificial sequence
<220> FEATURE:
<223> OTHER INFORMATION: sequence is synthesized

<400> SEQUENCE: 137

Tyr Ile Thr Thr Tyr Ser Gly Ala Thr Thr Tyr Asn Gln Lys Phe
 1               5                  10                  15

Lys Gly

<210> SEQ ID NO 138
<211> LENGTH: 12
<212> TYPE: PRT
<213> ORGANISM: Artificial sequence

```
<220> FEATURE:
<223> OTHER INFORMATION: sequence is synthesized

<400> SEQUENCE: 138

Asp Ser Asn Tyr Gly Glu Ala Tyr Ala Met Asp Tyr
                  5                  10

<210> SEQ ID NO 139
<211> LENGTH: 15
<212> TYPE: PRT
<213> ORGANISM: Artificial sequence
<220> FEATURE:
<223> OTHER INFORMATION: sequence is synthesized

<400> SEQUENCE: 139

Lys Ala Ser Gln Ser Val Asp Tyr Phe Ala Glu Ser Tyr Met Asn
 1               5                  10                  15

<210> SEQ ID NO 140
<211> LENGTH: 7
<212> TYPE: PRT
<213> ORGANISM: Artificial sequence
<220> FEATURE:
<223> OTHER INFORMATION: sequence is synthesized

<400> SEQUENCE: 140

Ala Ala Ser Tyr Arg Glu Ser
                  5

<210> SEQ ID NO 141
<211> LENGTH: 9
<212> TYPE: PRT
<213> ORGANISM: Artificial sequence
<220> FEATURE:
<223> OTHER INFORMATION: sequence is synthesized

<400> SEQUENCE: 141

Gln Gln Ile Asn Glu Asp Pro Phe Thr
                  5

<210> SEQ ID NO 142
<211> LENGTH: 10
<212> TYPE: PRT
<213> ORGANISM: Artificial sequence
<220> FEATURE:
<223> OTHER INFORMATION: sequence is synthesized

<400> SEQUENCE: 142

Gly Tyr Ser Phe Thr Asp Tyr Asp Met His
                  5                  10

<210> SEQ ID NO 143
<211> LENGTH: 17
<212> TYPE: PRT
<213> ORGANISM: Artificial sequence
<220> FEATURE:
<223> OTHER INFORMATION: sequence is synthesized

<400> SEQUENCE: 143

Tyr Ile Ser Ser Tyr Ser Gly Ala Thr Thr Tyr Asn Gln Lys Phe
 1               5                  10                  15

Lys Gly

<210> SEQ ID NO 144
<211> LENGTH: 12
<212> TYPE: PRT
```

<213> ORGANISM: Artificial sequence
<220> FEATURE:
<223> OTHER INFORMATION: sequence is synthesized

<400> SEQUENCE: 144

Asp Ser Asn Tyr Gly Glu Ala Tyr Ala Met Asp Tyr
                5                   10

<210> SEQ ID NO 145
<211> LENGTH: 15
<212> TYPE: PRT
<213> ORGANISM: Artificial sequence
<220> FEATURE:
<223> OTHER INFORMATION: sequence is synthesized

<400> SEQUENCE: 145

Lys Ala Ser Gln Ser Val Asp Tyr Ser Gly Asp Ser Tyr Met Asn
1               5                   10                  15

<210> SEQ ID NO 146
<211> LENGTH: 7
<212> TYPE: PRT
<213> ORGANISM: Artificial sequence
<220> FEATURE:
<223> OTHER INFORMATION: sequence is synthesized

<400> SEQUENCE: 146

Ala Ala Ser Asn Leu Glu Ser
                5

<210> SEQ ID NO 147
<211> LENGTH: 9
<212> TYPE: PRT
<213> ORGANISM: Artificial sequence
<220> FEATURE:
<223> OTHER INFORMATION: sequence is synthesized

<400> SEQUENCE: 147

Gln Gln Ile Asn Glu Asp Pro Phe Thr
                5

<210> SEQ ID NO 148
<211> LENGTH: 10
<212> TYPE: PRT
<213> ORGANISM: Artificial sequence
<220> FEATURE:
<223> OTHER INFORMATION: sequence is synthesized

<400> SEQUENCE: 148

Gly Tyr Ser Phe Val His Tyr Asp Met His
                5                   10

<210> SEQ ID NO 149
<211> LENGTH: 17
<212> TYPE: PRT
<213> ORGANISM: Artificial sequence
<220> FEATURE:
<223> OTHER INFORMATION: sequence is synthesized

<400> SEQUENCE: 149

Tyr Ile Ser Ser Tyr Ser Gly Ala Thr Ser Tyr Asn Gln Lys Phe
1               5                   10                  15

Lys Gly

<210> SEQ ID NO 150
<211> LENGTH: 12

```
<212> TYPE: PRT
<213> ORGANISM: Artificial sequence
<220> FEATURE:
<223> OTHER INFORMATION: sequence is synthesized

<400> SEQUENCE: 150

Asp Ser Asn Tyr Gly Glu Ala Tyr Ala Met Asp Tyr
                 5                  10

<210> SEQ ID NO 151
<211> LENGTH: 15
<212> TYPE: PRT
<213> ORGANISM: Artificial sequence
<220> FEATURE:
<223> OTHER INFORMATION: sequence is synthesized

<400> SEQUENCE: 151

Lys Ala Ser Gln Ser Leu Asp Tyr Tyr His Tyr Ser Tyr Met Asn
 1               5                  10                  15

<210> SEQ ID NO 152
<211> LENGTH: 7
<212> TYPE: PRT
<213> ORGANISM: Artificial sequence
<220> FEATURE:
<223> OTHER INFORMATION: sequence is synthesized

<400> SEQUENCE: 152

Ala Ala Ser Asn Arg Glu Ser
                 5

<210> SEQ ID NO 153
<211> LENGTH: 9
<212> TYPE: PRT
<213> ORGANISM: Artificial sequence
<220> FEATURE:
<223> OTHER INFORMATION: sequence is synthesized

<400> SEQUENCE: 153

Gln Gln Ile Asn Glu Asp Pro Phe Thr
                 5

<210> SEQ ID NO 154
<211> LENGTH: 10
<212> TYPE: PRT
<213> ORGANISM: Artificial sequence
<220> FEATURE:
<223> OTHER INFORMATION: sequence is synthesized

<400> SEQUENCE: 154

Gly Tyr Ser Leu Thr Asn Tyr Asp Met His
                 5                  10

<210> SEQ ID NO 155
<211> LENGTH: 17
<212> TYPE: PRT
<213> ORGANISM: Artificial sequence
<220> FEATURE:
<223> OTHER INFORMATION: sequence is synthesized

<400> SEQUENCE: 155

Tyr Ile His Ser Tyr Ser Gly Ser Thr Leu Tyr Asn Gln Lys Phe
 1               5                  10                  15
Lys Gly

<210> SEQ ID NO 156
```

```
<211> LENGTH: 12
<212> TYPE: PRT
<213> ORGANISM: Artificial sequence
<220> FEATURE:
<223> OTHER INFORMATION: sequence is synthesized

<400> SEQUENCE: 156

Asp Ser Asn Tyr Gly Glu Ala Tyr Ala Met Asp Tyr
                 5                  10

<210> SEQ ID NO 157
<211> LENGTH: 10
<212> TYPE: PRT
<213> ORGANISM: Artificial sequence
<220> FEATURE:
<223> OTHER INFORMATION: sequence is synthesized

<400> SEQUENCE: 157

Ser Ala Ser Ser Ser Val Phe Tyr Met His
                 5                  10

<210> SEQ ID NO 158
<211> LENGTH: 7
<212> TYPE: PRT
<213> ORGANISM: Artificial sequence
<220> FEATURE:
<223> OTHER INFORMATION: sequence is synthesized

<400> SEQUENCE: 158

Asp Thr Ser Lys Leu Ala Ser
                 5

<210> SEQ ID NO 159
<211> LENGTH: 9
<212> TYPE: PRT
<213> ORGANISM: Artificial sequence
<220> FEATURE:
<223> OTHER INFORMATION: sequence is synthesized

<400> SEQUENCE: 159

Gln Gln Trp Ser Ser Asp Pro Leu Thr
                 5

<210> SEQ ID NO 160
<211> LENGTH: 12
<212> TYPE: PRT
<213> ORGANISM: Artificial sequence
<220> FEATURE:
<223> OTHER INFORMATION: sequence is synthesized

<400> SEQUENCE: 160

Gly Phe Leu Leu Ser Thr Ser Gly Met Gly Val Ser
                 5                  10

<210> SEQ ID NO 161
<211> LENGTH: 16
<212> TYPE: PRT
<213> ORGANISM: Artificial sequence
<220> FEATURE:
<223> OTHER INFORMATION: sequence is synthesized

<400> SEQUENCE: 161

His Ile Tyr Trp Asp Asp Asp Thr Arg Tyr Asn Pro Ser Leu Lys
 1               5                  10                  15
Ser
```

```
<210> SEQ ID NO 162
<211> LENGTH: 10
<212> TYPE: PRT
<213> ORGANISM: Artificial sequence
<220> FEATURE:
<223> OTHER INFORMATION: sequence is synthesized

<400> SEQUENCE: 162

Arg Asp His Gly Tyr Tyr Trp Phe Thr Tyr
                  5                  10

<210> SEQ ID NO 163
<211> LENGTH: 10
<212> TYPE: PRT
<213> ORGANISM: Artificial sequence
<220> FEATURE:
<223> OTHER INFORMATION: sequence is synthesized

<400> SEQUENCE: 163

Ser Ala Ser Ser Ser Val Phe Tyr Met His
                  5                  10

<210> SEQ ID NO 164
<211> LENGTH: 7
<212> TYPE: PRT
<213> ORGANISM: Artificial sequence
<220> FEATURE:
<223> OTHER INFORMATION: sequence is synthesized

<400> SEQUENCE: 164

Asp Thr Ser Lys Leu Ala Ser
                  5

<210> SEQ ID NO 165
<211> LENGTH: 9
<212> TYPE: PRT
<213> ORGANISM: Artificial sequence
<220> FEATURE:
<223> OTHER INFORMATION: sequence is synthesized

<400> SEQUENCE: 165

Gln Gln Trp Ser Ser Asp Pro Leu Thr
                  5

<210> SEQ ID NO 166
<211> LENGTH: 12
<212> TYPE: PRT
<213> ORGANISM: Artificial sequence
<220> FEATURE:
<223> OTHER INFORMATION: sequence is synthesized

<400> SEQUENCE: 166

Gly Phe Leu Leu Ser Thr Ser Gly Met Gly Val Ser
                  5                  10

<210> SEQ ID NO 167
<211> LENGTH: 16
<212> TYPE: PRT
<213> ORGANISM: Artificial sequence
<220> FEATURE:
<223> OTHER INFORMATION: sequence is synthesized

<400> SEQUENCE: 167

His Ile Tyr Trp Asp Asp Asp Thr Arg Tyr Asn Pro Ser Leu Lys
  1               5                  10                  15
Ser
```

<210> SEQ ID NO 168
<211> LENGTH: 10
<212> TYPE: PRT
<213> ORGANISM: Artificial sequence
<220> FEATURE:
<223> OTHER INFORMATION: sequence is synthesized

<400> SEQUENCE: 168

Arg Asp His Gly Tyr Tyr Trp Phe Thr Tyr
                  5                  10

<210> SEQ ID NO 169
<211> LENGTH: 10
<212> TYPE: PRT
<213> ORGANISM: Artificial sequence
<220> FEATURE:
<223> OTHER INFORMATION: sequence is synthesized

<400> SEQUENCE: 169

Ser Ala Ser Ser Ser Val Phe Tyr Met His
                  5                  10

<210> SEQ ID NO 170
<211> LENGTH: 7
<212> TYPE: PRT
<213> ORGANISM: Artificial sequence
<220> FEATURE:
<223> OTHER INFORMATION: sequence is synthesized

<400> SEQUENCE: 170

Asp Thr Ser Lys Leu Ala Ser
                  5

<210> SEQ ID NO 171
<211> LENGTH: 9
<212> TYPE: PRT
<213> ORGANISM: Artificial sequence
<220> FEATURE:
<223> OTHER INFORMATION: sequence is synthesized

<400> SEQUENCE: 171

Gln Gln Trp Ser Phe Asp Pro Ile Thr
                  5

<210> SEQ ID NO 172
<211> LENGTH: 12
<212> TYPE: PRT
<213> ORGANISM: Artificial sequence
<220> FEATURE:
<223> OTHER INFORMATION: sequence is synthesized

<400> SEQUENCE: 172

Gly Phe Leu Leu Ser Thr Ser Gly Met Gly Val Ser
                  5                  10

<210> SEQ ID NO 173
<211> LENGTH: 16
<212> TYPE: PRT
<213> ORGANISM: Artificial sequence
<220> FEATURE:
<223> OTHER INFORMATION: sequence is synthesized

<400> SEQUENCE: 173

His Ile Tyr Trp Asp Asp Asp Thr Arg Tyr Asn Pro Ser Leu Lys
  1               5                  10                  15
Ser

<210> SEQ ID NO 174
<211> LENGTH: 10
<212> TYPE: PRT
<213> ORGANISM: Artificial sequence
<220> FEATURE:
<223> OTHER INFORMATION: sequence is synthesized

<400> SEQUENCE: 174

Arg Asp His Gly Tyr Tyr Trp Phe Asp Tyr
                 5                  10

<210> SEQ ID NO 175
<211> LENGTH: 10
<212> TYPE: PRT
<213> ORGANISM: Artificial sequence
<220> FEATURE:
<223> OTHER INFORMATION: sequence is synthesized

<400> SEQUENCE: 175

Ser Ala Ser Ser Ser Val Phe Tyr Met His
                 5                  10

<210> SEQ ID NO 176
<211> LENGTH: 7
<212> TYPE: PRT
<213> ORGANISM: Artificial sequence
<220> FEATURE:
<223> OTHER INFORMATION: sequence is synthesized

<400> SEQUENCE: 176

Asp Thr Ser Lys Leu Ala Ser
                 5

<210> SEQ ID NO 177
<211> LENGTH: 9
<212> TYPE: PRT
<213> ORGANISM: Artificial sequence
<220> FEATURE:
<223> OTHER INFORMATION: sequence is synthesized

<400> SEQUENCE: 177

Gln Gln Trp Ser Trp Glu Pro Leu Thr
                 5

<210> SEQ ID NO 178
<211> LENGTH: 12
<212> TYPE: PRT
<213> ORGANISM: Artificial sequence
<220> FEATURE:
<223> OTHER INFORMATION: sequence is synthesized

<400> SEQUENCE: 178

Gly Phe Leu Leu Ser Thr Ser Gly Met Gly Val Ser
                 5                  10

<210> SEQ ID NO 179
<211> LENGTH: 16
<212> TYPE: PRT
<213> ORGANISM: Artificial sequence
<220> FEATURE:
<223> OTHER INFORMATION: sequence is synthesized

<400> SEQUENCE: 179

His Ile Tyr Trp Asp Asp Asp Thr Arg Tyr Asn Pro Ser Leu Lys
 1               5                  10                  15

Ser

<210> SEQ ID NO 180
<211> LENGTH: 10
<212> TYPE: PRT
<213> ORGANISM: Artificial sequence
<220> FEATURE:
<223> OTHER INFORMATION: sequence is synthesized

<400> SEQUENCE: 180

Arg Asp His Gly Tyr Tyr Trp Phe Asp Tyr
                 5                  10

<210> SEQ ID NO 181
<211> LENGTH: 10
<212> TYPE: PRT
<213> ORGANISM: Artificial sequence
<220> FEATURE:
<223> OTHER INFORMATION: sequence is synthesized

<400> SEQUENCE: 181

Ser Ala Ser Ser Pro Val Phe Tyr Met His
                 5                  10

<210> SEQ ID NO 182
<211> LENGTH: 7
<212> TYPE: PRT
<213> ORGANISM: Artificial sequence
<220> FEATURE:
<223> OTHER INFORMATION: sequence is synthesized

<400> SEQUENCE: 182

Asp Thr Ser Asn Leu Ala Ser
                 5

<210> SEQ ID NO 183
<211> LENGTH: 9
<212> TYPE: PRT
<213> ORGANISM: Artificial sequence
<220> FEATURE:
<223> OTHER INFORMATION: sequence is synthesized

<400> SEQUENCE: 183

Gln Gln Trp Ser Tyr Glu Pro Leu Thr
                 5

<210> SEQ ID NO 184
<211> LENGTH: 12
<212> TYPE: PRT
<213> ORGANISM: Artificial sequence
<220> FEATURE:
<223> OTHER INFORMATION: sequence is synthesized

<400> SEQUENCE: 184

Gly Phe Leu Leu Ser Thr Ser Gly Met Gly Val Ser
                 5                  10

<210> SEQ ID NO 185
<211> LENGTH: 16
<212> TYPE: PRT
<213> ORGANISM: Artificial sequence
<220> FEATURE:
<223> OTHER INFORMATION: sequence is synthesized

<400> SEQUENCE: 185

His Ile Tyr Trp Asp Asp Asp Thr Arg Tyr Asn Pro Ser Leu Lys
  1              5                  10                  15

Ser

<210> SEQ ID NO 186
<211> LENGTH: 10
<212> TYPE: PRT
<213> ORGANISM: Artificial sequence
<220> FEATURE:
<223> OTHER INFORMATION: sequence is synthesized

<400> SEQUENCE: 186

Arg Asp His Gly Tyr Tyr Trp Phe Asp Tyr
                5                   10

<210> SEQ ID NO 187
<211> LENGTH: 10
<212> TYPE: PRT
<213> ORGANISM: Artificial sequence
<220> FEATURE:
<223> OTHER INFORMATION: sequence is synthesized

<400> SEQUENCE: 187

Ser Ala Ser Ser Ser Val Phe Tyr Met His
                5                   10

<210> SEQ ID NO 188
<211> LENGTH: 7
<212> TYPE: PRT
<213> ORGANISM: Artificial sequence
<220> FEATURE:
<223> OTHER INFORMATION: sequence is synthesized

<400> SEQUENCE: 188

Asp Thr Ser Lys Leu Ala Ser
                5

<210> SEQ ID NO 189
<211> LENGTH: 9
<212> TYPE: PRT
<213> ORGANISM: Artificial sequence
<220> FEATURE:
<223> OTHER INFORMATION: sequence is synthesized

<400> SEQUENCE: 189

Gln Gln Trp Ser Ser Asp Pro Leu Thr
                5

<210> SEQ ID NO 190
<211> LENGTH: 12
<212> TYPE: PRT
<213> ORGANISM: Artificial sequence
<220> FEATURE:
<223> OTHER INFORMATION: sequence is synthesized

<400> SEQUENCE: 190

Gly Phe Tyr Ile Ser Thr Pro Gly Met Gly Val Ser
                5                   10

<210> SEQ ID NO 191
<211> LENGTH: 16
<212> TYPE: PRT
<213> ORGANISM: Artificial sequence
<220> FEATURE:
<223> OTHER INFORMATION: sequence is synthesized

<400> SEQUENCE: 191

His Ile Tyr Trp Asp Asp Asp Thr Arg Tyr Asn Pro Ser Leu Lys

Ser

<210> SEQ ID NO 192
<211> LENGTH: 10
<212> TYPE: PRT
<213> ORGANISM: Artificial sequence
<220> FEATURE:
<223> OTHER INFORMATION: sequence is synthesized

<400> SEQUENCE: 192

Arg Asp His Gly Tyr Tyr Trp Phe Asp Tyr
                 5                  10

<210> SEQ ID NO 193
<211> LENGTH: 10
<212> TYPE: PRT
<213> ORGANISM: Artificial sequence
<220> FEATURE:
<223> OTHER INFORMATION: sequence is synthesized

<400> SEQUENCE: 193

Ser Ala Ser Ser Ser Val Phe Tyr Met His
                 5                  10

<210> SEQ ID NO 194
<211> LENGTH: 7
<212> TYPE: PRT
<213> ORGANISM: Artificial sequence
<220> FEATURE:
<223> OTHER INFORMATION: sequence is synthesized

<400> SEQUENCE: 194

Asp Thr Ser Lys Leu Ala Ser
                 5

<210> SEQ ID NO 195
<211> LENGTH: 9
<212> TYPE: PRT
<213> ORGANISM: Artificial sequence
<220> FEATURE:
<223> OTHER INFORMATION: sequence is synthesized

<400> SEQUENCE: 195

Gln Gln Trp Ser Tyr Asp Pro Met Thr
                 5

<210> SEQ ID NO 196
<211> LENGTH: 12
<212> TYPE: PRT
<213> ORGANISM: Artificial sequence
<220> FEATURE:
<223> OTHER INFORMATION: sequence is synthesized

<400> SEQUENCE: 196

Gly Phe Leu Leu Ser Thr Ser Gly Met Gly Val Ser
                 5                  10

<210> SEQ ID NO 197
<211> LENGTH: 16
<212> TYPE: PRT
<213> ORGANISM: Artificial sequence
<220> FEATURE:
<223> OTHER INFORMATION: sequence is synthesized

<400> SEQUENCE: 197

His Ile Tyr Trp Asp Asp Asp Thr Arg Tyr Asn Pro Ser Leu Lys
1               5                   10                  15

Ser

<210> SEQ ID NO 198
<211> LENGTH: 10
<212> TYPE: PRT
<213> ORGANISM: Artificial sequence
<220> FEATURE:
<223> OTHER INFORMATION: sequence is synthesized

<400> SEQUENCE: 198

Arg Asp His Gly Tyr Tyr Trp Phe Asp Tyr
                5                   10

<210> SEQ ID NO 199
<211> LENGTH: 15
<212> TYPE: PRT
<213> ORGANISM: Artificial sequence
<220> FEATURE:
<223> OTHER INFORMATION: sequence is synthesized

<400> SEQUENCE: 199

Glu Ala Ser Gln Ser Val Asp Tyr Asp Asp Ser Tyr Met Asn
1               5                   10                  15

<210> SEQ ID NO 200
<211> LENGTH: 7
<212> TYPE: PRT
<213> ORGANISM: Artificial sequence
<220> FEATURE:
<223> OTHER INFORMATION: sequence is synthesized

<400> SEQUENCE: 200

Ala Thr Ser Asn Leu Ala Ser
                5

<210> SEQ ID NO 201
<211> LENGTH: 9
<212> TYPE: PRT
<213> ORGANISM: Artificial sequence
<220> FEATURE:
<223> OTHER INFORMATION: sequence is synthesized

<400> SEQUENCE: 201

Gln Gln Ser Asn Glu Asp Pro Phe Thr
                5

<210> SEQ ID NO 202
<211> LENGTH: 10
<212> TYPE: PRT
<213> ORGANISM: Artificial sequence
<220> FEATURE:
<223> OTHER INFORMATION: sequence is synthesized

<400> SEQUENCE: 202

Gly Tyr Thr Phe Thr Asn Ser Trp Met Asn
                5                   10

<210> SEQ ID NO 203
<211> LENGTH: 17
<212> TYPE: PRT
<213> ORGANISM: Artificial sequence
<220> FEATURE:
<223> OTHER INFORMATION: sequence is synthesized

<400> SEQUENCE: 203

Arg Ile Asp Pro Ser Asp Ser Glu Thr His Tyr Asn Gln Lys Phe
 1               5                  10                  15

Lys Asp

<210> SEQ ID NO 204
<211> LENGTH: 12
<212> TYPE: PRT
<213> ORGANISM: Artificial sequence
<220> FEATURE:
<223> OTHER INFORMATION: sequence is synthesized

<400> SEQUENCE: 204

Asp Ser Ser Tyr Asp Gly Phe Tyr Ala Met Asp Tyr
                 5                  10

<210> SEQ ID NO 205
<211> LENGTH: 15
<212> TYPE: PRT
<213> ORGANISM: Artificial sequence
<220> FEATURE:
<223> OTHER INFORMATION: sequence is synthesized

<400> SEQUENCE: 205

Glu Ala Ser Gln Ser Val Asp Tyr Asp Asp Ser Tyr Met Asn
 1               5                  10                  15

<210> SEQ ID NO 206
<211> LENGTH: 7
<212> TYPE: PRT
<213> ORGANISM: Artificial sequence
<220> FEATURE:
<223> OTHER INFORMATION: sequence is synthesized

<400> SEQUENCE: 206

Ala Thr Ser Asn Leu Ala Ser
                 5

<210> SEQ ID NO 207
<211> LENGTH: 9
<212> TYPE: PRT
<213> ORGANISM: Artificial sequence
<220> FEATURE:
<223> OTHER INFORMATION: sequence is synthesized

<400> SEQUENCE: 207

Gln Gln Ser Asn Glu Asp Pro Phe Thr
                 5

<210> SEQ ID NO 208
<211> LENGTH: 10
<212> TYPE: PRT
<213> ORGANISM: Artificial sequence
<220> FEATURE:
<223> OTHER INFORMATION: sequence is synthesized

<400> SEQUENCE: 208

Gly Tyr Thr Phe Thr Asn Ser Trp Met Asn
                 5                  10

<210> SEQ ID NO 209
<211> LENGTH: 17
<212> TYPE: PRT
<213> ORGANISM: Artificial sequence
<220> FEATURE:
<223> OTHER INFORMATION: sequence is synthesized

```
<400> SEQUENCE: 209

Arg Ile Asp Pro Ser Asp Ser Glu Thr His Tyr Asn Gln Lys Phe
  1               5                  10                  15

Lys Asp

<210> SEQ ID NO 210
<211> LENGTH: 12
<212> TYPE: PRT
<213> ORGANISM: Artificial sequence
<220> FEATURE:
<223> OTHER INFORMATION: sequence is synthesized

<400> SEQUENCE: 210

Asp Ser Ser Tyr Asp Gly Phe Tyr Ala Met Asp Tyr
                  5                  10

<210> SEQ ID NO 211
<211> LENGTH: 11
<212> TYPE: PRT
<213> ORGANISM: Artificial sequence
<220> FEATURE:
<223> OTHER INFORMATION: sequence is synthesized

<400> SEQUENCE: 211

Lys Ser Ser Glu Tyr Val Ser Asn Ala Leu Ser
                  5                  10

<210> SEQ ID NO 212
<211> LENGTH: 7
<212> TYPE: PRT
<213> ORGANISM: Artificial sequence
<220> FEATURE:
<223> OTHER INFORMATION: sequence is synthesized

<400> SEQUENCE: 212

Gly Thr Asn Lys Leu Glu Asp
                  5

<210> SEQ ID NO 213
<211> LENGTH: 8
<212> TYPE: PRT
<213> ORGANISM: Artificial sequence
<220> FEATURE:
<223> OTHER INFORMATION: sequence is synthesized

<400> SEQUENCE: 213

Gln Gln Gly Tyr Asp Ile Pro Thr
                  5

<210> SEQ ID NO 214
<211> LENGTH: 10
<212> TYPE: PRT
<213> ORGANISM: Artificial sequence
<220> FEATURE:
<223> OTHER INFORMATION: sequence is synthesized

<400> SEQUENCE: 214

Gly Phe Thr Phe Ser Asp Tyr Phe Met Gly
                  5                  10

<210> SEQ ID NO 215
<211> LENGTH: 19
<212> TYPE: PRT
<213> ORGANISM: Artificial sequence
<220> FEATURE:
<223> OTHER INFORMATION: sequence is synthesized
```

<400> SEQUENCE: 215

Gly Ile Asp Thr Lys Ser Tyr Asn Tyr Ala Thr Tyr Tyr Ser Gly
 1               5                  10                  15

Ser Val Lys Gly

<210> SEQ ID NO 216
<211> LENGTH: 10
<212> TYPE: PRT
<213> ORGANISM: Artificial sequence
<220> FEATURE:
<223> OTHER INFORMATION: sequence is synthesized

<400> SEQUENCE: 216

Asn Tyr Gly Asn Tyr Gly Ala Phe Asp Ser
                 5                  10

<210> SEQ ID NO 217
<211> LENGTH: 108
<212> TYPE: PRT
<213> ORGANISM: Artificial sequence
<220> FEATURE:
<223> OTHER INFORMATION: sequence is synthesized

<400> SEQUENCE: 217

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Ser Ile Ser
                20                  25                  30

Asn Tyr Leu Ala Trp Tyr Gln Gln Lys Pro Gly Lys Ala Pro Lys
                35                  40                  45

Leu Leu Ile Tyr Ala Ala Ser Ser Leu Glu Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Tyr Asn Ser Leu Pro Trp Thr Phe Gly Gln Gly Thr Lys Val Glu
                95                  100                 105

Ile Lys Arg

<210> SEQ ID NO 218
<211> LENGTH: 112
<212> TYPE: PRT
<213> ORGANISM: Artificial sequence
<220> FEATURE:
<223> OTHER INFORMATION: sequence is synthesized

<400> SEQUENCE: 218

Asp Ile Val Leu Thr Gln Ser Pro Ala Ser Leu Ala Val Ser Leu
 1               5                  10                  15

Gly Gln Arg Ala Thr Ile Ser Cys Lys Ala Ser Gln Ser Val Asp
                20                  25                  30

Tyr Asp Gly Asp Ser Tyr Met Asn Trp Tyr Gln Gln Lys Pro Gly
                35                  40                  45

Gln Pro Pro Lys Leu Leu Ile Tyr Ala Ala Ser Asn Leu Glu Ser
                50                  55                  60

Gly Ile Pro Ala Arg Phe Ser Gly Ser Gly Ser Gly Thr Asp Phe
                65                  70                  75

Thr Leu Asn Ile His Pro Val Glu Glu Asp Ala Ala Thr Tyr
            80                  85                  90

Tyr Cys Gln Gln Ile Asn Glu Asp Pro Phe Thr Phe Gly Gln Gly
                95                 100                 105

Thr Lys Val Glu Ile Lys Arg
            110

<210> SEQ ID NO 219
<211> LENGTH: 112
<212> TYPE: PRT
<213> ORGANISM: Artificial sequence
<220> FEATURE:
<223> OTHER INFORMATION: sequence is synthesized

<400> SEQUENCE: 219

Asp Ile Gln Met Thr Gln Ser Pro Ser Ser Leu Ser Ala Ser Val
 1               5                  10                  15

Gly Asp Arg Val Thr Ile Thr Cys Lys Ala Ser Gln Ser Val Asp
                20                  25                  30

Tyr Asp Gly Asp Ser Tyr Met Asn Trp Tyr Gln Gln Lys Pro Gly
                35                  40                  45

Lys Ala Pro Lys Leu Leu Ile Tyr Ala Ala Ser Asn Leu Glu Ser
                50                  55                  60

Gly Val Pro Ser Arg Phe Ser Gly Ser Gly Ser Gly Thr Asp Phe
                65                  70                  75

Thr Leu Thr Ile Ser Ser Leu Gln Pro Glu Asp Phe Ala Thr Tyr
            80                  85                  90

Tyr Cys Gln Gln Ile Asn Glu Asp Pro Phe Thr Phe Gly Gln Gly
                95                 100                 105

Thr Lys Val Glu Ile Lys Arg
            110

<210> SEQ ID NO 220
<211> LENGTH: 112
<212> TYPE: PRT
<213> ORGANISM: Artificial sequence
<220> FEATURE:
<223> OTHER INFORMATION: sequence is synthesized

<400> SEQUENCE: 220

Asp Ile Val Met Thr Gln Ser Pro Asp Ser Leu Ala Val Ser Leu
 1               5                  10                  15

Gly Glu Arg Ala Thr Ile Asn Cys Lys Ala Ser Gln Ser Val Asp
                20                  25                  30

Tyr Asp Gly Asp Ser Tyr Met Asn Trp Tyr Gln Gln Lys Pro Gly
                35                  40                  45

Gln Pro Pro Lys Leu Leu Ile Tyr Ala Ala Ser Asn Leu Glu Ser
                50                  55                  60

Gly Val Pro Asp Arg Phe Ser Gly Ser Gly Ser Gly Thr Asp Phe
                65                  70                  75

Thr Leu Thr Ile Ser Ser Leu Gln Ala Glu Asp Val Ala Val Tyr
            80                  85                  90

Tyr Cys Gln Gln Ile Asn Glu Asp Pro Phe Thr Phe Gly Gln Gly
                95                 100                 105

Thr Lys Val Glu Ile Lys Arg
            110

<210> SEQ ID NO 221

```
<211> LENGTH: 121
<212> TYPE: PRT
<213> ORGANISM: Artificial sequence
<220> FEATURE:
<223> OTHER INFORMATION: sequence is synthesized

<400> SEQUENCE: 221

Glu Val Gln Leu Val Gln Ser Gly Ala Glu Val Lys Lys Pro Gly
 1               5                  10                  15

Ala Ser Val Lys Val Ser Cys Lys Ala Ser Gly Tyr Ser Phe Thr
                20                  25                  30

Asp Tyr Asp Met His Trp Val Arg Gln Ala Pro Gly Gln Gly Leu
                35                  40                  45

Glu Trp Ile Gly Tyr Ile Ser Cys Tyr Asn Gly Ala Thr Thr Tyr
                50                  55                  60

Asn Gln Lys Phe Lys Gly Arg Val Thr Ile Thr Val Asp Lys Ser
65                  70                  75

Thr Ser Thr Ala Tyr Leu Glu Leu Ser Ser Leu Arg Ser Glu Asp
                80                  85                  90

Thr Ala Val Tyr Tyr Cys Ala Arg Asp Gly Asn Tyr Gly Glu Ala
                95                 100                 105

Tyr Ala Met Asp Tyr Trp Gly Gln Gly Thr Leu Val Thr Val Ser
               110                 115                 120

Ser

<210> SEQ ID NO 222
<211> LENGTH: 115
<212> TYPE: PRT
<213> ORGANISM: Artificial sequence
<220> FEATURE:
<223> OTHER INFORMATION: sequence is synthesized

<400> SEQUENCE: 222

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Ser
                20                  25                  30

Ser Tyr Ala Met Ser Trp Asn Trp Val Arg Gln Ala Pro Gly Lys
                35                  40                  45

Gly Leu Glu Trp Val Ser Val Ile Ser Gly Asp Gly Gly Ser Thr
                50                  55                  60

Tyr Tyr Ala Asp Ser Val Lys Gly Arg Phe Thr Ile Ser Arg Asp
65                  70                  75

Asn Ser Lys Asn Thr Leu Tyr Leu Gln Met Asn Ser Leu Arg Ala
                80                  85                  90

Glu Asp Thr Ala Val Tyr Tyr Cys Ala Arg Gly Phe Asp Tyr Trp
                95                 100                 105

Gly Gln Gly Thr Leu Val Thr Val Ser Ser
               110                 115

<210> SEQ ID NO 223
<211> LENGTH: 121
<212> TYPE: PRT
<213> ORGANISM: Artificial sequence
<220> FEATURE:
<223> OTHER INFORMATION: sequence is synthesized

<400> SEQUENCE: 223

Glu Val Gln Leu Gln Gln Ser Gly Pro Glu Val Val Lys Thr Gly
```

```
                1               5                  10                 15
            Ala Ser Val Lys Ile Ser Cys Lys Ala Ser Gly Tyr Ser Phe Thr
                               20                  25                 30
            Asp Tyr Asp Met His Trp Val Lys Gln Ser Gln Gly Lys Ser Leu
                               35                  40                 45
            Glu Trp Ile Gly Tyr Ile Ser Cys Tyr Asn Gly Ala Thr Thr Tyr
                               50                  55                 60
            Asn Gln Lys Phe Lys Gly Lys Ala Thr Phe Thr Val Asp Lys Ser
                               65                  70                 75
            Ser Thr Thr Ala Tyr Met Gln Phe Asn Ser Leu Thr Ser Glu Asp
                               80                  85                 90
            Ser Ala Val Tyr Tyr Cys Ala Arg Asp Gly Asn Tyr Gly Glu Ala
                               95                  100                105
            Tyr Ala Met Asp Tyr Trp Gly Gln Gly Thr Ser Leu Thr Val Ser
                               110                 115                120
            Ser
```

<210> SEQ ID NO 224
<211> LENGTH: 121
<212> TYPE: PRT
<213> ORGANISM: Artificial sequence
<220> FEATURE:
<223> OTHER INFORMATION: sequence is synthesized

<400> SEQUENCE: 224

```
                1               5                  10                 15
            Glu Val Gln Leu Val Glu Ser Gly Gly Gly Leu Val Gln Pro Gly
                               20                  25                 30
            Gly Ser Leu Arg Leu Ser Cys Ala Ala Ser Gly Tyr Ser Phe Thr
                               35                  40                 45
            Asp Tyr Asp Met His Trp Val Arg Gln Ala Pro Gly Lys Gly Leu
                               50                  55                 60
            Glu Trp Val Gly Tyr Ile Ser Cys Tyr Asn Gly Ala Thr Thr Tyr
                               65                  70                 75
            Asn Gln Lys Phe Lys Gly Arg Phe Thr Ile Ser Val Asp Lys Ser
                               80                  85                 90
            Lys Asn Thr Ala Tyr Leu Gln Met Asn Ser Leu Arg Ala Glu Asp
                               95                  100                105
            Thr Ala Val Tyr Tyr Cys Ala Arg Asp Gly Asn Tyr Gly Glu Ala
                               110                 115                120
            Tyr Ala Met Asp Tyr Trp Gly Gln Gly Thr Leu Val Thr Val Ser
            Ser
```

<210> SEQ ID NO 225
<211> LENGTH: 35
<212> TYPE: DNA
<213> ORGANISM: Artificial sequence
<220> FEATURE:
<223> OTHER INFORMATION: sequence is synthesized
<220> FEATURE:
<221> NAME/KEY: Unsure
<222> LOCATION: 13
<223> OTHER INFORMATION: N is Guanine or Thymine
<220> FEATURE:
<221> NAME/KEY: Unsure
<222> LOCATION: 16
<223> OTHER INFORMATION: N is Guanine or Cytosine
<220> FEATURE:
<221> NAME/KEY: Unsure
<222> LOCATION: 19

<223> OTHER INFORMATION: N is Adenine or Cytosine
<220> FEATURE:
<221> NAME/KEY: Unsure
<222> LOCATION: 22
<223> OTHER INFORMATION: N is Adenine or Guanine
<220> FEATURE:
<221> NAME/KEY: Unsure
<222> LOCATION: 34
<223> OTHER INFORMATION: N is Adenine or Cytosine

<400> SEQUENCE: 225
gtcagatatc gtnctnacnc antctccagc aatna                                35

<210> SEQ ID NO 226
<211> LENGTH: 37
<212> TYPE: DNA
<213> ORGANISM: Artificial sequence
<220> FEATURE:
<223> OTHER INFORMATION: sequence is synthesized
<220> FEATURE:
<221> NAME/KEY: Unsure
<222> LOCATION: 23
<223> OTHER INFORMATION: N is Guanine or Thymine
<220> FEATURE:
<221> NAME/KEY: Unsure
<222> LOCATION: 29
<223> OTHER INFORMATION: N is Adenine or Guanine
<220> FEATURE:
<221> NAME/KEY: Unsure
<222> LOCATION: 35
<223> OTHER INFORMATION: N is Adenine or Thymine

<400> SEQUENCE: 226
gatcgacgta cgctcaggtg acnctgaang agtcngg                              37

<210> SEQ ID NO 227
<211> LENGTH: 27
<212> TYPE: DNA
<213> ORGANISM: Artificial sequence
<220> FEATURE:
<223> OTHER INFORMATION: sequence is synthesized
<220> FEATURE:
<221> NAME/KEY: Unsure
<222> LOCATION: 13
<223> OTHER INFORMATION: N is Guanine or Thymine
<220> FEATURE:
<221> NAME/KEY: Unsure
<222> LOCATION: 16
<223> OTHER INFORMATION: N is Guanine or Cytosine
<220> FEATURE:
<221> NAME/KEY: Unsure
<222> LOCATION: 22
<223> OTHER INFORMATION: N is Adenine or Guanine

<400> SEQUENCE: 227
gtacgatatc gtnctnaccc antctcc                                         27

<210> SEQ ID NO 228
<211> LENGTH: 37
<212> TYPE: DNA
<213> ORGANISM: Artificial sequence
<220> FEATURE:
<223> OTHER INFORMATION: sequence is synthesized
<220> FEATURE:
<221> NAME/KEY: Unsure
<222> LOCATION: 23
<223> OTHER INFORMATION: N is Guanine or Thymine
<220> FEATURE:
<221> NAME/KEY: Unsure
<222> LOCATION: 29
<223> OTHER INFORMATION: N is Adenine or Guanine
<220> FEATURE:
<221> NAME/KEY: Unsure
<222> LOCATION: 35
<223> OTHER INFORMATION: N is Adenine or Thymine

<400> SEQUENCE: 228
gatcgacgta cgctcaggtg acnctgaang agtcngg                              37

<210> SEQ ID NO 229
<211> LENGTH: 27
<212> TYPE: DNA
<213> ORGANISM: Artificial sequence
<220> FEATURE:
<223> OTHER INFORMATION: sequence is synthesized
<220> FEATURE:
<221> NAME/KEY: Unsure
<222> LOCATION: 13
<223> OTHER INFORMATION: N is Guanine or Thymine
<220> FEATURE:
<221> NAME/KEY: Unsure
<222> LOCATION: 16
<223> OTHER INFORMATION: N is Guanine or Cytosine
<220> FEATURE:
<221> NAME/KEY: Unsure
<222> LOCATION: 22
<223> OTHER INFORMATION: N is Adenine or Guanine

<400> SEQUENCE: 229
gtacgatatc gtnctnaccc antctcc                                         27

<210> SEQ ID NO 230
<211> LENGTH: 37
<212> TYPE: DNA
<213> ORGANISM: Artificial sequence
<220> FEATURE:
<223> OTHER INFORMATION: sequence is synthesized
<220> FEATURE:
<221> NAME/KEY: Unsure
<222> LOCATION: 20
<223> OTHER INFORMATION: N is Cytosine or Thymine
<220> FEATURE:
<221> NAME/KEY: Unsure
<222> LOCATION: 26
<223> OTHER INFORMATION: N is Guanine or Cytosine

<400> SEQUENCE: 230
gatcgacgta cgctgaggtn cagctncagc agtctgg                              37

<210> SEQ ID NO 231
<211> LENGTH: 27
<212> TYPE: DNA
<213> ORGANISM: Artificial sequence
<220> FEATURE:
<223> OTHER INFORMATION: sequence is synthesized
<220> FEATURE:
<221> NAME/KEY: Unsure
<222> LOCATION: 13
<223> OTHER INFORMATION: N is Adenine or Guanine
<220> FEATURE:
<221> NAME/KEY: Unsure
<222> LOCATION: 19
<223> OTHER INFORMATION: N is Adenine, Cytosine, Guanine or Thymine
<220> FEATURE:
<221> NAME/KEY: Unsure
<222> LOCATION: 22
<223> OTHER INFORMATION: N is Adenine or Guanine
<220> FEATURE:
<221> NAME/KEY: Unsure
<222> LOCATION: 25
<223> OTHER INFORMATION: N is Adenine, Cytosine, Guanine or Thymine

<400> SEQUENCE: 231
gatcgatatc canatgacnc anacncc                                         27

```
<210> SEQ ID NO 232
<211> LENGTH: 37
<212> TYPE: DNA
<213> ORGANISM: Artificial sequence
<220> FEATURE:
<223> OTHER INFORMATION: sequence is synthesized
<220> FEATURE:
<221> NAME/KEY: Unsure
<222> LOCATION: 17
<223> OTHER INFORMATION: N is Adenine or Guanine
<220> FEATURE:
<221> NAME/KEY: Unsure
<222> LOCATION: 23
<223> OTHER INFORMATION: N is Adenine or Guanine
<220> FEATURE:
<221> NAME/KEY: Unsure
<222> LOCATION: 24
<223> OTHER INFORMATION: N is Cytosine or Thymine
<220> FEATURE:
<221> NAME/KEY: Unsure
<222> LOCATION: 32
<223> OTHER INFORMATION: N is Adenine or Guanine

<400> SEQUENCE: 232
gatcgacgta cgctgangtg canntggtgg antctgg                              37

<210> SEQ ID NO 233
<211> LENGTH: 21
<212> TYPE: DNA
<213> ORGANISM: Artificial sequence
<220> FEATURE:
<223> OTHER INFORMATION: sequence is synthesized

<400> SEQUENCE: 233
gctgtaggtg ctgtctttgc t                                               21

<210> SEQ ID NO 234
<211> LENGTH: 23
<212> TYPE: DNA
<213> ORGANISM: Artificial sequence
<220> FEATURE:
<223> OTHER INFORMATION: sequence is synthesized
<220> FEATURE:
<221> NAME/KEY: Unsure
<222> LOCATION: 5
<223> OTHER INFORMATION: N is Adenine or Thymine
<220> FEATURE:
<221> NAME/KEY: Unsure
<222> LOCATION: 11
<223> OTHER INFORMATION: N is Adenine or Cytosine

<400> SEQUENCE: 234
ctggncaggg ntccagagtt cca                                             23

<210> SEQ ID NO 235
<211> LENGTH: 108
<212> TYPE: PRT
<213> ORGANISM: Homo sapiens

<400> SEQUENCE: 235

Met Arg Ser Leu Cys Cys Ala Pro Leu Leu Leu Leu Leu Leu Leu Leu
 1               5                  10                  15

Pro Pro Leu Leu Leu Thr Pro Arg Ala Gly Asp Ala Ala Val Ile
            20                  25                  30

Thr Gly Ala Cys Asp Lys Asp Ser Gln Cys Gly Gly Met Cys
        35                  40                  45

Cys Ala Val Ser Ile Trp Val Lys Ser Ile Arg Ile Cys Thr Pro
        50                  55                  60
```

```
Met Gly Lys Leu Gly Asp Ser Cys His Pro Leu Thr Arg Lys Val
            65                  70                  75

Pro Phe Phe Gly Arg Arg Met His His Thr Cys Pro Cys Leu Pro
            80                  85                  90

Gly Leu Ala Cys Leu Arg Thr Ser Phe Asn Arg Phe Ile Cys Leu
            95                  100                 105

Ala Gln Lys
```

<210> SEQ ID NO 236
<211> LENGTH: 107
<212> TYPE: PRT
<213> ORGANISM: Mouse

<400> SEQUENCE: 236

```
Met Gly Asp Pro Arg Cys Ala Pro Leu Leu Leu Leu Leu Leu Leu
  1               5                  10                  15

Pro Leu Leu Phe Thr Pro Pro Ala Gly Asp Ala Ala Val Ile Thr
            20                  25                  30

Gly Ala Cys Asp Lys Asp Ser Gln Cys Gly Gly Gly Met Cys Cys
            35                  40                  45

Ala Val Ser Ile Trp Val Lys Ser Ile Arg Ile Cys Thr Pro Met
            50                  55                  60

Gly Gln Val Gly Asp Ser Cys His Pro Leu Thr Arg Lys Val Pro
            65                  70                  75

Phe Trp Gly Arg Arg Met His His Thr Cys Pro Cys Leu Pro Gly
            80                  85                  90

Leu Ala Cys Leu Arg Thr Ser Phe Asn Arg Phe Ile Cys Leu Ala
            95                  100                 105

Arg Lys
```

<210> SEQ ID NO 237
<211> LENGTH: 81
<212> TYPE: PRT
<213> ORGANISM: Macaca mulatta

<400> SEQUENCE: 237

```
Ala Val Ile Thr Gly Ala Cys Asp Lys Asp Ser Gln Cys Gly Gly
  1               5                  10                  15

Gly Met Cys Cys Ala Val Ser Ile Trp Val Lys Ser Ile Arg Ile
            20                  25                  30

Cys Thr Pro Met Gly Lys Leu Gly Asp Ser Cys His Pro Leu Thr
            35                  40                  45

Arg Lys Val Pro Phe Val Gly Arg Arg Met His His Thr Cys Pro
            50                  55                  60

Cys Leu Pro Gly Leu Ala Cys Leu Arg Thr Ser Phe Asn Arg Phe
            65                  70                  75

Ile Cys Leu Ala Arg Lys
                  80
```

<210> SEQ ID NO 238
<211> LENGTH: 81
<212> TYPE: PRT
<213> ORGANISM: Homo sapiens

<400> SEQUENCE: 238

```
Ala Val Ile Thr Gly Ala Cys Asp Lys Asp Ser Gln Cys Gly Gly
  1               5                  10                  15
```

Gly Met Cys Cys Ala Val Ser Ile Trp Val Lys Ser Ile Arg Ile
            20                  25                  30

Cys Thr Pro Met Gly Lys Leu Gly Asp Ser Cys His Pro Leu Thr
                35                  40                  45

Arg Lys Val Pro Phe Phe Gly Arg Arg Met His His Thr Cys Pro
                50                  55                  60

Cys Leu Pro Gly Leu Ala Cys Leu Arg Thr Ser Phe Asn Arg Phe
                65                  70                  75

Ile Cys Leu Ala Gln Lys
                80

<210> SEQ ID NO 239
<211> LENGTH: 81
<212> TYPE: PRT
<213> ORGANISM: Mus musculus

<400> SEQUENCE: 239

Ala Val Ile Thr Gly Ala Cys Asp Lys Asp Ser Gln Cys Gly Gly
 1               5                  10                  15

Gly Met Cys Cys Ala Val Ser Ile Trp Val Lys Ser Ile Arg Ile
            20                  25                  30

Cys Thr Pro Met Gly Gln Val Gly Asp Ser Cys His Pro Leu Thr
                35                  40                  45

Arg Lys Val Pro Phe Trp Gly Arg Arg Met His His Thr Cys Pro
                50                  55                  60

Cys Leu Pro Gly Leu Ala Cys Leu Arg Thr Ser Phe Asn Arg Phe
                65                  70                  75

Ile Cys Leu Ala Arg Lys
                80

<210> SEQ ID NO 240
<211> LENGTH: 81
<212> TYPE: PRT
<213> ORGANISM: Artificial sequence
<220> FEATURE:
<223> OTHER INFORMATION: sequence is synthesized

<400> SEQUENCE: 240

Asp Ile Val Met Thr Gln Ser Pro Asp Ser Leu Ala Val Ser Leu
 1               5                  10                  15

Gly Glu Arg Ala Thr Ile Asn Cys Trp Tyr Gln Gln Lys Pro Gly
            20                  25                  30

Gln Pro Pro Lys Leu Leu Ile Tyr Gly Val Pro Asp Arg Phe Ser
                35                  40                  45

Gly Ser Gly Ser Gly Thr Asp Phe Thr Leu Thr Ile Ser Ser Leu
                50                  55                  60

Gln Ala Glu Asp Val Ala Val Tyr Tyr Cys Phe Gly Gln Gly Thr
                65                  70                  75

Lys Val Glu Ile Lys Arg
                80

<210> SEQ ID NO 241
<211> LENGTH: 82
<212> TYPE: PRT
<213> ORGANISM: Artificial sequence
<220> FEATURE:
<223> OTHER INFORMATION: sequence is synthesized

<400> SEQUENCE: 241

```
Glu Val Gln Leu Val Gln Ser Gly Ala Glu Val Lys Lys Pro Gly
 1               5                  10                  15

Ala Ser Val Lys Val Ser Cys Lys Ala Ser Trp Val Arg Gln Ala
                20                  25                  30

Pro Gly Gln Gly Leu Glu Trp Ile Gly Arg Val Thr Ile Thr Val
                35                  40                  45

Asp Lys Ser Thr Ser Thr Ala Tyr Leu Glu Leu Ser Ser Leu Arg
                50                  55                  60

Ser Glu Asp Thr Ala Val Tyr Tyr Cys Ala Arg Trp Gly Gln Gly
                65                  70                  75

Thr Leu Val Thr Val Ser Ser
                80
```

US 8,771,685 B2

ANTI-BV8 ANTIBODIES AND USES THEREOF

RELATED APPLICATIONS

This application is a non-provisional application filed under 37 CFR 1.53(b)(1), claiming priority under 35 USC 119(e) to provisional application No. 61/284,743 filed Dec. 23, 2009, and provisional application No. 61/414,052 filed Nov. 16, 2010, the contents of which are incorporated herein by reference.

FIELD OF THE INVENTION

The present invention relates generally to the field of molecular biology. More specifically, the invention concerns anti-Bv8 antibodies, and uses of same.

BACKGROUND OF THE INVENTION

It is now well established that angiogenesis, which involves the formation of new blood vessels from preexisting endothelium, is implicated in the pathogenesis of a variety of disorders. These include solid tumors and metastasis, atherosclerosis, retrolental fibroplasia, hemangiomas, chronic inflammation, intraocular neovascular syndromes such as proliferative retinopathies, e.g., diabetic retinopathy, age-related macular degeneration (AMD), neovascular glaucoma, immune rejection of transplanted corneal tissue and other tissues, rheumatoid arthritis, and psoriasis. Folkman et al., *J. Biol. Chem.*, 267: 10931-10934 (1992); Klagsbrun et al., *Annu. Rev. Physiol.*, 53: 217-239 (1991); and Garner A., "Vascular diseases", In: Pathobiology of Ocular Disease. A Dynamic Approach, Garner A., Klintworth G K, eds., 2nd Edition (Marcel Dekker, NY, 1994), pp 1625-1710.

In the case of tumor growth, angiogenesis appears to be crucial for the transition from hyperplasia to neoplasia, and for providing nourishment for the growth and metastasis of the tumor. Folkman et al., *Nature*, 339: 58 (1989). The neovascularization allows the tumor cells to acquire a growth advantage and proliferative autonomy compared to normal cells. A tumor usually begins as a single aberrant cell which can proliferate only to a size of a few cubic millimeters due to the distance from available capillary beds, and it can stay 'dormant' without further growth and dissemination for a long period of time. Some tumor cells then switch to the angiogenic phenotype to activate endothelial cells, which proliferate and mature into new capillary blood vessels. These newly formed blood vessels not only allow for continued growth of the primary tumor, but also for the dissemination and recolonization of metastatic tumor cells. Accordingly, a correlation has been observed between density of microvessels in tumor sections and patient survival in breast cancer as well as in several other tumors. Weidner et al., *N. Engl. J. Med*, 324: 1-6 (1991); Horak et al., *Lancet*, 340: 1120-1124 (1992); Macchiarini et al., *Lancet*, 340: 145-146 (1992). The precise mechanisms that control the angiogenic switch is not well understood, but it is believed that neovascularization of tumor mass results from the net balance of a multitude of angiogenesis stimulators and inhibitors (Folkman, 1995, Nat Med 1(1):27-31).

The process of vascular development is tightly regulated. To date, a significant number of molecules, mostly secreted factors produced by surrounding cells, have been shown to regulate EC differentiation, proliferation, migration and coalescence into cord-like structures. For example, vascular endothelial growth factor (VEGF) has been identified as the key factor involved in stimulating angiogenesis and in inducing vascular permeability. Ferrara et al., *Endocr. Rev.*, 18: 4-25 (1997). The finding that the loss of even a single VEGF allele results in embryonic lethality points to an irreplaceable role played by this factor in the development and differentiation of the vascular system. Furthermore, VEGF has been shown to be a key mediator of neovascularization associated with tumors and intraocular disorders. Ferrara et al., *Endocr. Rev.*, supra. The VEGF mRNA is overexpressed by the majority of human tumors examined Berkman et al., *J. Clin. Invest.*, 91: 153-159 (1993); Brown et al., *Human Pathol.*, 26: 86-91 (1995); Brown et al., *Cancer Res.*, 53: 4727-4735 (1993); Mattern et al., *Brit. J. Cancer*, 73: 931-934 (1996); Dvorak et al., *Am. J. Pathol.*, 146: 1029-1039 (1995).

Bv8 has been shown to induce proliferation, survival and migration of adrenal cortical capillary endothelial cells (LeCouter, J. et al., *Proc Natl Acad Sci USA* 100, 2685-2690 (2003)). Bv8 and EG-VEGF are two highly related secreted proteins, also referred to as prokineticin-1 and -2, which structurally belong to a larger class of peptides defined by a five disulphide bridge motif called a colipase fold (DeCouter, J. et al., *Nature* 420, 860-867 (2002); LeCouter, J. et al., *Proc Natl Acad Sci USA* 100, 2685-2690 (2003); Li, M. et al., *Mol Pharmacol* 59, 692-698 (2001)). Bv8 was initially identified as a secreted protein from the skin of the frog *Bombina variegate* (Mollay, C. et al., *Eur J Pharmacol* 374, 189-196 (1999)). The cloning and expression of Bv8 are described in WO 03/020892 published on Mar. 13, 2003. Bv8 and EG-VEGF bind two highly related G-protein coupled receptors (GPCR), EG-VEGF/PKR-1 (R1) and EG-VEGF/PKR-2 (R2) (Masuda, Y et al., *Biochem Biophys Res Commun* 293, 496-402 (2002); Lin, D. C. et al., *J Biol Chem* 277, 19276-19280 (2002)). EG-VEGF and Bv8 were characterized as mitogens selective for specific endothelial cell types (LeCouter, J. et al., *Nature* 412(6850):877-84 (2001) and LeCouter, J. et al., *Proc Natl Acad Sci USA* 100, 2685-2690 (2003)). Other activities have been ascribed to this family, including nociception (Mollay, C. et al., supra), gastrointestinal tract motility (Li, M. et al., supra), regulation of circadian locomotor rhythm (Cheng, M. Y., et al., *Nature* 417, 405-410 (2002)) and olfactory bulb neurogenesis (Matsumoto, S., et al., *Proc Natl Acad Sci USA* 103, 4140-4145 (2006)). Furthermore, Bv8 stimulated production of granulocytic and monocytic colonies in vitro (LeCouter, J. et al., (2003), supra; Dorsch, M. et al., *J. Leukoc Biol* 78(2), 426-34 (2005)). Bv8 has been characterized as a chemoattractact for macrophages (LeCouter et al., *Proc Natl Acad Sci USA* 101, 16813-16919 (2004)).

In view of the role of angiogenesis in many diseases and disorders, it is desirable to have a means of reducing or inhibiting one or more of the biological effects causing these processes. All references cited herein, including patent applications and publications, are incorporated by reference in their entirety.

SUMMARY OF THE INVENTION

The invention is in part based on a variety of antibodies to Bv8. Bv8 presents as an important and advantageous therapeutic target, and the invention provides antibodies as therapeutic and diagnostic agents for use in targeting pathological conditions associated with expression and/or activity of Bv8. Accordingly, the invention provides methods, compositions, kits and articles of manufacture related to Bv8.

In certain embodiments, an antibody that binds to Bv8 or a fragment thereof is provided, wherein the antibody comprises a variable domain comprising at least one, two, three, four, five or six hypervariable region (HVR) sequences selected from the group consisting of:
(i) HVR-L1 comprising KASQSX$_1$X$_2$YX$_3$X$_4$X$_5$SYMN, wherein X$_1$ is L or V; X$_2$ is D or I; X$_3$ is D, F, G, S, W or Y; X$_4$ is A, G, H or V; and X$_5$ is D, E or Y;
(ii) HVR-L2 comprising AASX$_1$X$_2$EX$_3$, wherein X$_1$ is N or Y; X$_2$ is L or R; and X$_3$ is S or T;
(iii) HVR-L3 comprising QQINEDPFT;
(iv) HVR-H1 comprising GYX$_1$X$_2$X$_3$X$_4$YDMH, wherein X$_1$ is S or T; X$_2$ is F or L; X$_3$ is F, M, P, T or V; X$_4$ is D, E, H, I, or N;
(v) HVR-H2 comprising YIX$_1$X$_2$YX$_3$GX$_4$TX$_5$YNQKFKG, wherein X$_1$ is H, S or T; X$_2$ is C, S or T; X$_3$ is A, L, N, S or T; X$_4$ is A, E or S; X$_5$ is I, L, S or T, and
(vi) HVR-H3 comprising DX$_1$NYGEAYAMDY, wherein X$_1$ is G or S.

In certain embodiments, the anti-Bv8 antibody comprises the following three HVR sequences:
(i) HVR-L1 comprising KASQSX$_1$X$_2$YX$_3$X$_4$X$_5$SYMN, wherein X$_1$ is L or V; X$_2$ is D or I; X$_3$ is D, F, G, S, W or Y; X$_4$ is A, G, H or V; and X$_5$ is D, E or Y;
(ii) HVR-L2 comprising AASX$_1$X$_2$EX$_3$, wherein X$_1$ is N or Y; X$_2$ is L or R; and X$_3$ is S or T; and
(iii) HVR-L3 comprising QQINEDPFT; and human VL kappa subgroup IV consensus framework sequence SEQ ID NO:240.

In certain embodiments, the anti-Bv8 antibody comprises the following three HVR sequences:
(i) HVR-H1 comprising GYX$_1$X$_2$X$_3$X$_4$YDMH, wherein X$_1$ is S or T; X$_2$ is F or L; X$_3$ is F, M, P, T or V; X$_4$ is D, E, H, I, or N;
(ii) HVR-H2 comprising YIX$_1$X$_2$YX$_3$GX$_4$TX$_5$YNQKFKG, wherein X$_1$ is H, S or T; X$_2$ is C, S or T; X$_3$ is A, L, N, S or T; X$_4$ is A, E or S; X$_5$ is I, L, S or T, and
(iii) HVR-H3 comprising DX$_1$NYGEAYAMDY, wherein X$_1$ is G or S and human VH subgroup I consensus framework sequence SEQ ID NO:241.

In certain embodiments, an antibody that binds to Bv8 or a fragment thereof is provided, wherein the antibody comprises a variable domain comprising the following six HVR sequences:
(i) HVR-L1 comprising KASQSX$_1$X$_2$YX$_3$X$_4$X$_5$SYMN, wherein X$_1$ is L or V; X$_2$ is D or I; X$_3$ is D, F, G, S, W or Y; X$_4$ is A, G, H or V; and X$_5$ is D, E or Y;
(ii) HVR-L2 comprising AASX$_1$X$_2$EX$_3$, wherein X$_1$ is N or Y; X$_2$ is L or R; and X$_3$ is S or T;
(iii) HVR-L3 comprising QQINEDPFT;
(iv) HVR-H1 comprising GYX$_1$X$_2$X$_3$X$_4$YDMH, wherein X$_1$ is S or T; X$_2$ is F or L; X$_3$ is F, M, P, T or V; X$_4$ is D, E, H, I, or N;
(v) HVR-H2 comprising YIX$_1$X$_2$YX$_3$GX$_4$TX$_5$YNQKFKG, wherein X$_1$ is H, S or T; X$_2$ is C, S or T; X$_3$ is A, L, N, S or T; X$_4$ is A, E or S; X$_5$ is I, L, S or T, and
(vi) HVR-H3 comprising DX$_1$NYGEAYAMDY, wherein X$_1$ is G or S.

In certain embodiments, the anti-Bv8 antibody further comprises a mutation compared to the murine/chimeric anti-Bv8 antibody at one or both of VL positions 28 and 29. In certain embodiments, the anti-Bv8 antibody further comprises a mutation compared to the murine/chimeric anti-Bv8 antibody at VH position 52a. In certain embodiments, the anti-Bv8 antibody further comprises a mutation compared to the murine/chimeric anti-Bv8 antibody at VH position 54. In certain embodiments, the anti-Bv8 antibody further comprises a mutation compared to the murine/chimeric anti-Bv8 antibody at one or both of VH positions 95 and 96. In certain embodiments, the anti-Bv8 antibody further comprises a mutation compared to the murine/chimeric anti-Bv8 antibody (1) at one or both of VL positions 28 and 29; and/or (2) at VH position 52a; and/or (3) VH position 54; and/or (4) one or both of VH positions 95 and 96. In certain embodiments, the anti-Bv8 antibody further comprises a mutation compared to the murine/chimeric anti-Bv8 antibody at VH positions 96 and no mutation at VH position 95.

In certain embodiments, an antibody that binds to Bv8 or a fragment thereof is provided, wherein HVR-L1 comprises an amino acid sequence selected from the group consisting of SEQ ID NOs:49, 55, 61, 67, 73, 79, 85, 91, 97, 103, 109, 115, 121, 127, 133, 139, 145 and 151, HVR-L2 comprises an amino acid sequence selected from the group consisting of SEQ ID NOs: 50, 56, 62, 68, 74, 80, 86, 92, 98, 104, 110, 116, 122, 128, 134, 140, 146 and 152, HVR-L3 comprises an amino acid sequence selected from the group consisting of SEQ ID NOs: 51, 57, 63, 69, 75, 81, 87, 93, 99, 105, 111, 117, 123, 129, 135, 141, 147 and 153, HVR-H1 comprises an amino acid sequence selected from the group consisting of SEQ ID NOs: 52, 58, 64, 70, 76, 82, 88, 94, 100, 106, 112, 118, 124, 130, 136, 142, 148 and 154, HVR-H2 comprises an amino acid sequence selected from the group consisting of SEQ ID NOs: 53, 59, 65, 71, 77, 83, 89, 95, 101, 107, 113, 119, 125, 131, 137, 143, 149 and 155, and HVR-H3 comprises an amino acid sequence selected from the group consisting of SEQ ID NOs: 54, 60, 66, 72, 78, 84, 90, 96, 102, 108, 114, 120, 126, 132, 138, 144, 150 and 156.

In certain embodiments, the anti-Bv8 antibody further comprises human VL kappa subgroup IV consensus framework sequence. In certain embodiments, the anti-Bv8 antibody further comprises human VH subgroup I consensus framework sequence. In certain embodiments, the anti-Bv8 antibody further comprises human VL kappa subgroup IV consensus framework sequence and human VH subgroup I consensus framework sequence. In certain embodiments, human VL kappa subgroup IV consensus framework sequence minus the three light chain HVR sequences is SEQ ID NO:240. In certain embodiments, the VH subgroup I consensus framework sequence minus the three heavy chain HVR sequences is SEQ ID NO:241.

In certain embodiments, an antibody that binds to Bv8 or a fragment thereof is provided, wherein the antibody comprises a variable domain comprising at least one, two, three, four, five or six hypervariable region (HVR) sequences selected from the group consisting of:
(i) HVR-L1 comprising KASQSX$_1$X$_2$YX$_3$X$_4$X$_5$SYMN, wherein X$_1$ is L or V; X$_2$ is D or I; X$_3$ is F, G, S, W or Y; X$_4$ is A, G, H or V; and X$_5$ is D, E or Y;
(ii) HVR-L2 comprising AASX$_1$X$_2$EX$_3$, wherein X$_1$ is N or Y; X$_2$ is L or R; and X$_3$ is S or T;
(iii) HVR-L3 comprising QQINEDPFT;
(iv) HVR-H1 comprising GYX$_1$X$_2$X$_3$X$_4$YDMH, wherein X$_1$ is S or T; X$_2$ is F or L; X$_3$ is F, M, P, T or V; X$_4$ is D, E, H, I, or N;
(v) HVR-H2 comprising YIX$_1$X$_2$YX$_3$GX$_4$TX$_5$YNQKFKG, wherein X$_1$ is H, S or T; X$_2$ is S or T; X$_3$ is A, L, S or T; X$_4$ is A, E or S; X$_5$ is I, L, S or T, and
(vi) HVR-H3 comprising DSNYGEAYAMDY.

In certain embodiments, the anti-Bv8 antibody comprises the following three HVR sequences:

(i) HVR-L1 comprising KASQSX$_1$X$_2$YX$_3$X$_4$X$_5$SYMN, wherein X$_1$ is L or V; X$_2$ is D or I; X$_3$ is F, G, S, W or Y; X$_4$ is A, G, H or V; and X$_5$ is D, E or Y;
(ii) HVR-L2 comprising AASX$_1$X$_2$EX$_3$, wherein X$_1$ is N or Y; X$_2$ is L or R; and X$_3$ is S or T;
(iii) HVR-L3 comprising QQINEDPFT; and
human VL kappa subgroup IV consensus framework sequence SEQ ID NO:240.

In certain embodiments, the anti-Bv8 antibody comprises the following three HVR sequences:
(i) HVR-H1 comprising GYX$_1$X$_2$X$_3$X$_4$YDMH, wherein X$_1$ is S or T; X$_2$ is F or L; X$_3$ is F, M, P, T or V; X$_4$ is D, E, H, I, or N;
(ii) HVR-H2 comprising YIX$_1$X$_2$YX$_3$GX$_4$TX$_5$YNQKFKG, wherein X$_1$ is H, S or T; X$_2$ is S or T; X$_3$ is A, L, S or T; X$_4$ is A, E or S; X$_5$ is I, L, S or T, and
(iii) HVR-H3 comprising DSNYGEAYAMDY, and human VH subgroup I consensus framework sequence SEQ ID NO:241.

In certain embodiments, an antibody that binds to Bv8 or a fragment thereof is provided, wherein the antibody comprises a variable domain comprising the following six HVR sequences:
(i) HVR-L1 comprising KASQSX$_1$X$_2$YX$_3$X$_4$X$_5$SYMN, wherein X$_1$ is L or V; X$_2$ is D or I; X$_3$ is F, G, S, W or Y; X$_4$ is A, G, H or V; and X$_5$ is D, E or Y;
(ii) HVR-L2 comprising AASX$_1$X$_2$EX$_3$, wherein X$_1$ is N or Y; X$_2$ is L or R; and X$_3$ is S or T;
(iii) HVR-L3 comprising QQINEDPFT;
(iv) HVR-H1 comprising GYX$_1$X$_2$X$_3$X$_4$YDMH, wherein X$_1$ is S or T; X$_2$ is F or L; X$_3$ is F, M, P, T or V; X$_4$ is D, E, H, I, or N;
(v) HVR-H2 comprising YIX$_1$X$_2$YX$_3$GX$_4$TX$_5$YNQKFKG, wherein X$_1$ is H, S or T; X$_2$ is S or T; X$_3$ is A, L, S or T; X$_4$ is A, E or S; X$_5$ is I, L, S or T, and
(vi) HVR-H3 comprising DSNYGEAYAMDY.

In certain embodiments, an antibody that binds to Bv8 or a fragment thereof is provided, wherein HVR-L1 comprises an amino acid sequence selected from the group consisting of SEQ ID NOs: 55, 61, 67, 73, 79, 85, 91, 97, 103, 109, 115, 121, 127, 133, 139, 145 and 151, HVR-L2 comprises an amino acid sequence selected from the group consisting of SEQ ID NOs: 56, 62, 68, 74, 80, 86, 92, 98, 104, 110, 116, 122, 128, 134, 140, 146 and 152, HVR-L3 comprises an amino acid sequence selected from the group consisting of SEQ ID NOs: 57, 63, 69, 75, 81, 87, 93, 99, 105, 111, 117, 123, 129, 135, 141, 147 and 153, HVR-H1 comprises an amino acid sequence selected from the group consisting of SEQ ID NOs: 58, 64, 70, 76, 82, 88, 94, 100, 106, 112, 118, 124, 130, 136, 142, 148 and 154, HVR-H2 comprises an amino acid sequence selected from the group consisting of SEQ ID NOs: 59, 65, 71, 77, 83, 89, 95, 101, 107, 113, 119, 125, 131, 137, 143, 149 and 155, and HVR-H3 comprises an amino acid sequence selected from the group consisting of SEQ ID NOs: 60, 66, 72, 78, 84, 90, 96, 102, 108, 114, 120, 126, 132, 138, 144, 150 and 156.

In certain embodiments, the anti-Bv8 antibody further comprises human VL kappa subgroup IV consensus framework sequence. In certain embodiments, the anti-Bv8 antibody further comprises human VH subgroup I consensus framework sequence. In certain embodiments, the anti-Bv8 antibody further comprises human VL kappa subgroup IV consensus framework sequence and human VH subgroup I consensus framework sequence. In certain embodiments, human VL kappa subgroup IV consensus framework sequence minus the three light chain HVR sequences is SEQ ID NO:240. In certain embodiments, the VH subgroup I consensus framework sequence minus the three heavy chain HVR sequences is SEQ ID NO:241.

In another embodiment, an antibody that binds to Bv8 or a fragment thereof is provided, wherein the antibody comprises:
(1) an HVR-H1 comprising the amino acid sequence of SEQ ID NO:61;
(2) an HVR-H2 comprising the amino acid sequence of SEQ ID NO:62;
(3) an HVR-H3 comprising the amino acid sequence of SEQ ID NO:63;
(4) an HVR-L1 comprising the amino acid sequence of SEQ ID NO:64;
(5) an HVR-L2 comprising the amino acid sequence of SEQ ID NO:65; and
(6) an HVR-L3 comprising the amino acid sequence of SEQ ID NO:66.

In another embodiment, an antibody that binds to Bv8 or a fragment thereof is provided, wherein the antibody comprises:
(1) an HVR-H1 comprising the amino acid sequence of SEQ ID NO:85;
(2) an HVR-H2 comprising the amino acid sequence of SEQ ID NO:86;
(3) an HVR-H3 comprising the amino acid sequence of SEQ ID NO:87;
(4) an HVR-L1 comprising the amino acid sequence of SEQ ID NO:88;
(5) an HVR-L2 comprising the amino acid sequence of SEQ ID NO:89; and
(6) an HVR-L3 comprising the amino acid sequence of SEQ ID NO:90.

In another embodiment, an antibody that binds to Bv8 or a fragment thereof is provided, wherein the antibody comprises:
(1) an HVR-H1 comprising the amino acid sequence of SEQ ID NO:91;
(2) an HVR-H2 comprising the amino acid sequence of SEQ ID NO:92;
(3) an HVR-H3 comprising the amino acid sequence of SEQ ID NO:93;
(4) an HVR-L1 comprising the amino acid sequence of SEQ ID NO:94;
(5) an HVR-L2 comprising the amino acid sequence of SEQ ID NO:95; and
(6) an HVR-L3 comprising the amino acid sequence of SEQ ID NO:96.

In another embodiment, an antibody that binds to Bv8 or a fragment thereof is provided, wherein the antibody comprises:
(1) an HVR-H1 comprising the amino acid sequence of SEQ ID NO:121;
(2) an HVR-H2 comprising the amino acid sequence of SEQ ID NO:122;
(3) an HVR-H3 comprising the amino acid sequence of SEQ ID NO:123;
(4) an HVR-L1 comprising the amino acid sequence of SEQ ID NO:124;
(5) an HVR-L2 comprising the amino acid sequence of SEQ ID NO:125; and
(6) an HVR-L3 comprising the amino acid sequence of SEQ ID NO:126.

In certain embodiments, the anti-Bv8 antibody further comprises human VL kappa subgroup IV consensus framework sequence. In certain embodiments, the anti-Bv8 antibody further comprises human VH subgroup I consensus framework sequence. In certain embodiments, the anti-Bv8 antibody further comprises human VL kappa subgroup IV consensus framework sequence and human VH subgroup I consensus framework sequence. In certain embodiments, human VL kappa subgroup IV consensus framework sequence minus the three light chain HVR sequences is SEQ ID NO:240. In certain embodiments, the VH subgroup I consensus framework sequence minus the three heavy chain HVR sequences is SEQ ID NO:241.

In one embodiment, an antibody that binds to Bv8 or a fragment thereof is provided, wherein the antibody comprises a light chain variable domain comprising SEQ ID NO:7 and the heavy chain variable domain comprising SEQ ID NO:8.

In another embodiment, an antibody that binds to Bv8 or a fragment thereof is provided, wherein the antibody comprises a light chain variable domain comprising SEQ ID NO:9 and the heavy chain variable domain comprising SEQ ID NO:10.

In another embodiment, an antibody that binds to Bv8 or a fragment thereof is provided, wherein the antibody comprises a light chain variable domain comprising SEQ ID NO:11 and the heavy chain variable domain comprising SEQ ID NO:12.

In another embodiment, an antibody that binds to Bv8 or a fragment thereof is provided, wherein the antibody comprises a light chain variable domain comprising SEQ ID NO:13 and the heavy chain variable domain comprising SEQ ID NO:14.

In certain embodiments, an antibody that binds to Bv8 or a fragment thereof is provided, wherein the antibody comprises a light chain variable domain having at least 90% sequence identity to the amino acid sequence selected from the group consisting of SEQ ID NOs:3, 5, 7, 9, 11, 13 and 15.

In certain embodiments, an antibody that binds to Bv8 or a fragment thereof is provided, wherein the antibody comprises a light chain variable domain comprising the amino acid sequence selected from the group consisting of SEQ ID NOs: 3, 5, 7, 9, 11, 13 and 15.

In one embodiment, an antibody that binds to Bv8 or a fragment thereof is provided, wherein the antibody comprises the light chain variable domain comprises the amino acid sequence of SEQ ID NO:7.

In another embodiment, an antibody that binds to Bv8 or a fragment thereof is provided, wherein the antibody comprises the light chain variable domain comprises the amino acid sequence of SEQ ID NO:9.

In another embodiment, an antibody that binds to Bv8 or a fragment thereof is provided, wherein the antibody comprises the light chain variable domain comprises the amino acid sequence of SEQ ID NO:11.

In another embodiment, an antibody that binds to Bv8 or a fragment thereof is provided, wherein the antibody comprises the light chain variable domain comprises the amino acid sequence of SEQ ID NO:13.

In certain embodiments, an antibody that binds to Bv8 or a fragment thereof is provided, wherein the antibody comprises a heavy chain variable domain having at least 90% sequence identity to the amino acid sequence selected from the group consisting of SEQ ID NOs:4, 6, 8, 10, 12, 14 and 16.

In certain embodiments, an antibody that binds to Bv8 or a fragment thereof is provided, wherein the antibody comprises a heavy chain variable domain comprising the amino acid sequence selected from the group consisting of SEQ ID NOs: 4, 6, 8, 10, 12, 14 and 16.

In one embodiment, an antibody that binds to Bv8 or a fragment thereof is provided, wherein the antibody comprises the heavy chain variable domain comprises the amino acid sequence of SEQ ID NO:8.

In another embodiment, an antibody that binds to Bv8 or a fragment thereof is provided, wherein the antibody comprises the heavy chain variable domain comprises the amino acid sequence of SEQ ID NO:10.

In another embodiment, an antibody that binds to Bv8 or a fragment thereof is provided, wherein the antibody comprises the heavy chain variable domain comprises the amino acid sequence of SEQ ID NO:12.

In another embodiment, an antibody that binds to Bv8 or a fragment thereof is provided, wherein the antibody comprises the heavy chain variable domain comprises the amino acid sequence of SEQ ID NO:14.

In certain embodiments, an antibody that binds to Bv8 or a fragment thereof is provided, wherein the antibody comprises a light chain variable domain having at least 90% sequence identity to the amino acid sequence selected from the group consisting of SEQ ID NOs:3, 5, 7, 9, 11, 13 and 15 and a heavy chain variable domain having at least 90% sequence identity to the amino acid sequence selected from the group consisting of SEQ ID NOs:4, 6, 8, 10, 12, 14 and 16. In certain embodiments, an antibody that binds to Bv8 or a fragment thereof is provided, wherein the antibody comprises a light chain variable domain comprising the amino acid sequence selected from the group consisting of SEQ ID NOs:3, 5, 7, 9, 11, 13 and 15 and a heavy chain variable domain comprising the amino acid sequence selected from the group consisting of SEQ ID NOs:4, 6, 8, 10, 12, 14 and 16.

In certain embodiments, an antibody that binds to Bv8 or a fragment thereof is provided, wherein the anti-Bv8 antibody binds to human Bv8 with Kd value of less than about 0.02 nM.

In certain embodiments, an antibody that binds to Bv8 or a fragment thereof is provided, wherein the anti-Bv8 antibody binds to human Bv8 with Kd value of about 0.01 nM or less.

In certain embodiments, an antibody that binds to Bv8 or a fragment thereof is provided, wherein the anti-Bv8 antibody binds to human Bv8 at least two fold tighter than the chimeric 2G9 anti-Bv8 antibody. In certain embodiments, an antibody that binds to Bv8 or a fragment thereof is provided, wherein the anti-Bv8 antibody binds to human Bv8 at least five fold tighter than the chimeric 2G9 anti-Bv8 antibody.

In certain embodiments, the Kd value is measured by using A surface plasmon resonance assay. In certain embodiments, the Kd value is measured using a full-length anti-Bv8 antibody. In certain embodiments, the Kd value is measured using a the Fab version of the anti-Bv8 antibody.

In certain embodiments, an antibody that binds to Bv8 or a fragment thereof is provided, wherein the antibody comprises at least one, two, three, four, five or six hypervariable region (HVR) sequences selected from the group consisting of:
  (i) HVR-L1 comprising SASS $X_1$VFYMH, wherein $X_1$ is P or S;
  (ii) HVR-L2 comprising DTS$X_1$LAS, wherein $X_1$ is K or N;
  (iii) HVR-L3 comprising QQWS $X_1X_2$P$X_3$T, wherein $X_1$ is F, S, W or Y; $X_2$ is D or E; $X_3$ is I, L or M;
  (iv) HVR-H1 comprising GF$X_1X_2$ST$X_3$GMGVS, wherein $X_1$ is L or Y; $X_2$ is I or L; $X_3$ is P or S;
  (v) HVR-H2 comprising HIYWDDDTRYNPSLKS, and
  (vi) HVR-H3 comprising RDHGYYWF$X_1$Y, wherein $X_1$ is D or T.

In certain embodiments, an antibody that binds to Bv8 or a fragment thereof is provided, wherein the antibody comprises a variable domain comprising the following six HVR sequences:

(i) HVR-L1 comprising SASS $X_1$VFYMH, wherein $X_1$ is P or S;
(ii) HVR-L2 comprising DTS$X_1$LAS, wherein $X_1$ is K or N;
(iii) HVR-L3 comprising QQWS $X_1X_2PX_3$T, wherein $X_1$ is F, S, W or Y; $X_2$ is D or E; $X_3$ is I, L or M;
(iv) HVR-H1 comprising GF$X_1X_2$ST$X_3$GMGVS, wherein $X_1$ is L or Y; $X_2$ is I or L; $X_3$ is P or S;
(v) HVR-H2 comprising HIYWDDDTRYNPSLKS, and
(vi) HVR-H3 comprising RDHGYYWF$X_1$Y, wherein $X_1$ is D or T.

In certain embodiments, an antibody that binds to Bv8 or a fragment thereof is provided, wherein HVR-L1 comprises an amino acid sequence selected from the group consisting of SEQ ID NOs:157, 163, 169, 175, 181, 187 and 193, HVR-L2 comprises an amino acid sequence selected from the group consisting of SEQ ID NOs:158, 164, 170, 176, 182, 188 and 194, HVR-L3 comprises an amino acid sequence selected from the group consisting of SEQ ID NOs:159, 165, 171, 177, 183, 189 and 195, HVR-H1 comprises an amino acid sequence selected from the group consisting of SEQ ID NOs: 160, 166, 172, 178, 184, 190 and 196, HVR-H2 comprises an amino acid sequence selected from the group consisting of SEQ ID NOs:161, 167, 173, 179, 185, 191 and 197, and HVR-H3 comprises an amino acid sequence selected from the group consisting of SEQ ID NOs:162, 168, 174, 180, 186, 192 and 198.

In certain embodiments, the anti-Bv8 antibody further comprises human VL kappa subgroup I consensus framework sequence. In certain embodiments, the anti-Bv8 antibody further comprises human VH subgroup III consensus framework sequence. In certain embodiments, the anti-Bv8 antibody further comprises human VL kappa subgroup I consensus framework sequence and human VH subgroup III consensus framework sequence.

In certain embodiments, an antibody that binds to Bv8 or a fragment thereof is provided, wherein the antibody comprises at least one, two, three, four, five or six hypervariable region (HVR) sequences selected from the group consisting of:
(i) HVR-L1 comprising SASS $X_1$VFYMH, wherein $X_1$ is P or S;
(ii) HVR-L2 comprising DTS$X_1$LAS, wherein $X_1$ is K or N;
(iii) HVR-L3 comprising QQWS $X_1X_2PX_3$T, wherein $X_1$ is F, S, W or Y; $X_2$ is D or E; $X_3$ is I, L or M;
(iv) HVR-H1 comprising GF$X_1X_2$ST$X_3$GMGVS, wherein $X_1$ is L or Y; $X_2$ is I or L; $X_3$ is P or S;
(v) HVR-H2 comprising HIYWDDDTRYNPSLKS, and
(vi) HVR-H3 comprising RDHGYYWFDY.

In certain embodiments, an antibody that binds to Bv8 or a fragment thereof is provided, wherein the antibody comprises the following six HVR sequences:
(i) HVR-L1 comprising SASS $X_1$VFYMH, wherein $X_1$ is P or S;
(ii) HVR-L2 comprising DTS$X_1$LAS, wherein $X_1$ is K or N;
(iii) HVR-L3 comprising QQWS $X_1X_2PX_3$T, wherein $X_1$ is F, S, W or Y; $X_2$ is D or E; $X_3$ is I, L or M;
(iv) HVR-H1 comprising GF$X_1X_2$ST$X_3$GMGVS, wherein $X_1$ is L or Y; $X_2$ is I or L; $X_3$ is P or S;
(v) HVR-H2 comprising HIYWDDDTRYNPSLKS, and
(vi) HVR-H3 comprising RDHGYYWFDY.

In certain embodiments, an antibody that binds to Bv8 or a fragment thereof is provided, wherein the antibody comprises HVR-L1 comprises an amino acid sequence selected from the group consisting of SEQ ID NOs:157, 163, 169, 175, 181, 187 and 193, HVR-L2 comprises an amino acid sequence selected from the group consisting of SEQ ID NOs:158, 164, 170, 176, 182, 188 and 194, HVR-L3 comprises an amino acid sequence selected from the group consisting of SEQ ID NOs:159, 165, 171, 177, 183, 189 and 195, HVR-H1 comprises an amino acid sequence selected from the group consisting of SEQ ID NOs:160, 166, 172, 178, 184, 190 and 196, HVR-H2 comprises an amino acid sequence selected from the group consisting of SEQ ID NOs:161, 167, 173, 179, 185, 191 and 197, and HVR-H3 comprises an amino acid sequence selected from the group consisting of SEQ ID NOs:174, 180, 186, 192 and 198.

In certain embodiments, the anti-Bv8 antibody further comprises human VL kappa subgroup I consensus framework sequence. In certain embodiments, the anti-Bv8 antibody further comprises human VH subgroup III consensus framework sequence. In certain embodiments, the anti-Bv8 antibody further comprises human VL kappa subgroup I consensus framework sequence and human VH subgroup III consensus framework sequence.

In another embodiment, an antibody that binds to Bv8 or a fragment thereof is provided, wherein the antibody comprises a light chain variable domain comprising SEQ ID NO:23 and the heavy chain variable domain comprising SEQ ID NO:24.

In certain embodiments, an antibody that binds to Bv8 or a fragment thereof is provided, wherein the antibody comprises at least one, two, three, four, five or six hypervariable region (HVR) sequences selected from the group consisting of:
(i) HVR-L1 comprising EASQSVDYDDDSYMN;
(ii) HVR-L2 comprising ATSNLAS;
(iii) HVR-L3 comprising QQSNEDPFT;
(iv) HVR-H1 comprising GYTFTNSWMN;
(v) HVR-H2 comprising RIDPSDSETHYNQKFKD; and
(vi) HVR-H3 comprising DSSYDGFYAMDY.

In certain embodiments, an antibody that binds to Bv8 or a fragment thereof is provided, wherein the antibody comprises the following six HVR sequences:
(i) HVR-L1 comprising EASQSVDYDDDSYMN;
(ii) HVR-L2 comprising ATSNLAS;
(iii) HVR-L3 comprising QQSNEDPFT;
(iv) HVR-H1 comprising GYTFTNSWMN;
(v) HVR-H2 comprising RIDPSDSETHYNQKFKD; and
(vi) HVR-H3 comprising DSSYDGFYAMDY.

In certain embodiments, an antibody that binds to Bv8 or a fragment thereof is provided, wherein the antibody comprises HVR-L1 comprises an amino acid sequence selected from the group consisting of SEQ ID NOs:199 and 205, HVR-L2 comprises an amino acid sequence selected from the group consisting of SEQ ID NOs:200 and 206, HVR-L3 comprises an amino acid sequence selected from the group consisting of SEQ ID NOs:201 and 207, HVR-H1 comprises an amino acid sequence selected from the group consisting of SEQ ID NOs: 202 and 208, HVR-H2 comprises an amino acid sequence selected from the group consisting of SEQ ID NOs:203 and 209, and HVR-H3 comprises an amino acid sequence selected from the group consisting of SEQ ID NOs:204 and 210.

In certain embodiments, the anti-Bv8 antibody further comprises human VL kappa subgroup I consensus framework sequence. In certain embodiments, the anti-Bv8 antibody further comprises human VH subgroup III consensus framework sequence. In certain embodiments, the anti-Bv8 antibody further comprises human VL kappa subgroup I consensus framework sequence and human VH subgroup III consensus framework sequence.

In certain embodiments, an antibody that binds to Bv8 or a fragment thereof is provided, wherein the antibody comprises at least one, two, three, four, five or six hypervariable region (HVR) sequences selected from the group consisting of:
(i) HVR-L1 comprising KSSEYVSNALS;
(ii) HVR-L2 comprising GTNKLED;
(iii) HVR-L3 comprising QQGYDIPT;
(iv) HVR-H1 comprising GFTFSDYFMG;
(v) HVR-H2 comprising GIDTKSYNYATYYSGSVKG; and
(vi) HVR-H3 comprising NYGNYGAFDS.

In certain embodiments, an antibody that binds to Bv8 or a fragment thereof is provided, wherein the antibody comprises the following six HVR sequences:
(i) HVR-L1 comprising KSSEYVSNALS;
(ii) HVR-L2 comprising GTNKLED;
(iii) HVR-L3 comprising QQGYDIPT;
(iv) HVR-H1 comprising GFTFSDYFMG;
(v) HVR-H2 comprising GIDTKSYNYATYYSGSVKG; and
(vi) HVR-H3 comprising NYGNYGAFDS.

In certain embodiments, an antibody that binds to Bv8 or a fragment thereof is provided, wherein the antibody comprises HVR-L1 comprises an amino acid sequence SEQ ID NO:211, HVR-L2 comprises an amino acid sequence SEQ ID NO:212, HVR-L3 comprises an amino acid sequence SEQ ID NO:213, HVR-H1 comprises an amino acid sequence SEQ ID NO:214, HVR-H2 comprises an amino acid sequence SEQ ID NO:215, and HVR-H3 comprises an amino acid sequence SEQ ID NO:216.

In certain embodiments, the anti-Bv8 antibody further comprises human VL kappa subgroup I consensus framework sequence. In certain embodiments, the anti-Bv8 antibody further comprises human VH subgroup III consensus framework sequence. In certain embodiments, the anti-Bv8 antibody further comprises human VL kappa subgroup I consensus framework sequence and human VH subgroup III consensus framework sequence.

In certain embodiments, the anti-Bv8 antibody is a monoclonal antibody. In certain embodiments, the anti-Bv8 antibody is humanized. In certain embodiments, the anti-Bv8 antibody is human. In certain embodiments, at least a portion of the framework sequence of the anti-Bv8 antibody is a human consensus framework sequence. In one embodiment, the antibody is an antibody fragment selected from a Fab, Fab'-SH, Fv, scFv, or (Fab')$_2$ fragment.

In certain embodiments, a polynucleotide or nucleic acid encoding any of the antibodies described herein is provided. In one embodiment, a vector comprising the polynucleotide or the nucleic acid is provided. In one embodiment, the vector is an expression vector. In one embodiment, a host cell comprising the vector is provided. In one embodiment, the host cell is eukaryotic. In one embodiment, the host cell is prokaryotic. In one embodiment, the host cell is a CHO cell. In one embodiment, a method of making an anti-Bv8 antibody is provided, wherein the method comprises culturing the host cell under conditions suitable for expression of the polynucleotide encoding the antibody, and isolating the antibody.

In certain embodiments, the invention further concerns a composition comprising any of the anti-Bv8 antibodies above. In certain embodiments, the invention concerns a pharmaceutical composition comprising any of the anti-Bv8 antibodies above in admixture with a pharmaceutically acceptable carrier.

In certain embodiments, the invention concerns a pharmaceutical composition for the prevention or treatment of tumor metastasis comprising an effective amount of any of the anti-Bv8 antibodies described herein in admixture with a pharmaceutically acceptable carrier.

In certain embodiments, methods of detecting the presence of Bv8 in a biological sample is provided, the method comprising contacting the biological sample with an anti-Bv8 antibody of the invention under conditions permissive for binding of the antibody to Bv8, and detecting whether a complex is formed between the antibody and Bv8.

In certain embodiments, methods for treating a tumor, a cancer, or a cell proliferative disorder comprising administering to a subject an effective amount of any of the anti-Bv8 antibodies described herein are provided. In certain embodiments, the cancer is selected from the group consisting of breast cancer, colorectal cancer, lung cancer, renal cancer, glioblastoma, esophageal cancer, melanoma, bladder cancer, ovarian cancer, pancreatic cancer, and hepatocellular carcinoma. In certain embodiments, the cancer is breast cancer, colorectal cancer, lung cancer, renal cancer, ovarian cancer or glioblastoma. An exemplary and non-limiting list of cancers contemplated is provided herein under "Definitions."

In certain embodiments, methods for reducing or inhibiting angiogenesis in a subject having a pathological condition associated with angiogenesis, comprising administering to the subject an effective amount of any of the anti-Bv8 antibodies described herein are provided. In certain embodiments, the pathological condition is a neoplastic condition. In certain embodiments, the pathological condition in a non-neoplastic condition. An exemplary and non-limiting list of non-neoplastic conditions contemplated is provided herein under "Definitions." In certain embodiments, the non-neoplastic condition is selected from the group consisting of diabetic and other proliferative retinopathies, retinopathy of prematurity, neovascular glaucoma, age-related macular degeneration, diabetic macular edema, corneal neovascularization, corneal graft neovascularization, retinal/choroidal neovascularization and rheumatoid arthritis.

In certain embodiments, methods for inhibiting endothelial cell proliferation comprising administering to a subject an effective amount of any of the anti-Bv8 antibodies described herein are provided. In certain embodiments, the endothelial cells are adrenal cortical endothelial cells.

In certain embodiments, methods for inhibiting neutrophil migration comprising administering to a subject an effective amount of any of the anti-Bv8 antibodies described herein are provided.

In certain embodiments, methods for inhibiting tumor metastasis comprising administering to a subject an effective amount of any of the anti-Bv8 antibodies described herein are provided. In certain embodiments, the metastasis is in the lymphatic system. In certain embodiments, the metastasis is in a distant organ.

In certain embodiments, methods for treating, preventing or reducing pain comprising administering to a subject an effective amount of any of the anti-Bv8 antibodies described herein are provided. In certain embodiments, the pain is acute or chronic pain. In certain embodiments, the pain is acute or chronic inflammatory pain. In certain embodiments, methods for treating rheumatoid arthritis comprising administering to a subject an effective amount of any one of the anti-Bv8 antibodies described herein are provided.

In certain embodiments, the methods described herein and above further comprise administering to the subject an effective amount of a second medicament, wherein the anti-Bv8 antibody is the first medicament. In certain embodiments, the second medicament is another antibody, a chemotherapeutic agent, a cytotoxic agent, an anti-angiogenic agent, an immunosuppressive agent, a prodrug, a cytokine, a cytokine antagonist, cytotoxic radiotherapy, a corticosteroid, an anti-emetic, a cancer vaccine, an analgesic, or a growth-inhibitory agent. In certain embodiments, the second medicament is an anti-angiogenic agent. In certain embodiments, the second medicament or the anti-angiogenic agent is an anti-VEGF antibody. In certain embodiments, the anti-VEGF antibody is bevacizumab. In certain embodiments, the second medicament is administered prior to or subsequent to the administration of the anti-Bv8 antibody. In certain embodiments, the second medicament is administered concurrently with the anti-Bv8 antibody. In certain embodiments, the methods further comprise administering to the subject an effective amount of a third medicament, wherein the third medicament is a chemotherapeutic agent.

An exemplary and non-limiting list of chemotherapeutic agents contemplated is provided herein under "Definitions." In certain embodiments, the chemotherapeutic agent is selected from the group consisting of paclitaxel, carboplatin, cisplatin, gemcitabine and pemetrexed.

In certain embodiments, methods for enhancing efficacy of an anti-angiogenic agent in a subject having a pathological condition associated with angiogenesis is provided, the methods comprising administering to the subject an effective amount of any of the anti-Bv8 antibodies described herein in combination with the anti-angiogenic agent, thereby enhancing said anti-angiogenic agent's inhibitory activity. In certain embodiments, the pathological condition associated with angiogenesis is a tumor, cancer or cell proliferative disorder. In certain embodiments, the pathological condition associated with angiogenesis is a non-neoplastic condition. In certain embodiments, the non-neoplastic condition is selected from the group consisting of diabetic and other proliferative retinopathies, retinopathy of prematurity, neovascular glaucoma, age-related macular degeneration, diabetic macular edema, corneal neovascularization, corneal graft neovascularization, retinal/choroidal neovascularization and rheumatoid arthritis. In certain embodiments, the non-neoplastic condition is rheumatoid arthritis.

In certain embodiments, the subject is a human patient. In certain embodiments, the subject is a human cancer patient. In certain embodiments, the subject is a human cancer patient who may have been diagnosed or may be at risk of developing metastasis. In certain embodiments, the subject is relapsed from or refractory to a VEGF antagonist. In certain embodiments, the VEGF antagonist is an anti-VEGF antibody. In certain embodiments, the anti-VEGF antibody is bevacizumab.

In certain embodiments, the anti-angiogenic agent is administered prior to or subsequent to the administration of the anti-Bv8 antibody. In certain embodiments, the anti-angiogenic agent is administered concurrently with the anti-Bv8 antibody. In certain embodiments, the anti-antigenic agent is an anti-VEGF agent. In certain embodiments, the anti-VEGF agent is an anti-VEGF antibody. In certain embodiments, the anti-VEGF antibody is bevacizumab.

Any embodiment described herein or any combination thereof applies to any and all anti-Bv8 antibodies and methods of the invention described herein.

BRIEF DESCRIPTION OF THE FIGURES

FIG. 1A-F: Light chain and heavy chain HVR loop sequences of anti-Bv8 antibodies. The Figures show the light chain HVR sequences, Li, L2, and L3, and heavy chain HVR sequences, H1, H2 and H3. Sequence numbering for each antibody is as follows: Chimeric 2G9 (HVR-H1 is SEQ ID NO:49; HVR-H2 is SEQ ID NO:50; HVR-H3 is SEQ ID NO:51; HVR-L1 is SEQ ID NO:52; HVR-L2 is SEQ ID NO:53; HVR-L3 is SEQ ID NO:54); h2G9.K4G1.Polish (HVR-L1 is SEQ ID NO:55; HVR-L2 is SEQ ID NO:56; HVR-L3 is SEQ ID NO:57; HVR-H1 is SEQ ID NO:58; HVR-H2 is SEQ ID NO:59; HVR-H3 is SEQ ID NO:60); h2G9.K4G1.v19 (HVR-L1 is SEQ ID NO:61; HVR-L2 is SEQ ID NO:62; HVR-L3 is SEQ ID NO:63; HVR-H1 is SEQ ID NO:64; HVR-H2 is SEQ ID NO:65; HVR-H3 is SEQ ID NO:66); h2G9.K4G1.v25 (HVR-L1 is SEQ ID NO:67; HVR-L2 is SEQ ID NO:68; HVR-L3 is SEQ ID NO:69; HVR-H1 is SEQ ID NO:70; HVR-H2 is SEQ ID NO:71; HVR-H3 is SEQ ID NO:72); h2G9.K4G1.v27 (HVR-L1 is SEQ ID NO:73; HVR-L2 is SEQ ID NO:74; HVR-L3 is SEQ ID NO:75; HVR-H1 is SEQ ID NO:76; HVR-H2 is SEQ ID NO:77; HVR-H3 is SEQ ID NO:78); h2G9.K4G1.v37 (HVR-L1 is SEQ ID NO:79; HVR-L2 is SEQ ID NO:80; HVR-L3 is SEQ ID NO:81; HVR-H1 is SEQ ID NO:82; HVR-H2 is SEQ ID NO:83; HVR-H3 is SEQ ID NO:84); h2G9.K4G1.v52 (HVR-L1 is SEQ ID NO:85; HVR-L2 is SEQ ID NO:86; HVR-L3 is SEQ ID NO:87; HVR-H1 is SEQ ID NO:88; HVR-H2 is SEQ ID NO:89; HVR-H3 is SEQ ID NO:90); h2G9.K4G1.v55 (HVR-L1 is SEQ ID NO:91; HVR-L2 is SEQ ID NO:92; HVR-L3 is SEQ ID NO:93; HVR-H1 is SEQ ID NO:94; HVR-H2 is SEQ ID NO:95; HVR-H3 is SEQ ID NO:96); h2G9.K4G1.v63 (HVR-L1 is SEQ ID NO:97; HVR-L2 is SEQ ID NO:98; HVR-L3 is SEQ ID NO:99; HVR-H1 is SEQ ID NO:100; HVR-H2 is SEQ ID NO:101; HVR-H3 is SEQ ID NO:102); h2G9.K4G1.v64 (HVR-L1 is SEQ ID NO:103; HVR-L2 is SEQ ID NO:104; HVR-L3 is SEQ ID NO:105; HVR-H1 is SEQ ID NO:106; HVR-H2 is SEQ ID NO:107; HVR-H3 is SEQ ID NO:108); h2G9.K4G1.v65 (HVR-L1 is SEQ ID NO:109; HVR-L2 is SEQ ID NO:110; HVR-L3 is SEQ ID NO:111; HVR-H1 is SEQ ID NO:112; HVR-H2 is SEQ ID NO:113; HVR-H3 is SEQ ID NO:114); h2G9.K4G1.v67 (HVR-L1 is SEQ ID NO:115; HVR-L2 is SEQ ID NO:116; HVR-L3 is SEQ ID NO:117; HVR-H1 is SEQ ID NO:118; HVR-H2 is SEQ ID NO:119; HVR-H3 is SEQ ID NO:120); h2G9.K4G1.v73 (HVR-L1 is SEQ ID NO:121; HVR-L2 is SEQ ID NO:122; HVR-L3 is SEQ ID NO:123; HVR-H1 is SEQ ID NO:124; HVR-H2 is SEQ ID NO:125; HVR-H3 is SEQ ID NO:126); h2G9.K4G1.v75 (HVR-L1 is SEQ ID NO:127; HVR-L2 is SEQ ID NO:128; HVR-L3 is SEQ ID NO:129; HVR-H1 is SEQ ID NO:130; HVR-H2 is SEQ ID NO:131; HVR-H3 is SEQ ID NO:132); h2G9.K4G1.v77 (HVR-L1 is SEQ ID NO:133; HVR-L2 is SEQ ID NO:134; HVR-L3 is SEQ ID NO:135; HVR-H1 is SEQ ID NO:136; HVR-H2 is SEQ ID NO:137; HVR-H3 is SEQ ID NO:138); h2G9.K4G1.v80 (HVR-L1 is SEQ ID NO:139; HVR-L2 is SEQ ID NO:140; HVR-L3 is SEQ ID NO:141; HVR-H1 is SEQ ID NO:142; HVR-H2 is SEQ ID NO:143; HVR-H3 is SEQ ID NO:144); h2G9.K4G1.v92 (HVR-L1 is SEQ ID NO:145; HVR-L2 is SEQ ID NO:146; HVR-L3 is SEQ ID NO:147; HVR-H1 is SEQ ID NO:148; HVR-H2 is SEQ ID NO:149; HVR-H3 is SEQ ID NO:150); h2G9.K4G1.v19H/v55L (HVR-L1 is SEQ ID NO:151; HVR-L2 is SEQ ID NO:152; HVR-L3 is SEQ ID NO:153; HVR-H1 is SEQ ID NO:154; HVR-H2 is SEQ ID NO:155; HVR-H3 is SEQ ID NO:156); chimeric 2B9 (HVR-L1 is SEQ ID NO:157; HVR-L2 is SEQ ID NO:158; HVR-L3 is SEQ ID NO:159; HVR-H1 is SEQ ID NO:160; HVR-H2 is SEQ ID NO:161; HVR-H3 is SEQ ID NO:162); h2B9.v1 (HVR-L1 is SEQ ID NO:163; HVR-L2 is SEQ ID NO:164; HVR-L3 is SEQ ID NO:165; HVR-H1 is SEQ ID NO:166; HVR-H2 is SEQ ID NO:167; HVR-H3 is SEQ ID NO:168); h2B9.v10 (HVR-L1 is SEQ ID NO:169; HVR-L2 is SEQ ID NO:170; HVR-L3 is SEQ ID NO:171; HVR-H1 is SEQ ID NO:172; HVR-H2 is SEQ ID NO:173; HVR-H3 is SEQ ID NO:174); h2B9.v23 (HVR-L1 is SEQ ID NO:175; HVR-L2 is SEQ ID NO:176; HVR-L3 is SEQ ID NO:177; HVR-H1 is SEQ ID NO:178; HVR-H2 is SEQ ID NO:179; HVR-H3 is SEQ ID NO:180); h2B9.v37 (HVR-L1 is SEQ ID NO:181; HVR-L2 is SEQ ID NO:182; HVR-L3 is SEQ ID NO:183; HVR-H1 is SEQ ID NO:184; HVR-H2 is SEQ ID NO:185; HVR-H3 is SEQ ID NO:186); h2B9.v56 (HVR-L1 is SEQ ID NO:187; HVR-L2 is SEQ ID NO:188; HVR-L3 is SEQ ID NO:189; HVR-H1 is SEQ ID NO:190; HVR-H2 is SEQ ID NO:191; HVR-H3 is SEQ ID NO:192); h2B9.v76 (HVR-L1 is SEQ ID NO:193; HVR-L2 is SEQ ID NO:194; HVR-L3 is SEQ ID NO:195; HVR-H1 is SEQ ID NO:196; HVR-H2 is SEQ ID NO:197; HVR-H3 is SEQ ID NO:198); chimeric 3F1 (HVR-L1 is SEQ ID NO:199; HVR-L2 is SEQ ID NO:200; HVR-L3 is SEQ ID NO:201; HVR-H1 is SEQ ID NO:202; HVR-H2 is SEQ ID NO:203; HVR-H3 is SEQ ID NO:204); h3F1.v1(HVR-L1 is SEQ ID NO:205; HVR-L2 is SEQ ID NO:206; HVR-L3 is SEQ ID NO:207; HVR-H1 is SEQ ID NO:208; HVR-H2 is SEQ ID NO:209; HVR-H3 is SEQ ID NO:210); and chimeric 2D3 (HVR-L1 is SEQ ID NO:211; HVR-L2 is SEQ ID NO:212; HVR-L3 is SEQ ID NO:213; HVR-H1 is SEQ ID NO:214; HVR-H2 is SEQ ID NO:215; HVR-H3 is SEQ ID NO:216).

Amino acid positions are numbered according to the Kabat numbering system as described below.

FIG. 1G. Human VL kappa subgroup IV consensus framework sequence minus Kabat light chain HVR sequences is shown in SEQ ID NO:240. Human VH subgroup I consensus framework sequence minus Kabat heavy chain HVR sequences is shown in SEQ ID NO:241.

Figure 2A-2:
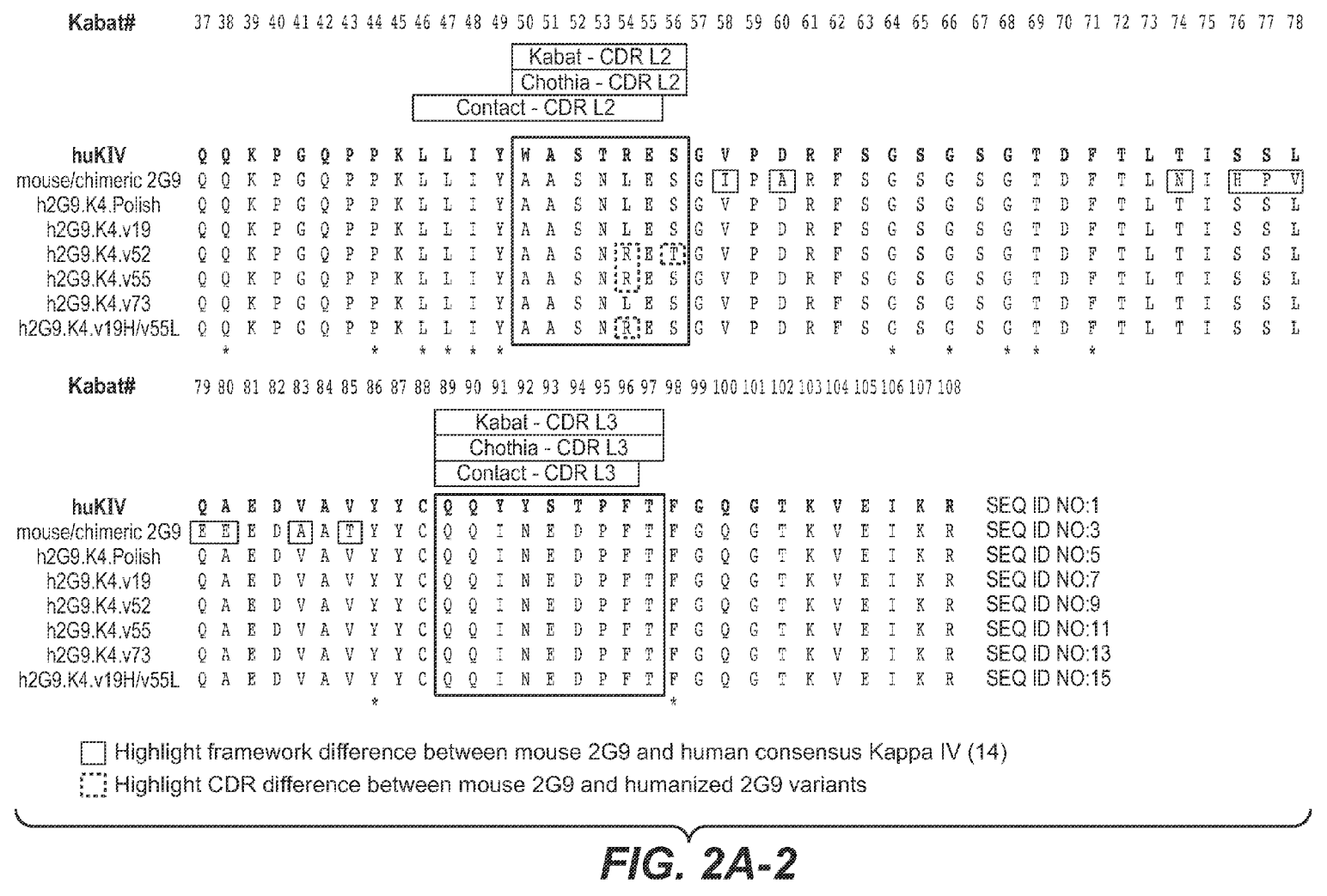
Figure 2B-2:
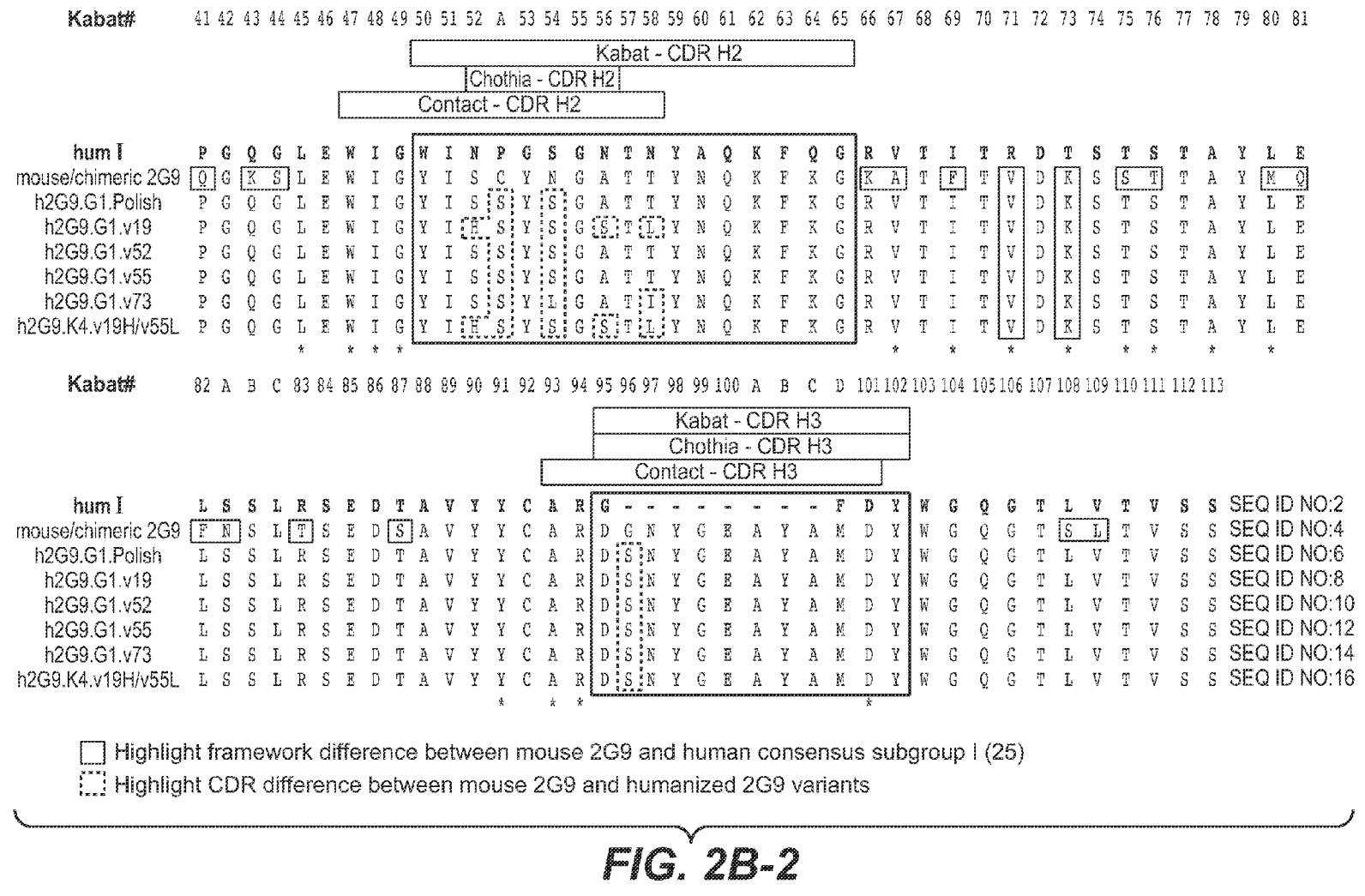

FIG. 2A-B. The amino acid sequences of (A) the light chain variable domain and (B) heavy chain variable domain of anti-Bv8 antibody 2G9 variants. Positions are numbered according to Kabat and hypervariable regions are boxed.

Figure 3B:
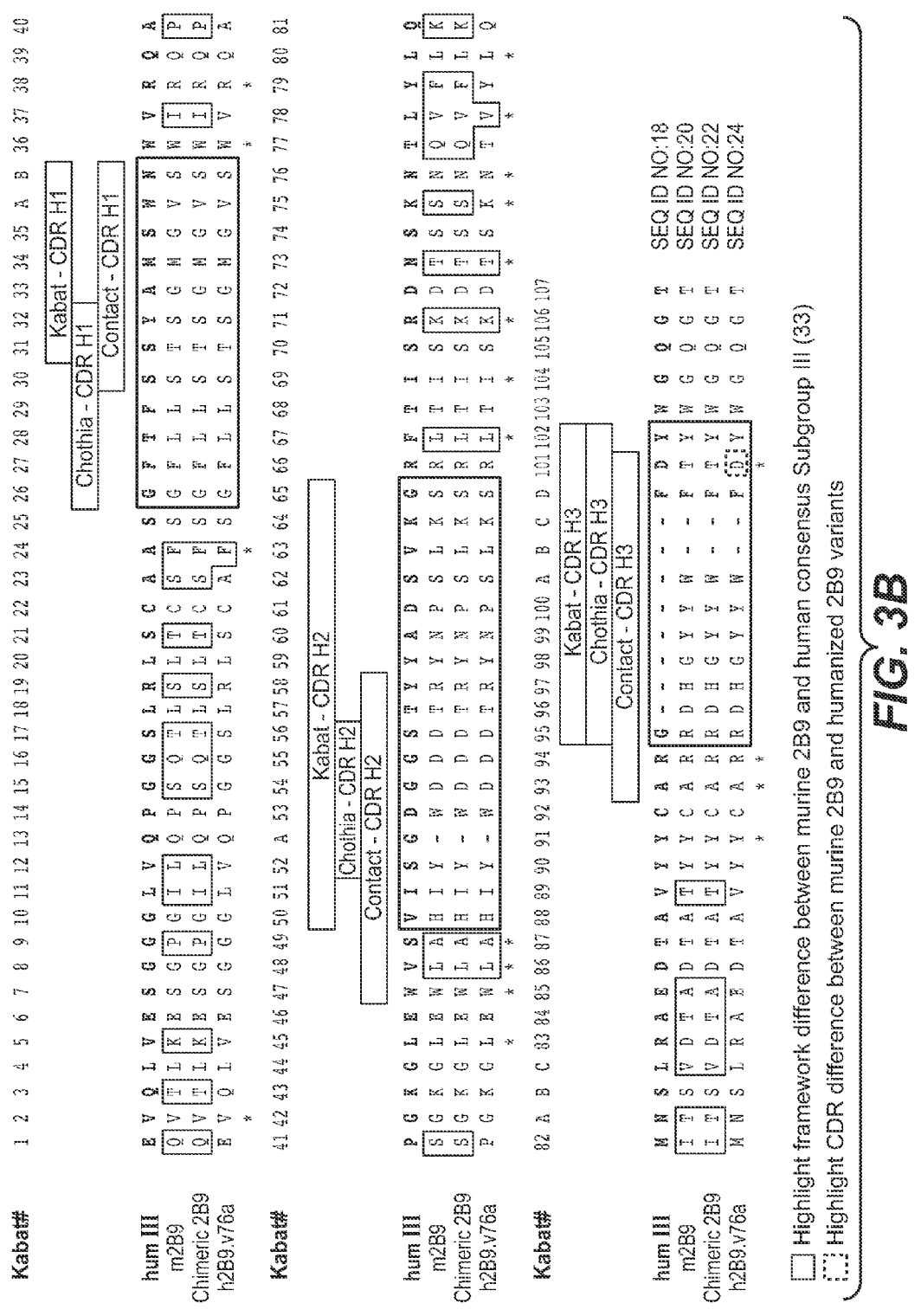

FIG. 3A-B. The amino acid sequences of (A) the light chain variable domain and (B) heavy chain variable domain of anti-Bv8 antibody 2B9 variants. Positions are numbered according to Kabat and hypervariable regions are boxed.

Figure 4A:
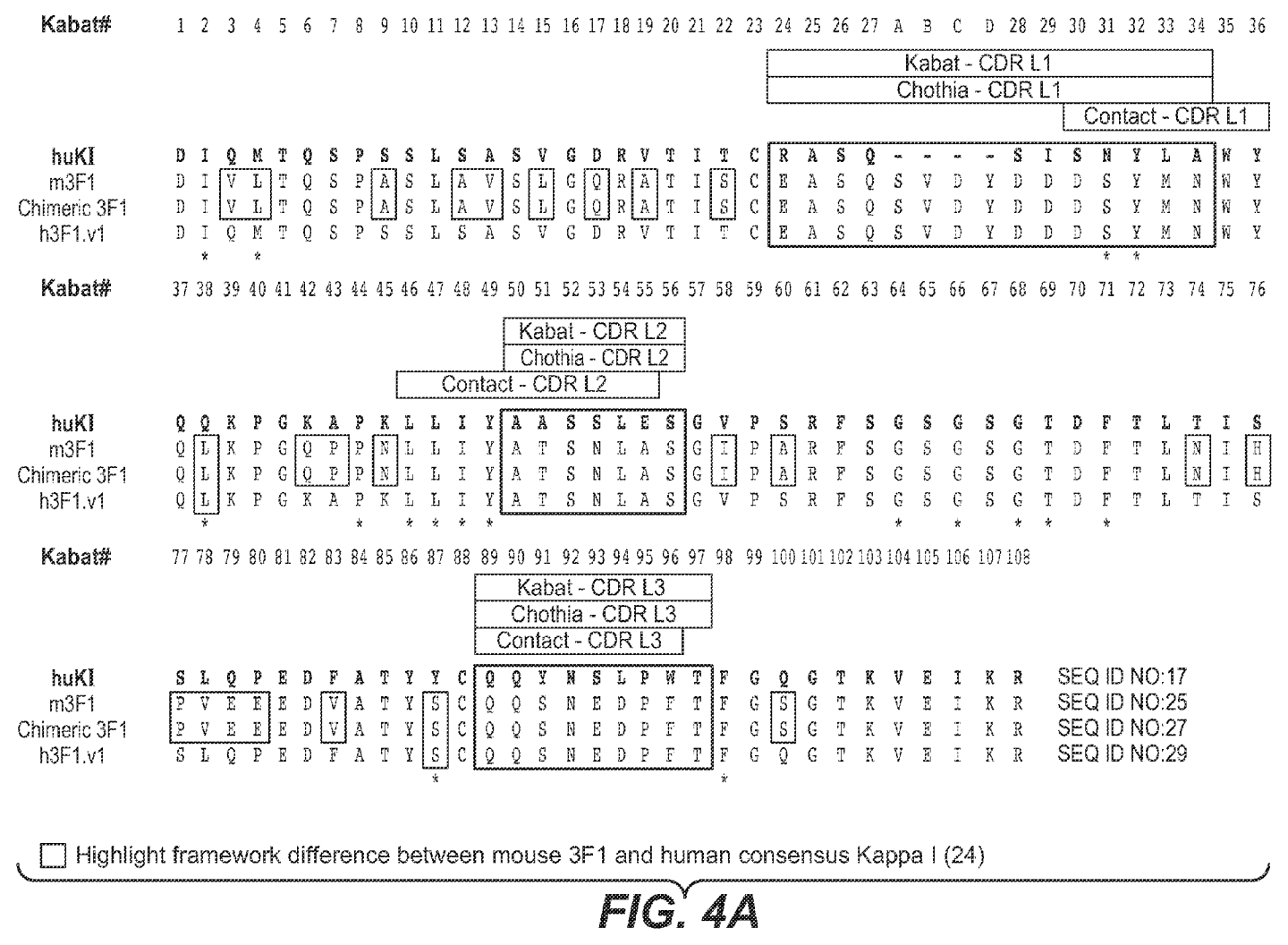

FIG. 4A-B. The amino acid sequences of (A) the light chain variable domain and (B) heavy chain variable domain of anti-Bv8 antibody 3F1 variants. Positions are numbered according to Kabat and hypervariable regions are boxed.

FIG. 5A-B. The amino acid sequences of (A) the light chain variable domain and (B) heavy chain variable domain of anti-Bv8 antibody 2D3 variants. Positions are numbered according to Kabat and hypervariable regions are boxed.

Figure 6B-2:
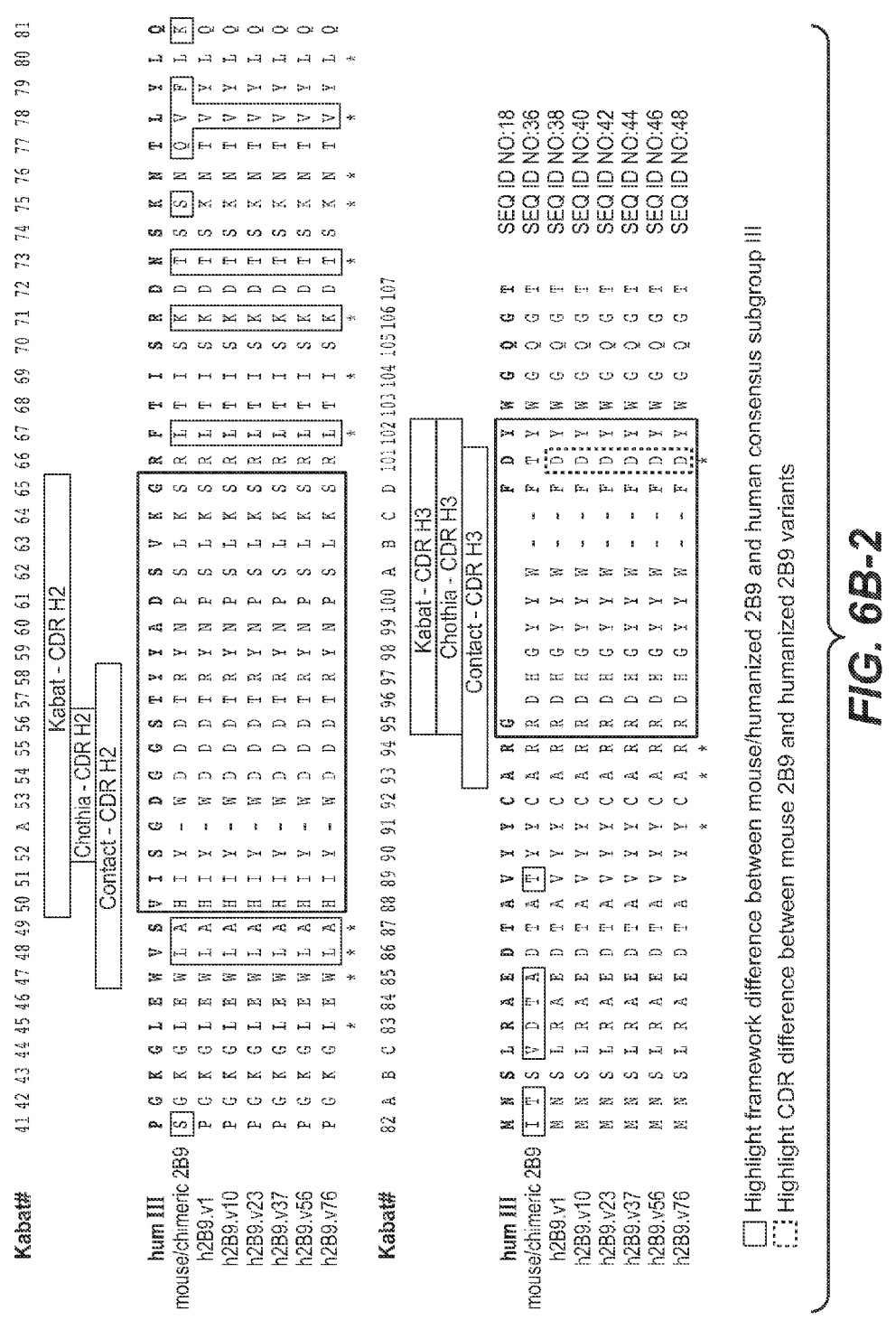

FIG. 6A-B. The amino acid sequences of (A) the light chain variable domain and (B) heavy chain variable domain of humanized anti-Bv8 antibody 2B9 variants. Positions are numbered according to Kabat and hypervariable regions are boxed.

Figure 7B:
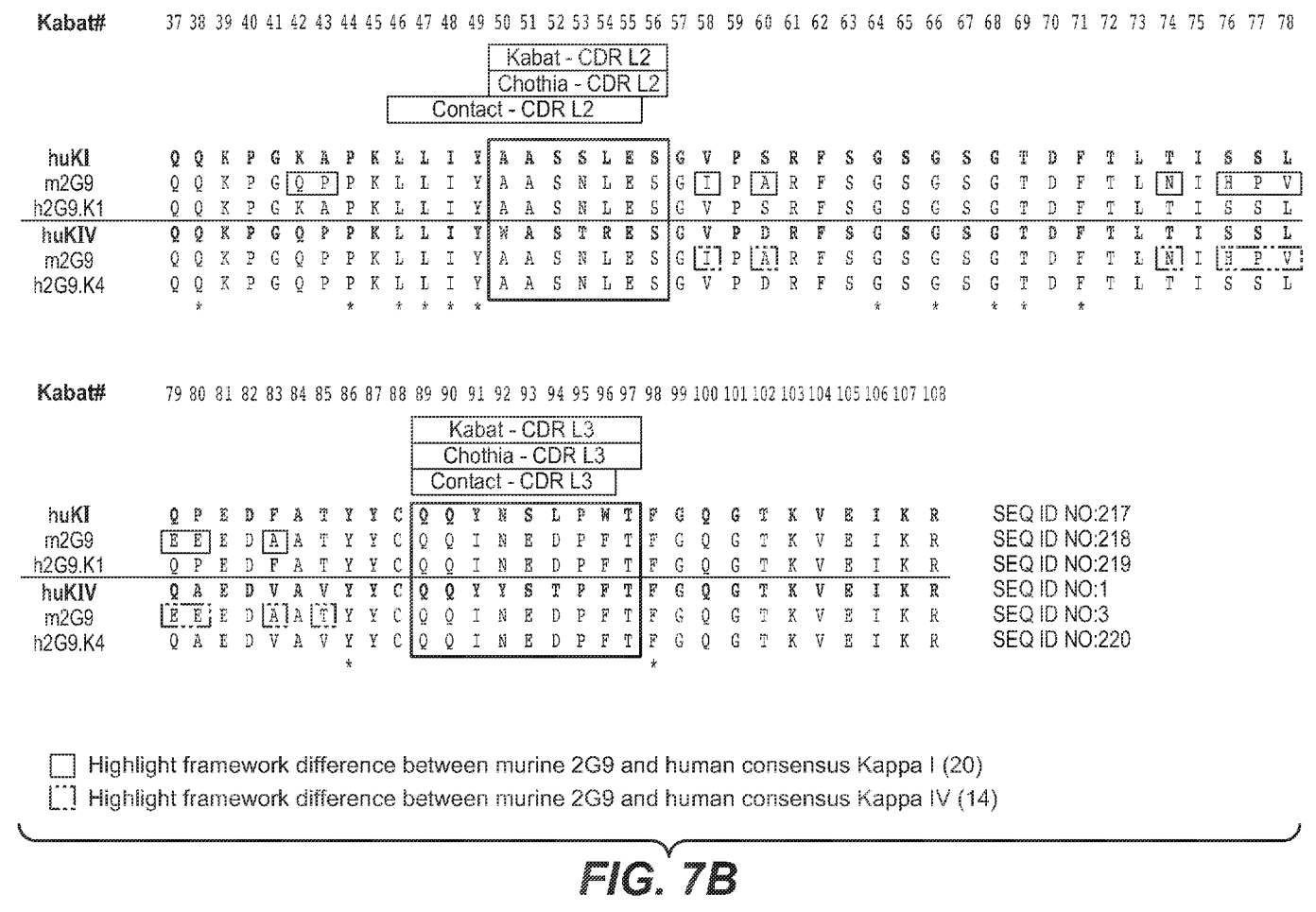

FIG. 7. The light chain variable domain amino acid sequences showing the difference between (1) the mouse 2G9 (m2G9) framework sequence and human concensus Kappa I framework sequence and (2) the m2G9 framework sequence and human concensus Kappa IV framework sequence. Positions are numbered according to Kabat and hypervariable regions are boxed.

Figure 8B:
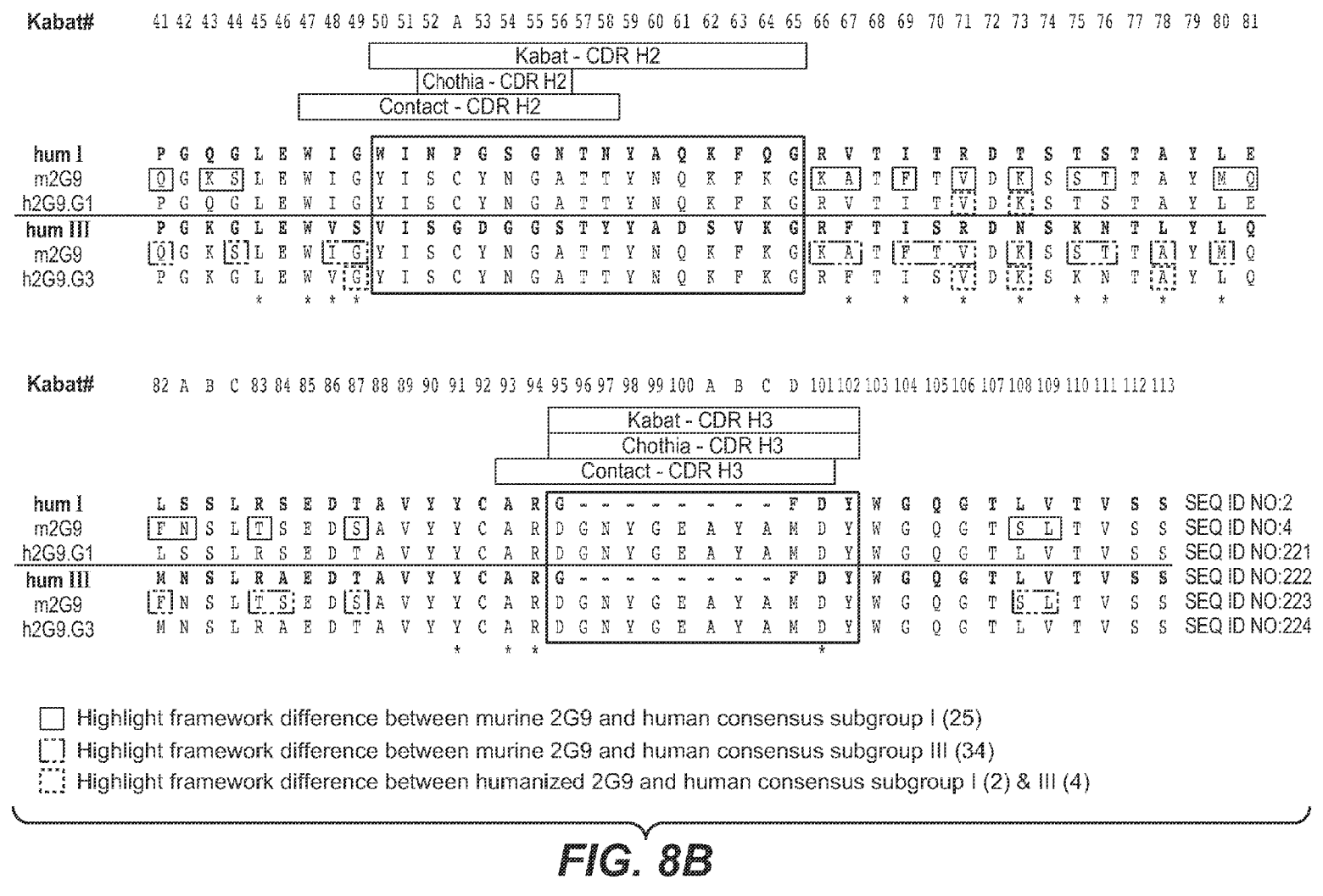

FIG. 8. The heavy chain variable domain amino acid sequences showing the difference between (1) the mouse 2G9 (m2G9) framework sequence and human concensus subgroup I (GI) framework sequence and (2) the m2G9 framework sequence and human concensus subgroup III (G3) framework sequence. Positions are numbered according to Kabat and hypervariable regions are boxed.

FIG. 9. The Li, L2 and L3 amino acid sequences for anti-Bv8 antibodies h2G9.K4G1.Polish, h2G9.K4G1.v27, h2G9.K4G1.v52, h2G9.K4G1.v55, h2G9.K4G1.v63, h2G9.K4G1.v64, h2G9.K4G1.v67, h2G9.K4G1.v77 and h2G9.K4G1.v80.

FIG. 10. The H1, H2 and H3 amino acid sequences for anti-Bv8 antibodies h2G9.K4G1.Polish, h2G9.K4G1.v19, h2G9.K4G1.v25, h2G9.K4G1.v37, h2G9.K4G1.v65, h2G9.K4G1.v73, h2G9.K4G1.v75, h2G9.K4G1.v77, h2G9.K4G1.v92.

Figure 11:
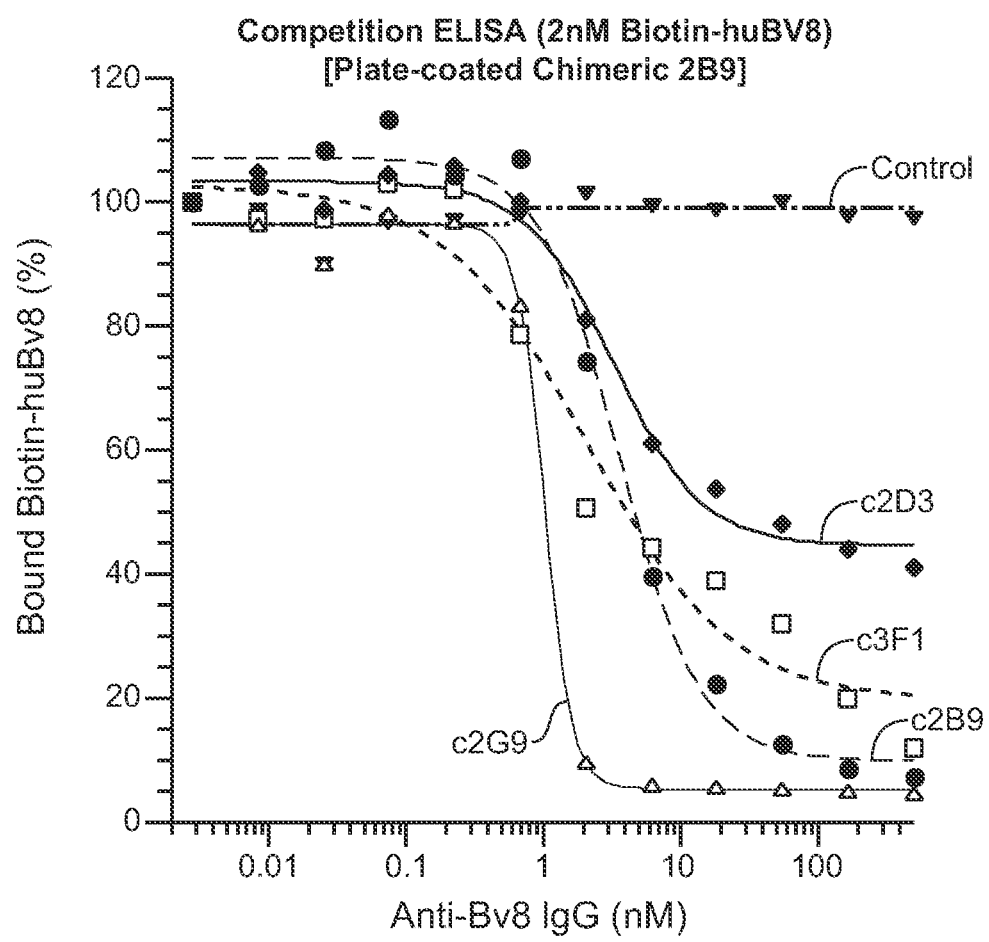

FIG. 11 shows chimeric 2D3 antibody may have distinct epitope(s) from chimeric 2B9 as well as chimeric 3F1 and chimeric 2G9 antibodies. ELISA competition assay show that chimeric 3F1 and chimeric 2G9 antibodies competed with chimeric 2B9 binding to human Bv8. Chimeric 2D3 only partially competed with chimeric 2B9 antibody binding to human Bv8.

Figure 12:
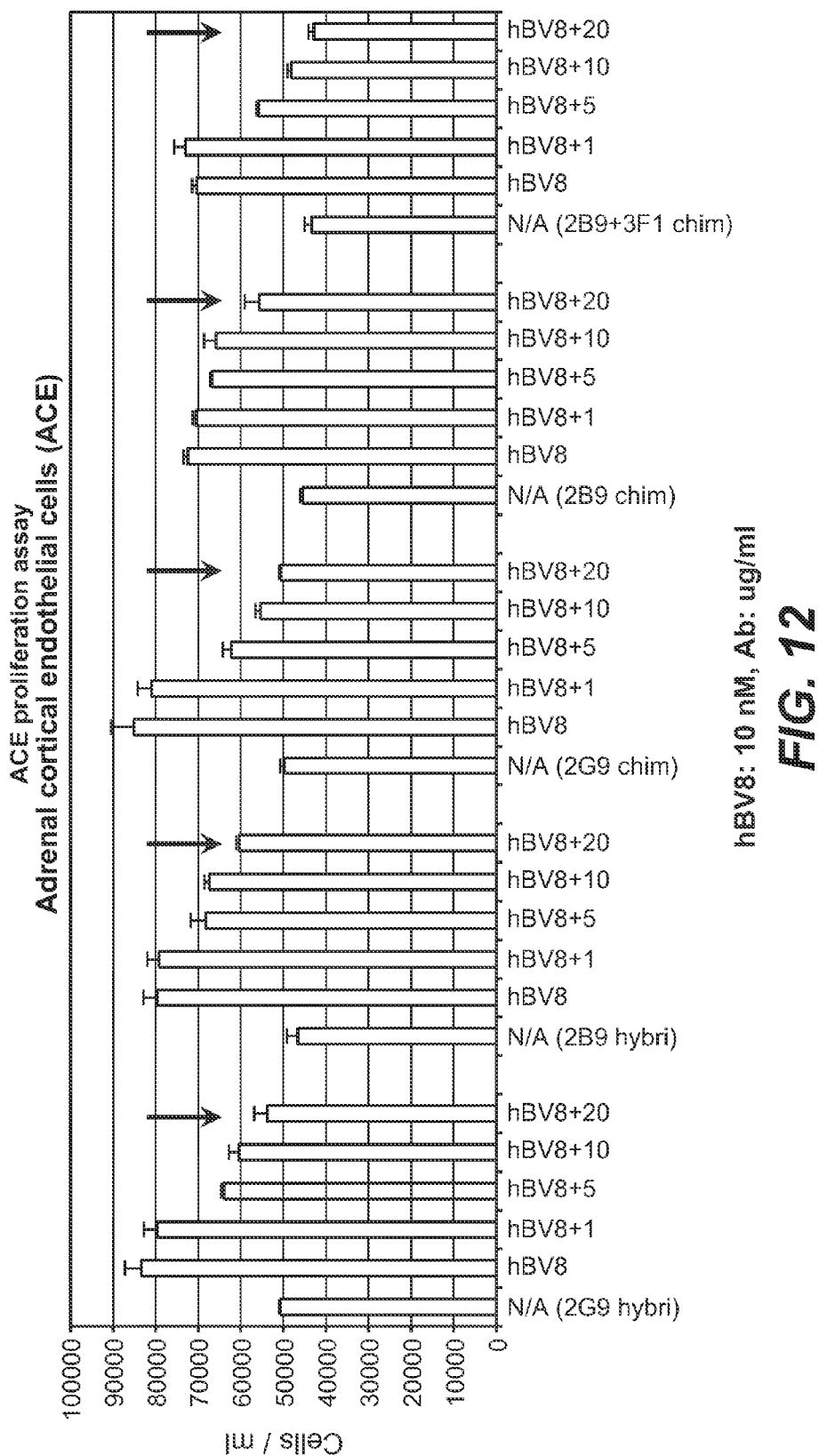

FIG. 12 shows the blocking of human Bv8-induced ACE cell proliferation by mouse 2G9, chimeric 2G9, mouse 2B9, chimeric 2B9 and chimeric 3F1. The results of the assay show that chimeric 2G9 is able to completely inhibit the human Bv8-induced ACE cell proliferation.

Figure 13:
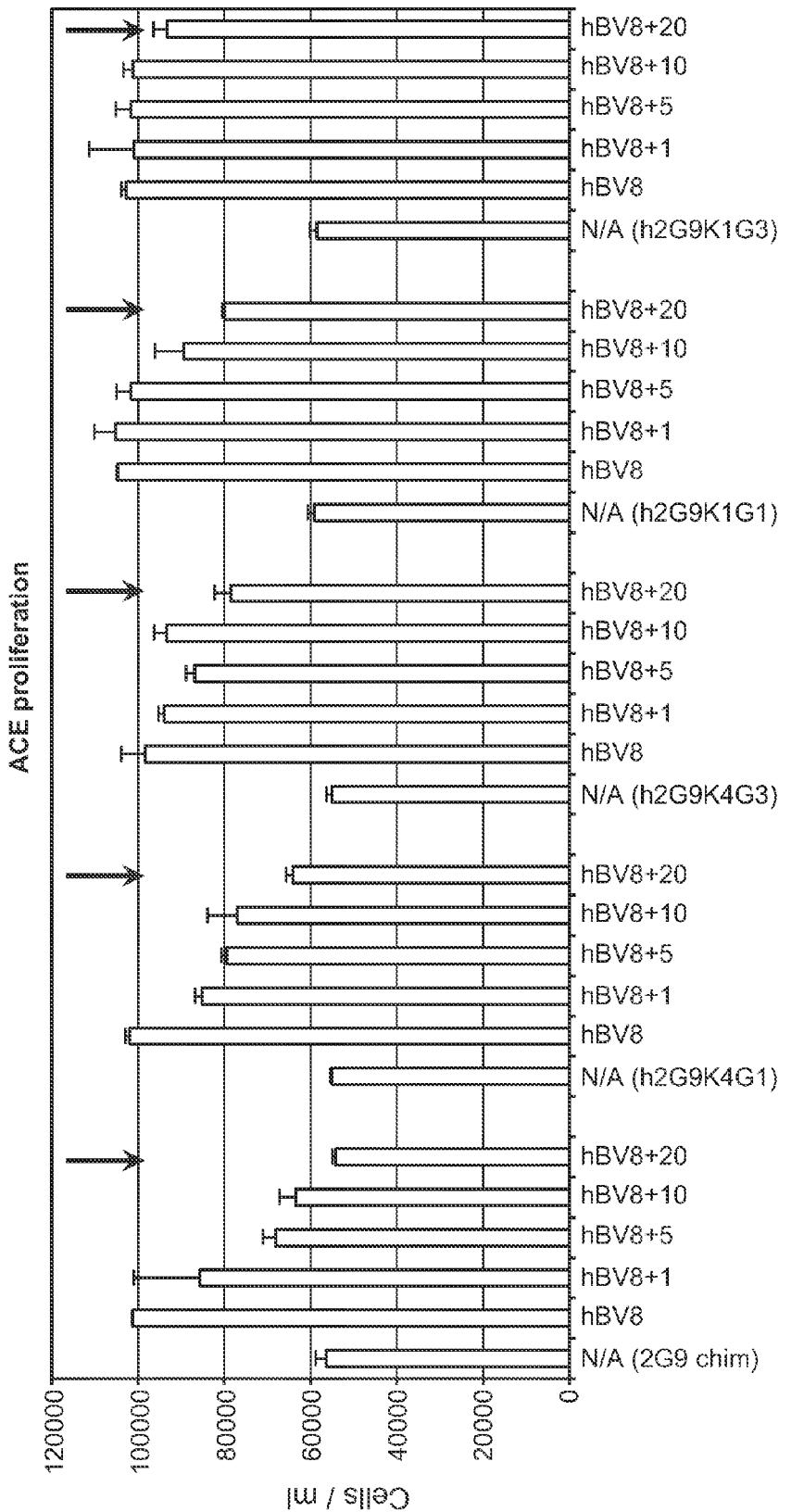

FIG. 13 shows the blocking of human Bv8-induced ACE cell proliferation by chimeric 2G9, h2G9.K4G1, h2G9.K4G3, h2G9.K1G1 and h2G9.K1G3 anti-Bv8 antibodies. The results of the assay show that chimeric 2G9 anti-Bv8 antibody has the highest blocking activity at 20 µg/mL antibody concentration.

Figure 14A:
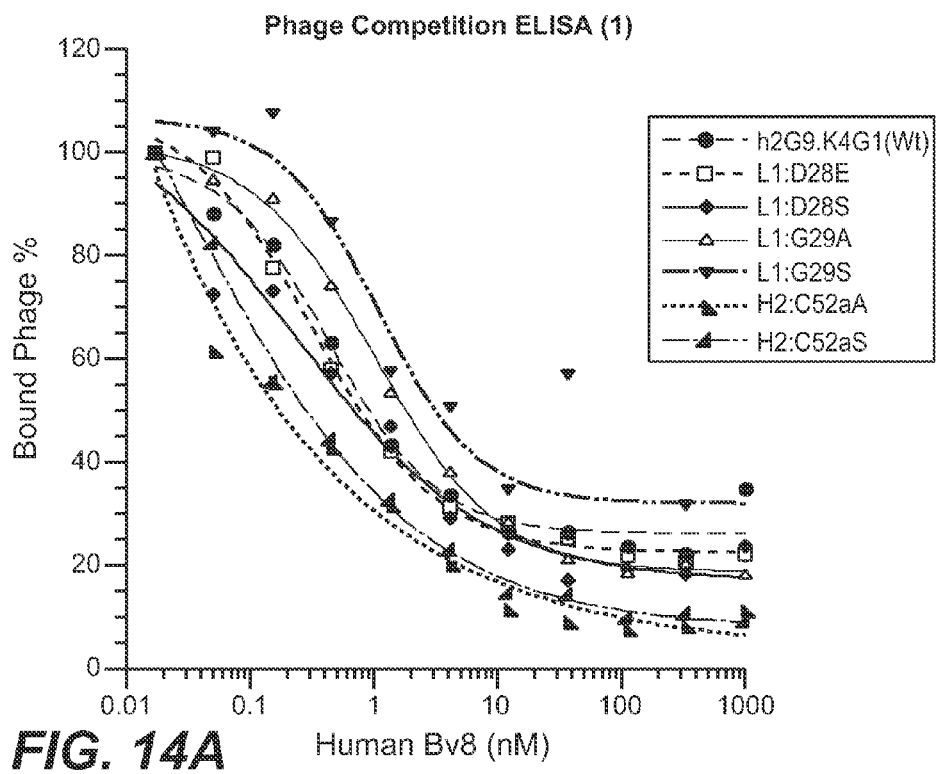
Figure 14B:
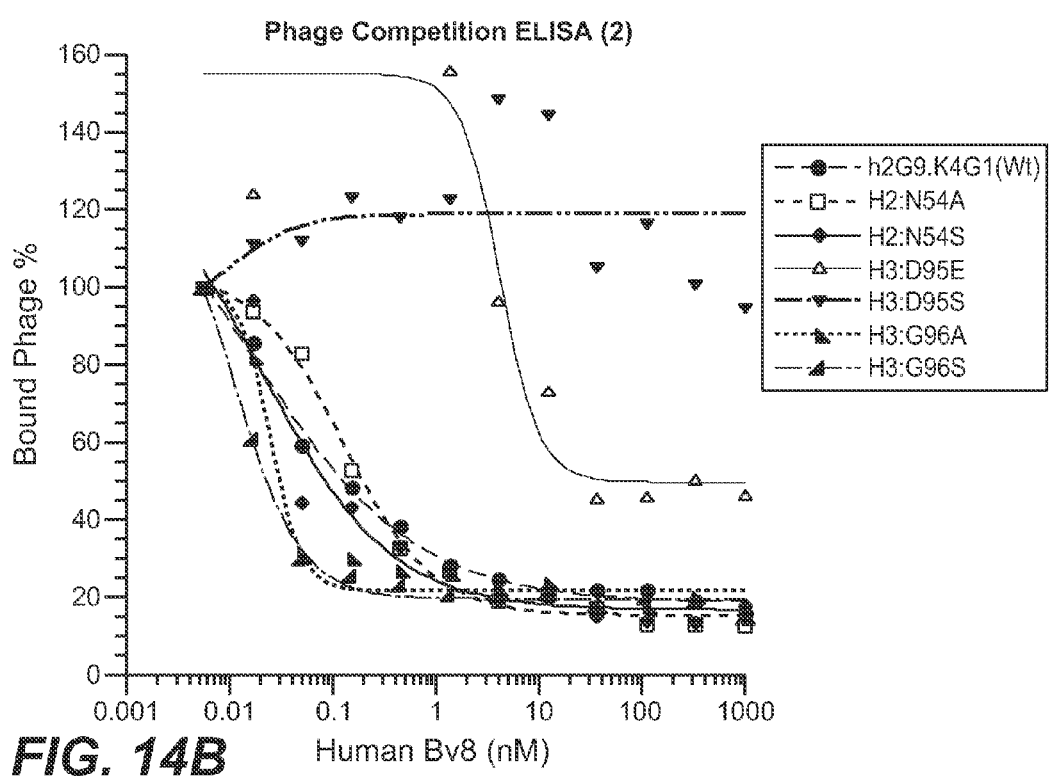

FIG. 14A-B depict results from a phage competition assay demonstrating the binding of h2G9.K4G1 variants (Ll: D28E, D28S, G29A, G29S, H2: C52aA, C52aS, N54A, N54S, H3: D95E, D95S, G96A and G96S) against human Bv8.

Figure 15:
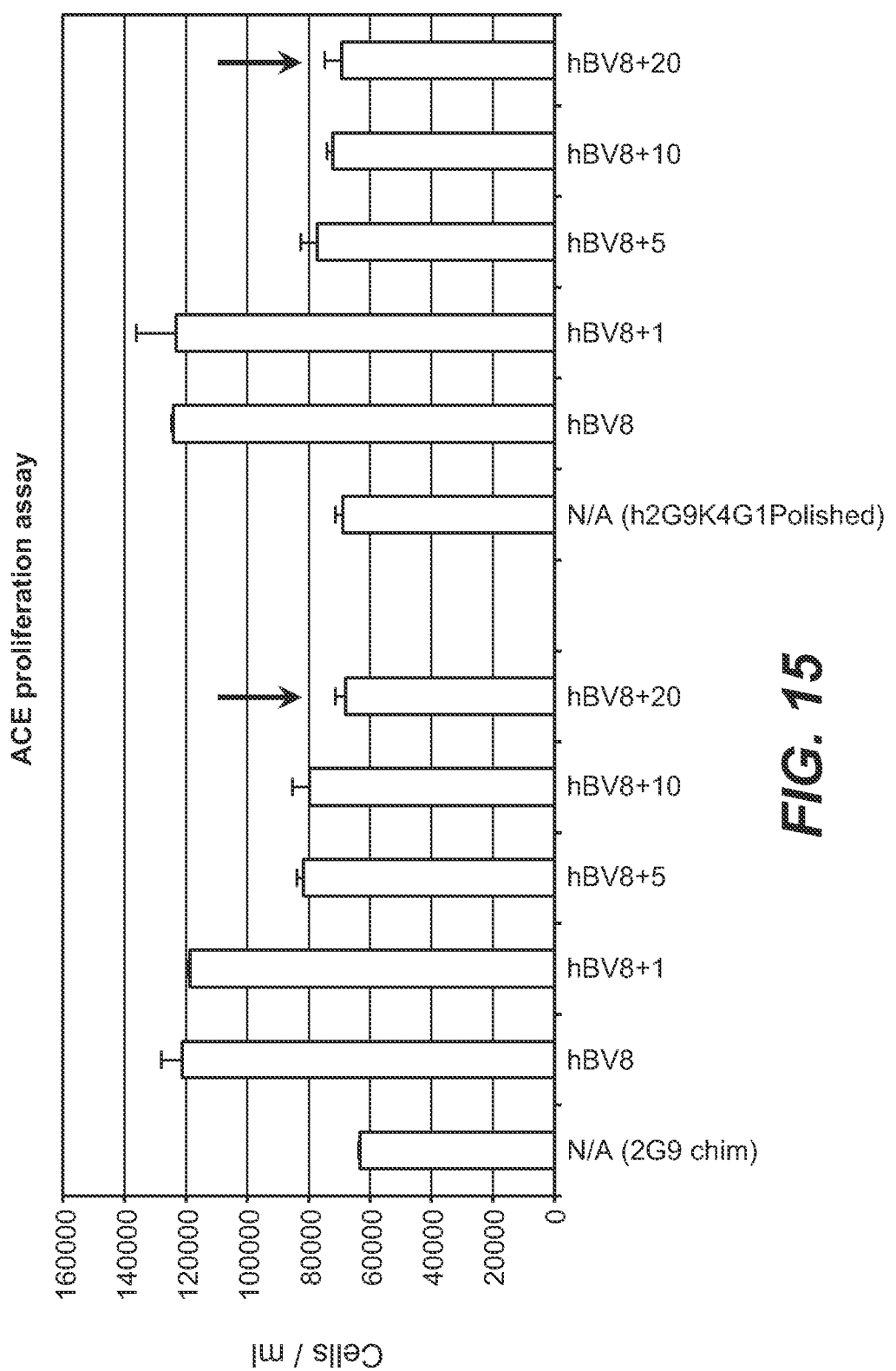

FIG. 15 shows the blocking of human Bv8-induced ACE cell proliferation by chimeric 2G9 and h2G9.K4G1.Polish anti-Bv8 antibodies.

Figure 16:
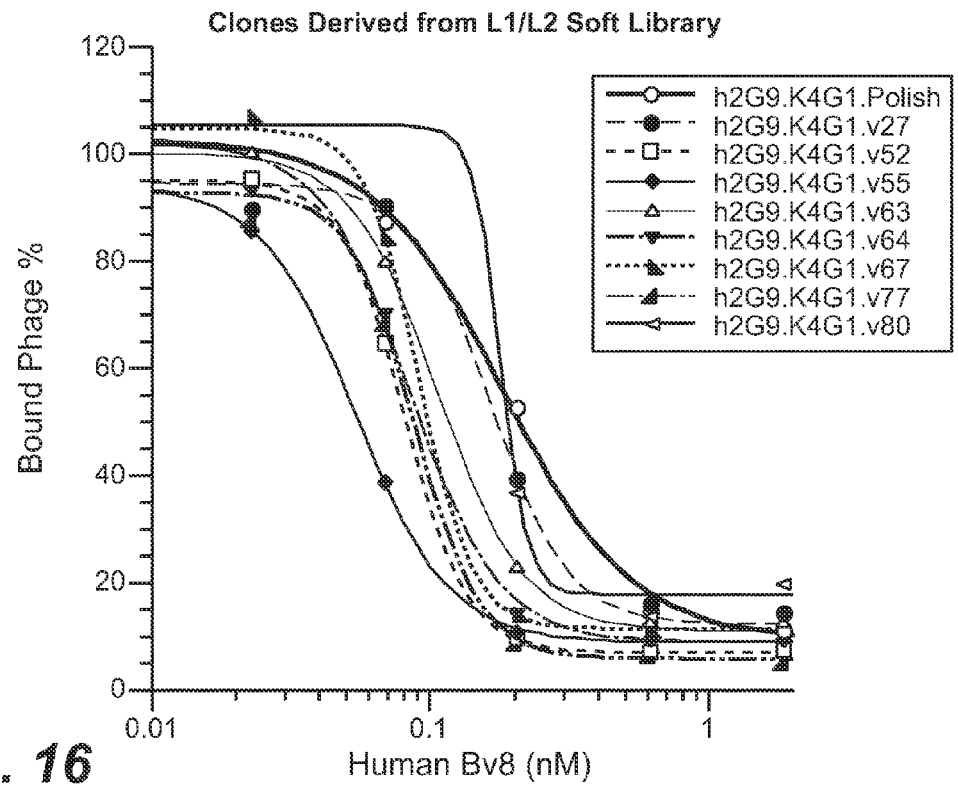

FIG. 16 depicts results from a phage competition assay demonstrating the binding of affinity-improved h2G9.K4G1.Polish variants (h2G9.K4G1.v27, v52, v55, v63, v64, v67, v77, v80 from L1/L2 soft-randomized library) against human Bv8.

Figure 17:
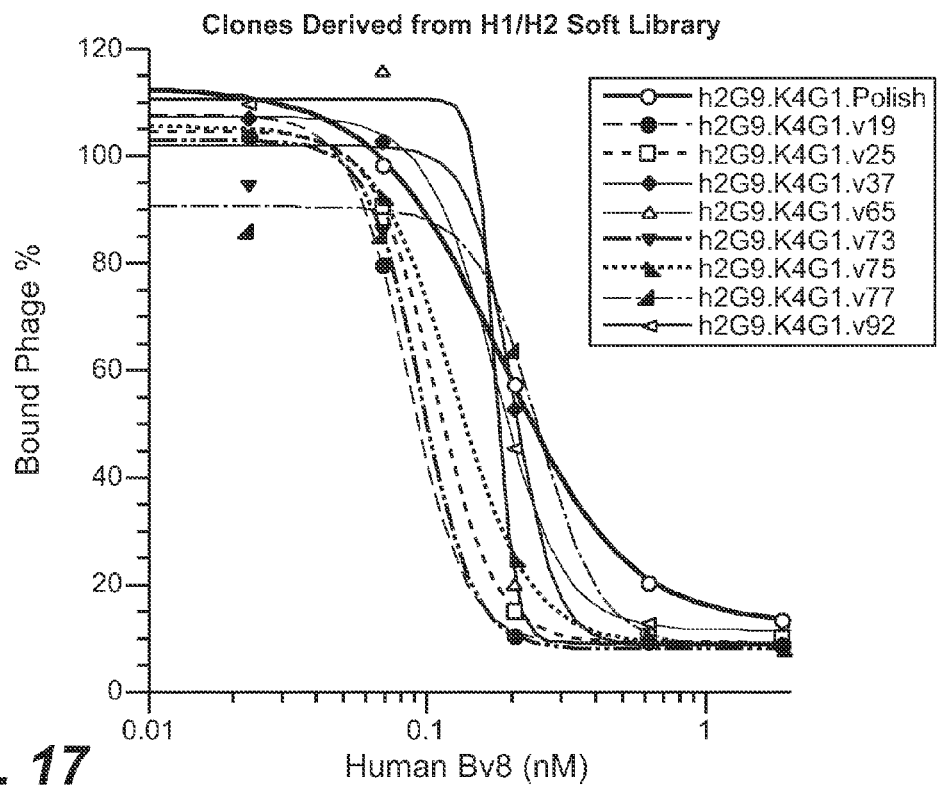

FIG. 17 depict results from a phage competition assay demonstrating the binding of affinity-improved h2G9.K4G1.Polish variants (h2G9.K4G1.v19, v25, v37, v65, v73, v75, v77. v92 from H1/H2 soft-randomized library) against human Bv8.

FIG. 18 shows dissociation constants of the following anti-Bv8 antibodies (Fab) against human Bv8: h2G9.K4G1.Polish, h2G9.K4G1.v19, h2G9.K4G1.v52, h2G9.K4G1.v55 and h2G9.K4G1.v73.

FIG. 19 shows dissociation constants of humanized anti-Bv8 antibodies (Fab and IgG) h2G9.K4G1.v19 and h2G9.K4G1.v55 against human Bv8 and cynomologus monkey Bv8.

FIG. 20 shows the sensograms for injection of 50 nM anti-Bv8 Fab antibodies at 25° C. over human Bv8 immobilized BIAcore chip demonstrating the off-rate improvements.

FIG. 21 shows dissociation constants of the following anti-Bv8 antibodies (IgG) against human Bv8 and cynomologus monkey Bv8: chimeric 2G9, h2G9.K4G1.v19 and h2G9.K4G1.v55. The results show that the affinities of humanized anti-Bv8 antibodies, h2G9.K4G1.v19 and h2G9.K4G1.v55, appear to be at least two fold tighter than the chimeric 2G9 anti-Bv8 antibody.

Figure 22:
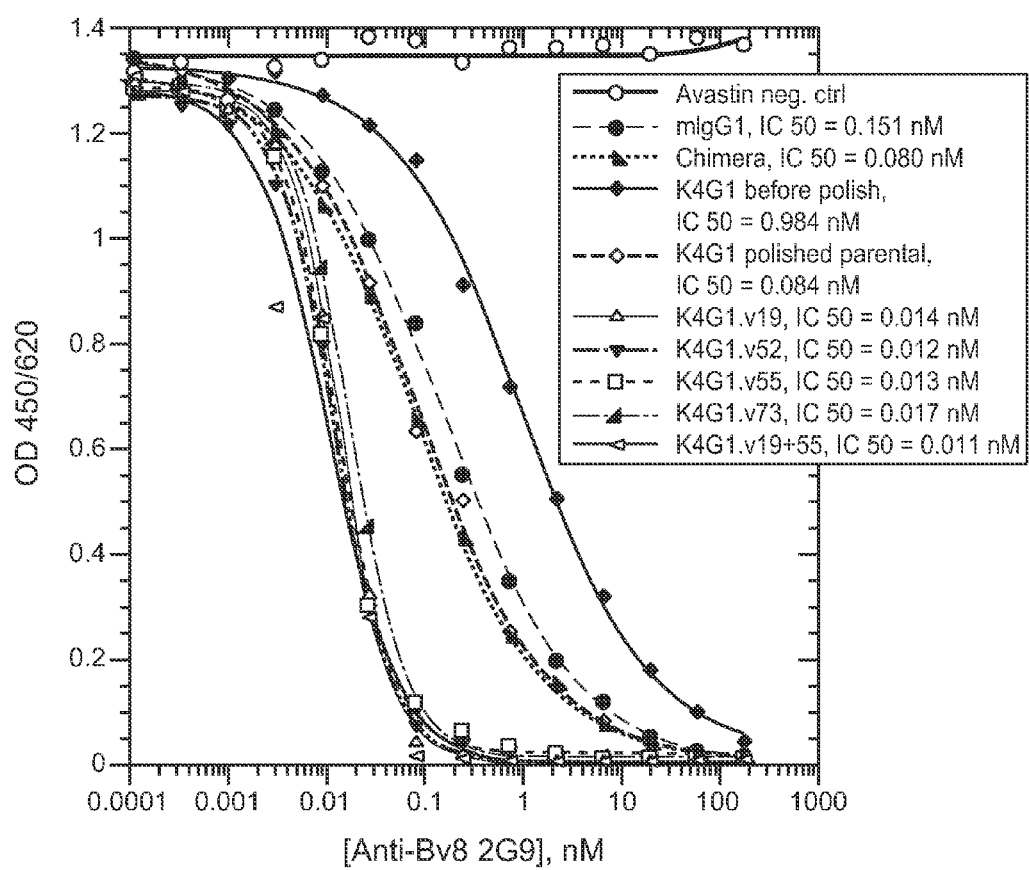

FIG. 22 shows that humanized anti-Bv8 antibodies block binding of human Bv8 to mouse 2G9 antibody. The five affinity matured humanized anti-Bv8 antibodies (h2G9.K4G1.v19, h2G9.K4G1.v52, h2G9.K4G1.v55, h2G9.K4G1.v73 and h2G9.K4G1.v19H/v55L) have approximately 5-8 fold stronger blocking abilities compared to the parental polished K4G1 molecule.

Figure 23:
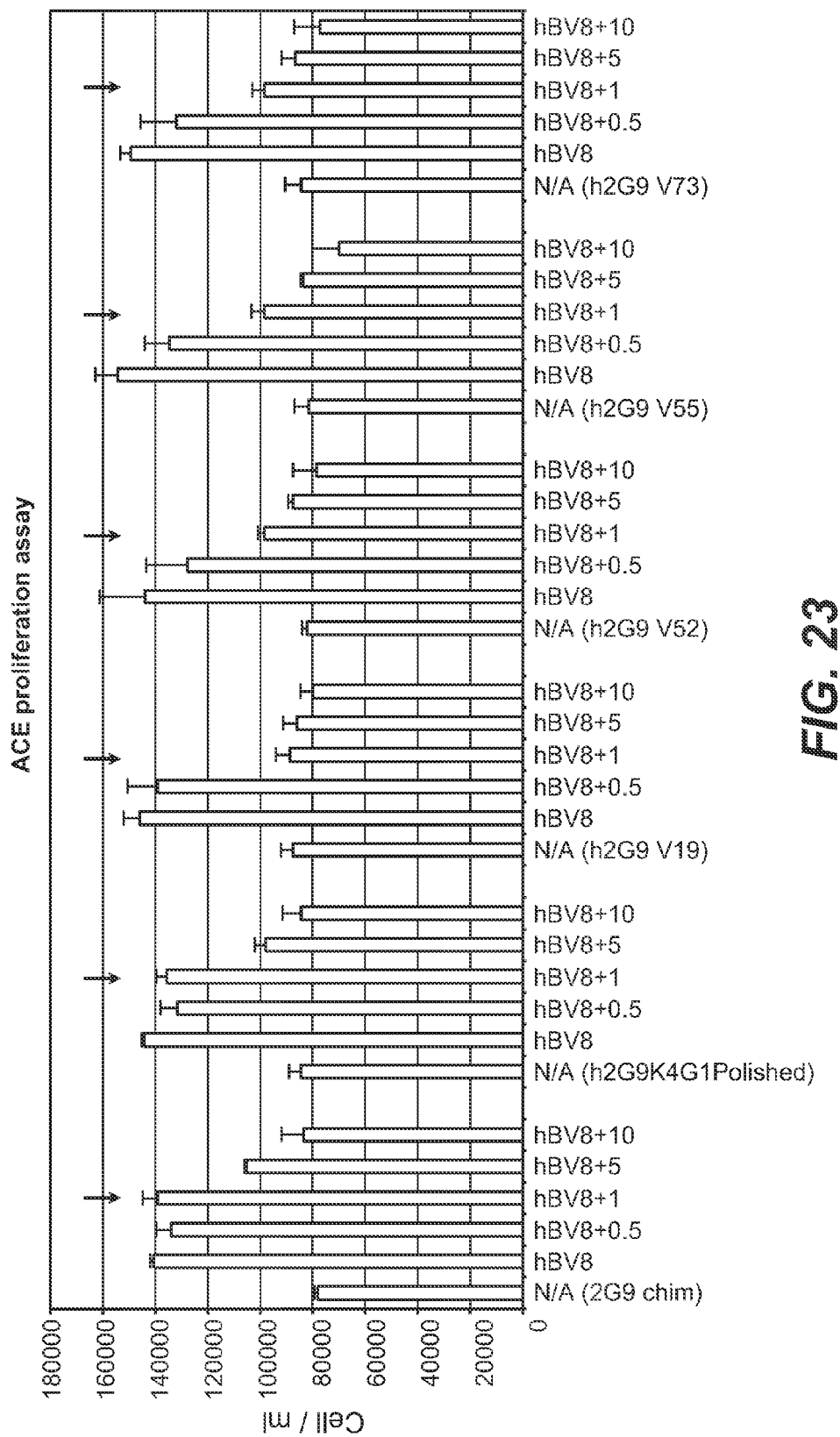

FIG. 23 shows the blocking of human Bv8-induced ACE cell proliferation by chimeric 2G9, h2G9K4G1.Polish, h2G9K4G1.v19, h2G9K4G1.v52, h2G9K4G1.v55 and h2G9K4G1.v73 anti-Bv8 antibodies at indicated concentrations (µg/mL). Humanized anti-Bv8 antibodies h2G9K4G1.v19, h2G9K4G1.v52, h2G9K4G1.v55 and h2G9K4G1.v73 showed significant improvement in blocking human Bv8-induced ACE proliferation.

Figure 24:
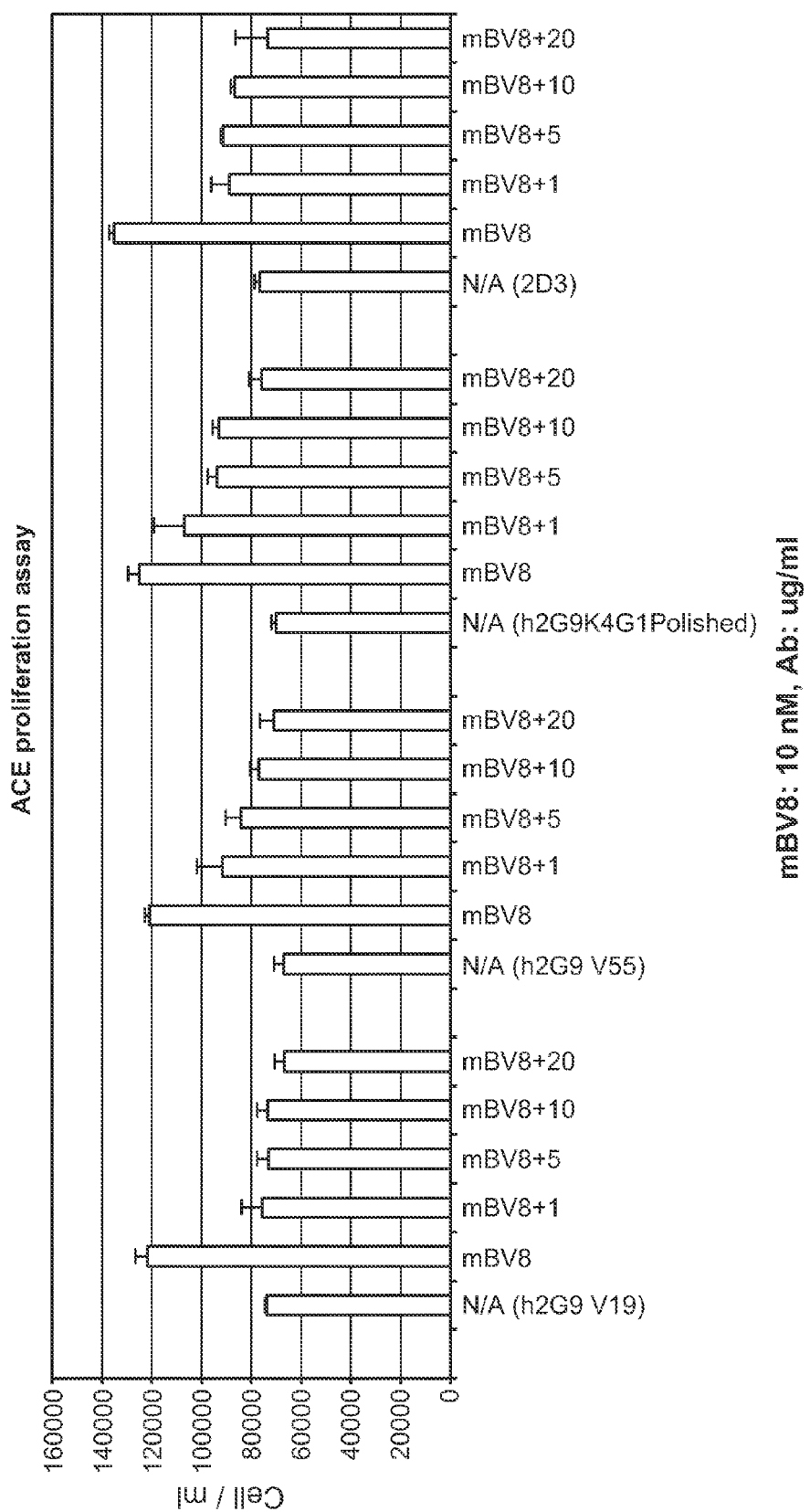

FIG. 24 shows the blocking of mouse Bv8-induced ACE cell proliferation by h2G9K4G1.Polished, h2G9K4G1.v19, h2G9K4G1.v55 and chimeric 2D3 anti-Bv8 antibodies at indicated concentrations (µg/mL).

Figure 25:
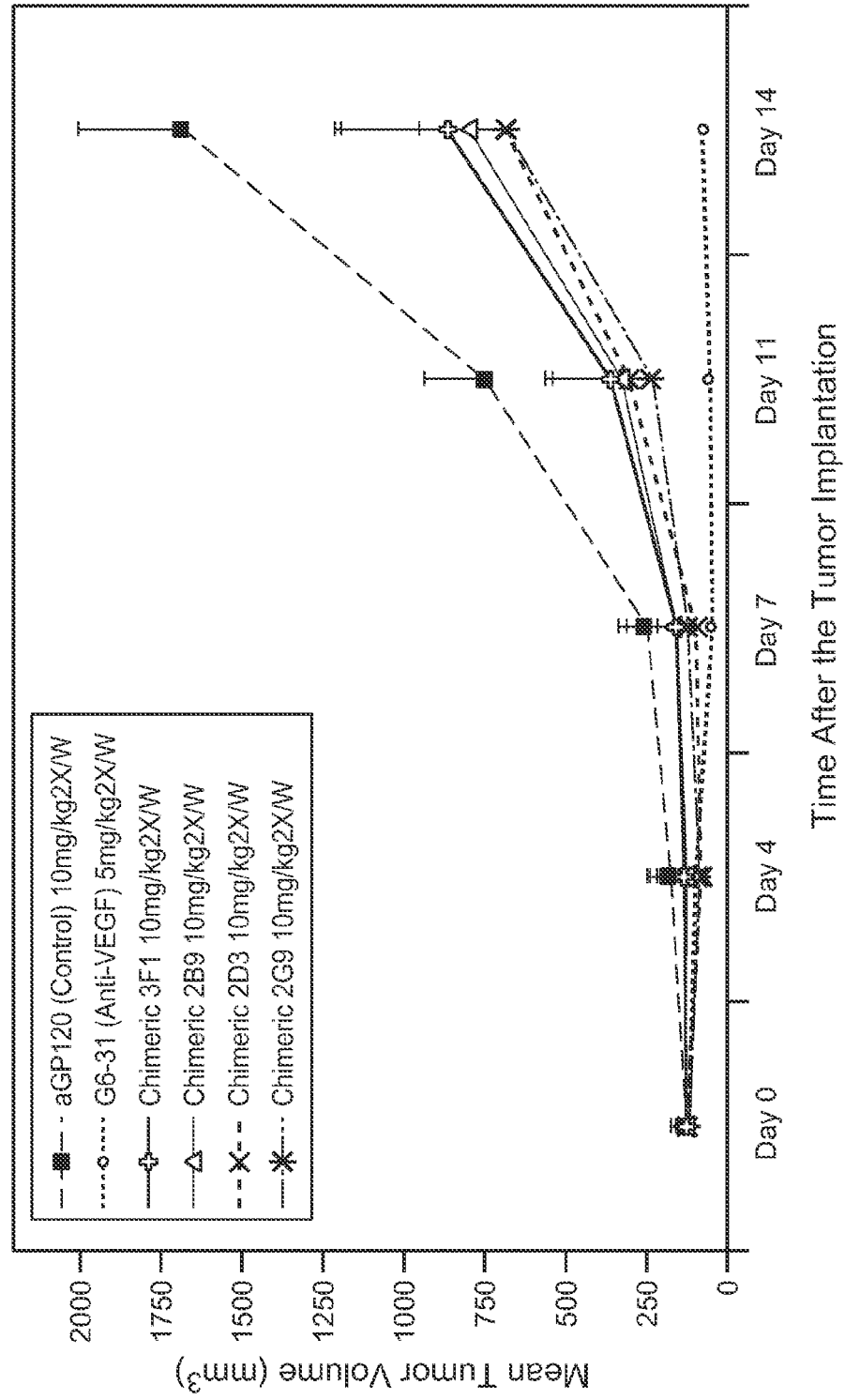

FIG. 25. Efficacy study of chimeric 3F1, chimeric 2B9, chimeric 2D3 and chimeric 2G9 anti-Bv8 antibodies in treating HM7 human colon cancer.

Figure 26:
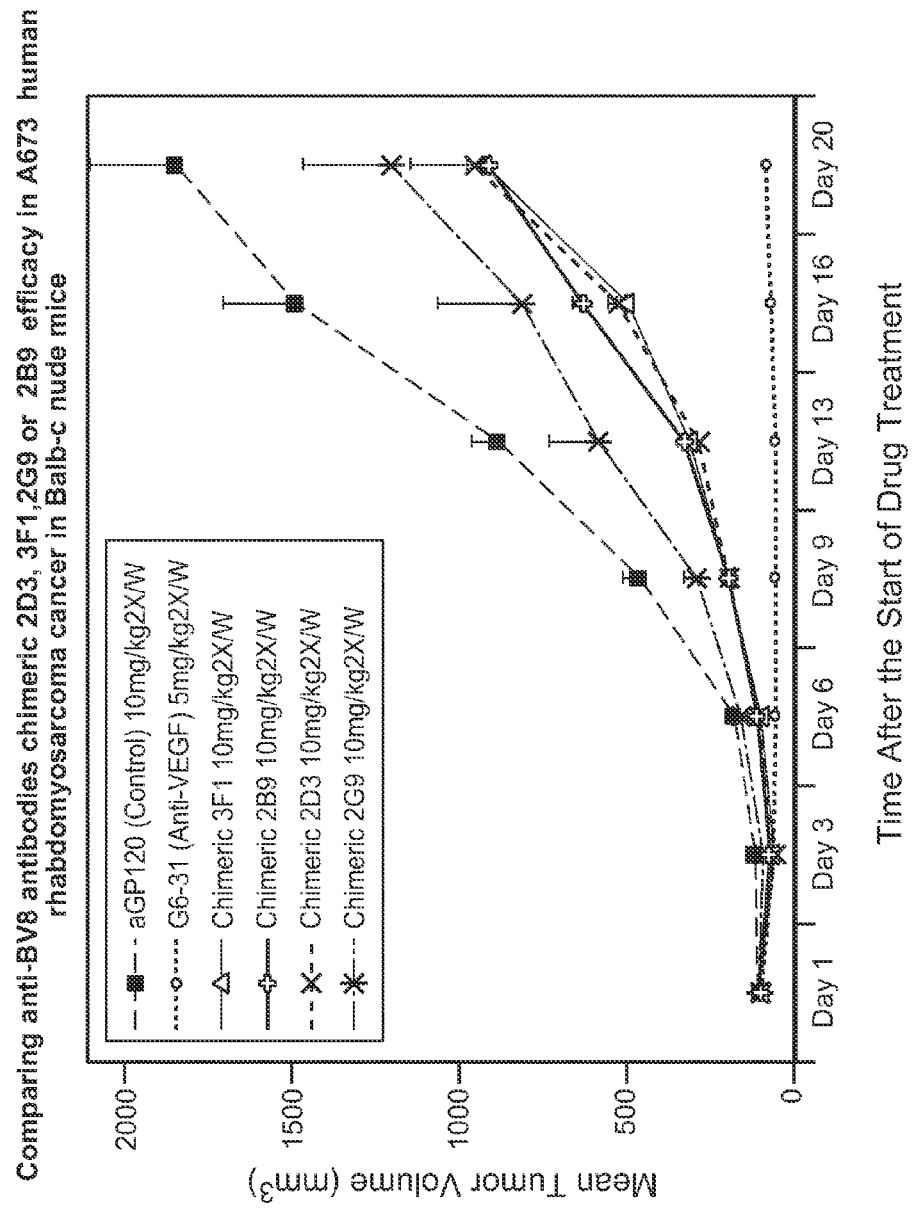

FIG. 26. Efficacy study of chimeric 3F1, chimeric 2B9, chimeric 2D3 and chimeric 2G9 anti-Bv8 antibodies in treating A673 human rhabdomyosarcoma cancer.

Figure 27:
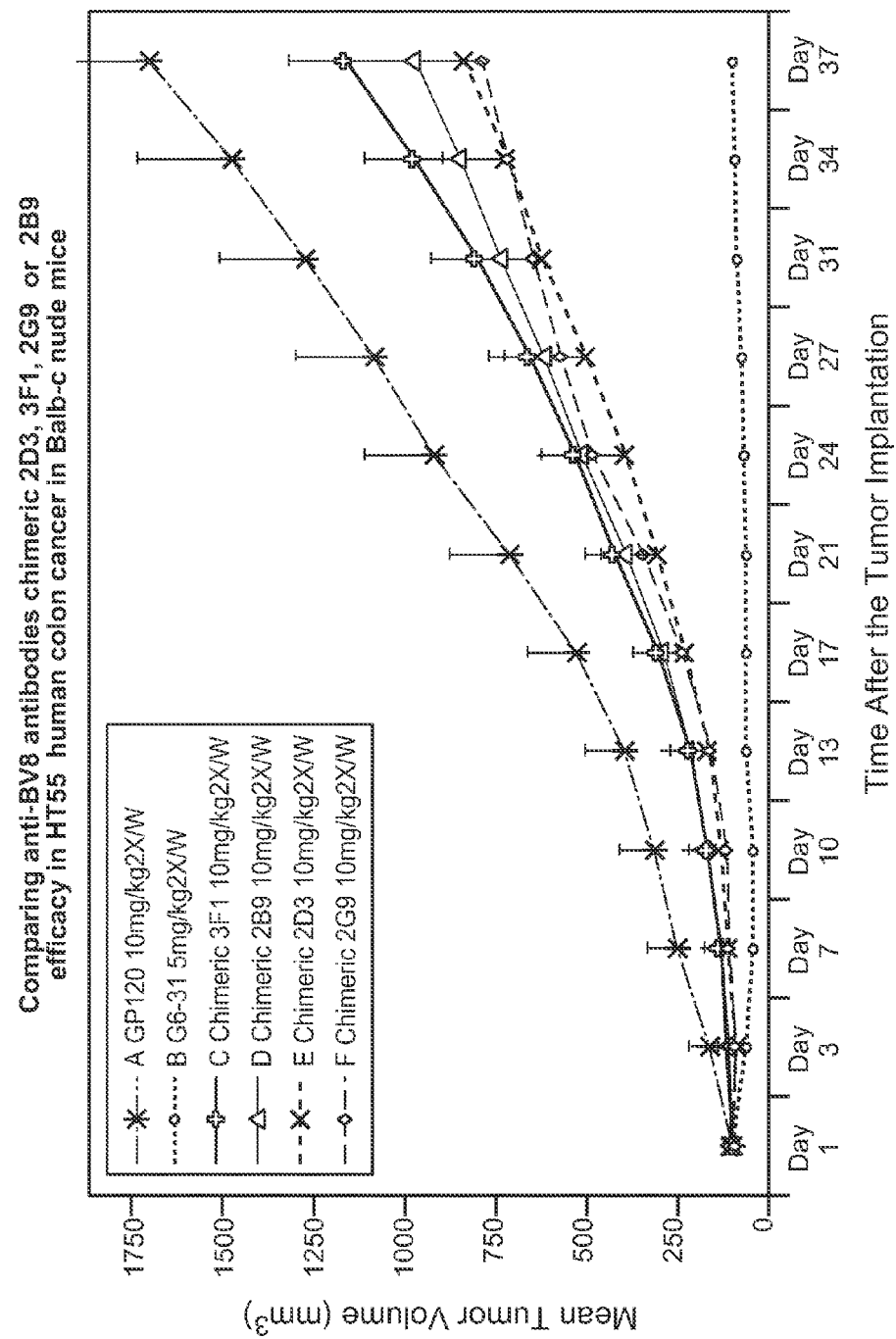

FIG. 27. Efficacy study of chimeric 3F1, chimeric 2B9, chimeric 2D3 and chimeric 2G9 anti-Bv8 antibodies in treating HT55 human colon cancer.

Figure 28:
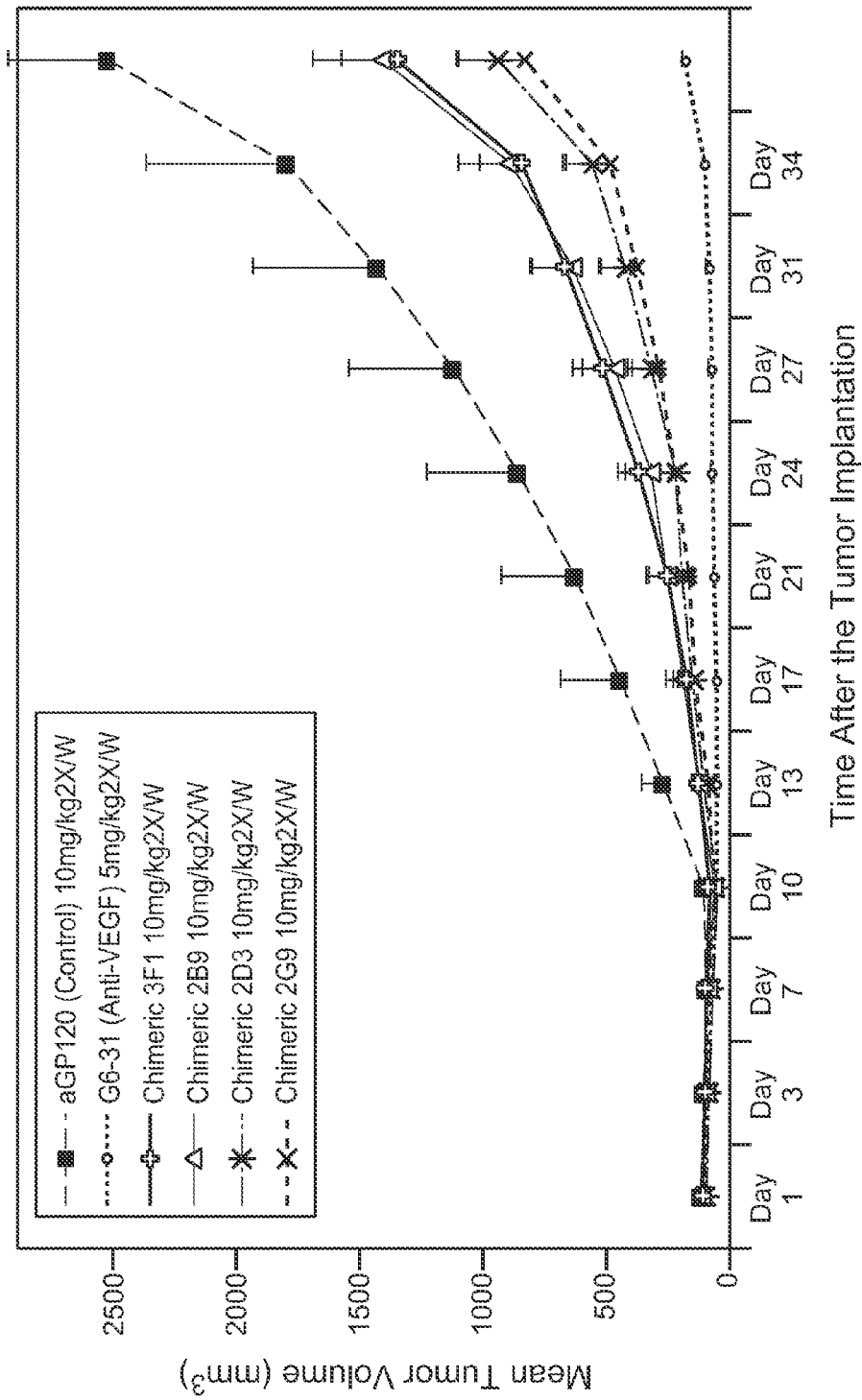

FIG. 28. Efficacy study of chimeric 3F1, chimeric 2B9, chimeric 2D3 and chimeric 2G9 anti-Bv8 antibodies in treating Calu-6 human lung cancer.

Figure 29:
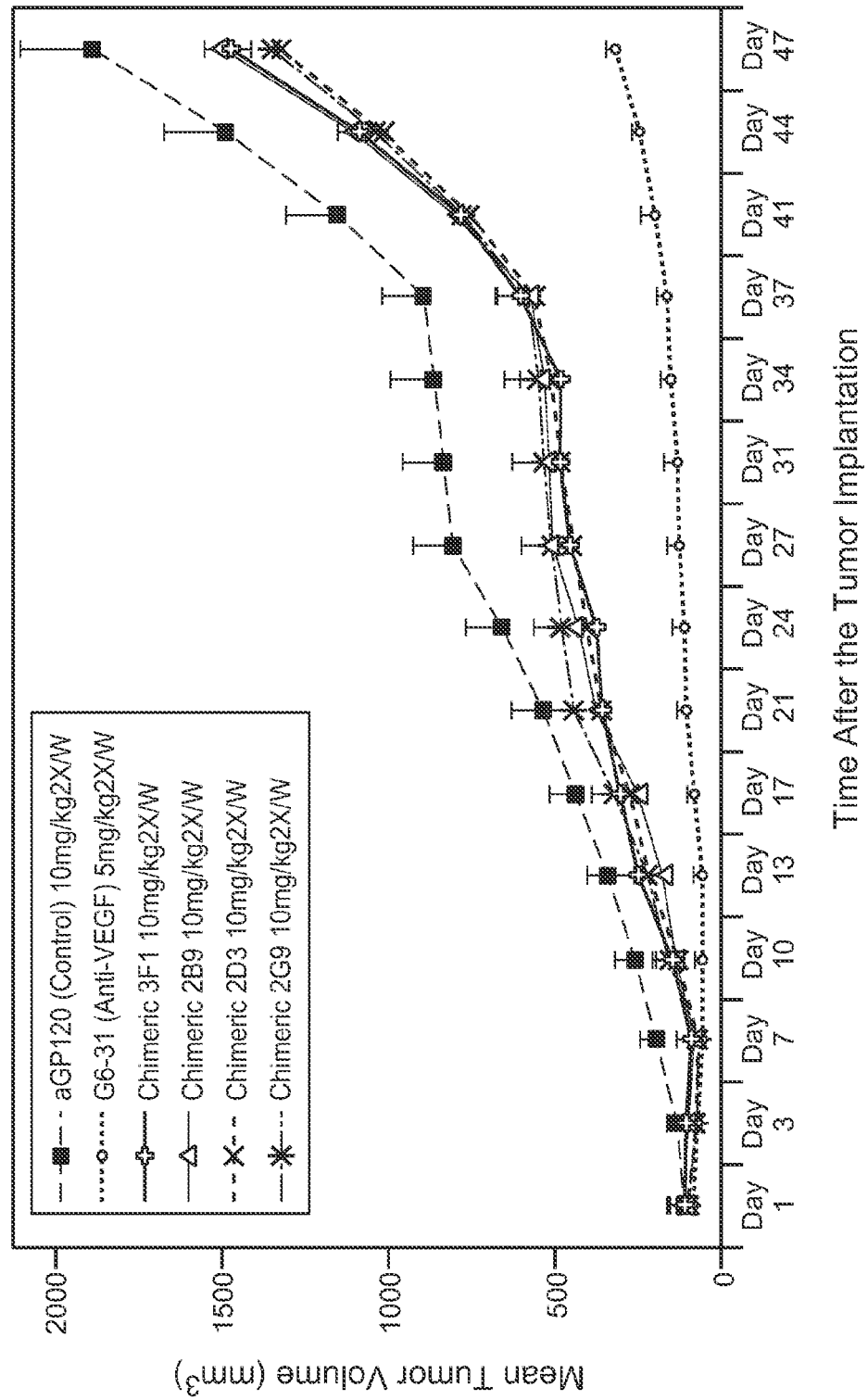

FIG. 29. Efficacy study of chimeric 3F1, chimeric 2B9, chimeric 2D3 and chimeric 2G9 anti-Bv8 antibodies in treating Colo-205 human colon cancer.

Figure 30:
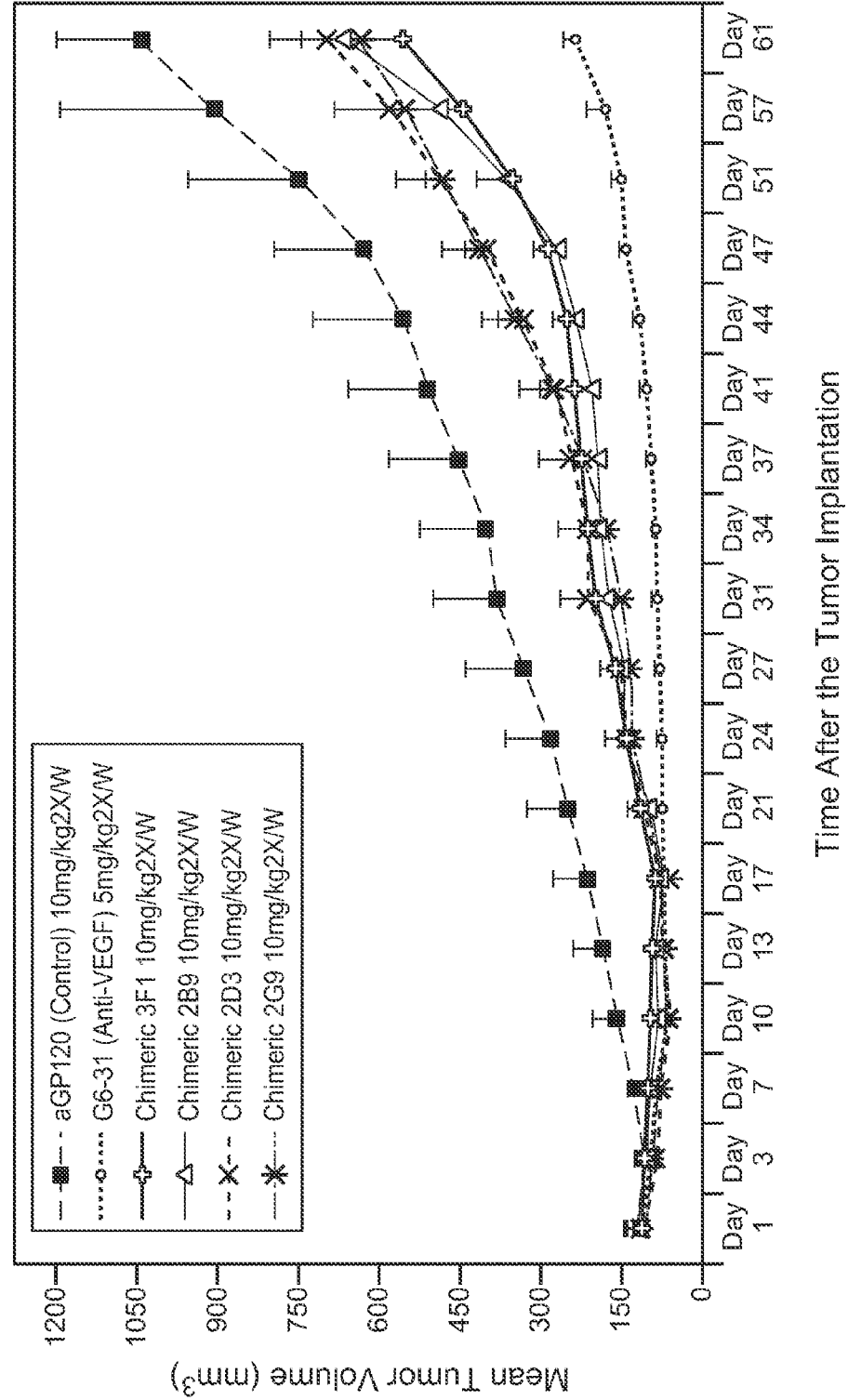

FIG. 30. Efficacy study of chimeric 3F1, chimeric 2B9, chimeric 2D3 and chimeric 2G9 anti-Bv8 antibodies in treating HPAC human pancreatic cancer.

Figure 31:
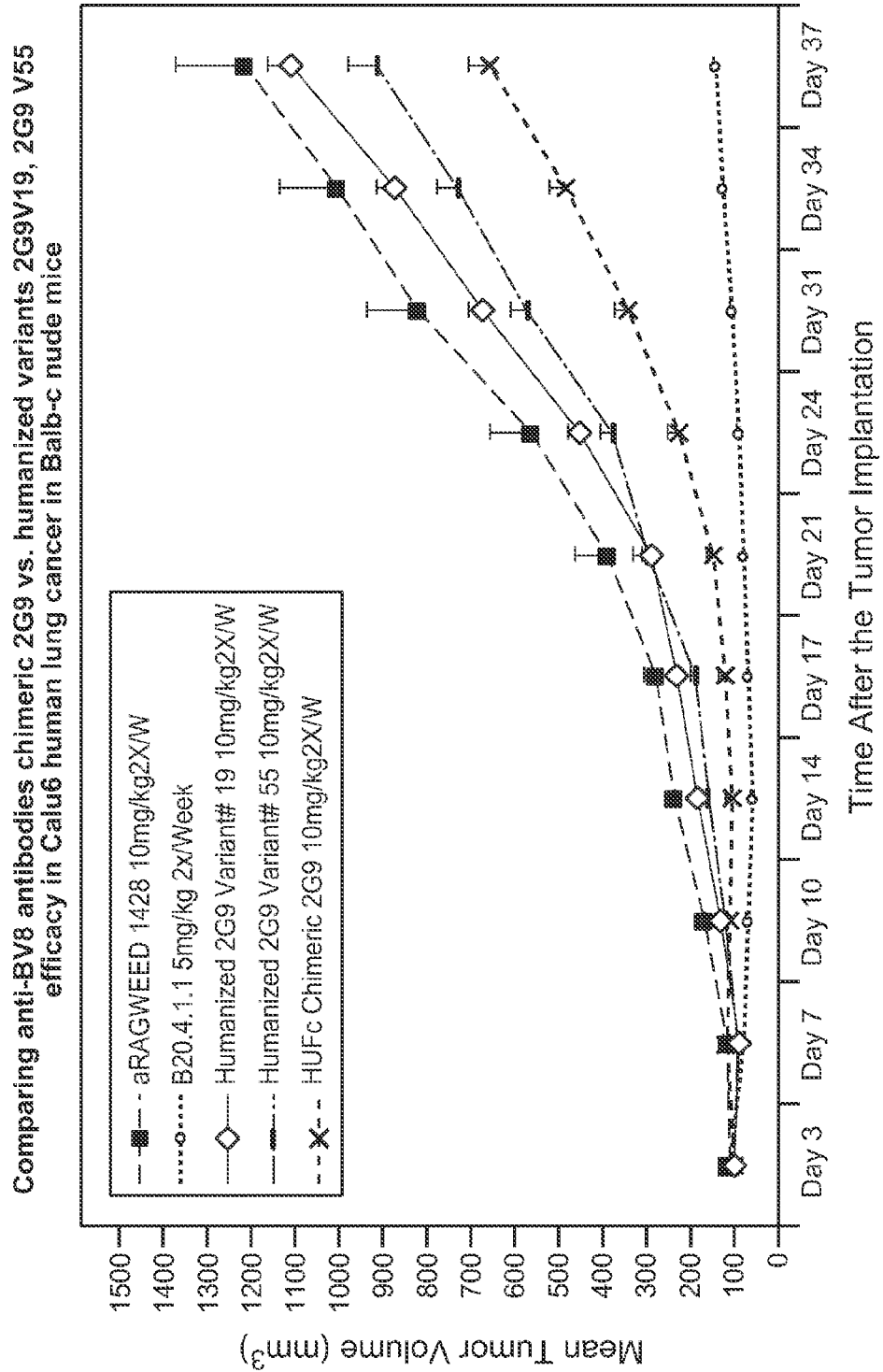

FIG. 31. Efficacy study of chimeric 2G9, h2G9.K4G1.v19 and h2G9.K4G1.v55 anti-Bv8 antibodies in treating Calu-6 human lung cancer.

Figure 32:
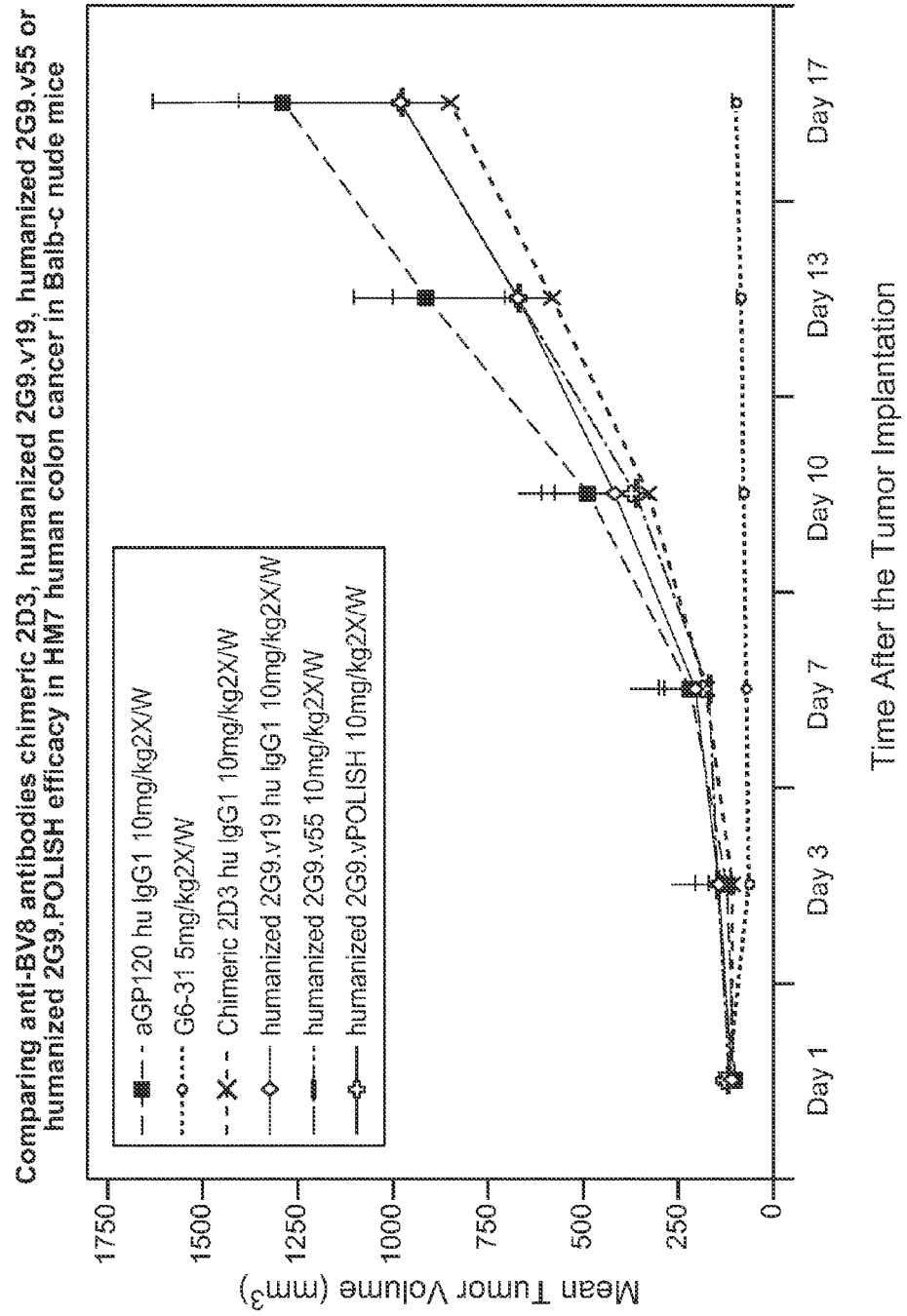

FIG. 32. Efficacy study of chimeric 2D3, h2G9.K4G1.Polish, h2G9.K4G1.v19 and h2G9.K4G1.v55 anti-Bv8 antibodies in treating HM7 human colon cancer.

Figure 33:
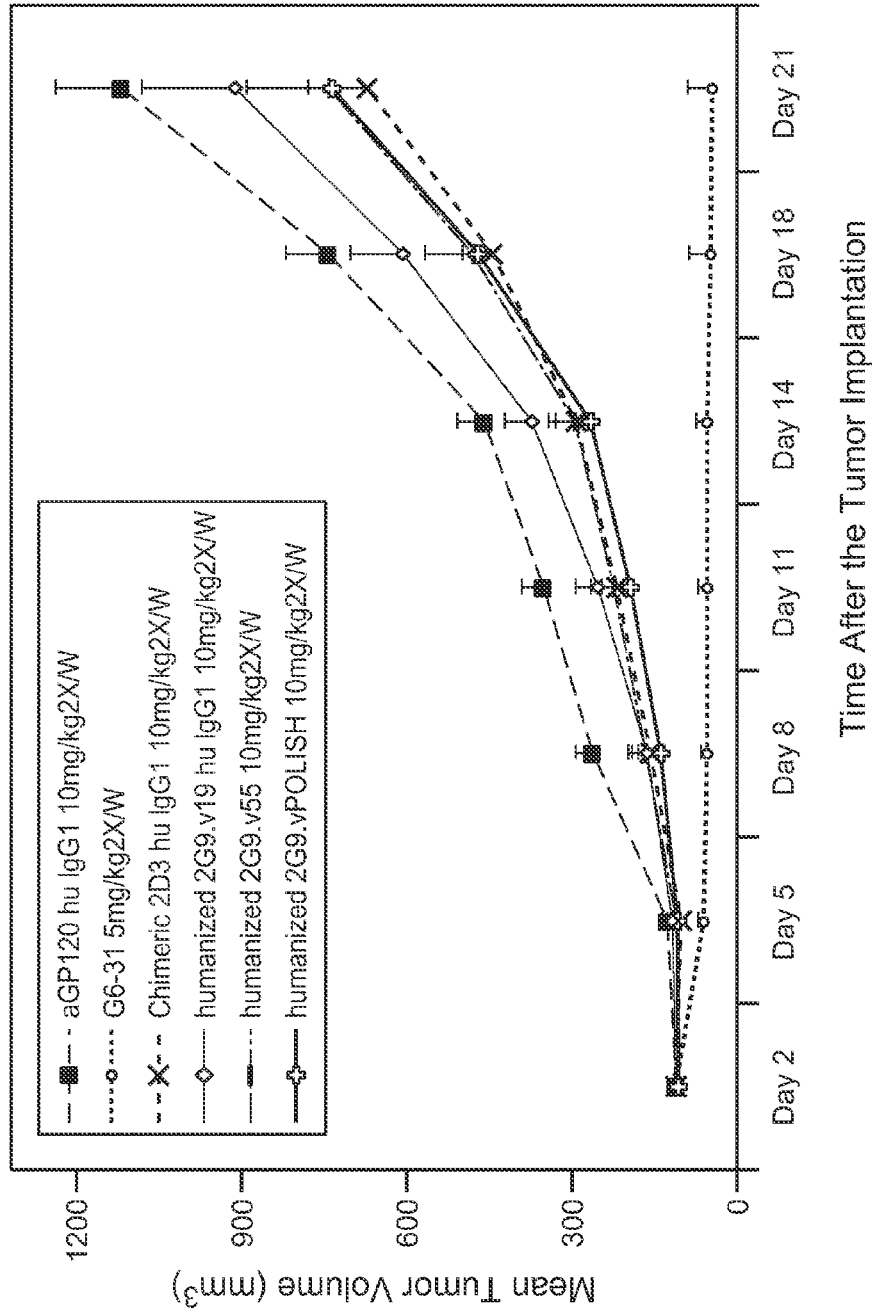

FIG. 33. Efficacy study of chimeric 2G9, h2G9.K4G1.v19 and h2G9.K4G1.v55 anti-Bv8 antibodies in treating A673 human rhabdomyosarcoma cancer.

Figure 34:
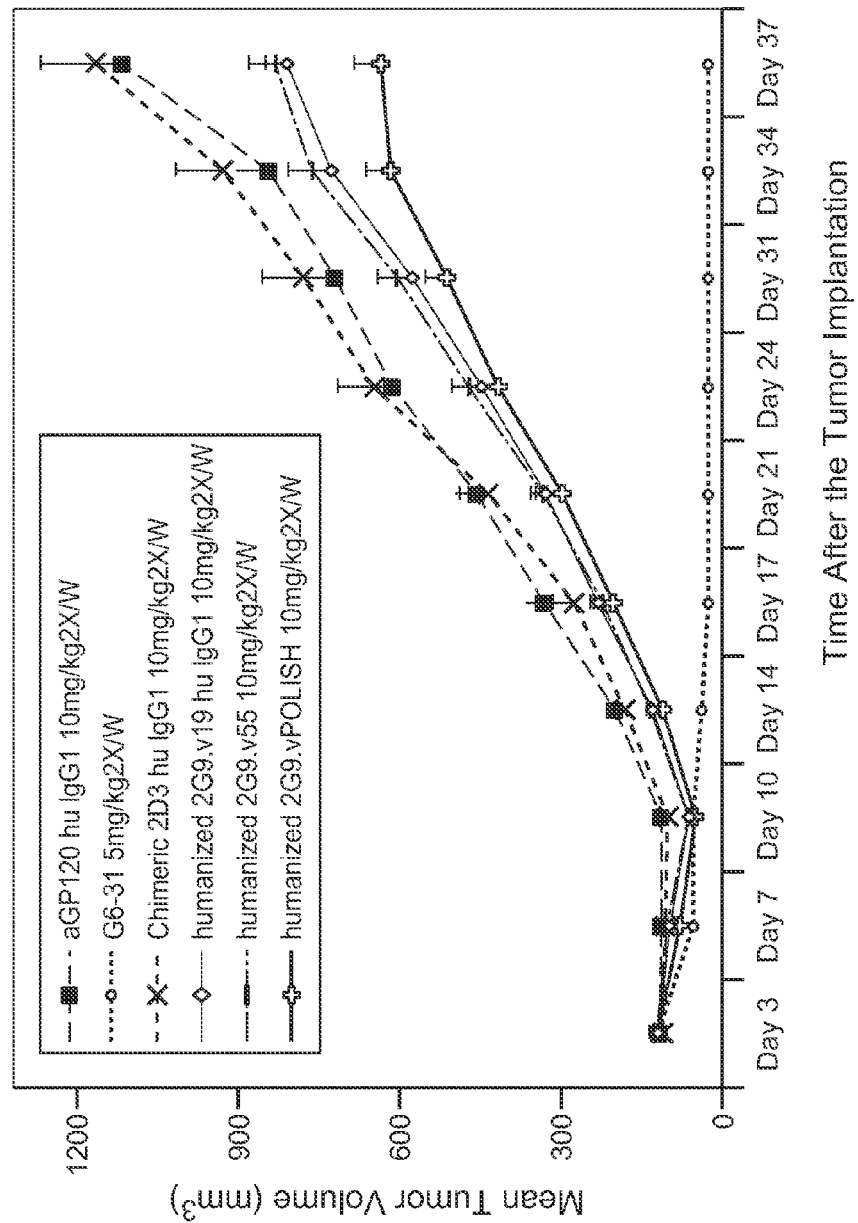

FIG. 34. Efficacy study of chimeric 2G9, h2G9.K4G1.v19 and h2G9.K4G1.v55 anti-Bv8 antibodies in treating HT55 human colon cancer.

Figure 35:
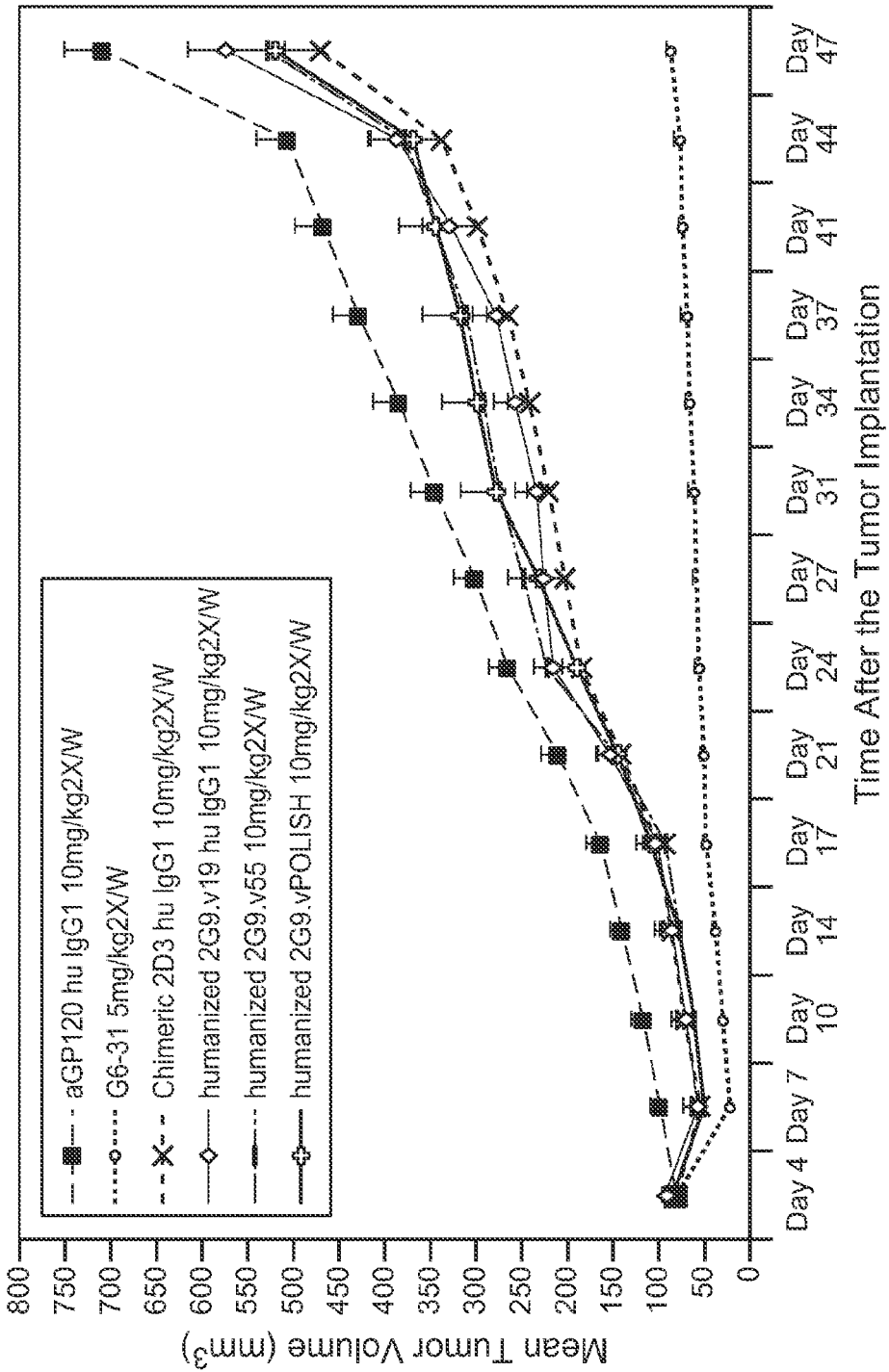

FIG. 35. Efficacy study of chimeric 2G9, h2G9.K4G1.v19 and h2G9.K4G1.v55 anti-Bv8 antibodies in treating Colo-205 human colon cancer.

Figure 36:
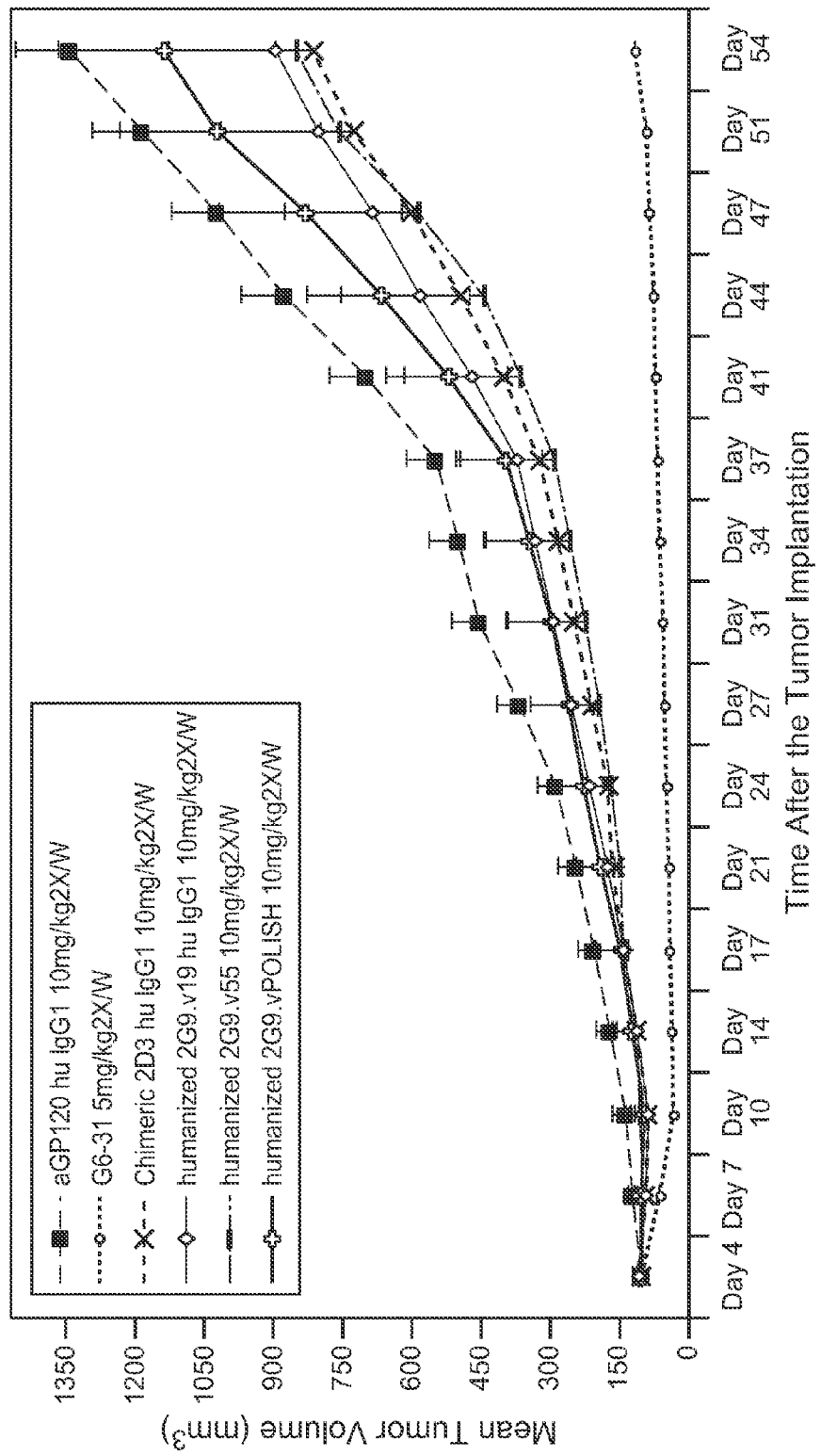

FIG. 36. Efficacy study of chimeric 2G9, h2G9.K4G1.v19 and h2G9.K4G1.v55 anti-Bv8 antibodies in treating HPAC human pancreatic cancer.

Figure 37:
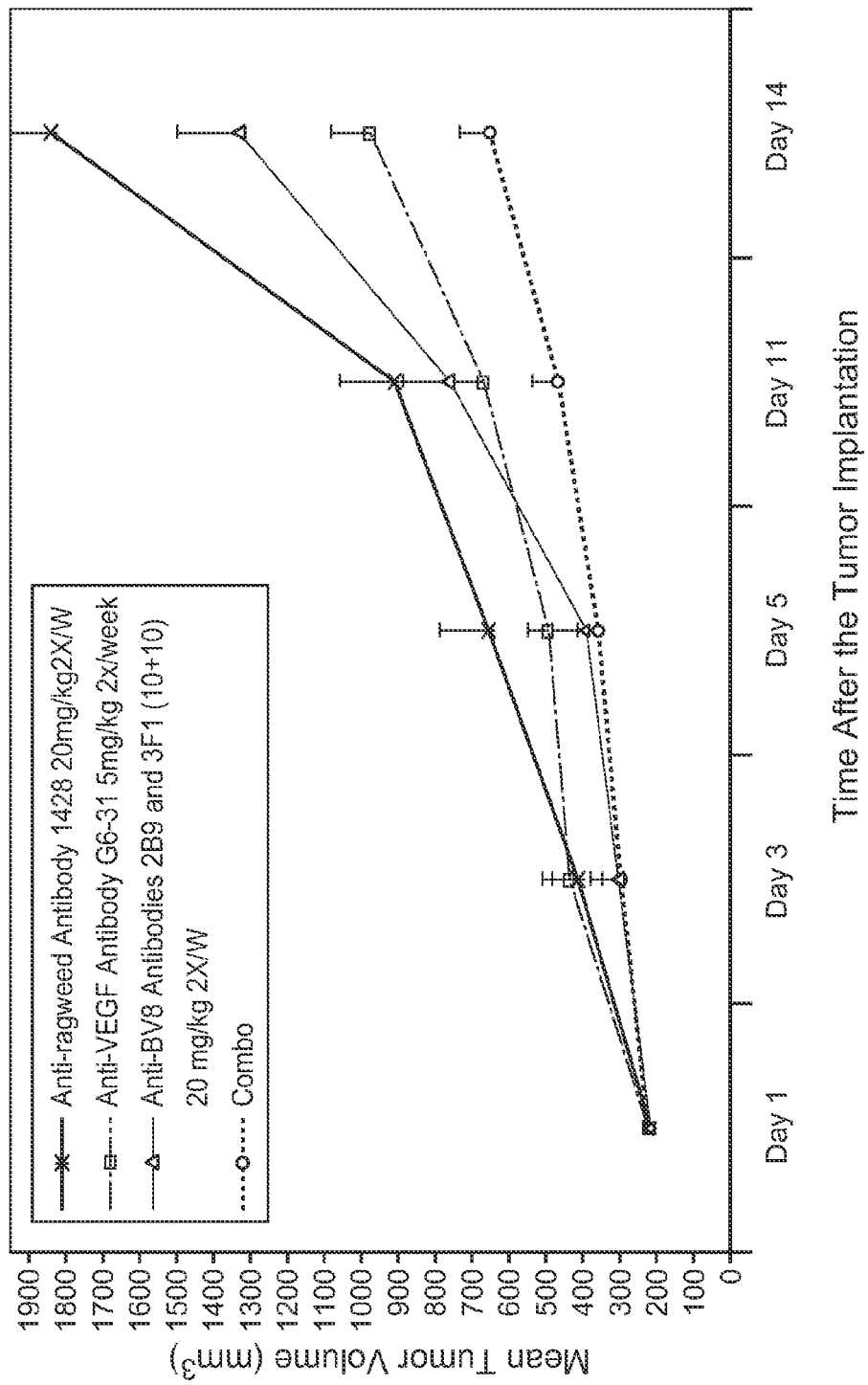

FIG. 37. Efficacy study of anti-Bv8 mouse antibodies (3F1 and 2B9) in treating LXFL529 human lung non-small cell carcinoma cells with and without anti-VEGF antibody.

Figure 38:
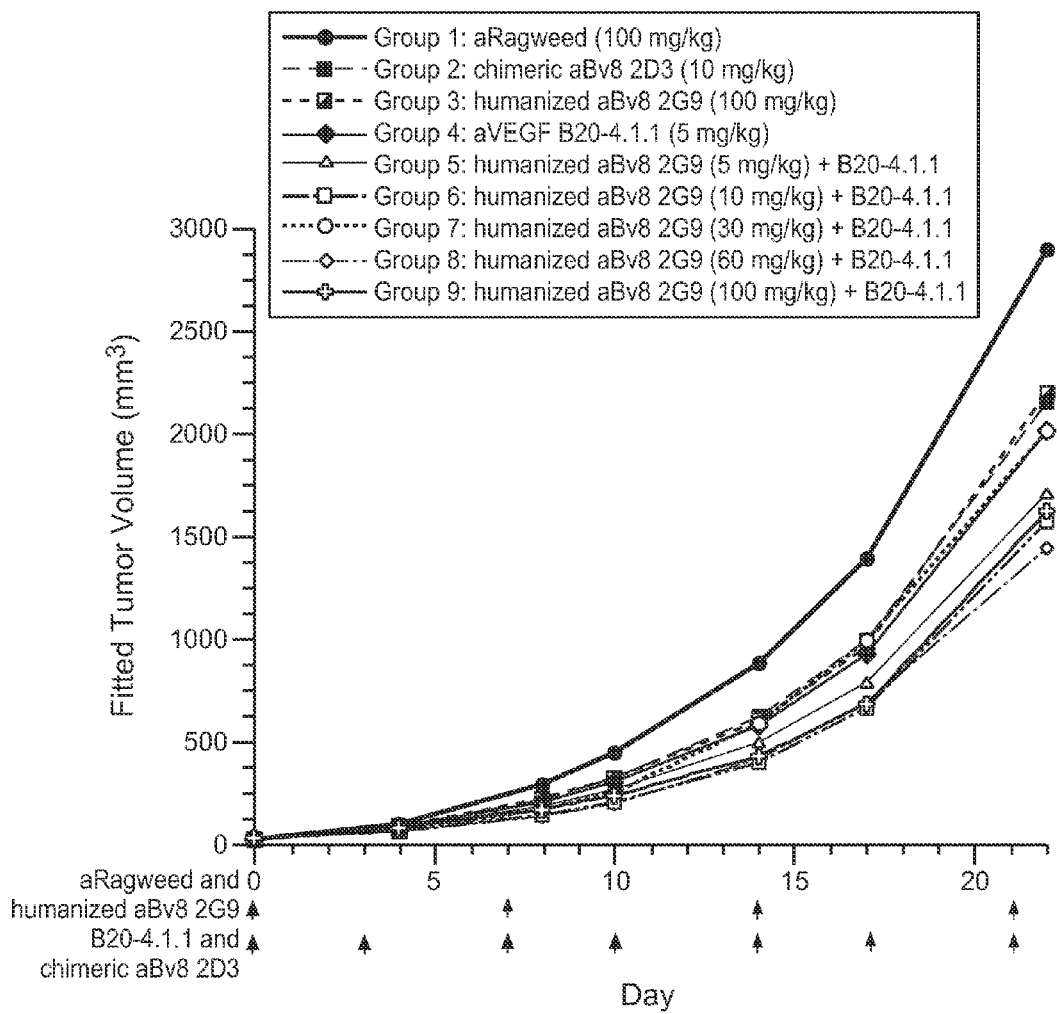

FIG. 38 shows growth inhibition of lewis lung carcinoma (LLC) allografts in response to anti-Bv8 antibody as a single agent or in combination with anti-VEGF antibody.

Figure 39:
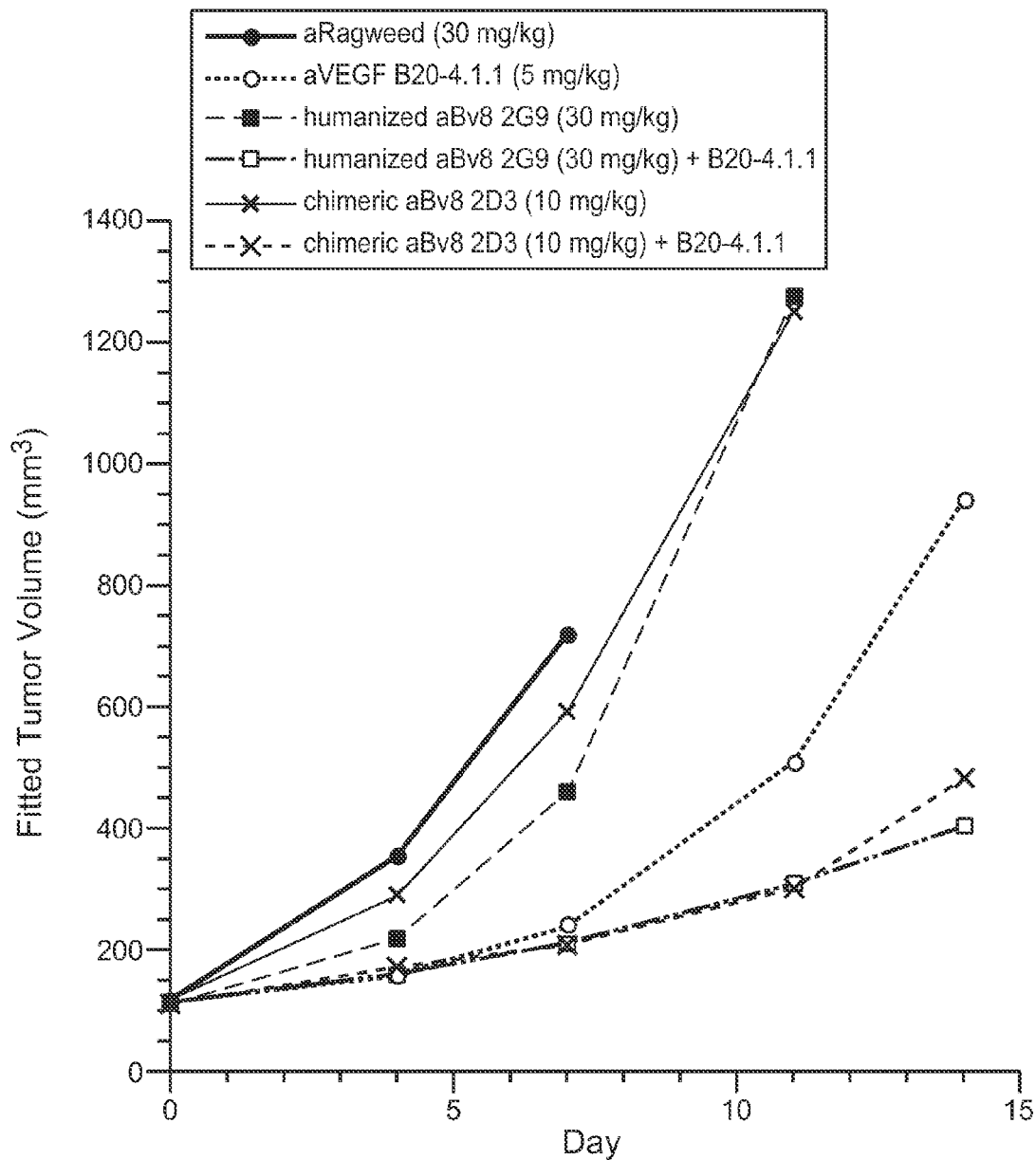

FIG. 39 shows growth inhibition of HM7 human colorectal carcinoma xenografts in response to anti-Bv8 antibody as a single agent or in combination with anti-VEGF antibody.

Figure 40:
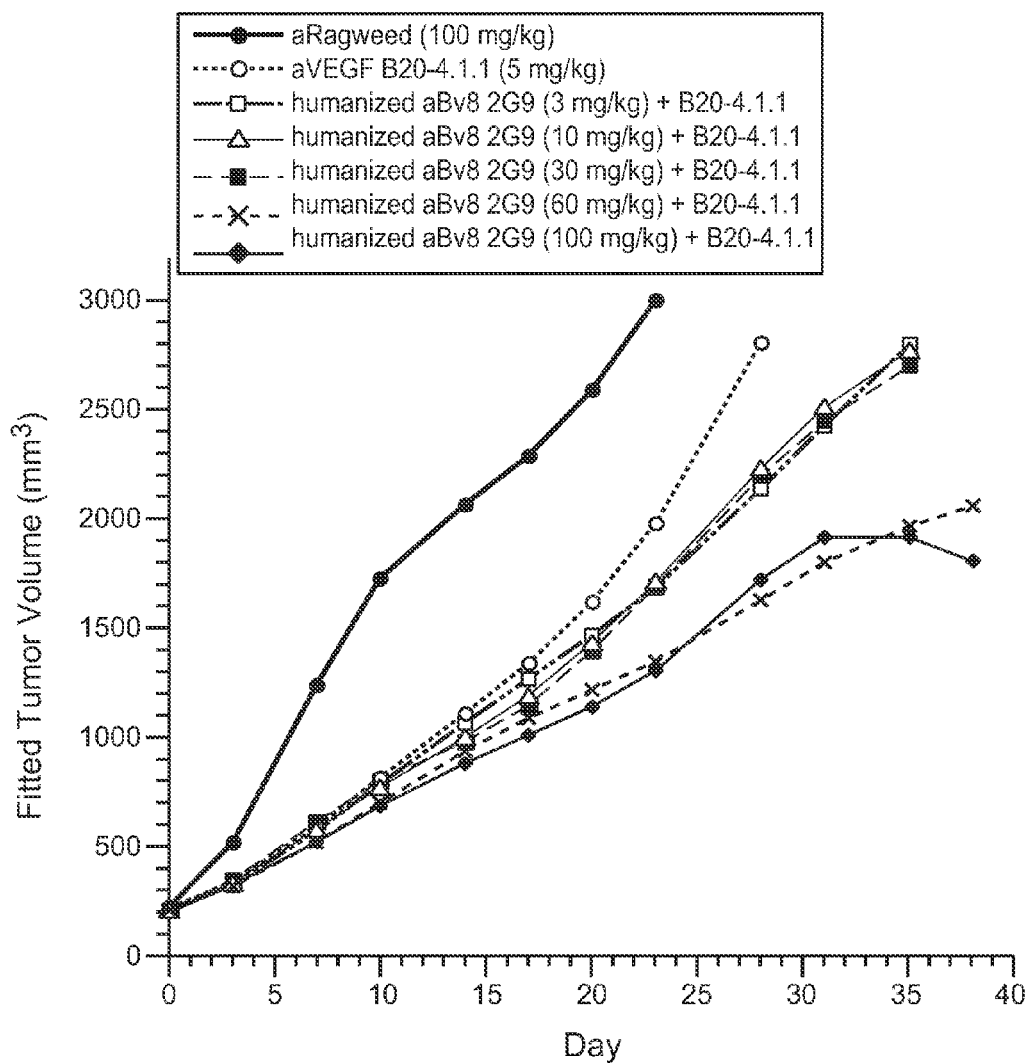

FIG. 40 shows growth inhibition of H460 human non-small cell lung carcinoma xenografts in response to anti-Bv8 antibody in combination with anti-VEGF antibody.

Figure 41:
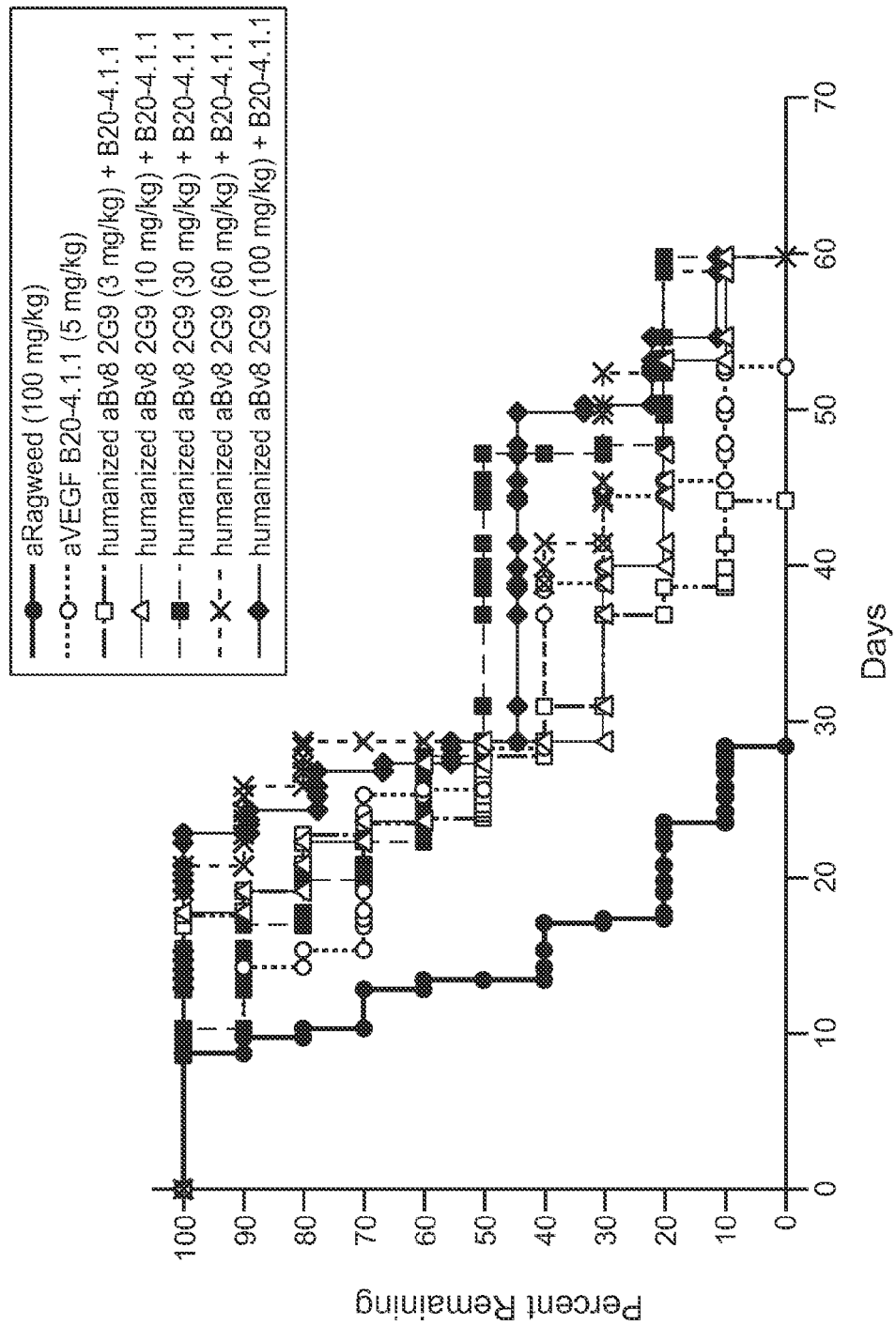

FIG. 41 shows prolonged survival of mice bearing H460 human non-small cell lung carcinoma xenografts in response to anti-Bv8 antibody in combination with anti-VEGF antibody.

Figure 42:
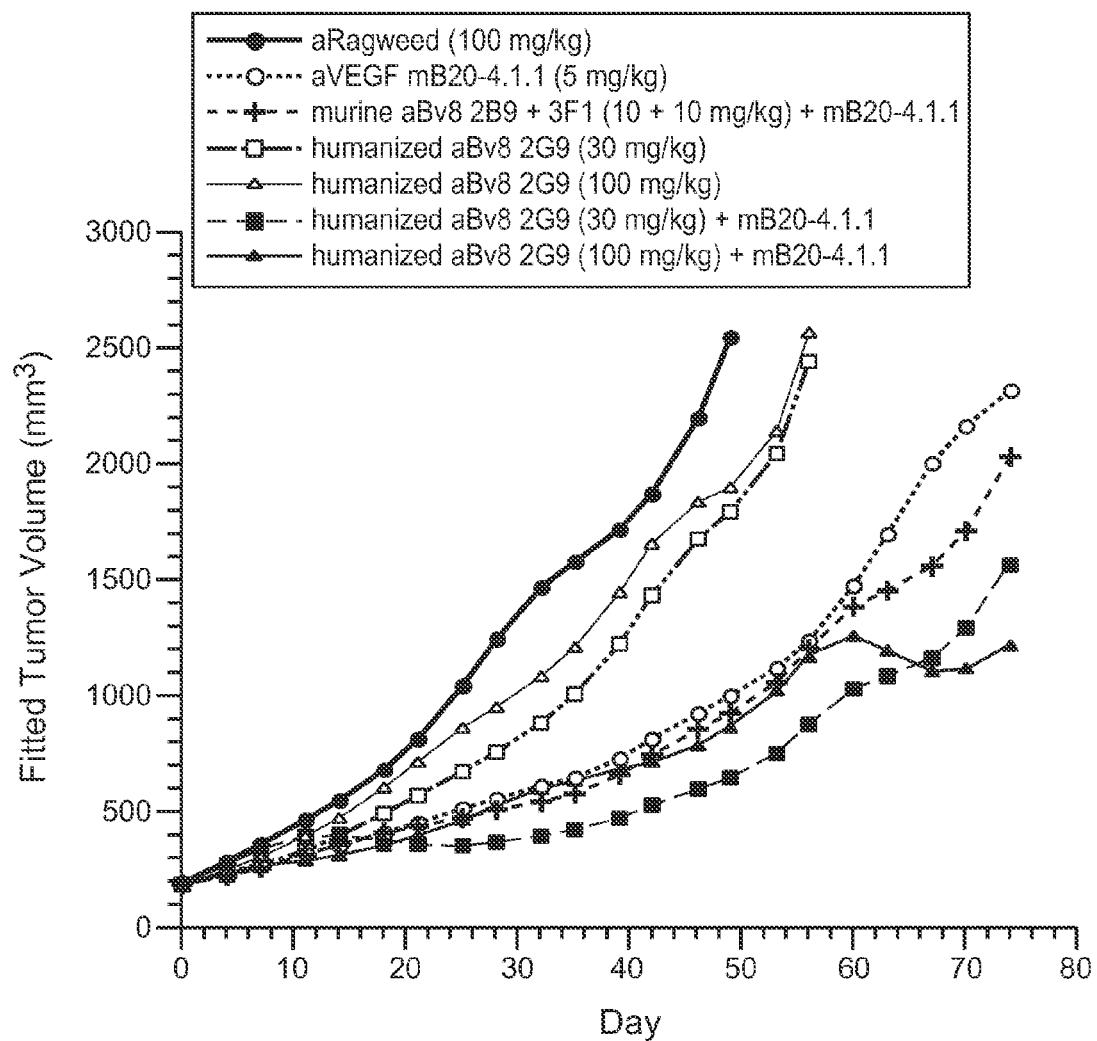

FIG. 42 shows growth inhibition of HT29 human colorectal carcinoma xenografts in response to anti-Bv8 antibodies alone or in combination with anti-VEGF antibody.

Figure 43:
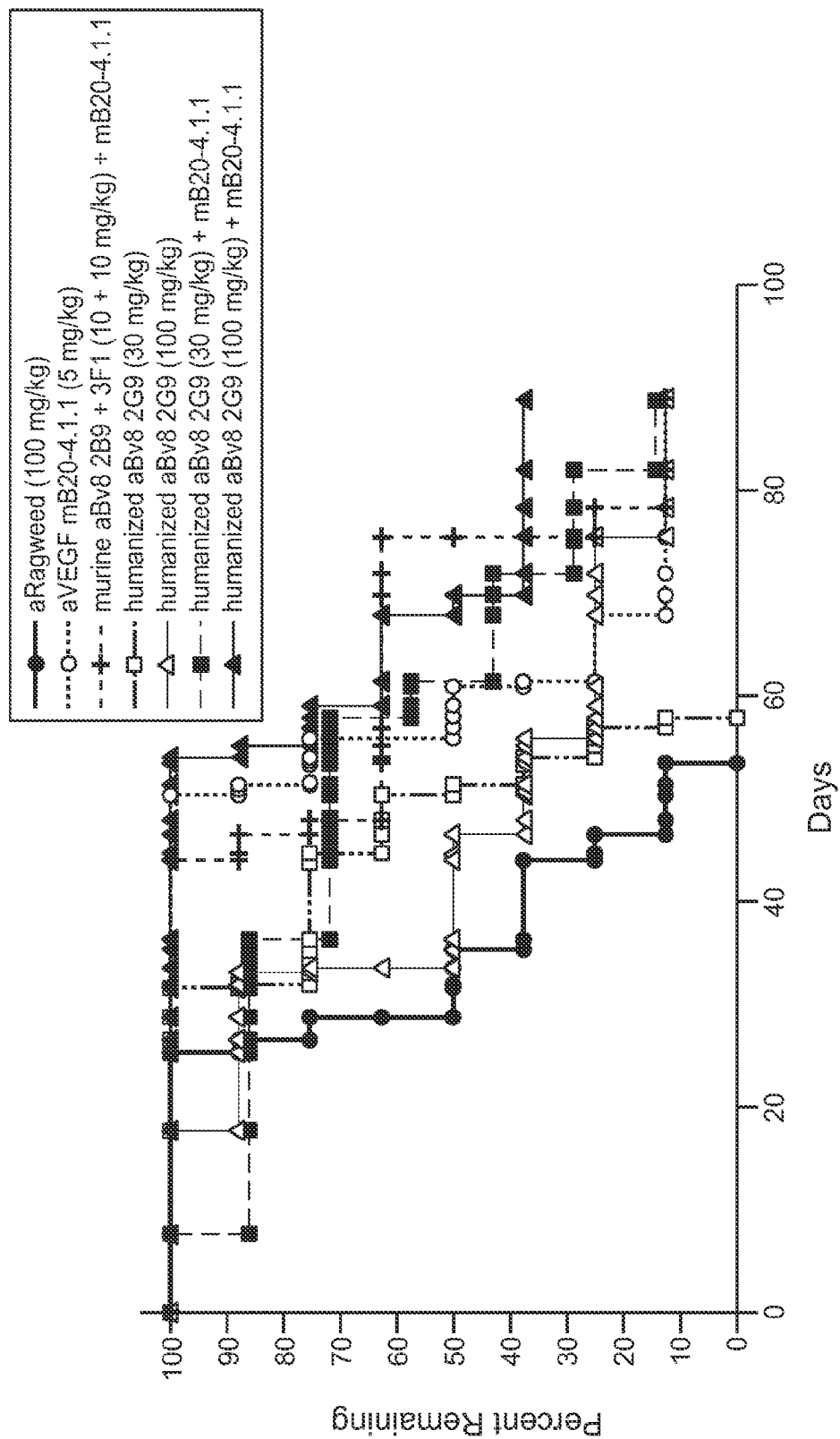

FIG. 43 shows prolonged survival of mice bearing HT29 human colorectal carcinoma xenografts in response to anti-Bv8 antibody alone or in combination with anti-VEGF antibody.

DETAILED DESCRIPTION OF THE INVENTION

The invention provides methods, compositions, kits and articles of manufacture for anti-Bv8 antibodies. Details of these methods, compositions, kits and articles of manufacture are provided herein.

General Techniques

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3rd. edition (2001) Cold Spring Harbor Laboratory Press, Cold Spring Harbor, N.Y. CURRENT PROTOCOLS IN MOLECULAR BIOLOGY (F. M. Ausubel, et al. eds., (2003)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

DEFINITIONS

Terms "Bv8," "Bv8 homologue," "prokineticin-2," (also known as "PK2," KAL4," and "MIT1") are used herein interchangeably and refer to the full-length polypeptide and/or the active fragments of the full-length polypeptide. Native sequence Bv8 encompasses naturally occurring prepro, pro and mature forms and truncated forms of Bv8, naturally occurring variant forms (e.g. alternatively spliced forms and naturally occurring allelic variants. In certain embodiments, native Bv8 amino acid sequences are shown in SEQ ID NOs: 235 to 239. Human and murine Bv8 sequences are also disclosed, for example, in Wechselberger et al. (*FEBS Lett.* 462: 177-181 (1999)) and Li et al. (*Mol. Pharm.* 59:692-698 (2001)).

"Bv8 receptor" is a molecule to which Bv8 binds and which mediates the biological properties of Bv8. Therefore, the term "Bv8 receptor" includes within its meaning PKR1/GPR73/EG-VEGF receptor-1/PROKR1 and PKR2/GPR73L1/EG-VEGF receptor-2/PROKR2 (LeCouter et al., 2003, *Proc. Natl. Acad. Sci. USA,* 100:2685-2690; Lin et al., 2002, J. Biol. Chem., 277:19276-19280; Masuda et al., 2002, Biochem. Biophys. Res. Commun., 293:396-402).

The term "biological activity" and "biologically active" with regard to a polypeptide refer to the ability of a molecule to specifically bind to and regulate cellular responses, e.g., proliferation, migration, etc. Cellular responses also include those mediated through a receptor, including, but not limited to, migration, and/or proliferation.

"Active" or "activity," in connection with Bv8, for the purposes herein refers to form(s) of Bv8 which retain a biological and/or an immunological activity of native or naturally-occurring Bv8, wherein "biological" activity refers to a biological function (either inhibitory or stimulatory) caused by a native or naturally-occurring Bv8, other than the ability to induce the production of an antibody against an antigenic epitope, possessed by a native or naturally-occurring Bv8, and an "immunological" activity refers to the ability to induce the production of an antibody against an antigenic epitope possessed by a native or naturally-occurring Bv8. In certain embodiments, the biological activity of Bv8 is the ability to modulate myeloid cell mobilization, promote tumor angiogenesis and/or promote tumor metastasis.

The term "anti-Bv8 antibody" or "an antibody that binds to Bv8" refers to an antibody that is capable of binding Bv8 with sufficient affinity such that the antibody is useful as a diagnostic and/or therapeutic agent in targeting Bv8. In certain embodiments, an antibody that binds to Bv8 has a dissociation constant (Kd) of ≤1 µM, ≤100 nM, ≤10 nM, ≤1 nM, ≤0.1 nM, or ≤0.01 nM. In certain embodiments, an anti-Bv8 antibody binds to an epitope of Bv8 that is conserved among Bv8 from different species. In certain embodiments, anti-Bv8 antibody binds to a same epitope on human Bv8 as an antibody selected from the group consisting of chimeric 2G9, h2G9.K4G1.v19, h2G9.K4G1.v52, h2G9.K4G1.v55, h2G9.K4G1.v73 and chimeric 2D3. In certain embodiments, anti-Bv8 antibody competes for binding to human Bv8 with an antibody selected from the group consisting of chimeric 2G9, h2G9.K4G1.v19, h2G9.K4G1.v52, h2G9.K4G1.v55, h2G9.K4G1.v73 and chimeric 2D3.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

In certain embodiments, the "Kd" or "Kd value" according is measured by a radiolabeled antigen binding assay (RIA) performed with the Fab version of an anti-Bv8 antibody and its antigen as described by the following assay that measures solution binding affinity of Fabs for antigen by equilibrating Fab with a minimal concentration of ($^{125}$I)-labeled antigen in the presence of a titration series of unlabeled antigen, then capturing bound antigen with an anti-Fab antibody-coated plate (Chen, et al., (1999) J. Mol. Biol 293:865-881). To establish conditions for the assay, microtiter plates (Dynex) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate (Nunc #269620), 100 pM or 26 pM [$^{125}$I]-antigen are mixed with serial dilutions of a Fab of interest (e.g., consistent with assessment of an anti-VEGF antibody, Fab-12, in Presta et al., (1997) Cancer Res. 57:4593-4599). The Fab of interest is then incubated overnight; however, the incubation may continue for a longer period (e.g., 65 hours) to insure that equilibrium is reached. Thereafter, the mixtures are transferred to the capture plate for incubation at room temperature (e.g., for one hour). The solution is then removed and the plate washed eight times with 0.1% Tween™-20 in PBS. When the plates have dried, 150 µL1/well of scintillant (MicroScint™-20; Packard) is added, and the plates are counted on a TopCount gamma counter (Packard) for ten minutes. Concentrations of each Fab that give less than or equal to 20% of maximal binding are chosen for use in competitive binding assays. According to another embodiment, the Kd or Kd value is measured by using surface plasmon resonance assays using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 µg/ml (~0.2 µM) before injection at a flow rate of 5 µl/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween™ 20 (PBST) at 25° C. at a flow rate of approximately 25 µl/min. Association rates ($k_{on}$) and dissociation rates ($k_{off}$) are calculated using a simple one-to-one Langmuir binding model (BIAcore™ Evaluation Software version 3.2) by simultaneous fitting the association and dissociation sensorgram. The equilibrium dissociation constant (Kd) is calculated as the ratio $k_{off}/k_{on}$. See, e.g., Chen, Y., et al., (1999) J. Mol. Biol. 293:865-881. If the on-rate exceeds $10^6 M^{-1} S^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM Aminco spectrophotometer (ThermoSpectronic) with a stirred cuvette.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors" or "expression vectors"). In general, expression vectors of utility in recombinant DNA techniques are often in the form of plasmids. In the present specification, "plasmid" and "vector" may be used interchangeably.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and a basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR$_2$ ("amidate"), P(O) R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

The terms "antibody" and "immunoglobulin" are used interchangeably in the broadest sense and include monoclonal antibodies (for e.g., full length or intact monoclonal antibodies), polyclonal antibodies, multivalent antibodies, multispecific antibodies (e.g., bispecific antibodies so long as they exhibit the desired biological activity) and may also include certain antibody fragments (as described in greater detail herein). An antibody can be human, humanized and/or affinity matured.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions or hypervariable regions (CDRs or HVRs, used interchangeably herein) both in the light-chain and the heavy-chain variable domains. The more highly conserved portions of variable domains are called the framework (FR). The variable domains of native heavy and light chains each comprise four FR regions, largely adopting a β-sheet configuration, connected by three HVRs, which form loops connecting, and in some cases forming part of, the β-sheet structure. The HVRs in each chain are held together in close proximity by the FR regions and, with the HVRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., IgG$_1$, IgG$_2$, IgG$_3$, IgG$_4$, IgA$_1$, and IgA$_2$. The heavy-chain constant domains that correspond to the different classes of immunoglobulins are called α, δ, ε, γ, and μ, respectively. The subunit structures and three-dimensional configurations of different classes of immunoglobulins are well known.

"Antibody fragments" comprise only a portion of an intact antibody, wherein the portion preferably retains at least one, preferably most or all, of the functions normally associated with that portion when present in an intact antibody. Examples of antibody fragments include Fab, Fab', F(ab')2, and Fv fragments; diabodies; linear antibodies; single-chain antibody molecules; and multispecific antibodies formed from antibody fragments. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For e.g., such an antibody fragment may comprise on antigen binding arm linked to an Fc sequence capable of conferring in vivo stability to the fragment.

The term "hypervariable region," "HVR," or "HV," when used herein refers to the regions of an antibody variable domain which are hypervariable in sequence and/or form structurally defined loops. Generally, antibodies comprise six HVRs; three in the VH(H1, H2, H3), and three in the VL (Li, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|------|-------|-----|---------|---------|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B (Kabat Numbering) | H26-H32 | H30-H35B |
| H1 | H31-H35 | H26-H35 (Chothia Numbering) | H26-H32 | H30-H35 |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the hypervariable region residues as herein defined.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a HVR of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, e.g., Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

Human antibodies can be produced using various techniques known in the art, including phage-display libraries. Hoogenboom and Winter, *J. Mol. Biol.*, 227:381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147 (1):86-95 (1991). See also van Dijk and van de Winkel, *Curr. Opin. Pharmacol.*, 5: 368-74 (2001). Human antibodies can be prepared by administering the antigen to a transgenic animal that has been modified to produce such antibodies in response to antigenic challenge, but whose endogenous loci have been disabled., e.g., immunized xenomice (see, e.g., U.S. Pat. Nos. 6,075,181 and 6,150,584 regarding XENOMOUSE™ technology). See also, for example, Li et al. *Proc. Natl. Acad. Sci. USA*, 103:3557-3562 (2006) regarding human antibodies generated via a human B-cell hybridoma technology.

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein, *Nature*, 256:495-97 (1975); Hongo et al., *Hybridoma*, 14 (3): 253-260 (1995), Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816, 567; and Morrison et al., *Proc. Natl. Acad. Sci. USA* 81:6851-6855 (1984)). Chimeric antibodies include PRIMATIZED® antibodies wherein the antigen-binding region of the antibody is derived from an antibody produced by, e.g., immunizing macaque monkeys with the antigen of interest.

The term "multispecific antibody" is used in the broadest sense and specifically covers an antibody that has polyeptopic specificity. Such multispecific antibodies include, but are not limited to, an antibody comprising a heavy chain variable domain ($V_H$) and a light chain variable domain ($V_L$), wherein the $V_H V_L$ unit has polyepitopic specificity, antibodies having two or more $V_L$ and $V_H$ domains with each $V_H V_L$ unit binding to a different epitope, antibodies having two or more single variable domains with each single variable domain binding to a different epitope, full length antibodies, antibody fragments such as Fab, Fv, dsFv, scFv, diabodies, bispecific diabodies and triabodies and antibody fragments that have been linked covalently or non-covalently. According to one embodiment the multispecific antibody is an IgG antibody that binds to each epitope with an affinity of 5 µM to 0.001 pM, 3 µM to 0.001 pM, 1 µM to 0.001 pM, 0.5 µM to 0.001 pM, or 0.1 µM to 0.001 pM.

"Polyepitopic specificity" refers to the ability to specifically bind to two or more different epitopes on the same or different antigen(s). For example, "bispecific" as used herein refers to the ability to bind two different epitopes. "Monospecific" refers to the ability to bind only one epitope.

The expression "single domain antibodies" (sdAbs) or "single variable domain (SVD) antibodies" generally refers to antibodies in which a single variable domain ($V_H$ or $V_L$) can confer antigen binding. In other words, the single variable domain does not need to interact with another variable domain in order to recognize the target antigen. Examples of single domain antibodies include those derived from camelids (lamas and camels) and cartilaginous fish (e.g., nurse sharks) and those derived from recombinant methods from humans and mouse antibodies (Nature (1989) 341:544-546; Dev Comp Immunol (2006) 30:43-56; Trend Biochem Sci (2001) 26:230-235; Trends Biotechnol (2003):21:484-490; WO 2005/035572; WO 03/035694; Febs Lett (1994) 339: 285-290; WO00/29004; WO 02/051870).

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv see Pluckthun, in *The Pharmacology of Monoclonal Antibodies*, vol. 113, Rosenburg and Moore eds., Springer-Verlag, New York, pp. 269-315 (1994).

An "antigen" is a predetermined antigen to which an antibody can selectively bind. The target antigen may be polypeptide, carbohydrate, nucleic acid, lipid, hapten or other naturally occurring or synthetic compound.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993). Triabodies and tetrabodies are also described in Hudson et al., *Nat. Med.* 9:129-134 (2003).

"The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g, Kabat et al., *Sequences of Immunological Interest*. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system (e.g., see U.S. Provisional Application No. 60/640,323, Figures for EU numbering).

A "blocking" antibody or an "antagonist" antibody is one which inhibits or reduces biological activity of the antigen it binds. Certain blocking antibodies or antagonist antibodies substantially or completely inhibit the biological activity of the antigen.

The term "substantially similar" or "substantially the same," as used herein, denotes a sufficiently high degree of similarity between two numeric values (for example, one associated with an antibody of the invention and the other associated with a reference/comparator antibody), such that one of skill in the art would consider the difference between the two values to be of little or no biological and/or statistical significance within the context of the biological characteristic measured by said values (e.g., Kd values). The difference between said two values is, for example, less than about 50%, less than about 40%, less than about 30%, less than about 20%, and/or less than about 10% as a function of the reference/comparator value.

The phrase "substantially reduced," or "substantially different," as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

A "functional Fc region" possesses an "effector function" of a native sequence Fc region. Exemplary "effector functions" include C1q binding; CDC; Fc receptor binding; ADCC; phagocytosis; down regulation of cell surface receptors (e.g. B cell receptor; BCR), etc. Such effector functions generally require the Fc region to be combined with a binding domain (e.g., an antibody variable domain) and can be assessed using various assays as disclosed, for example, in definitions herein.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

"Fc receptor" or "FcR" describes a receptor that binds to the Fc region of an antibody. In some embodiments, an FcR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. (see, e.g., Daëron, *Annu. Rev. Immunol.* 15:203-234 (1997)). FcRs are reviewed, for example, in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulation of homeostasis of immunoglobulins. Methods of measuring binding to FcRn are known (see, e.g., Ghetie and Ward., *Immunol. Today* 18(12):592-598 (1997); Ghetie et al., *Nature Biotechnology,* 15(7):637-640 (1997); Hinton et al., *J. Biol. Chem.* 279(8):6213-6216 (2004); WO 2004/92219 (Hinton et al.).

Binding to human FcRn in vivo and serum half life of human FcRn high affinity binding polypeptides can be assayed, e.g., in transgenic mice or transfected human cell lines expressing human FcRn, or in primates to which the polypeptides with a variant Fc region are administered. PCT Publication WO 2000/42072 (Presta) and U.S. application Ser. No. 12/577,967 (Lowman) describe antibody variants with improved or diminished binding to FcRs. See also, e.g., Shields et al. *J. Biol. Chem.* 9(2):6591-6604 (2001).

"Human effector cells" are leukocytes which express one or more FcRs and perform effector functions. In certain embodiments, the cells express at least FcγRIII and perform ADCC effector function(s). Examples of human leukocytes which mediate ADCC include peripheral blood mononuclear cells (PBMC), natural killer (NK) cells, monocytes, cytotoxic T cells, and neutrophils. The effector cells may be isolated from a native source, e.g., from blood.

"Antibody-dependent cell-mediated cytotoxicity" or "ADCC" refers to a form of cytotoxicity in which secreted Ig bound onto Fc receptors (FcRs) present on certain cytotoxic cells (e.g. NK cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 or U.S. Pat. No. 6,737,056 (Presta), may be performed. Useful effector cells for such assays include PBMC and NK cells. Alternatively, or additionally, ADCC activity of the molecule of interest may be assessed in vivo, e.g., in an animal model such as that disclosed in Clynes et al. *PNAS* (USA) 95:652-656 (1998).

"Complement dependent cytotoxicity" or "CDC" refers to the lysis of a target cell in the presence of complement. Activation of the classical complement pathway is initiated by the binding of the first component of the complement system (Clq) to antibodies (of the appropriate subclass), which are bound to their cognate antigen. To assess complement activation, a CDC assay, e.g., as described in Gazzano-Santoro et al., *J. Immunol. Methods* 202:163 (1996), may be performed. Polypeptide variants with altered Fc region amino acid sequences (polypeptides with a variant Fc region) and increased or decreased Clq binding capability are described, e.g., in U.S. Pat. No. 6,194,551 B1 and WO 1999/51642. See also, e.g., Idusogie et al. *J. Immunol.* 164: 4178-4184 (2000).

The term "Fc region-comprising antibody" refers to an antibody that comprises an Fc region. The C-terminal lysine (residue 447 according to the EU numbering system) of the Fc region may be removed, for example, during purification of the antibody or by recombinant engineering of the nucleic acid encoding the antibody. Accordingly, a composition comprising an antibody having an Fc region according to this invention can comprise an antibody with K447, with all K447 removed, or a mixture of antibodies with and without the K447 residue.

An "acceptor human framework" for the purposes herein is a framework comprising the amino acid sequence of a VL or VH framework derived from a human immunoglobulin framework, or from a human consensus framework. An acceptor human framework "derived from" a human immunoglobulin framework or human consensus framework may comprise the same amino acid sequence thereof, or may contain pre-existing amino acid sequence changes. Where pre-existing amino acid changes are present, preferably no more than 5 and preferably 4 or less, or 3 or less, pre-existing amino acid changes are present. Where pre-existing amino acid changes are present in a VH, preferably those changes are only at three, two or one of positions 71H, 73H and 78H; for instance, the amino acid residues at those positions may be 71A, 73T and/or 78A. In one embodiment, the VL acceptor human framework is identical in sequence to the VL human immunoglobulin framework sequence or human consensus framework sequence.

A "human consensus framework" is a framework which represents the most commonly occurring amino acid residue in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al. In one embodiment, for the VL, the subgroup is subgroup kappa IV as in Kabat et al. In one embodiment, for the VH, the subgroup is subgroup I as in Kabat et al. A "VH subgroup I consensus framework" comprises the consensus sequence obtained from the amino acid sequences in variable heavy subgroup I of Kabat et al.

A "VH subgroup I consensus framework" comprises the consensus sequence obtained from the amino acid sequences in variable heavy subgroup I of Kabat et al.

A "VH subgroup III consensus framework" comprises the consensus sequence obtained from the amino acid sequences in variable heavy subgroup III of Kabat et al.

A "VL subgroup IV consensus framework" comprises the consensus sequence obtained from the amino acid sequences in variable light kappa subgroup IV of Kabat et al.

A "VL subgroup I consensus framework" comprises the consensus sequence obtained from the amino acid sequences in variable light kappa subgroup I of Kabat et al.

A "medicament" is an active drug to treat the disorder in question or its symptoms, or side effects.

A "disorder" or "disease" is any condition that would benefit from treatment with a substance/molecule or method of the invention. This includes chronic and acute disorders or diseases including those pathological conditions which predispose the mammal to the disorder in question. Non-limiting examples of disorders to be treated herein include malignant and benign tumors; carcinoma, blastoma, and sarcoma.

The "pathology" of a disease includes all phenomena that compromise the well-being of the patient. For cancer, this includes, without limitation, abnormal or uncontrollable cell growth, metastasis, interference with the normal functioning of neighboring cells, release of cytokines or other secretory products at abnormal levels, suppression or aggravation of inflammatory or immunological response, etc.

The terms "cell proliferative disorder" and "proliferative disorder" refer to disorders that are associated with some degree of abnormal cell proliferation. In one embodiment, the cell proliferative disorder is cancer.

"Tumor", as used herein, refers to all neoplastic cell growth and proliferation, whether malignant or benign, and all precancerous and cancerous cells and tissues. The terms "cancer", "cancerous", "cell proliferative disorder", "proliferative disorder" and "tumor" are not mutually exclusive as referred to herein.

The terms "cancer" and "cancerous" refer to or describe the physiological condition in mammals that is typically characterized by unregulated cell growth/proliferation. Examples of cancer include but are not limited to, carcinoma, lymphoma, blastoma, sarcoma, and leukemia. More particular examples of such cancers include squamous cell cancer, small-cell lung cancer, pituitary cancer, esophageal cancer, astrocytoma, soft tissue sarcoma, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, renal cancer, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, and various types of head and neck cancer.

Dysregulation of angiogenesis can lead to many disorders that can be treated by compositions and methods of the invention. These disorders include both non-neoplastic and neoplastic conditions. Neoplastics include but are not limited those described above.

Non-neoplastic conditions that are amenable to treatment with antibodies and antibody fragments of the invention include, but are not limited to, e.g., undesired or aberrant hypertrophy, benign prostatic hypertrophy, pain (acute and chronic), including inflammatory pain, arthritis, rheumatoid arthritis ($R^4$), psoriatic arthritis, neurodegenerative diseases (e.g. Alzheimer's disease, AIDS-related dementia, Parkinson's disease, amyotrophic lateral sclerosis, retinitis pigmentosa, spinal muscular atrophy and cerebellar degeneration), autoimmune disease, psoriasis, psoriatic plaques, sarcoidosis, atherosclerosis, atherosclerotic plaques, Hashimoto's thyroiditis, angiogenic disorders, ocular disease such as presumed ocular histoplasmosis syndrome, retinal vascularization, diabetic and other proliferative retinopathies including retinopathy of prematurity, diabetic nephropathy, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular disease, conditions involving abnormal proliferation of vascular epithelial cells, vascular restenosis, Guillain-Barre Syndrome, polyps such as colon polyps, familial adenomatosis polyposis, nasal polyps or gastrointestinal polyps, gastrointestinal ulcers, infantile hypertrophic pyloric stenosis, urinary obstructive syndrome, Menetrier's disease, secreting adenomas or protein loss syndrome, fibroadenoma, respiratory disease, cholecystitis, neurofibromatosis, arteriovenous malformations (AVM), meningioma, hemangioma, angiofibroma, thyroid hyperplasias (including Grave's disease), corneal and other tissue transplantation, inflammatory diseases, chronic inflammation, lung inflammation, acute lung injury/ARDS, sepsis, chronic occlusive pulmonary disease, primary pulmonary hypertension, malignant pulmonary effusions, atheroma, edema following burns, trauma, radiation, stroke, hypoxia or ischemia, edema from myocardial infarction, ischemic injury, damage following a cerebral ischemic event, cerebral edema (e.g., associated with acute stroke/closed head injury/trauma), thrombus caused by platelet aggregation, fibrotic or edemia diseases such as hepatic cirrhosis, lung fibrosis, carcoidosis, throiditis, hyperviscosity syndrome systemic, synovial inflammation, pannus formation in RA, myositis ossificans, hypertropic bone formation, bone associated pathologies such as osteoarthritis, rickets and osteoporosis, refractory ascites, bone or joint inflammation, Myelodysplastic Syndrome, aplastic anemia, kidney or liver; T-cell mediated hypersensitivity disease, Paget's disease, polycystic kidney disease, 3rd spacing of fluid diseases (pancreatitis, compartment syndrome, burns, bowel disease), chronic inflammation such as IBD (Crohn's disease and ulcerative colitis), renal disorders, renal allograft rejection, graft versus host disease or transplant rejection, inflammatory bowel disease, acute and chronic nephropathies (including proliferative glomerulonephritis and diabetes-induced renal disease), nephrotic syndrome, undesired or aberrant tissue mass growth (non-cancer), obesity, adipose tissue mass growth, hemophilic joints, hypertrophic scars, inhibition of hair growth, Osler Weber-Rendu Syndrome, pyogenic granuloma retrolental fibroplasias, scleroderma, trachoma, vascular adhesions, synovitis, hypersensitivity reaction of the skin, skin disorders including psoriasis and dermatitis, eczema, photoaging (e.g. caused by UV radiation of human skin), hypertrophic scar formation, reproductive conditions such as endometriosis, ovarian hyperstimulation syndrome, polycystic ovarian disease, preeclampsia, dysfunctional uterine bleeding, or menometrorrhagia, uterine fibroids, premature labor, ascites, pericardial effusion (such as that associated with pericarditis), pleural effusion, endotoxic shock and fungal infection, certain microbial infections including microbial pathogens selected from adenovirus, hantaviruses, *Borrelia burgdorferi*, *Yersinia* spp., *Bordetella pertussis* and psychiatric disorders (e.g. schizophrenia, bipolar depression, autism, and attention deficit disorder).

The term "pre-cancerous" refers to a condition or a growth that typically precedes or develops into a cancer. A "pre-cancerous" growth will have cells that are characterized by abnormal cell cycle regulation, proliferation, or differentiation, which can be determined by markers of cell cycle regulation, cellular proliferation, or differentiation.

By "dysplasia" is meant any abnormal growth or development of tissue, organ, or cells. In certain embodiments, the dysplasia is high grade or precancerous.

By "metastasis" is meant the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream or lymphatics, and stopping at a distant site. At the new site, the cells establish a blood supply and can grow to form a life-threatening mass. In certain embodiments, the term metastatic tumor refers to a tumor that is capable of metastasizing, but has not yet metastasized to tissues or organs elsewhere in the body. In certain embodiments, the term metastatic tumor refers to a tumor that has metastasized to tissues or organs elsewhere in the body.

Both stimulatory and inhibitory molecular pathways within the tumor cell regulate this behavior, and interactions between the tumor cell and host cells in the distant site are also significant.

By "non-metastatic" is meant a cancer that is benign or that remains at the primary site and has not penetrated into the lymphatic or blood vessel system or to tissues other than the primary site. Generally, a non-metastatic cancer is any cancer that is a Stage 0, I, or II cancer, and occasionally a Stage III cancer.

The "pre-metastatic organ" or "pre-metastatic tissue" as used herein, refers to an organ or a tissue in which no cancer cells from a primary tumor or from another part of the body have been detected. In certain embodiments, the pre-metastatic organ or pre-metastatic tissue as used herein, refers to an organ or tissue that is in the phase before the spread of cancer cells from a primary tumor or from another part of the body to this organ or tissue have occurred. Examples of pre-metastatic organ or pre-metastatic tissue include, but not limited to, lung, liver, brain, ovary, bone and bone marrow.

By "primary tumor" or "primary cancer" is meant the original cancer and not a metastatic lesion located in another tissue, organ, or location in the subject's body.

The "metastatic organ" or "metastatic tissue" is used in the broadest sense, refers to an organ or a tissue in which the cancer cells from a primary tumor or the cancer cells from another part of the body have spread. Examples of metastatic organ and metastatic tissue include, but not limited to, lung, liver, brain, ovary, bone and bone marrow.

"Cancer recurrence" herein refers to a return of cancer following treatment, and includes return of cancer in the primary organ, as well as distant recurrence, where the cancer returns outside of the primary organ.

By "tumor burden" is meant the number of cancer cells, the size of a tumor, or the amount of cancer in the body. Tumor burden is also referred to as tumor load.

By "tumor number" is meant the number of tumors.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, decreasing the rate of disease progression, amelioration or palliation of the disease state, and remission or improved prognosis. In some embodiments, antibodies of the invention are used to delay development of a disease or disorder.

The term "anti-neoplastic composition" refers to a composition useful in treating cancer comprising at least one active therapeutic agent, e.g., "anti-cancer agent." Examples of therapeutic agents (e.g., anti-cancer agents) include, but are limited to, e.g., chemotherapeutic agents, growth inhibitory agents, cytotoxic agents, agents used in radiation therapy, anti-angiogenesis agents, apoptotic agents, anti-tubulin agents, and other-agents to treat cancer, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib (TARCEVA®), platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also included in the invention.

The term "anti-cancer therapy" or "cancer therapy" refers to a therapy useful in treating cancer. Examples of anti-cancer therapeutic agents include, but are limited to, e.g., chemotherapeutic agents, growth inhibitory agents, cytotoxic agents, agents used in radiation therapy, anti-angiogenic agents, apoptotic agents, anti-tubulin agents, and other agents to treat cancer, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib (TARCEVA®), platelet derived growth factor inhibitors (e.g., GLEEVEC® (Imatinib Mesylate)), a COX-2 inhibitor (e.g., celecoxib), Erbitux® (cetuximab, Imclone), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also included in the invention.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one time administration and typical dosages range from 10 to 200 units (Grays) per day.

The term "VEGF" or "VEGF-A" as used herein refers to the 165-amino acid human vascular endothelial cell growth factor and related 121-, 189-, and 206-amino acid human vascular endothelial cell growth factors, as described by Leung et al. (1989) Science 246:1306, and Houck et al. (1991) Mol. Endocrin, 5:1806, together with the naturally occurring allelic and processed forms thereof. The term "VEGF" also refers to VEGFs from non-human species such as mouse, rat or primate. Sometimes the VEGF from a specific species are indicated by terms such as hVEGF for human VEGF, mVEGF for murine VEGF, and etc. The term "VEGF" is also used to refer to truncated forms of the polypeptide comprising amino acids 8 to 109 or 1 to 109 of the 165-amino acid human vascular endothelial cell growth factor. Reference to any such forms of VEGF may be identified in the present application, e.g., by "VEGF (8-109)," "VEGF (1-109)," "VEGF-$A_{109}$" or "VEGF165." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF.

A "VEGF antagonist" refers to a molecule capable of neutralizing, blocking, inhibiting, abrogating, reducing or interfering with VEGF activities including, but not limited to, its binding to one or more VEGF receptors. VEGF antagonists include, without limitation, anti-VEGF antibodies and antigen-binding fragments thereof, receptor molecules and derivatives which bind specifically to VEGF thereby sequestering its binding to one or more receptors, anti-VEGF receptor antibodies, VEGF receptor antagonists such as small molecule inhibitors of the VEGFR tyrosine kinases and immunoadhesins that binds to VEGF such as VEGF Trap. The term "VEGF antagonist," as used herein, specifically includes molecules, including antibodies, antibody fragments, other binding polypeptides, peptides, and non-peptide small molecules, that bind to VEGF and are capable of neutralizing, blocking, inhibiting, abrogating, reducing or interfering with VEGF activities. Thus, the term "VEGF activities" specifically includes VEGF mediated biological activities of VEGF.

The terms "biological activity" and "biologically active" with regard to VEGF polypeptide or "VEGF activity" refer to physical/chemical properties and biological functions associated with full-length and/or truncated VEGF. In certain embodiments, VEGF activity is inducing and/or stimulating and/or promoting angiogenesis. In certain embodiments, VEGF activity is inducing and/or stimulating and/or promoting neovascularization. In certain embodiments, VEGF activity is inducing and/or modulating vascular permeability. In certain embodiments, VEGF activity is inducing and/or stimulating and/or promoting endothelial cell migration and/or endothelial cell proliferation.

Anti-VEGF neutralizing antibodies suppress the growth of a variety of human tumor cell lines in nude mice (Kim et al., *Nature* 362:841-844 (1993); Warren et al., *J. Clin. Invest.* 95:1789-1797 (1995); Borgström et al., *Cancer Res.* 56:4032-4039 (1996); Melnyk et al., *Cancer Res.* 56:921-924 (1996)) and also inhibit intraocular angiogenesis in models of ischemic retinal disorders. Adamis et al., *Arch. Ophthalmol.* 114:66-71 (1996).

The term "anti-VEGF antibody" or "an antibody that binds to VEGF" refers to an antibody that is capable of binding to VEGF with sufficient affinity and specificity that the antibody is useful as a diagnostic and/or therapeutic agent in targeting VEGF. For example, the anti-VEGF antibody of the invention can be used as a therapeutic agent in targeting and interfering with diseases or conditions wherein the VEGF activity is involved. See, e.g., U.S. Pat. Nos. 6,582,959, 6,703,020; WO98/45332; WO 96/30046; WO94/10202, WO2005/044853; EP 0666868B1; US Patent Applications 20030206899, 20030190317, 20030203409, 20050112126, 20050186208, and 20050112126; Popkov et al., *Journal of Immunological Methods* 288:149-164 (2004); and WO2005012359. The antibody selected will normally have a sufficiently strong binding affinity for VEGF. For example, the antibody may bind hVEGF with a $K_d$ value of between 100 nM-1 pM. Antibody affinities may be determined by a surface plasmon resonance based assay (such as the BIAcore assay as described in PCT Application Publication No. WO2005/012359); enzyme-linked immunoabsorbent assay (ELISA); and competition assays (e.g. RIA's), for example. The antibody may be subjected to other biological activity assays, e.g., in order to evaluate its effectiveness as a therapeutic. Such assays are known in the art and depend on the target antigen and intended use for the antibody. Examples include the HUVEC inhibition assay; tumor cell growth inhibition assays (as described in WO 89/06692, for example); antibody-dependent cellular cytotoxicity (ADCC) and complement-mediated cytotoxicity (CDC) assays (U.S. Pat. No. 5,500,362); and agonistic activity or hematopoiesis assays (see WO 95/27062). An anti-VEGF antibody will usually not bind to other VEGF homologues such as VEGF-B, VEGF-C, VEGF-D or VEGF-E, nor other growth factors such as P1GF, PDGF or bFGF. In one embodiment, anti-VEGF antibodies include a monoclonal antibody that binds to the same epitope as the monoclonal anti-VEGF antibody A4.6.1 produced by hybridoma ATCC HB 10709; a recombinant humanized anti-VEGF monoclonal antibody (see Presta et al. (1997) *Cancer Res.* 57:4593-4599), including but not limited to the antibody known as "bevacizumab (BV)," also known as "rhuMAb VEGF" or "AVASTIN®." AVASTIN® is presently commercially available. Bevacizumab comprises mutated human $IgG_1$ framework regions and antigen-binding complementarity-determining regions from the murine antibody A.4.6.1 that blocks binding of human VEGF to its receptors. Approximately 93% of the amino acid sequence of bevacizumab, including most of the framework regions, is derived from human $IgG_1$, and about 7% of the sequence is derived from A4.6.1. Bevacizumab has a molecular mass of about 149,000 daltons and is glycosylated. Bevacizumab and other humanized anti-VEGF antibodies are further described in U.S. Pat. No. 6,884,879, issued Feb. 26, 2005. Additional anti-VEGF antibodies include the G6 or B20 series antibodies (e.g., G6-23, G6-31, B20-4.1), as described in PCT Application Publication No. WO2005/012359. For additional preferred antibodies see U.S. Pat. Nos. 7,060,269, 6,582,959, 6,703,020; 6,054,297; WO98/45332; WO 96/30046; WO94/10202; EP 0666868B1; U.S. Patent Application Publication Nos. 2006009360, 20050186208, 20030206899, 20030190317, 20030203409, and 20050112126; and Popkov et al., *Journal of Immunological Methods* 288:149-164 (2004).

The term "B20 series polypeptide" as used herein refers to a polypeptide, including an antibody that binds to VEGF. B20 series polypeptides includes, but not limited to, antibodies derived from a sequence of the B20 antibody or a B20-derived antibody described in US Publication No. 20060280747, US Publication No. 20070141065 and/or US Publication No. 20070020267, the content of these patent applications are expressly incorporated herein by reference. In one embodiment, B20 series polypeptide is B20-4.1 as described in US Publication No. 20060280747, US Publication No. 20070141065 and/or US Publication No. 20070020267. In another embodiment, B20 series polypeptide is B20-4.1.1 described in PCT Publication No. WO 2009/073160, the entire disclosure of which is expressly incorporated herein by reference.

The term "G6 series polypeptide" as used herein refers to a polypeptide, including an antibody that binds to VEGF. G6 series polypeptides includes, but not limited to, antibodies derived from a sequence of the G6 antibody or a G6-derived antibody described in US Publication No. 20060280747, US Publication No. 20070141065 and/or US Publication No. 20070020267. G6 series polypeptides, as described in US Publication No. 20060280747, US Publication No. 20070141065 and/or US Publication No. 20070020267 include, but not limited to, G6-8, G6-23 and G6-31.

An "angiogenic factor or agent" is a growth factor which stimulates the development of blood vessels, e.g., promote angiogenesis, endothelial cell growth, stabiliy of blood vessels, and/or vasculogenesis, etc. For example, angiogenic factors, include, but are not limited to, e.g., VEGF and members of the VEGF family (VEGF-B, VEGF-C and VEGF-D), P1GF, PDGF family, fibroblast growth factor family (FGFs), TIE ligands (Angiopoietins), ephrins, delta-like ligand 4 (DLL4), Del-1, fibroblast growth factors: acidic (aFGF) and basic (bFGF), follistatin, granulocyte colony-stimulating factor (G-CSF), hepatocyte growth factor (HGF)/scatter factor (SF), Interleukin-8 (IL-8), leptin, midkine, neuropilins, placental growth factor, platelet-derived endothelial cell growth factor (PD-ECGF), platelet-derived growth factor, especially PDGF-BB or PDGFR-beta, pleiotrophin (PTN), progranulin, proliferin, transforming growth factor-alpha (TGF-alpha), transforming growth factor-beta (TGF-beta), tumor necrosis factor-alpha (TNF-alpha), etc. It would also include factors that accelerate wound healing, such as growth hormone, insulin-like growth factor-I (IGF-I), VIGF, epidermal growth factor (EGF), CTGF and members of its family, and TGF-alpha and TGF-beta. See, e.g., Klagsbrun and D'Amore (1991) *Annu. Rev. Physiol.* 53:217-39; Streit and Detmar (2003) *Oncogene* 22:3172-3179; Ferrara & Alitalo (1999) *Nature Medicine* 5(12):1359-1364; Tonini et al. (2003) *Oncogene* 22:6549-6556 (e.g., Table 1 listing known angiogenic factors); and, Sato (2003) *Int. J. Clin. Oncol.* 8:200-206.

An "anti-angiogenic agent" or "angiogenesis inhibitor" refers to a small molecular weight substance, a polynucleotide, a polypeptide, an isolated protein, a recombinant protein, an antibody, or conjugates or fusion proteins thereof, that inhibits angiogenesis, vasculogenesis, or undesirable vascular permeability, either directly or indirectly. For example, an anti-angiogenic agent is an antibody or other antagonist to an angiogenic agent as defined above, e.g., antibodies to VEGF, antibodies to VEGF receptors, small molecules that block VEGF receptor signaling (e.g., PTK787/ZK2284, SU6668, SUTENT®/SU11248 (sunitinib malate), AMG706). Anti-angiogenic agents also include native angiogenesis inhibitors, e.g., angiostatin, endostatin, etc. See, e.g., Klagsbrun and D'Amore, Annu. Rev. Physiol., 53:217-39 (1991); Streit and Detmar, Oncogene, 22:3172-3179 (2003) (e.g., Table 3 listing anti-angiogenic therapy in malignant melanoma); Ferrara & Alitalo, Nature Medicine 5(12):1359-1364 (1999); Tonini et al., Oncogene, 22:6549-6556 (2003) (e.g., Table 2 listing anti-angiogenic factors); and, Sato Int. J. Clin. Oncol., 8:200-206 (2003) (e.g., Table 1 lists Anti-angiogenic agents used in clinical trials). In certain embodiments, anti-angiogenic agent is an anti-VEGF agent, such as an anti-VEGF antibody (e.g., bevacizumab).

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "toxin" is any substance capable of having a detrimental effect on the growth or proliferation of a cell.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Nicolaou et al., *Angew. Chem. Intl. Ed. Engl.*, 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including ADRIAMYCINO, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), pemetrexed (ALIMTA®); tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®);

dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g. celecoxib or etoricoxib), proteosome inhibitor (e.g. PS341); bortezomib (VELCADE®); CCl-779; tipifarnib (R11577); orafenib, ABT510; Bcl-2 inhibitor such as oblimersen sodium (GENASENSE®); pixantrone; EGFR inhibitors (see definition below); tyrosine kinase inhibitors (see definition below); serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents as defined herein include "anti-hormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and nonsteroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releaseing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

A "growth inhibitory agent" when used herein refers to a compound or composition which inhibits growth of a cell (such as a cell expressing Bv8) either in vitro or in vivo. Thus, the growth inhibitory agent may be one which significantly reduces the percentage of cells (such as a cell expressing Bv8) in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., *The Molecular Basis of Cancer*, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Doxorubicin" is an anthracycline antibiotic. The full chemical name of doxorubicin is (8S-cis)-10-[(3-amino-2,3, 6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione.

The term "Fc region-comprising polypeptide" refers to a polypeptide, such as an antibody or immunoadhesin (see definitions below), which comprises an Fc region. The C-terminal lysine (residue 447 according to the EU numbering system) of the Fc region may be removed, for example, during purification of the polypeptide or by recombinant engineering the nucleic acid encoding the polypeptide. Accordingly, a composition comprising a polypeptide having an Fc region according to this invention can comprise polypeptides with K447, with all K447 removed, or a mixture of polypeptides with and without the K447 residue.

An "individual," "subject," or "patient" is a vertebrate. In certain embodiments, the vertebrate is a mammal. Mammals include, but are not limited to, farm animals (such as cows), sport animals, pets (such as cats, dogs, and horses), primates, mice and rats. In certain embodiments, a mammal is a human.

An "effective amount" refers to an amount effective, at dosages and for periods of time necessary, to achieve the desired therapeutic or prophylactic result.

A "therapeutically effective amount" of a substance/molecule of the invention, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

"Refractory" refers to the resistance or non-responsiveness of a disease or condition to a treatment (e.g., the number of neoplastic plasma cells increases even though treatment if given). In certain embodiments, the term "refractory" refers a resistance or non-responsiveness to any previous treatment including, but not limited to, VEGF antagonist, anti-angiogenic agents and chemotherapy treatments. In certain embodiments, the term "refractory" refers an intrinsically non-responsiveness of a disease or condition to any previous treatment comprising a VEGF antagonist, anti-angiogenic agents and/or chemotherapy treatments. In certain embodiments, the VEGF antagonist is an anti-VEGF antibody.

"Relapsed" refers to the regression of the patient's illness back to its former diseased state, especially the return of symptoms following an apparent recovery or partial recovery. In certain embodiments, relapsed state refers to the process of returning to or the return to illness before the previous treatment including, but not limited to, VEGF antagonist, anti-angiogenic agents and/or chemotherapy treatments. In certain embodiments, relapsed state refers to the process of returning to or the return to illness after an initial strong response to a cancer therapy comprising a VEGF antagonist, anti-angiogenic agents and/or chemotherapy treatments. In certain embodiments, the VEGF antagonist is an anti-VEGF antibody.

The term "efficacy" is used herein in the broadest sense and refers to immunoglobuin's, antibody's or Fc fusion protein's ability to produce a desired effect. In certain embodiments, efficacy refers to the maximal observed effect of an immunoglobulin, antibody or Fc fusion protein at saturating levels. In certain embodiments, efficacy refers to the $EC_{50}$ of an immunoglobulin, antibody or Fc fusion protein. In certain embodiments, efficacy refers to the potency of an immunoglobulin, antibody or Fc fusion protein. In certain embodiments, efficacy refers to immunoglobulin's, antibody's or Fc fusion protein's ability to produce beneficial effects on the course or duration of a disease, including clinical benefit as defined herein.

The term "$EC_{50}$" refers to the concentration of an immunoglobulin, antibody or Fc fusion protein which induces a response halfway between the baseline and maximum. In certain embodiments, $EC_{50}$ represents the concentration of an immunoglobulin, antibody or Fc fusion protein where 50% of its maximal effect is observed. In certain embodiments, $EC_{50}$ represents the plasma or serum concentration required for obtaining 50% of the maximum effect in vivo.

Efficacy in treating cancer may be demonstrated by detecting the ability of an antibody, a fusion protein, a conjugated molecule, or a composition of the invention to inhibit or reduce the growth or metastasis of cancerous cells or to ameliorate or alleviate one or more symptoms associated with cancer. The treatment is considered therapeutic if there is, for example, a reduction in the growth or metastasis of cancerous cells, amelioration of one or more symptoms associated with cancer, or a decrease in mortality and/or morbidity following administration of an antibody, a fusion protein, a conjugated molecule, or a composition of the invention. Antibodies, fusion proteins or compositions of the invention can be tested for their ability to reduce tumor formation in in vitro, ex vivo, and in vivo assays. For cancer therapy, efficacy in vivo can, for example, be also measured by assessing the duration of survival, time to disease progression (TTP), the response rates (RR), duration of response, and/or quality of life.

Clinical benefit can be measured by assessing various endpoints, e.g., inhibition, to some extent, of disease progression, including slowing down and complete arrest; reduction in the number of disease episodes and/or symptoms; reduction in lesion size; inhibition (i.e., reduction, slowing down or complete stopping) of disease cell infiltration into adjacent peripheral organs and/or tissues; inhibition (i.e. reduction, slowing down or complete stopping) of disease spread; decrease of auto-immune response, which may, but does not have to, result in the regression or ablation of the disease lesion; relief, to some extent, of one or more symptoms associated with the disorder; increase in the length of disease-free presentation following treatment, e.g., progression-free survival; increased overall survival; higher response rate; and/or decreased mortality at a given point of time following treatment.

By "maintenance therapy" is meant a therapeutic regimen that is given to reduce the likelihood of disease recurrence or progression. Maintenance therapy can be provided for any length of time, including extended time periods up to the life-span of the subject. Maintenance therapy can be provided after initial therapy or in conjunction with initial or additional therapies. Dosages used for maintenance therapy can vary and can include diminished dosages as compared to dosages used for other types of therapy.

"Adjuvant therapy" herein refers to therapy given after surgery, where no evidence of residual disease can be detected, so as to reduce the risk of disease recurrence. The goal of adjuvant therapy is to prevent recurrence of the cancer, and therefore to reduce the chance of cancer-related death.

Administration "in combination with" one or more further therapeutic agents includes simultaneous (concurrent) and consecutive administration in any order.

The term "simultaneously" or "concurrently" is used herein to refer to administration of two or more therapeutic agents, where at least part of the administration overlaps in time. Accordingly, concurrent administration includes a dosing regimen when the administration of one or more agent(s) continues after discontinuing the administration of one or more other agent(s).

A "biological sample" (interchangeably termed "sample" or "tissue or cell sample") encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes cells in culture, cell supernatants, cell lysates, serum, plasma, biological fluid, and tissue samples. The source of the biological sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. In some embodiments, the biological sample is obtained from a primary or metastatic tumor. The biological sample may contain compounds which are not naturally intermixed with the tissue in nature such as preservatives, anticoagulants, buffers, fixatives, nutrients, antibiotics, or the like.

For the purposes herein a "section" of a tissue sample is meant a single part or piece of a tissue sample, e.g. a thin slice of tissue or cells cut from a tissue sample. It is understood that multiple sections of tissue samples may be taken and subjected to analysis according to the present invention. In some embodiments, the same section of tissue sample is analyzed at both morphological and molecular levels, or is analyzed with respect to both protein and nucleic acid.

The term "pharmaceutical formulation", "pharmaceutical composition" or "therapeutic formulation" refers to a preparation which is in such form as to permit the biological activity of the active ingredient to be effective, and which contains no additional components which are unacceptably toxic to a subject to which the formulation would be administered. Such formulations may be sterile.

A "sterile" formulation is aseptic or free from all living microorganisms and their spores.

The word "label" when used herein refers to a compound or composition which is conjugated or fused directly or indirectly to a reagent such as a nucleic acid probe or an antibody and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which is detectable.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

A "liposome" is a small vesicle composed of various types of lipids, phospholipids and/or surfactant which is useful for delivery of a drug to a mammal The components of the liposome are commonly arranged in a bilayer formation, similar to the lipid arrangement of biological membranes.

Compositions

The anti-Bv8 antibodies of the invention are preferably monoclonal. Also encompassed within the scope of the invention are Fab, Fab', Fab'-SH and F(ab')$_2$ fragments of the anti-Bv8 antibodies provided herein. These antibody fragments can be created by traditional means, such as enzymatic digestion, or may be generated by recombinant techniques. Such antibody fragments may be chimeric or humanized. These fragments are useful for the diagnostic and therapeutic purposes set forth below.

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

The anti-Bv8 monoclonal antibodies of the invention can be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized to elicit lymphocytes that produce or are capable of producing antibodies that will specifically bind to the protein used for immunization. Antibodies to Bv8 may be raised in animals by multiple subcutaneous (sc) or intraperitoneal (ip) injections of Bv8 and an adjuvant. Bv8 may be prepared using methods well-known in the art, some of which are further described herein. For example, recombinant production of human and mouse Bv8 is described below. In one embodiment, animals are immunized with a Bv8 fused to the Fc portion of an immunoglobulin heavy chain. In a preferred embodiment, animals are immunized with a Bv8-IgG1 fusion protein. Animals ordinarily are immunized against immunogenic conjugates or derivatives of Bv8 with monophosphoryl lipid A (MPL)/trehalose dicrynomycolate (TDM) (Ribi Immunochem. Research, Inc., Hamilton, Mont.) and the solution is injected intradermally at multiple sites. Two weeks later the animals are boosted. 7 to 14 days later animals are bled and the serum is assayed for anti-Bv8 titer. Animals are boosted until titer plateaus.

Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against Bv8. Preferably, the binding specificity of monoclonal antibodies produced by hybridoma cells is determined by immunoprecipitation or by an in vitro binding assay, such as radioimmunoassay (RIA) or enzyme-linked immunoadsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

The anti-Bv8 antibodies of the invention can be made by using combinatorial libraries to screen for synthetic antibody clones with the desired activity or activities. In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the anti-Bv8 antibodies of the invention can be obtained by designing a suitable antigen screening procedure to select for the phage clone of interest followed by construction of a full length anti-Bv8 antibody clone using the Fv sequences from the phage clone of interest and suitable constant region (Fc) sequences described in Kabat et al., *Sequences of Proteins of Immunological Interest*, Fifth Edition, NIH Publication 91-3242, Bethesda Md. (1991), vols. 1-3.

The antigen-binding domain of an antibody is formed from two variable (V) regions of about 110 amino acids, one each from the light (VL) and heavy (VH) chains, that both present three hypervariable loops or complementarity-determining regions (CDRs). Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described in Winter et al., *Ann. Rev. Immunol.*, 12: 433-455 (1994). As used herein, scFv encoding phage clones and Fab encoding phage clones are collectively referred to as "Fv phage clones" or "Fv clones".

Repertoires of VH and VL genes can be separately cloned by polymerase chain reaction (PCR) and recombined randomly in phage libraries, which can then be searched for antigen-binding clones as described in Winter et al., *Ann. Rev. Immunol.*, 12: 433-455 (1994). Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., *EMBO J*, 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, *J. Mol. Biol.*, 227: 381-388 (1992).

Filamentous phage is used to display antibody fragments by fusion to the minor coat protein pIII. The antibody fragments can be displayed as single chain Fv fragments, in which VH and VL domains are connected on the same polypeptide chain by a flexible polypeptide spacer, e.g., as described by Marks et al., *J. Mol. Biol.*, 222: 581-597 (1991), or as Fab fragments, in which one chain is fused to pIII and the other is secreted into the bacterial host cell periplasm where assembly of a Fab-coat protein structure which becomes displayed on the phage surface by displacing some of the wild type coat proteins, e.g., as described in Hoogenboom et al., *Nuci. Acids Res.*, 19: 4133-4137 (1991).

In general, nucleic acids encoding antibody gene fragments are obtained from immune cells harvested from humans or animals. If a library biased in favor of anti-Bv8 clones is desired, the individual is immunized with Bv8 to generate an antibody response, and spleen cells and/or circulating B cells other peripheral blood lymphocytes (PBLs) are recovered for library construction. In a preferred embodiment, a human antibody gene fragment library biased in favor of anti-Bv8 clones is obtained by generating an anti-Bv8 antibody response in transgenic mice carrying a functional human immunoglobulin gene array (and lacking a functional endogenous antibody production system) such that Bv8 immunization gives rise to B cells producing human antibodies against Bv8. The generation of human antibody-producing transgenic mice is described below.

Additional enrichment for anti-Bv8 reactive cell populations can be obtained by using a suitable screening procedure to isolate B cells expressing Bv8-specific membrane bound antibody, e.g., by cell separation with Bv8 affinity chromatography or adsorption of cells to fluorochrome-labeled Bv8 followed by flow-activated cell sorting (FACS).

Alternatively, the use of spleen cells and/or B cells or other PBLs from an unimmunized donor provides a better representation of the possible antibody repertoire, and also permits the construction of an antibody library using any animal (human or non-human) species in which Bv8 is not antigenic. For libraries incorporating in vitro antibody gene construction, stem cells are harvested from the individual to provide nucleic acids encoding unrearranged antibody gene segments. The immune cells of interest can be obtained from a variety of animal species, such as human, mouse, rat, lagomorpha, luprine, canine, feline, porcine, bovine, equine, and avian species, etc.

Nucleic acid encoding antibody variable gene segments (including VH and VL segments) are recovered from the cells of interest and amplified. In the case of rearranged VH and VL gene libraries, the desired DNA can be obtained by isolating genomic DNA or mRNA from lymphocytes followed by polymerase chain reaction (PCR) with primers matching the 5' and 3' ends of rearranged VH and VL genes as described in Orlandi et al., *Proc. Natl. Acad. Sci.* (USA), 86: 3833-3837 (1989), thereby making diverse V gene repertoires for expression. The V genes can be amplified from cDNA and genomic DNA, with back primers at the 5' end of the exon encoding the mature V-domain and forward primers based within the J-segment as described in Orlandi et al. (1989) and in Ward et al., *Nature*, 341: 544-546 (1989). However, for amplifying from cDNA, back primers can also be based in the leader exon as described in Jones et al., *Biotechnol.*, 9: 88-89 (1991), and forward primers within the constant region as described in Sastry et al., *Proc. Natl. Acad. Sci.* (USA), 86: 5728-5732 (1989). To maximize complementarity, degeneracy can be incorporated in the primers as described in Orlandi et al. (1989) or Sastry et al. (1989). Preferably, the library diversity is maximized by using PCR primers targeted to each V-gene family in order to amplify all available VH and VL arrangements present in the immune cell nucleic acid sample, e.g. as described in the method of Marks et al., *J. Mol. Biol.,* 222: 581-597 (1991) or as described in the method of Orum et al., *Nucleic Acids Res.,* 21: 4491-4498 (1993). For cloning of the amplified DNA into expression vectors, rare restriction sites can be introduced within the PCR primer as a tag at one end as described in Orlandi et al. (1989), or by further PCR amplification with a tagged primer as described in Clackson et al., *Nature,* 352: 624-628 (1991).

Repertoires of synthetically rearranged V genes can be derived in vitro from V gene segments. Most of the human VH-gene segments have been cloned and sequenced (reported in Tomlinson et al., *J. Mol. Biol.,* 227: 776-798 (1992)), and mapped (reported in Matsuda et al., *Nature Genet.,* 3: 88-94 (1993); these cloned segments (including all the major conformations of the H1 and H2 loop) can be used to generate diverse VH gene repertoires with PCR primers encoding H3 loops of diverse sequence and length as described in Hoogenboom and Winter, J. Mol. Biol., 227: 381-388 (1992). VH repertoires can also be made with all the sequence diversity focused in a long H3 loop of a single length as described in Barbas et al., *Proc. Natl. Acad. Sci. USA,* 89: 4457-4461 (1992). Human Vκ and Vλ segments have been cloned and sequenced (reported in Williams and Winter, *Eur. J. Immunol.,* 23: 1456-1461 (1993)) and can be used to make synthetic light chain repertoires. Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, *J. Mol. Biol.,* 227: 381-388 (1992).

Repertoires of antibody fragments can be constructed by combining VH and VL gene repertoires together in several ways. Each repertoire can be created in different vectors, and the vectors recombined in vitro, e.g., as described in Hogrefe et al., *Gene,* 128:119-126 (1993), or in vivo by combinatorial infection, e.g., the loxP system described in Waterhouse et al., *Nuci. Acids Res.,* 21:2265-2266 (1993). The in vivo recombination approach exploits the two-chain nature of Fab fragments to overcome the limit on library size imposed by *E. coli* transformation efficiency. Naive VH and VL repertoires are cloned separately, one into a phagemid and the other into a phage vector. The two libraries are then combined by phage infection of phagemid-containing bacteria so that each cell contains a different combination and the library size is limited only by the number of cells present (about $10^{12}$ clones). Both vectors contain in vivo recombination signals so that the VH and VL genes are recombined onto a single replicon and are co-packaged into phage virions. These huge libraries provide large numbers of diverse antibodies of good affinity ($K_d^{-1}$ of about $10^{-8}$ M).

Alternatively, the repertoires may be cloned sequentially into the same vector, e.g., as described in Barbas et al., *Proc. Natl. Acad. Sci. USA,* 88:7978-7982 (1991), or assembled together by PCR and then cloned, e.g. as described in Clackson et al., *Nature,* 352: 624-628 (1991). PCR assembly can also be used to join VH and VL DNAs with DNA encoding a flexible peptide spacer to form single chain Fv (scFv) repertoires. In yet another technique, "in cell PCR assembly" is used to combine VH and VL genes within lymphocytes by PCR and then clone repertoires of linked genes as described in Embleton et al., *Nuci. Acids Res.,* 20:3831-3837 (1992).

The antibodies produced by naive libraries (either natural or synthetic) can be of moderate affinity ($K_d^{-1}$ of about $10^6$ to $10^7$ $M^{-1}$), but affinity maturation can also be mimicked in vitro by constructing and reselecting from secondary libraries as described in Winter et al. (1994), supra. For example, mutations can be introduced at random in vitro by using error-prone polymerase (reported in Leung et al., *Technique,* 1:11-15 (1989)) in the method of Hawkins et al., *J. Mol. Biol.,* 226: 889-896 (1992) or in the method of Gram et al., *Proc. Natl. Acad. Sci. USA,* 89: 3576-3580 (1992). Additionally, affinity maturation can be performed by randomly mutating one or more CDRs, e.g. using PCR with primers carrying random sequence spanning the CDR of interest, in selected individual Fv clones and screening for higher affinity clones. WO 96/07754 (published 14 Mar. 1996) described a method for inducing mutagenesis in a complementarity determining region of an immunoglobulin light chain to create a library of light chain genes. Another effective approach is to recombine the VH or VL domains selected by phage display with repertoires of naturally occurring V domain variants obtained from unimmunized donors and screen for higher affinity in several rounds of chain reshuffling as described in Marks et al., *Biotechnol.,* 10:779-783 (1992). This technique allows the production of antibodies and antibody fragments with affinities in the $10^{-9}$ M range.

Bv8 nucleic acid and amino acid sequences are known in the art, for example, in Wechselberger et al. (*FEBS Lett.* 462:177-181 (1999)) and Li et al. (*Mol. Pharm.* 59:692-698 (2001)). Nucleic acids encoding Bv8 can be prepared by a variety of methods known in the art. These methods include, but are not limited to, chemical synthesis by any of the methods described in Engels et al., *Agnew. Chem. Int. Ed. Engl.,* 28: 716-734 (1989), such as the triester, phosphite, phosphoramidite and H-phosphonate methods. In one embodiment, codons preferred by the expression host cell are used in the design of the Bv8 encoding DNA. Alternatively, DNA encoding the Bv8 can be isolated from a genomic or cDNA library.

Following construction of the DNA molecule encoding the Bv8, the DNA molecule is operably linked to an expression control sequence in an expression vector, such as a plasmid, wherein the control sequence is recognized by a host cell transformed with the vector. In general, plasmid vectors contain replication and control sequences which are derived from species compatible with the host cell. The vector ordinarily carries a replication site, as well as sequences which encode proteins that are capable of providing phenotypic selection in transformed cells. Suitable vectors for expression in prokaryotic and eukaryotic host cells are known in the art and some are further described herein. Eukaryotic organisms, such as yeasts, or cells derived from multicellular organisms, such as mammals, may be used.

Optionally, the DNA encoding the Bv8 is operably linked to a secretory leader sequence resulting in secretion of the expression product by the host cell into the culture medium. Examples of secretory leader sequences include stII, ecotin, lamB, herpes GD, 1 pp, alkaline phosphatase, invertase, and alpha factor. Also suitable for use herein is the 36 amino acid leader sequence of protein A (Abrahmsen et al., *EMBO J.,* 4: 3901 (1985)).

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ precipitation and electroporation. Successful transfection is generally recognized when any indication of the operation of this vector occurs within the host cell. Methods for transfection are well known in the art, and some are further described herein.

Transformation means introducing DNA into an organism so that the DNA is replicable, either as an extrachromosomal element or by chromosomal integrant. Depending on the host cell used, transformation is done using standard techniques appropriate to such cells. Methods for transformation are well known in the art, and some are further described herein.

Prokaryotic host cells used to produce the Bv8 can be cultured as described generally in Sambrook et al., supra.

The mammalian host cells used to produce the Bv8 can be cultured in a variety of media, which is well known in the art and some of which is described herein.

The host cells referred to in this disclosure encompass cells in in vitro culture as well as cells that are within a host animal.

Purification of Bv8 may be accomplished using art-recognized methods, some of which are described herein.

The purified Bv8 can be attached to a suitable matrix such as agarose beads, acrylamide beads, glass beads, cellulose, various acrylic copolymers, hydroxylmethacrylate gels, polyacrylic and polymethacrylic copolymers, nylon, neutral and ionic carriers, and the like, for use in the affinity chromatographic separation of phage display clones. Attachment of the Bv8 protein to the matrix can be accomplished by the methods described in *Methods in Enzymology*, vol. 44 (1976). A commonly employed technique for attaching protein ligands to polysaccharide matrices, e.g. agarose, dextran or cellulose, involves activation of the carrier with cyanogen halides and subsequent coupling of the peptide ligand's primary aliphatic or aromatic amines to the activated matrix.

Alternatively, Bv8 can be used to coat the wells of adsorption plates, expressed on host cells affixed to adsorption plates or used in cell sorting, or conjugated to biotin for capture with streptavidin-coated beads, or used in any other art-known method for panning phage display libraries.

The phage library samples are contacted with immobilized Bv8 under conditions suitable for binding of at least a portion of the phage particles with the adsorbent. Normally, the conditions, including pH, ionic strength, temperature and the like are selected to mimic physiological conditions. The phages bound to the solid phase are washed and then eluted by acid, e.g. as described in Barbas et al., *Proc. Natl. Acad. Sci. USA*, 88: 7978-7982 (1991), or by alkali, e.g. as described in Marks et al., *J. Mol. Biol.*, 222: 581-597 (1991), or by Bv8 antigen competition, e.g. in a procedure similar to the antigen competition method of Clackson et al., *Nature*, 352: 624-628 (1991). Phages can be enriched 20-1.000-fold in a single round of selection. Moreover, the enriched phages can be grown in bacterial culture and subjected to further rounds of selection.

The efficiency of selection depends on many factors, including the kinetics of dissociation during washing, and whether multiple antibody fragments on a single phage can simultaneously engage with antigen. Antibodies with fast dissociation kinetics (and weak binding affinities) can be retained by use of short washes, multivalent phage display and high coating density of antigen in solid phase. The high density not only stabilizes the phage through multivalent interactions, but favors rebinding of phage that has dissociated. The selection of antibodies with slow dissociation kinetics (and good binding affinities) can be promoted by use of long washes and monovalent phage display as described in Bass et al., *Proteins*, 8: 309-314 (1990) and in WO 92/09690, and a low coating density of antigen as described in Marks et al., *Biotechnol.*, 10: 779-783 (1992).

It is possible to select between phage antibodies of different affinities, even with affinities that differ slightly, for Bv8. However, random mutation of a selected antibody (e.g. as performed in some of the affinity maturation techniques described above) is likely to give rise to many mutants, most binding to antigen, and a few with higher affinity. With limiting Bv8, rare high affinity phage could be competed out. To retain all the higher affinity mutants, phages can be incubated with excess biotinylated Bv8, but with the biotinylated Bv8 at a concentration of lower molarity than the target molar affinity constant for Bv8. The high affinity-binding phages can then be captured by streptavidin-coated paramagnetic beads. Such "equilibrium capture" allows the antibodies to be selected according to their affinities of binding, with sensitivity that permits isolation of mutant clones with as little as two-fold higher affinity from a great excess of phages with lower affinity. Conditions used in washing phages bound to a solid phase can also be manipulated to discriminate on the basis of dissociation kinetics.

Bv8 clones may be activity selected. In one embodiment, the invention provides Bv8 antibodies that block the binding between a Bv8 and its ligand (e.g., Bv8 receptors PKR1 and PKR2). Fv clones corresponding to such Bv8 antibodies can be selected by (1) isolating Bv8 clones from a phage library as described above, and optionally amplifying the isolated population of phage clones by growing up the population in a suitable bacterial host; (2) selecting Bv8 and a second protein against which blocking and non-blocking activity, respectively, is desired; (3) adsorbing the anti-Bv8 phage clones to immobilized Bv8; (4) using an excess of the second protein to elute any undesired clones that recognize Bv8-binding determinants which overlap or are shared with the binding determinants of the second protein; and (5) eluting the clones which remain adsorbed following step (4). Optionally, clones with the desired blocking/non-blocking properties can be further enriched by repeating the selection procedures described herein one or more times.

DNA encoding the hybridoma-derived monoclonal antibodies or phage display Fv clones of the invention is readily isolated and sequenced using conventional procedures (e.g., by using oligonucleotide primers designed to specifically amplify the heavy and light chain coding regions of interest from hybridoma or phage DNA template). Once isolated, the DNA can be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of the desired monoclonal antibodies in the recombinant host cells. Review articles on recombinant expression in bacteria of antibody-encoding DNA include Skerra et al., *Curr. Opinion in Immunol.*, 5: 256 (1993) and Pluckthun, *Immunol. Revs*, 130:151 (1992).

DNA encoding the Fv clones of the invention can be combined with known DNA sequences encoding heavy chain and/or light chain constant regions (e.g., the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. A Fv clone derived from the variable domain DNA of one animal (such as human) species and then fused to constant region DNA of another animal species to form coding sequence(s) for "hybrid," full length heavy chain and/or light chain is included in the definition of "chimeric" and "hybrid" antibody as used herein. In a preferred embodiment, a Fv clone derived from human variable DNA is fused to human constant region DNA to form coding sequence(s) for all human, full or partial length heavy and/or light chains.

DNA encoding anti-Bv8 antibody derived from a hybridoma of the invention can also be modified, for example, by substituting the coding sequence for human heavy- and light-chain constant domains in place of homologous murine sequences derived from the hybridoma clone (e.g., as in the method of Morrison et al., *Proc. Natl. Acad. Sci. USA*, 81:6851-6855 (1984)). DNA encoding a hybridoma or Fv clone-derived antibody or fragment can be further modified by covalently joining to the immunoglobulin coding sequence all or part of the coding sequence for a non-immunoglobulin polypeptide. In this manner, "chimeric" or "hybrid" antibodies are prepared that have the binding specificity of the Fv clone or hybridoma clone-derived antibodies of the invention.

Antibody Fragments

The present invention encompasses antibody fragments. Antibody fragments may be generated by traditional means, such as enzymatic digestion, or by recombinant techniques. In certain circumstances there are advantages of using antibody fragments, rather than whole antibodies. The smaller size of the fragments allows for rapid clearance, and may lead to improved access to solid tumors. For a review of certain antibody fragments, see Hudson et al. (2003) Nat. Med. 9:129-134.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science*, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Fab and F(ab')$_2$ fragment with increased in vivo half-life comprising salvage receptor binding epitope residues are described in U.S. Pat. No. 5,869,046. Other techniques for the production of antibody fragments will be apparent to the skilled practitioner. In certain embodiments, an antibody is a single chain Fv fragment (scFv). See WO 93/16185; U.S. Pat. Nos. 5,571,894; and 5,587,458. Fv and scFv are the only species with intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. See *Antibody Engineering*, ed. Borrebaeck, supra. The antibody fragment may also be a "linear antibody", e.g., as described in U.S. Pat. No. 5,641,870, for example. Such linear antibodies may be monospecific or bispecific.

Humanized Antibodies

The invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) *Nature* 321:522-525; Riechmann et al. (1988) *Nature* 332:323-327; Verhoeyen et al. (1988) *Science* 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies can be important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody. See, e.g., Sims et al. (1993) *J. Immunol.* 151:2296; Chothia et al. (1987) *J. Mol. Biol.* 196:901. Another method uses a particular framework derived from the consensus sequence of all human antibodies of a particular subgroup of light or heavy chains. The same framework may be used for several different humanized antibodies. See, e.g., Carter et al. (1992) *Proc. Natl. Acad. Sci. USA*, 89:4285; Presta et al. (1993) *J. Immunol.*, 151:2623.

It is further generally desirable that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Human Antibodies

Human antibodies of the invention can be constructed by combining Fv clone variable domain sequence(s) selected from human-derived phage display libraries with known human constant domain sequences(s) as described above. Alternatively, human monoclonal antibodies of the invention can be made by the hybridoma method. Human myeloma and mouse-human heteromyeloma cell lines for the production of human monoclonal antibodies have been described, for example, by Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).

It is now possible to produce transgenic animals (e.g. mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA,* 90: 2551 (1993); Jakobovits et al., *Nature,* 362: 255 (1993); Bruggermann et al., *Year in Immunol.,* 7: 33 (1993).

Gene shuffling can also be used to derive human antibodies from non-human, e.g. rodent, antibodies, where the human antibody has similar affinities and specificities to the starting non-human antibody. According to this method, which is also called "epitope imprinting", either the heavy or light chain variable region of a non-human antibody fragment obtained by phage display techniques as described herein is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (see PCT WO 93/06213 published Apr. 1, 1993). Unlike traditional humanization of non-human antibodies by HVR grafting, this technique provides completely human antibodies, which have no FR or HVR residues of non-human origin.

Multispecific Antibodies

One example of a multispecific antibody of this invention includes an antibody that binds to Bv8 and to another antigen. In other embodiments, multispecific antibodies may bind to two different epitopes of Bv8. Multispecific antibodies may also be used to localize cytotoxic agents to cells which express Bv8. These antibodies possess a Bv8-binding arm and an arm which binds a cytotoxic agent, such as, e.g., saporin, anti-interferon-α, vinca alkaloid, ricin A chain, methotrexate or radioactive isotope hapten. Multispecific antibodies can be prepared as full length antibodies or antibody fragments (e.g. F(ab')$_2$ bispecific antibodies).

Various methods for making bispecific antibodies have been described in the art. One of the first approaches involved co-expression of two immunoglobulin heavy chain-light chain pairs, where the two heavy chains have different specificities (Milstein and Cuello, *Nature,* 305: 537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829 published May 13, 1993, and in Traunecker et al., *EMBO J.,* 10: 3655 (1991).

According to a different approach, antibody variable domains are fused to immunoglobulin constant domain sequences. The fusion, for example, is with an immunoglobulin heavy chain constant domain, comprising at least part of the hinge, CH2, and CH3 regions. In certain embodiments, the first heavy-chain constant region (CH1) is present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology,* 121:210 (1986).

According to another approach, "knob-into-hole" or "KnH" technology refers to a technology that directs the pairing of two polypeptides together in vitro or in vivo by introducing a pertuberance (knob) into one polypeptide and a cavity (hole) into the other polypeptide at an interface in which they interact. For example, KnHs have been introduced in the Fc:Fc binding interfaces, CL:CH$_1$ interfaces or VH/VL interfaces of antibodies (e.g., US20007/0178552, WO 96/027011, WO 98/050431 and Zhu et al. (1997) Protein Science 6:781-788). This is especially useful in driving the pairing of two different heavy chains together during the manufacture of multispecific antibodies. For example, multispecific antibodies having KnH in their Fc regions can further comprise single variable domains linked to each Fc region, or further comprise different heavy chain variable domains that pair with similar or different light chain variable domains. According to one embodiment, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Multipecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/00373, and EP 03089). Heteroconjugate antibodies may be made using any convenient cross-linking method. Suitable cross-linking agents and techniques are known (e.g., U.S. Pat. No. 4,676,980).

Techniques for generating multispecific antibodies from antibody fragments have also been described in the literature. For example, bispecific antibodies can be prepared using chemical linkage. Brennan et al., *Science,* 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab'-SH fragments can be recovered from *E. coli* and can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. In certain embodiments, the dimerization domain comprises (or consists of) an Fc region or a hinge region. In this scenario, the antibody will comprise an Fc region and three or more antigen binding sites amino-terminal to the Fc region. In certain embodiments, a multivalent antibody comprises (or consists of) three to about eight antigen binding sites. In one such embodiment, a multivalent antibody comprises (or consists of) four antigen binding sites. The multivalent antibody comprises at least one polypeptide chain (for example, two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is one polypeptide chain of an Fc region, X$_1$ and X$_2$ represent an amino acid or polypeptide, and n is 0 or 1. For instance, the polypeptide chain(s) may comprise: VH—CH1-flexible linker-VH—CH1-Fc region chain; or VH—CH1-VH—CH1-Fc region chain. The multivalent antibody herein may further comprise at least two (for example, four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Single-Domain Antibodies

In certain embodiments, an anti-Bv8 antibody of the invention is a single-domain antibody. A single-domain antibody is a single polypeptide chain comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1). In one embodiment, a single-domain antibody consists of all or a portion of the heavy chain variable domain of an antibody.

Antibody Variants

In some embodiments, amino acid sequence modification(s) of the anti-Bv8 antibodies described herein are contemplated. For example, it may be desirable to improve the binding affinity and/or other biological properties of the antibody Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) *Science*, 244: 1081-1085. Here, a residue or group of target residues are identified (e.g., charged residues such as arg, asp, his, lys, and glu) and replaced by a neutral or negatively charged amino acid (e.g., alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

In certain embodiments, an antibody of the invention is altered to increase or decrease the extent to which the antibody is glycosylated. Glycosylation of polypeptides is typically either N-linked or O-linked. N-linked refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition or deletion of glycosylation sites to the antibody is conveniently accomplished by altering the amino acid sequence such that one or more of the above-described tripeptide sequences (for N-linked glycosylation sites) is created or removed. The alteration may also be made by the addition, deletion, or substitution of one or more serine or threonine residues to the sequence of the original antibody (for O-linked glycosylation sites).

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. (1997) *TIBTECH* 15:26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

For example, antibody variants are provided having a carbohydrate structure that lacks fucose attached (directly or indirectly) to an Fc region. Such variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336: 1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

In certain embodiments, an antibody variant comprises an Fc region with one or more amino acid substitutions which further improve ADCC, for example, substitutions at positions 298, 333, and/or 334 of the Fc region (Eu numbering of residues). Such substitutions may occur in combination with any of the variations described above.

In certain embodiments, the invention contemplates an antibody variant that possesses some but not all effector functions, which make it a desirable candidate for many applications in which the half life of the antibody in vivo is important yet certain effector functions (such as complement and ADCC) are unnecessary or deleterious. In certain embodiments, the Fc activities of the antibody are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol. 9:457-92 (1991). Non-limiting examples of in vitro assays to assess ADCC activity of a molecule of interest is described in U.S. Pat. No. 5,500,362 (see, e.g. Hellstrom, I., et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. To assess complement activation, a CDC assay may be performed (see, for example, Gazzano-Santoro et al., *J. Immunol. Methods* 202: 163 (1996); Cragg, M. S. et al., *Blood* 101:1045-1052 (2003); and Cragg, M.S, and M. J. Glennie, *Blood* 103:2738-2743 (2004)). FcRn binding and in vivo clearance/half life determinations can also be performed using methods known in the art (see, for example, Petkova, S. B. et al., *Int'l Immunol.* 18(12):1759-1769 (2006)).

Other antibody variants having one or more amino acid substitutions are provided. Sites of interest for substitutional mutagenesis include the hypervariable regions, but FR alterations are also contemplated. Conservative substitutions are shown in Table 1 under the heading of "preferred substitutions." More substantial changes, denominated "exemplary substitutions" are provided in Table 1, or as further described below in reference to amino acid classes Amino acid substitutions may be introduced into an antibody of interest and the products screened, e.g., for a desired activity, such as improved antigen binding, decreased immunogenicity, improved ADCC or CDC, etc.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Modifications in the biological properties of an antibody may be accomplished by selecting substitutions that affect (a) the structure of the polypeptide backbone in the area of the substitution, for example, as a sheet or helical conformation, (b) the charge or hydrophobicity of the molecule at the target site, or (c) the bulk of the side chain Amino acids may be grouped according to similarities in the properties of their side chains (in A. L. Lehninger, in Biochemistry, second ed., pp. 73-75, Worth Publishers, New York (1975)):

(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (O)
(3) acidic: Asp (D), Glu (E)
(4) basic: Lys (K), Arg (R), H is (H)

Alternatively, naturally occurring residues may be divided into groups based on common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: H is, Lys, Arg;
(5) residues that influence chain orientation: Gly, Pro;
(6) aromatic: Trp, Tyr, Phe.

Non-conservative substitutions will entail exchanging a member of one of these classes for another class. Such substituted residues also may be introduced into the conservative substitution sites or, into the remaining (non-conserved) sites.

One type of substitutional variant involves substituting one or more hypervariable region residues of a parent antibody (e.g. a humanized or human antibody). Generally, the resulting variant(s) selected for further development will have modified (e.g., improved) biological properties relative to the parent antibody from which they are generated. An exemplary substitutional variant is an affinity matured antibody, which may be conveniently generated using phage display-based affinity maturation techniques. Briefly, several hypervariable region sites (e.g. 6-7 sites) are mutated to generate all possible amino acid substitutions at each site. The antibodies thus generated are displayed from filamentous phage particles as fusions to at least part of a phage coat protein (e.g., the gene III product of M13) packaged within each particle. The phage-displayed variants are then screened for their biological activity (e.g. binding affinity). In order to identify candidate hypervariable region sites for modification, scanning mutagenesis (e.g., alanine scanning) can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to techniques known in the art, including those elaborated herein. Once such variants are generated, the panel of variants is subjected to screening using techniques known in the art, including those described herein, and variants with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of antibodies of the invention, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

In accordance with this description and the teachings of the art, it is contemplated that in some embodiments, an antibody of the invention may comprise one or more alterations as compared to the wild type counterpart antibody, e.g. in the Fc region. These antibodies would nonetheless retain substantially the same characteristics required for therapeutic utility as compared to their wild type counterpart. For example, it is thought that certain alterations can be made in the Fc region that would result in altered (i.e., either improved or diminished) Clq binding and/or Complement Dependent Cytotoxicity (CDC), e.g., as described in WO99/51642. See also Duncan & Winter, Nature 322:738-40 (1988); U.S. Pat. No. 5,648,260; U.S. Pat. No. 5,624,821; and WO94/29351 concerning other examples of Fc region variants. WO00/42072 (Presta) and WO 2004/056312 (Lowman) describe antibody variants with improved or diminished binding to FcRs. See, also, Shields et al. J. Biol. Chem. 9(2): 6591-6604 (2001). Antibodies with increased half lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). These antibodies comprise an Fc region with one or more substitutions therein which improve binding of the Fc region to FcRn. Polypeptide variants with altered Fc region amino acid sequences and increased or decreased Clq binding capability are described in U.S. Pat. No. 6,194,551B1, WO99/51642. See, also, Idusogie et al. J. Immunol. 164: 4178-4184 (2000).

In another aspect, the invention provides antibodies comprising modifications in the interface of Fc polypeptides comprising the Fc region, wherein the modifications facilitate and/or promote heterodimerization. These modifications comprise introduction of a protuberance into a first Fc polypeptide and a cavity into a second Fc polypeptide, wherein the protuberance is positionable in the cavity so as to promote complexing of the first and second Fc polypeptides. Methods of generating antibodies with these modifications are known in the art, e.g., as described in U.S. Pat. No. 5,731,168.

In yet another aspect, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region.

Antibody Derivatives

The anti-Bv8 antibodies of the present invention can be further modified to contain additional nonproteinaceous moieties that are known in the art and readily available. Preferably, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Nall. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Activity Assays

The antibodies of the present invention can be characterized for their physical/chemical properties and biological functions by various assays known in the art.

In one aspect, assays are provided for identifying anti-Bv8 antibodies thereof having biological activity. Biological activity may include, e.g., the modulation of one or more aspects of Bv8-associated effects, including but not limited to Bv8 binding, Bv8-mediated endothelial cell proliferation, tumor metastasis.

In certain embodiments of the invention, the immunoglobulins produced herein are analyzed for their biological activity. In some embodiments, the immunoglobulins of the present invention are tested for their antigen binding activity. The antigen binding assays that are known in the art and can be used herein include without limitation any direct or competitive binding assays using techniques such as western blots, radioimmunoassays, ELISA (enzyme linked immunosorbent assay), "sandwich" immunoassays, immunoprecipitation assays, fluorescent immunoassays, and protein A immunoassays. An illustrative antigen binding assay is provided below in the Examples section.

The purified antibodies can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

In some embodiments, the present invention contemplates altered antibodies that possess some but not all effector functions, which make it a desired candidate for many applications in which the half life of the antibody in vivo is important yet certain effector functions (such as complement and ADCC) are unnecessary or deleterious. In certain embodiments, the Fc activities of the produced immunoglobulin are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). An example of an in vitro assay to assess ADCC activity of a molecule of interest is described in U.S. Pat. No. 5,500,362 or 5,821,337. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998). Clq binding assays may also be carried out to confirm that the antibody is unable to bind Clq and hence lacks CDC activity. To assess complement activation, a CDC assay, e.g. as described in Gazzano-Santoro et al., J. Immunol. Methods 202:163 (1996), may be performed. FcRn binding and in vivo clearance/half life determinations can also be performed using methods known in the art.

In some embodiments, the invention provides altered antibodies that possess increased effector functions and/or increased half-life. See e.g., U.S. application Ser. No. 12/577, 967.

Vectors, Host Cells and Recombinant Methods

For recombinant production of an antibody of the invention, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian) origin. It will be appreciated that constant regions of any isotype can be used for this a. Generating Antibodies Using Prokaryotic Host Cells:
i. Vector Construction Polynucleotide sequences encoding polypeptide components of the antibody of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM.™-11 may be utilized in making a recombinant vector which can be used to transform susceptible host cells such as E. coli LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, lpp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the E. coli trxB- strains) provide cytoplasm conditions that are favorable for disulfide bond formation, thereby permitting proper folding and assembly of expressed protein subunits. Proba and Pluckthun Gene, 159:203 (1995).

Prokaryotic host cells suitable for expressing antibodies of the invention include Archaebacteria and Eubacteria, such as Gram-negative or Gram-positive organisms. Examples of useful bacteria include Escherichia (e.g., E. coli), Bacilli (e.g., B. subtilis), Enterobacteria, Pseudomonas species (e.g., P. aeruginosa), Salmonella typhimurium, Serratia marcescans, Klebsiella, Proteus, Shigella, Rhizobia, Vitreoscilla, or Paracoccus. In one embodiment, gram-negative cells are used. In one embodiment, E. coli cells are used as hosts for the invention. Examples of E. coli strains include strain W3110 (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ(nmpc-fepE) degP41 kanR (U.S. Pat. No. 5,639,635). Other strains and derivatives thereof, such as E. coli 294 (ATCC 31,446), E. coli B, E. coli λ 1776 (ATCC 31,537) and E. coli RV308(ATCC 31,608) are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, *E. coli*, *Serratia*, or *Salmonella* species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

ii. Antibody Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., J. Immunol. Methods (2002), 263:133-147). A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) J Bio Chem 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun (2000) J. Biol. Chem. 275: 17106-17113; Arie et al. (2001) Mol. Microbiol. 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), supra; Georgiou et al., U.S. Pat. No. 5,264,365; Georgiou et al., U.S. Pat. No. 5,508,192; Hara et al., Microbial Drug Resistance, 2:63-72 (1996).

In one embodiment, *E. coli* strains deficient for proteolytic enzymes and transformed with plasmids overexpressing one or more chaperone proteins are used as host cells in the expression system of the invention.

iii. Antibody Purification

Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex® G-75.

In one aspect, Protein A immobilized on a solid phase is used for immunoaffinity purification of the full length antibody products of the invention. Protein A is a 41 kD cell wall protein from *Staphylococcus aureas* which binds with a high affinity to the Fc region of antibodies. Lindmark et al (1983) J. Immunol. Meth. 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the antibody of interest to Protein A. The solid phase is then washed to remove contaminants non-specifically bound to the solid phase. Finally the antibody of interest is recovered from the solid phase by elution.

b. Generating Antibodies Using Eukaryotic Host Cells:

The vector components generally include, but are not limited to, one or more of the following: a signal sequence, an origin of replication, one or more marker genes, an enhancer element, a promoter, and a transcription termination sequence.

(i) Signal Sequence Component

A vector for use in a eukaryotic host cell may also contain a signal sequence or other polypeptide having a specific cleavage site at the N-terminus of the mature protein or polypeptide of interest. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the antibody.

(ii) Origin of Replication

Generally, an origin of replication component is not needed for mammalian expression vectors. For example, the SV40 origin may typically be used only because it contains the early promoter.

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC® CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

(iv) Promoter Component

Expression and cloning vectors usually contain a promoter that is recognized by the host organism and is operably linked to the antibody polypeptide nucleic acid. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT (SEQ ID NO: 206) region where N may be any nucleotide. At the 3' end of most eukaryotic genes is an AATAAA (SEQ ID NO: 207) sequence that may be the signal for addition of the poly A tail to the 3' end of the coding sequence. All of these sequences are suitably inserted into eukaryotic expression vectors.

Antibody polypeptide transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. Alternatively, the Rous Sarcoma Virus long terminal repeat can be used as the promoter.

(v) Enhancer Element Component

Transcription of DNA encoding the antibody polypeptide of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the antibody polypeptide-encoding sequence, but is preferably located at a site 5' from the promoter.

(vi) Transcription Termination Component

Expression vectors used in eukaryotic host cells will typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC® CRL 1651); human embryonic kidney line (293 or 293 cells subcloned for growth in suspension culture, Graham et al., J. Gen Virol. 36:59 (1977)); baby hamster kidney cells (BHK, ATCC® CCL 10); Chinese hamster ovary cells/–DHFR(CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC® CCL 70); African green monkey kidney cells (VERO-76, ATCC® CRL-1587); human cervical carcinoma cells (HELA, ATCC® CCL 2); canine kidney cells (MDCK, ATCC® CCL 34); buffalo rat liver cells (BRL 3A, ATCC® CRL 1442); human lung cells (W138, ATCC® CCL 75); human liver cells (Hep G2, HB 8065); mouse mammary tumor (MMT 060562, ATCC® CCL51); TR1 cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

(viii) Culturing the Host Cells

The host cells used to produce an antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. No. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCINT™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Purification of Antibody

When using recombinant techniques, the antibody can be produced intracellularly, or directly secreted into the medium. If the antibody is produced intracellularly, as a first step, the particulate debris, either host cells or lysed fragments, are removed, for example, by centrifugation or ultrafiltration. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Immunoconjugates

The invention also provides immunoconjugates (interchangeably referred to as "antibody-drug conjugates," or "ADCs") comprising an antibody conjugated to one or more cytotoxic agents, such as a chemotherapeutic agent, a drug, a growth inhibitory agent, a toxin (e.g., a protein toxin, an enzymatically active toxin of bacterial, fungal, plant, or animal origin, or fragments thereof), or a radioactive isotope (i.e., a radioconjugate).

Immunoconjugates have been used for the local delivery of cytotoxic agents, i.e., drugs that kill or inhibit the growth or proliferation of cells, in the treatment of cancer (Lambert, J. (2005) *Curr. Opinion in Pharmacology* 5:543-549; Wu et al (2005) *Nature Biotechnology* 23(9):1137-1146; Payne, G. (2003) i 3:207-212; Syrigos and Epenetos (1999) *Anticancer Research* 19:605-614; Niculescu-Duvaz and Springer (1997) *Adv. Drug Deliv. Rev.* 26:151-172; U.S. Pat. No. 4,975,278) Immunoconjugates allow for the targeted delivery of a drug moiety to a tumor, and intracellular accumulation therein, where systemic administration of unconjugated drugs may result in unacceptable levels of toxicity to normal cells as well as the tumor cells sought to be eliminated (Baldwin et al., *Lancet* (Mar. 15, 1986) pp. 603-05; Thorpe (1985) "Antibody Carriers Of Cytotoxic Agents In Cancer Therapy: A Review," in *Monoclonal Antibodies '84: Biological And Clinical Applications* (A. Pinchera et al., eds) pp. 475-506. Both polyclonal antibodies and monoclonal antibodies have been reported as useful in these strategies (Rowland et al., (1986) *Cancer Immunol. Immunother.* 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) *J. Nat. Cancer Inst.* 92(19):1573-1581; Mandler et al (2000) *Bioorganic & Med. Chem. Letters* 10:1025-1028; Mandler et al (2002) *Bioconjugate Chem.* 13:786-791), maytansinoids (EP 1391213; Liu et al., (1996) *Proc. Natl. Acad. Sci. USA* 93:8618-8623), and calicheamicin (Lode et al (1998) *Cancer Res.* 58:2928; Hinman et al (1993) *Cancer Res.* 53:3336-3342). The toxins may exert their cytotoxic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and 111In or 90Y radioisotope bound by a thiourea linker-chelator (Wiseman et al (2000) *Eur. Jour. Nucl. Med.* 27(7):766-77; Wiseman et al (2002) *Blood* 99(12):4336-42; Witzig et al (2002) *J. Clin. Oncol.* 20(10):2453-63; Witzig et al (2002) *J. Clin. Oncol.* 20(15):3262-69). Although ZEVALIN has activity against B-cell non-Hodgkin's Lymphoma (NHL), administration results in severe and prolonged cytopenias in most patients. MYLOTARG™ (gemtuzumab ozogamicin, Wyeth Pharmaceuticals), an antibody-drug conjugate composed of a huCD33 antibody linked to calicheamicin, was approved in 2000 for the treatment of acute myeloid leukemia by injection (*Drugs of the Future* (2000) 25(7):686; U.S. Pat. Nos. 4,970,198; 5,079,233; 5,585,089; 5,606,040; 5,693,762; 5,739,116; 5,767,285; 5,773,001). Cantuzumab mertansine (Immunogen, Inc.), an antibody-drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and other cancers. MLN-2704 (Millennium Pharm., BZL Biologics, Immunogen Inc.), an antibody-drug conjugate composed of the anti-prostate specific membrane antigen (PSMA) monoclonal antibody linked to the maytansinoid drug moiety, DM1, is under development for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al (2003) *Nature Biotechnol.* 21(7):778-784) and are under therapeutic development.

In certain embodiments, an immunoconjugate comprises an antibody and a chemotherapeutic agent or other toxin. Chemotherapeutic agents useful in the generation of immunoconjugates are described herein (e.g., above). Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, dolastatins, aurostatins, a trichothecene, and CC1065, and the derivatives of these toxins that have toxin activity, are also contemplated herein.

Maytansine and Maytansinoids

In some embodiments, the immunoconjugate comprises an antibody (full length or fragments) conjugated to one or more maytansinoid molecules.

Maytansinoids are mitototic inhibitors which act by inhibiting tubulin polymerization. Maytansine was first isolated from the east African shrub Maytenus serrata (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248, 870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Immunoconjugates containing maytansinoids, methods of making same, and their therapeutic use are disclosed, for example, in U.S. Pat. Nos. 5,208,020, 5,416,064 and European Patent EP 0 425 235 B1. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansinoid conjugate was tested in vitro on the human breast cancer cell line SK-BR-3, which expresses 3×10$^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-maytansinoid conjugates are prepared by chemically linking an antibody to a maytansinoid molecule without significantly diminishing the biological activity of either the antibody or the maytansinoid molecule. See, e.g., U.S. Pat. No. 5,208,020. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, Chari et al., Cancer Research 52:127-131 (1992), and U.S. patent application Ser. No. 10/960,602, filed Oct. 8, 2004. Antibody-maytansinoid conjugates comprising the linker component SMCC may be prepared as disclosed in U.S. patent application Ser. No. 10/960,602, filed Oct. 8, 2004. The linking groups include disulfide groups, thioether groups, acid labile groups, photolabile groups, peptidase labile groups, or esterase labile groups, as disclosed in the above-identified patents, disulfide and thioether groups being preferred. Additional linking groups are described and exemplified herein.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., *Biochem. J.* 173:723-737 (1978)) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

Auristatins and Dolastatins

In some embodiments, the immunoconjugate comprises an antibody conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Monomethylvaline Compounds Capable of Conjugation to Ligands", U.S. Ser. No. 10/983,340, filed Nov. 5, 2004.

Typically, peptide-based drug moieties can be prepared by forming a peptide bond between two or more amino acids and/or peptide fragments. Such peptide bonds can be prepared, for example, according to the liquid phase synthesis method (see E. Schroder and K. Lake, "The Peptides", volume 1, pp 76-136, 1965, Academic Press) that is well known in the field of peptide chemistry. The auristatin/dolastatin drug moieties may be prepared according to the methods of: U.S. Pat. No. 5,635,483; U.S. Pat. No. 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; and Pettit et al (1996) J. Chem. Soc. Perkin Trans. 1 5:859-863. See also Doronina (2003) Nat Biotechno121(7):778-784; "Monomethylvaline Compounds Capable of Conjugation to Ligands", U.S. Ser. No. 10/983, 340, filed Nov. 5, 2004 (disclosing, e.g., linkers and methods of preparing monomethylvaline compounds such as MMAE and MMAF conjugated to linkers).

Calicheamicin

In other embodiments, the immunoconjugate comprises an antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, γ1I, α2I, α3I, N-acetyl-γ1I, PSAG and θI1 (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the antibodies include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $sm^{153}$, $Bi^{212}$, $P^{32}$, $Pb^{212}$ and radioactive isotopes of Lu. When the conjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99}m$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57) can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

Preparation of Antibody Drug Conjugates

In the antibody drug conjugates (ADC), an antibody (Ab) is conjugated to one or more drug moieties (D), e.g. about 1 to about 20 drug moieties per antibody, through a linker (L). The ADC of Formula I may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody. Additional methods for preparing ADC are described herein.

$$Ab-(L-D)_p \qquad \qquad I$$

The linker may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio) pentanoate ("SPP"), N-Succinimidyl 4-(N-maleimidomethyl)cyclohexane-1 carboxylate ("SMCC"), and N-Succinimidyl (4-iodo-acetyl) aminobenzoate ("SIAB"). Additional linker components are known in the art and some are described herein. See also "Monomethylvaline Compounds Capable of Conjugation to Ligands", U.S. Ser. No. 10/983,340, filed Nov. 5, 2004.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly) Amino acid residues which comprise an amino acid linker component include those occurring naturally, as well as minor amino acids and non-naturally occurring amino acid analogs, such as citrulline Amino acid linker components can be designed and optimized in their selectivity for enzymatic cleavage by a particular enzymes, for example, a tumor-associated protease, cathepsin B, C and D, or a plasmin protease.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Antibody drug conjugates may also be produced by modification of the antibody to introduce electrophilic moieties, which can react with nucleophilic substituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan & Stroh, (1992) *Bioconjugate Chem.* 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

Compositions of the Invention

This invention also encompasses compositions, including pharmaceutical compositions, comprising an anti-Bv8 antibody, and polynucleotides comprising sequences encoding an anti-Bv8 antibody. As used herein, compositions comprise one or more antibodies that bind to Bv8, and/or one or more polynucleotides comprising sequences encoding one or more antibodies that bind to Bv8. These compositions may further comprise suitable carriers, such as pharmaceutically acceptable excipients including buffers, which are well known in the art.

Therapeutic formulations comprising anti-Bv8 antibody of the invention are prepared for storage by mixing the antibody having the desired degree of purity with optional physiologically acceptable carriers, excipients or stabilizers (*Remington: The Science and Practice of Pharmacy* 20th edition (2000)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington: The Science and Practice of Pharmacy* 20th edition (2000).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the immunoglobulin of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated immunoglobulins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Uses

An antibody of the present invention may be used in, for example, in vitro, ex vivo and in vivo therapeutic methods.

The invention provides methods and compositions useful for modulating disease states associated with expression and/or activity of Bv8, such as increased expression and/or activity or undesired expression and/or activity, said methods comprising administration of an effective dose of an anti-Bv8 antibody to an individual in need of such treatment.

In one aspect, the invention provides methods for treating or preventing a tumor, a cancer, and/or a cell proliferative disorder, the methods comprising administering an effective amount of an anti-Bv8 antibody to an individual in need of such treatment.

In one aspect, the invention provides methods for inhibiting angiogenesis, the methods comprising administering an effective amount of an anti-Bv8 antibody to an individual in need of such treatment.

In one aspect, the invention provides methods for inhibiting tumor metastasis, the methods comprising administering an effective amount of an anti-Bv8 antibody to an individual in need of such treatment.

In one aspect, the invention provides methods for inhibiting endothelial cell proliferation, the methods comprising administering an effective amount of an anti-Bv8 antibody to an individual in need of such treatment.

In one aspect, the invention provides methods for enhancing the efficacy of another anti-angiogenic agent, the methods comprising administering an effective amount of an anti-Bv8 antibody to an individual in need of such treatment. In some embodiments, the individual has a tumor, a cancer, and/or a cell proliferative disorder. In some embodiments, the other anti-angiogenic agent targets VEGF, e.g. an anti-VEGF antibody It is understood that any suitable anti-Bv8 antibody may be used in methods of treatment, including monoclonal and/or polyclonal antibodies, a human antibody, a chimeric antibody, an affinity-matured antibody, a humanized antibody, and/or an antibody fragment. In some embodiments, any anti-Bv8 antibody described herein is used for treatment.

In any of the methods herein, one may administer to the subject or patient along with the anti-Bv8 antibody herein an effective amount of a second medicament (where the anti-Bv8 antibody herein is the first medicament), which is another active agent that can treat the condition in the subject that requires treatment. For instance, an antibody of the invention may be co-administered with another antibody, chemotherapeutic agent(s) (including cocktails of chemotherapeutic agents), anti-angiogenic agent(s), immunosuppressive agents(s), cytokine(s), cytokine antagonist(s), and/or growth-inhibitory agent(s). The type of such second medicament depends on various factors, including the type of disorder, the severity of the disease, the condition and age of the patient, the type and dose of first medicament employed, etc.

Where an antibody of the invention inhibits tumor growth, for example, it may be particularly desirable to combine it with one or more other therapeutic agents that also inhibit tumor growth. For instance, an antibody of the invention may be combined with an anti-angiogenic agent, such as an anti-VEGF antibody (e.g., AVASTIN®) and/or anti-ErbB antibodies (e.g. HERCEPTIN® trastuzumab anti-HER2 antibody or EGFR inhibitor (e.g., erlotinib (TARCEVA®)) or an anti-HER2 antibody that binds to Domain II of HER2, such as OMNITARG™ pertuzumab anti-HER2 antibody) in a treatment scheme, e.g. in treating any of the disease described herein, including colorectal cancer, lung cancer, hepatocellular carcinoma, breast cancer and/or pancreatic cancer. Alternatively, or additionally, the patient may receive combined radiation therapy (e.g. external beam irradiation or therapy with a radioactive labeled agent, such as an antibody). Such combined therapies noted above include combined administration (where the two or more agents are included in the same or separate formulations), and separate administration, in which case, administration of the antibody of the invention can occur prior to, and/or following, administration of the adjunct therapy or therapies. In addition, combining an antibody of this invention with a relatively non-cytotoxic agent such as another biologic molecule, e.g., another antibody is expected to reduce cytotoxicity versus combining the antibody with a chemotherapeutic agent of other agent that is highly toxic to cells.

Treatment with a combination of the antibody herein with one or more second medicaments preferably results in an improvement in the signs or symptoms of cancer. For instance, such therapy may result in an improvement in survival (overall survival and/or progression-free survival) relative to a patient treated with the second medicament only (e.g., a chemotherapeutic agent only), and/or may result in an objective response (partial or complete). Moreover, treatment with the combination of an antibody herein and one or more second medicament(s) preferably results in an additive, and more preferably synergistic (or greater than additive), therapeutic benefit to the patient. In certain embodiments, the timing between at least one administration of the second medicament and at least one administration of the antibody herein is about one month or less. In certain embodiments, the timing between at least one administration of the second medicament and at least one administration of the antibody herein is about two weeks or less. In certain embodiments, the antibody herein and the second medicament is administered concurrently.

For treatment of cancers, the second medicament is preferably another antibody, chemotherapeutic agent (including cocktails of chemotherapeutic agents), anti-angiogenic agent, immunosuppressive agent, prodrug, cytokine, cytokine antagonist, cytotoxic radiotherapy, corticosteroid, anti-emetic, cancer vaccine, analgesic, anti-vascular agent, and/or growth-inhibitory agent. The cytotoxic agent includes an agent interacting with DNA, the antimetabolites, the topoisomerase I or II inhibitors, or the spindle inhibitor or stabilizer agents (e.g., preferably vinca alkaloid, more preferably selected from vinblastine, deoxyvinblastine, vincristine, vindesine, vinorelbine, vinepidine, vinfosiltine, vinzolidine and vinfunine), or any agent used in chemotherapy such as 5-FU, a taxane, doxorubicin, or dexamethasone.

In some embodiments, the second medicament is another antibody used to treat cancers such as those directed against the extracellular domain of the HER2/neu receptor, e.g., trastuzumab, or one of its functional fragments, pan-HER inhibitor, a Src inhibitor, a MEK inhibitor, or an EGFR inhibitor (e.g., an anti-EGFR antibody (such as one inhibiting the tyrosine kinase activity of the EGFR), such as cetuximab (ERBITUX®), dianilinophthalimides, pyrazolo- or pyrrolopyridopyrimidines, quinazilines, gefitinib, erlotinib, cetuximab, ABX-EFG, canertinib, EKB-569 and PKI-166), or dual-EGFR/HER-2 inhibitor such as lapatanib. Additional second medicaments include alemtuzumab (CAMPATH™), FavID (IDKLH), CD20 antibodies with altered glycosylation, such as GA-101/GLYCARTT™, oblimersen (GENASENSE™), thalidomide and analogs thereof, such as lenalidomide (REVLIMID™), imatinib, sorafenib, ofatumumab (HUMAX-CD20™), anti-CD40 antibody, e.g. SGN-40, and anti-CD-80 antibody, e.g. galiximab.

The anti-emetic agent is preferably ondansetron hydrochloride, granisetron hydrochloride, metroclopramide, domperidone, haloperidol, cyclizine, lorazepam, prochlorperazine, dexamethasone, levomepromazine, or tropisetron. The vaccine is preferably GM-CSF DNA and cell-based vaccines, dendritic cell vaccine, recombinant viral vaccines, heat shock protein (HSP) vaccines, allogeneic or autologous tumor vaccines. The analgesic agent preferably is ibuprofen, naproxen, choline magnesium trisalicylate, or oxycodone hydrochloride. The anti-vascular agent preferably is bevacizumab, or rhuMAb-VEGF. Further second medicaments include anti-proliferative agents such a farnesyl protein transferase inhibitors, anti-VEGF inhibitors, p53 inhibitors, or PDGFR inhibitors. The second medicament herein includes also biologic-targeted therapy such as treatment with antibodies as well as small-molecule-targeted therapy, for example, against certain receptors.

Many anti-angiogenic agents have been identified and are known in the art, including those listed herein, e.g., listed under Definitions, and by, e.g., Carmeliet and Jain, Nature 407:249-257 (2000); Ferrara et al., Nature Reviews:Drug Discovery, 3:391-400 (2004); and Sato Int. J. Clin. Oncol., 8:200-206 (2003). See also, US Patent Application US20030055006. In one embodiment, an anti-Bv8 antibody is used in combination with an anti-VEGF neutralizing antibody (or fragment) and/or another VEGF antagonist or a VEGF receptor antagonist including, but not limited to, for example, soluble VEGF receptor (e.g., VEGFR-1, VEGFR-2, VEGFR-3, neuropilins (e.g., NRP1, NRP2)) fragments, aptamers capable of blocking VEGF or VEGFR, neutralizing anti-VEGFR antibodies, low molecule weight inhibitors of VEGFR tyrosine kinases (RTK), antisense strategies for VEGF, ribozymes against VEGF or VEGF receptors, antagonist variants of VEGF; and any combinations thereof. Alternatively, or additionally, two or more angiogenesis inhibitors may optionally be co-administered to the patient in addition to VEGF antagonist and other agent. In certain embodiment, one or more additional therapeutic agents, e.g., anti-cancer agents, can be administered in combination with anti-Bv8 antibody, the VEGF antagonist, and an anti-angiogenic agent.

Chemotherapeutic agents useful herein are described supra, e.g., in the definition of "chemotherapeutic agent".

Such second medicaments may be administered within 48 hours after the antibodies herein are administered, or within 24 hours, or within 12 hours, or within 3-12 hours after said agent, or may be administered over a pre-selected period of time, which is preferably about 1 to 2 days. Further, the dose of such agent may be sub-therapeutic.

The antibodies herein can be administered concurrently, sequentially, or alternating with the second medicament or upon non-responsiveness with other therapy. Thus, the combined administration of a second medicament includes co-administration (concurrent administration), using separate formulations or a single pharmaceutical formulation, and consecutive administration in either order, wherein preferably there is a time period while both (or all) medicaments simultaneously exert their biological activities. All these second medicaments may be used in combination with each other or by themselves with the first medicament, so that the express "second medicament" as used herein does not mean it is the only medicament besides the first medicament, respectively. Thus, the second medicament need not be one medicament, but may constitute or comprise more than one such drug.

These second medicaments as set forth herein are generally used in the same dosages and with administration routes as the first medicaments, or about from 1 to 99% of the dosages of the first medicaments. If such second medicaments are used at all, preferably, they are used in lower amounts than if the first medicament were not present, especially in subsequent dosings beyond the initial dosing with the first medicament, so as to eliminate or reduce side effects caused thereby.

The invention also provides methods and compositions for inhibiting or preventing refractory tumor, relapsed tumor growth or relapsed cancer cell growth. In certain embodiments, relapsed tumor growth or relapsed cancer cell growth is used to describe a condition in which patients undergoing or treated with one or more currently available therapies (e.g., cancer therapies, such as chemotherapy, radiation therapy, surgery, hormonal therapy and/or biological therapy/immunotherapy, anti-VEGF antibody therapy, particularly a standard therapeutic regimen for the particular cancer) is not clinically adequate to treat the patients or the patients are no longer receiving any beneficial effect from the therapy such that these patients need additional effective therapy. In certain embodiments, a cancer is relapsed tumor growth or relapsed cancer cell growth where the number of cancer cells has not been significantly reduced, or has increased, or tumor size has not been significantly reduced, or has increased, or fails any further reduction in size or in number of cancer cells. In certain embodiments, patients with relapsed tumor trowth or relapsed cancer cell growth have developed resistance to one or more currently available therapies. In certain embodiments, the term refractory is used to describe a condition in which patients undergoing or treated with one or more currently available therapies (e.g., cancer therapies, such as chemotherapy, radiation therapy, surgery, hormonal therapy and/or biological therapy/immunotherapy, anti-VEGF antibody therapy, particularly a standard therapeutic regimen for the particular cancer) is not clinically adequate to treat the patients. In certain embodiments, the non-responsive/refractory patients are patients who respond to therapy yet suffer from side effects, do not respond to the therapy, or do not respond satisfactorily to the therapy, etc. In certain embodiments, a cancer is a non-responsive/refractory tumor where the tumor is intrinsically non-responsive or resistant to previous treatments. In certain embodiments, refractory refers to an intrinsically non-responsiveness of a disease or condition to a therapy comprising a VEGF-antagonist. The determination of whether the cancer cells are refractory, relapsed tumor growth or relapsed cancer cell growth can be made either in vivo or in vitro by any method known in the art for assaying the effectiveness of treatment on cancer cells, using the art-accepted meanings of "relapse" or "refractory" or "non-responsive" in such context.

The invention provides methods of blocking or reducing relapsed tumor growth or relapsed cancer cell growth in a subject by administering an effective amount of anti-Bv8 antibody to block or reduce the relapsed tumor growth or relapsed cancer cell growth in subject. The invention provides methods of treating patients refractory to a therapy comprising a VEGF antagonist by administering an effective amount of anti-Bv8 antibody to the patient. In certain embodiments, the anti-Bv8 antibody can be administered subsequent to the other cancer therapeutic. In certain embodiments, the anti-Bv8 antibody is administered simultaneously with cancer therapy. Alternatively, or additionally, the anti-Bv8 antibody therapy alternates with another cancer therapy, which can be performed in any order. The invention also encompasses methods for administering one or more inhibitory antibodies to prevent the onset or recurrence of cancer in patients predisposed to having cancer. Generally, the subject was or is concurrently undergoing cancer therapy. In one embodiment, the cancer therapy is treatment with an anti-angiogenic agent, e.g., a VEGF antagonist. The anti-angiogenic agent includes those known in the art and those found under the Definitions herein. In one embodiment, the anti-angiogenic agent is an anti-VEGF neutralizing antibody or fragment (e.g., humanized A4.6.1, AVASTIN® (Genentech, South San Francisco, Calif.), Y0317, M4, G6, B20, 2C3, etc.). See, e.g., U.S. Pat. Nos. 6,582,959, 6,884,879, 6,703,020; WO98/45332; WO 96/30046; WO94/10202; EP 0666868B1; US Patent Applications 20030206899, 20030190317, 20030203409, and 20050112126; Popkov et al., Journal of Immunological Methods 288:149-164 (2004); and, WO2005012359. Additional agents can be administered in combination with VEGF antagonist and an anti-Bv8 antibody for treating refractory tumor, blocking or reducing relapsed tumor growth or relapsed cancer cell growth.

The anti-Bv8 antibodies of the invention (and adjunct therapeutic agent) is/are administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the anti-Bv8 antibodies are suitably administered by pulse infusion, particularly with declining doses of the antibody. Dosing can be by any suitable route, e.g. by injections, such as intravenous or subcutaneous injections, depending in part on whether the administration is brief or chronic.

The location of the binding target of an antibody of the invention may be taken into consideration in preparation and administration of the antibody. When the binding target is an intracellular molecule, certain embodiments of the invention provide for the antibody or antigen-binding fragment thereof to be introduced into the cell where the binding target is located. In one embodiment, an anti-Bv8 antibody of the invention can be expressed intracellularly as an intrabody. The term "intrabody," as used herein, refers to an antibody or antigen-binding portion thereof that is expressed intracellularly and that is capable of selectively binding to a target molecule, as described, e.g., in Marasco, *Gene Therapy* 4: 11-15 (1997); Kontermann, *Methods* 34: 163-170 (2004); U.S. Pat. Nos. 6,004,940 and 6,329,173; U.S. Patent Application Publication No. 2003/0104402, and PCT Publication No. WO2003/077945. See also, for example, WO96/07321 published Mar. 14, 1996, concerning the use of gene therapy to generate intracellular antibodies.

Intracellular expression of an intrabody may be effected by introducing a nucleic acid encoding the desired antibody or antigen-binding portion thereof (lacking the wild-type leader sequence and secretory signals normally associated with the gene encoding that antibody or antigen-binding fragment) into a target cell. One or more nucleic acids encoding all or a portion of an antibody of the invention can be delivered to a target cell, such that one or more intrabodies are expressed which are capable of binding to an intracellular target polypeptide and modulating the activity of the target polypeptide. Any standard method of introducing nucleic acids into a cell may be used, including, but not limited to, microinjection, ballistic injection, electroporation, calcium phosphate precipitation, liposomes, and transfection with retroviral, adenoviral, adeno-associated viral and vaccinia vectors carrying the nucleic acid of interest.

In certain embodiments, nucleic acid (optionally contained in a vector) may be introduced into a patient's cells by in vivo and ex vivo methods. In one example of in vivo delivery, nucleic acid is injected directly into the patient, e.g., at the site where therapeutic intervention is required. In a further example of in vivo delivery, nucleic acid is introduced into a cell using transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). For review of certain gene marking and gene therapy protocols, see Anderson et al., *Science* 256:808-813 (1992), and WO 93/25673 and the references cited therein. In an example of ex vivo treatment, a patient's cells are removed, nucleic acid is introduced into those isolated cells, and the modified cells are administered to the patient either directly or, for example, encapsulated within porous membranes which are implanted into the patient (see, e.g., U.S. Pat. Nos. 4,892,538 and 5,283,187). A commonly used vector for ex vivo delivery of a nucleic acid is a retroviral vector.

In another embodiment, internalizing antibodies are provided. Antibodies can possess certain characteristics that enhance delivery of antibodies into cells, or can be modified to possess such characteristics. Techniques for achieving this are known in the art. For example, cationization of an antibody is known to facilitate its uptake into cells (see, e.g., U.S. Pat. No. 6,703,019). Lipofections or liposomes can also be used to deliver the antibody into cells. Where antibody fragments are used, the smallest inhibitory fragment that specifically binds to the target protein may be advantageous. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA*, 90: 7889-7893 (1993).

Entry of antibodies into target cells can be enhanced by other methods known in the art. For example, certain sequences, such as those derived from HIV Tat or the Antennapedia homeodomain protein are able to direct efficient uptake of heterologous proteins across cell membranes. See, e.g., Chen et al., *Proc. Natl. Acad. Sci. USA* (1999), 96:4325-4329.

When the binding target of an antibody is located in the brain, certain embodiments of the invention provide for the antibody to traverse the blood-brain barrier. Several art-known approaches exist for transporting molecules across the blood-brain barrier, including, but not limited to, physical methods, lipid-based methods, stem cell-based methods, and receptor and channel-based methods.

Physical methods of transporting an antibody across the blood-brain barrier include, but are not limited to, circumventing the blood-brain barrier entirely, or by creating openings in the blood-brain barrier. Circumvention methods include, but are not limited to, direct injection into the brain (see, e.g., Papanastassiou et al., *Gene Therapy* 9: 398-406 (2002)), interstitial infusion/convection-enhanced delivery (see, e.g., Bobo et al., *Proc. Natl. Acad. Sci. USA* 91: 2076-2080 (1994)), and implanting a delivery device in the brain (see, e.g., Gill et al., *Nature Med.* 9: 589-595 (2003); and Gliadel Wafers™, Guildford Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., *Implication of the Blood-Brain Barrier and its Manipulation*, Vols 1 & 2, Plenum Press, N.Y. (1989)), permeabilization by, e.g., bradykinin or permeabilizer A-7 (see, e.g., U.S. Pat. Nos. 5,112,596, 5,268,164, 5,506,206, and 5,686,416), and transfection of neurons that straddle the blood-brain barrier with vectors containing genes encoding the antibody (see, e.g., U.S. Patent Publication No. 2003/0083299).

Lipid-based methods of transporting an antibody across the blood-brain barrier include, but are not limited to, encapsulating the antibody in liposomes that are coupled to antibody binding fragments that bind to receptors on the vascular endothelium of the blood-brain barrier (see, e.g., U.S. Patent Application Publication No. 20020025313), and coating the antibody in low-density lipoprotein particles (see, e.g., U.S. Patent Application Publication No. 20040204354) or apolipoprotein E (see, e.g., U.S. Patent Application Publication No. 20040131692).

Stem-cell based methods of transporting an antibody across the blood-brain barrier entail genetically engineering neural progenitor cells (NPCs) to express the antibody of interest and then implanting the stem cells into the brain of the individual to be treated. See Behrstock et al. (2005) *Gene Ther.* 15 Dec. 2005 advanced online publication (reporting that NPCs genetically engineered to express the neurotrophic factor GDNF reduced symptoms of Parkinson disease when implanted into the brains of rodent and primate models).

Receptor and channel-based methods of transporting an antibody across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating antibodies with a transferrin and modulating activity of the one or more transferrin receptors (see, e.g., U.S. Patent Application Publication No. 2003/0129186), and cationizing the antibodies (see, e.g., U.S. Pat. No. 5,004,697).

Anti-Bv8 antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The anti-Bv8 antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 μg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 50 mg/kg. Thus, one or more doses of about 0.5 mg/kg, 2.0 mg/kg, 4.0 mg/kg, 10 mg/kg, 15 mg/kg, 20 mg.kg or 25 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

Diagnostic Methods and Methods of Detection

The anti-Bv8 antibodies of the invention are useful in assays detecting Bv8 expression (such as diagnostic or prognostic assays) in specific cells or tissues wherein the antibodies are labeled as described below and/or are immobilized on an insoluble matrix.

In another aspect, the invention provides methods for detection of Bv8, the methods comprising detecting Bv8-anti-Bv8 antibody complex in the sample. The term "detection" as used herein includes qualitative and/or quantitative detection (measuring levels) with or without reference to a control.

In another aspect, the invention provides any of the anti-Bv8 antibodies described herein, wherein the anti-Bv8 antibody comprises a detectable label.

In another aspect, the invention provides a complex of any of the anti-Bv8 antibodies described herein and Bv8. In some embodiments, the complex is in vivo or in vitro. In some embodiments, the complex comprises a cancer cell. In some embodiments, the anti-Bv8 antibody is detectably labeled.

Anti-Bv8 antibodies (e.g., any of the Bv8 antibodies described herein) can be used for the detection of Bv8 in any one of a number of well known detection assay methods.

For example, a biological sample may be assayed for Bv8 by obtaining the sample from a desired source, admixing the sample with anti-Bv8 antibody to allow the antibody to form antibody/Bv8 complex with any Bv8 present in the mixture, and detecting any antibody/Bv8 complex present in the mixture. The biological sample may be prepared for assay by methods known in the art which are suitable for the particular sample. The methods of admixing the sample with antibodies and the methods of detecting antibody/Bv8 complex are chosen according to the type of assay used. Such assays include immunohistochemistry, competitive and sandwich assays, and steric inhibition assays. For sample preparation, a tissue or cell sample from a mammal (typically a human patient) may be used. Examples of samples include, but are not limited to, cancer cells such as colon, breast, prostate, ovary, lung, stomach, pancreas, lymphoma, and leukemia cancer cells. Bv8 may also be measured in serum. The sample can be obtained by a variety of procedures known in the art including, but not limited to surgical excision, aspiration or biopsy. The tissue may be fresh or frozen. In one embodiment, the sample is fixed and embedded in paraffin or the like. The tissue sample may be fixed (i.e. preserved) by conventional methodology (See e.g., "Manual of Histological Staining Method of the Armed Forces Institute of Pathology," 3$^{rd}$ edition (1960) Lee G. Luna, H T (ASCP) Editor, The Blakston Division McGraw-Hill Book Company, New York; *The Armed Forces Institute of Pathology Advanced Laboratory Methods in Histology and Pathology* (1994) Ulreka V. Mikel, Editor, Armed Forces Institute of Pathology, American Registry of Pathology, Washington, D.C.). One of ordinary skill in the art will appreciate that the choice of a fixative is determined by the purpose for which the sample is to be histologically stained or otherwise analyzed. One of ordinary skill in the art will also appreciate that the length of fixation depends upon the size of the tissue sample and the fixative used. By way of example, neutral buffered formalin, Bouin's or paraformaldehyde, may be used to fix a sample. Generally, the sample is first fixed and is then dehydrated through an ascending series of alcohols, infiltrated and embedded with paraffin or other sectioning media so that the tissue sample may be sectioned. Alternatively, one may section the tissue and fix the sections obtained. By way of example, the tissue sample may be embedded and processed in paraffin by conventional methodology (See e.g., "Manual of Histological Staining Method of the Armed Forces Institute of Pathology", supra). Examples of paraffin that may be used include, but are not limited to, Paraplast, Broloid, and Tissuemay. Once the tissue sample is embedded, the sample may be sectioned by a microtome or the like (See e.g., "Manual of Histological Staining Method of the Armed Forces Institute of Pathology", supra). By way of example for this procedure, sections may range from about three microns to about five microns in thickness. Once sectioned, the sections may be attached to slides by several standard methods. Examples of slide adhesives include, but are not limited to, silane, gelatin, poly-L-lysine and the like. By way of example, the paraffin embedded sections may be attached to positively charged slides and/or slides coated with poly-L-lysine. If paraffin has been used as the embedding material, the tissue sections are generally deparaffinized and rehydrated to water. The tissue sections may be deparaffinized by several conventional standard methodologies. For example, xylenes and a gradually descending series of alcohols may be used (See e.g., "Manual of Histological Staining Method of the Armed Forces Institute of Pathology", supra). Alternatively, commercially available deparaffinizing non-organic agents such as Hemo-De7 (CMS, Houston, Tex.) may be used.

Analytical methods for Bv8 all use one or more of the following reagents: labeled Bv8 analogue, immobilized Bv8 analogue, labeled anti-Bv8 antibody, immobilized anti-Bv8 antibody and steric conjugates. The labeled reagents also are known as "tracers."

The label used is any detectable functionality that does not interfere with the binding of Bv8 and anti-Bv8 antibody. Numerous labels are known for use in immunoassay, examples including moieties that may be detected directly, such as fluorochrome, chemiluminescent, and radioactive labels, as well as moieties, such as enzymes, that must be reacted or derivatized to be detected.

The label used is any detectable functionality that does not interfere with the binding of Bv8 and anti-Bv8 antibody. Numerous labels are known for use in immunoassay, examples including moieties that may be detected directly, such as fluorochrome, chemiluminescent, and radioactive labels, as well as moieties, such as enzymes, that must be reacted or derivatized to be detected. Examples of such labels include the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Conventional methods are available to bind these labels covalently to proteins or polypeptides. For instance, coupling agents such as dialdehydes, carbodiimides, dimaleimides, bis-imidates, bis-diazotized benzidine, and the like may be used to tag the antibodies with the above-described fluorescent, chemiluminescent, and enzyme labels. See, for example, U.S. Pat. No. 3,940,475 (fluorimetry) and U.S. Pat. No. 3,645,090 (enzymes); Hunter et al., *Nature*, 144: 945 (1962); David et al., *Biochemistry*, 13: 1014-1021 (1974); Pain et al., *J. Immunol. Methods*, 40: 219-230 (1981); and Nygren, *J. Histochem. and Cytochem.*, 30: 407-412 (1982). Preferred labels herein are enzymes such as horseradish peroxidase and alkaline phosphatase. The conjugation of such label, including the enzymes, to the antibody is a standard manipulative procedure for one of ordinary skill in immunoassay techniques. See, for example, O'Sullivan et al., "Methods for the Preparation of Enzyme-antibody Conjugates for Use in Enzyme Immunoassay," in *Methods in Enzymology*, ed. J. J. Langone and H. Van Vunakis, Vol. 73 (Academic Press, New York, N.Y., 1981), pp. 147-166.

Immobilization of reagents is required for certain assay methods Immobilization entails separating the anti-Bv8 antibody from any Bv8 that remains free in solution. This conventionally is accomplished by either insolubilizing the anti-Bv8 antibody or Bv8 analogue before the assay procedure, as by adsorption to a water-insoluble matrix or surface (Bennich et al., U.S. Pat. No. 3,720,760), by covalent coupling (for example, using glutaraldehyde cross-linking), or by insolubilizing the anti-Bv8 antibody or Bv8 analogue afterward, e.g., by immunoprecipitation.

The expression of proteins in a sample may be examined using immunohistochemistry and staining protocols. Immunohistochemical staining of tissue sections has been shown to be a reliable method of assessing or detecting presence of proteins in a sample. Immunohistochemistry ("IHC") techniques utilize an antibody to probe and visualize cellular antigens in situ, generally by chromogenic or fluorescent methods. For sample preparation, a tissue or cell sample from a mammal (typically a human patient) may be used. The sample can be obtained by a variety of procedures known in the art including, but not limited to surgical excision, aspiration or biopsy. The tissue may be fresh or frozen. In one embodiment, the sample is fixed and embedded in paraffin or the like. The tissue sample may be fixed (i.e. preserved) by conventional methodology. One of ordinary skill in the art will appreciate that the choice of a fixative is determined by the purpose for which the sample is to be histologically stained or otherwise analyzed. One of ordinary skill in the art will also appreciate that the length of fixation depends upon the size of the tissue sample and the fixative used.

IHC may be performed in combination with additional techniques such as morphological staining and/or fluorescence in-situ hybridization. Two general methods of IHC are available; direct and indirect assays. According to the first assay, binding of antibody to the target antigen (e.g., Bv8) is determined directly. This direct assay uses a labeled reagent, such as a fluorescent tag or an enzyme-labeled primary antibody, which can be visualized without further antibody interaction. In a typical indirect assay, unconjugated primary antibody binds to the antigen and then a labeled secondary antibody binds to the primary antibody. Where the secondary antibody is conjugated to an enzymatic label, a chromogenic or fluorogenic substrate is added to provide visualization of the antigen. Signal amplification occurs because several secondary antibodies may react with different epitopes on the primary antibody.

The primary and/or secondary antibody used for immunohistochemistry typically will be labeled with a detectable moiety. Numerous labels are available.

Aside from the sample preparation procedures discussed above, further treatment of the tissue section prior to, during or following IHC may be desired, For example, epitope retrieval methods, such as heating the tissue sample in citrate buffer may be carried out (see, e.g., Leong et al. *Appl. Immunohistochem.* 4(3):201 (1996)).

Following an optional blocking step, the tissue section is exposed to primary antibody for a sufficient period of time and under suitable conditions such that the primary antibody binds to the target protein antigen in the tissue sample. Appropriate conditions for achieving this can be determined by routine experimentation. The extent of binding of antibody to the sample is determined by using any one of the detectable labels discussed above. Preferably, the label is an enzymatic label (e.g. HRPO) which catalyzes a chemical alteration of the chromogenic substrate such as 3,3'-diaminobenzidine chromogen. Preferably the enzymatic label is conjugated to antibody which binds specifically to the primary antibody (e.g. the primary antibody is rabbit polyclonal antibody and secondary antibody is goat anti-rabbit antibody).

Specimens thus prepared may be mounted and coverslipped. Slide evaluation is then determined, e.g. using a microscope, and staining intensity criteria, routinely used in the art, may be employed.

Other assay methods, known as competitive or sandwich assays, are well established and widely used in the commercial diagnostics industry.

Competitive assays rely on the ability of a tracer Bv8 analogue to compete with the test sample Bv8 for a limited number of anti-Bv8 antibody antigen-binding sites. The anti-Bv8 antibody generally is insolubilized before or after the competition and then the tracer and Bv8 bound to the anti-Bv8 antibody are separated from the unbound tracer and Bv8. This separation is accomplished by decanting (where the binding partner was preinsolubilized) or by centrifuging (where the binding partner was precipitated after the competitive reaction). The amount of test sample Bv8 is inversely proportional to the amount of bound tracer as measured by the amount of marker substance. Dose-response curves with known amounts of Bv8 are prepared and compared with the test results to quantitatively determine the amount of Bv8 present in the test sample. These assays are called ELISA systems when enzymes are used as the detectable markers.

Another species of competitive assay, called a "homogeneous" assay, does not require a phase separation. Here, a conjugate of an enzyme with the Bv8 is prepared and used such that when anti-Bv8 antibody binds to the Bv8 the presence of the anti-Bv8 antibody modifies the enzyme activity. In this case, the Bv8 or its immunologically active fragments are conjugated with a bifunctional organic bridge to an enzyme such as peroxidase. Conjugates are selected for use with anti-Bv8 antibody so that binding of the anti-Bv8 antibody inhibits or potentiates the enzyme activity of the label. This method per se is widely practiced under the name of EMIT.

Steric conjugates are used in steric hindrance methods for homogeneous assay. These conjugates are synthesized by covalently linking a low-molecular-weight hapten to a small Bv8 fragment so that antibody to hapten is substantially unable to bind the conjugate at the same time as anti-Bv8 antibody. Under this assay procedure the Bv8 present in the test sample will bind anti-Bv8 antibody, thereby allowing anti-hapten to bind the conjugate, resulting in a change in the character of the conjugate hapten, e.g., a change in fluorescence when the hapten is a fluorophore.

Sandwich assays particularly are useful for the determination of Bv8 or anti-Bv8 antibodies. In sequential sandwich assays an immobilized anti-Bv8 antibody is used to adsorb test sample Bv8, the test sample is removed as by washing, the bound Bv8 is used to adsorb a second, labeled anti-Bv8 antibody and bound material is then separated from residual tracer. The amount of bound tracer is directly proportional to test sample Bv8. In "simultaneous" sandwich assays the test sample is not separated before adding the labeled anti-Bv8. A sequential sandwich assay using an anti-Bv8 monoclonal antibody as one antibody and a polyclonal anti-Bv8 antibody as the other is useful in testing samples for Bv8.

The foregoing are merely exemplary detection assays for Bv8. Other methods now or hereafter developed that use anti-Bv8 antibody for the determination of Bv8 are included within the scope hereof, including the bioassays described herein.

In one aspect, the invention provides methods to detect (e.g., presence or absence of or amount) a polynucleotide(s) (e.g., Bv8 polynucleotides) in a biological sample from an individual, such as a human subject. A variety of methods for detecting polynucleotides can be employed and include, for example, RT-PCR, taqman, amplification methods, polynucleotide microarray, and the like.

Methods for the detection of polynucleotides (such as mRNA) are well known and include, for example, hybridization assays using complementary DNA probes (such as in situ hybridization using labeled Bv8 riboprobes), Northern blot and related techniques, and various nucleic acid amplification assays (such as RT-PCR using complementary primers specific for Bv8, and other amplification type detection methods, such as, for example, branched DNA, SPIA, Ribo-SPIA, SISBA, TMA and the like).

Biological samples from mammals can be conveniently assayed for, e.g., Bv8 mRNAs using Northern, dot blot or PCR analysis. For example, RT-PCR assays such as quantitative PCR assays are well known in the art. In an illustrative embodiment of the invention, a method for detecting Bv8 mRNA in a biological sample comprises producing cDNA from the sample by reverse transcription using at least one primer; amplifying the cDNA so produced using an Bv8 polynucleotide as sense and antisense primers to amplify Bv8 cDNAs therein; and detecting the presence or absence of the amplified Bv8 cDNA. In addition, such methods can include one or more steps that allow one to determine the amount (levels) of Bv8 mRNA in a biological sample (e.g. by simultaneously examining the levels a comparative control mRNA sequence of a housekeeping gene such as an actin family member). Optionally, the sequence of the amplified Bv8 cDNA can be determined Probes and/or primers may be labeled with a detectable marker, such as, for example, a radioisotope, fluorescent compound, bioluminescent compound, a chemiluminescent compound, metal chelator or enzyme. Such probes and primers can be used to detect the presence of Bv8 polynucleotides in a sample and as a means for detecting a cell expressing Bv8 proteins. As will be understood by the skilled artisan, a great many different primers and probes may be prepared (e.g., based on the sequences provided in herein) and used effectively to amplify, clone and/or determine the presence or absence of and/or amount of Bv8 mRNAs.

Optional methods of the invention include protocols comprising detection of polynucleotides, such as Bv8 polynucleotide, in a tissue or cell sample using microarray technologies. For example, using nucleic acid microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. For example, a selection of genes that have potential to be expressed in certain disease states may be arrayed on a solid support. Hybridization of a labeled probe with a particular array member indicates that the sample from which the probe was derived expresses that gene. Differential gene expression analysis of disease tissue can provide valuable information. Microarray technology utilizes nucleic acid hybridization techniques and computing technology to evaluate the mRNA expression profile of thousands of genes within a single experiment. (see, e.g., WO 01/75166 published Oct. 11, 2001; (See, for example, U.S. Pat. No. 5,700,637, U.S. Pat. No. 5,445,934, and U.S. Pat. No. 5,807,522, Lockart, Nature Biotechnology, 14:1675-1680 (1996); Cheung, V. G. et al., Nature Genetics 21(Suppl):15-19 (1999) for a discussion of array fabrication). DNA microarrays are miniature arrays containing gene fragments that are either synthesized directly onto or spotted onto glass or other substrates. Thousands of genes are usually represented in a single array. A typical microarray experiment involves the following steps: 1. preparation of fluorescently labeled target from RNA isolated from the sample, 2. hybridization of the labeled target to the microarray, 3. washing, staining, and scanning of the array, 4. analysis of the scanned image and 5. generation of gene expression profiles. Currently two main types of DNA microarrays are being used: oligonucleotide (usually 25 to 70 mers) arrays and gene expression arrays containing PCR products prepared from cDNAs. In forming an array, oligonucleotides can be either prefabricated and spotted to the surface or directly synthesized on to the surface (in situ).

The Affymetrix GeneChip® system is a commercially available microarray system which comprises arrays fabricated by direct synthesis of oligonucleotides on a glass surface. Probe/Gene Arrays: Oligonucleotides, usually 25 mers, are directly synthesized onto a glass wafer by a combination of semiconductor-based photolithography and solid phase chemical synthesis technologies. Each array contains up to 400,000 different oligos and each oligo is present in millions of copies. Since oligonucleotide probes are synthesized in known locations on the array, the hybridization patterns and signal intensities can be interpreted in terms of gene identity and relative expression levels by the Affymetrix Microarray Suite software. Each gene is represented on the array by a series of different oligonucleotide probes. Each probe pair consists of a perfect match oligonucleotide and a mismatch oligonucleotide. The perfect match probe has a sequence exactly complimentary to the particular gene and thus measures the expression of the gene. The mismatch probe differs from the perfect match probe by a single base substitution at the center base position, disturbing the binding of the target gene transcript. This helps to determine the background and nonspecific hybridization that contributes to the signal measured for the perfect match oligo. The Microarray Suite software subtracts the hybridization intensities of the mismatch probes from those of the perfect match probes to determine the absolute or specific intensity value for each probe set. Probes are chosen based on current information from GenBank® and other nucleotide repositories. The sequences are believed to recognize unique regions of the 3' end of the gene. A GeneChip® Hybridization Oven ("rotisserie" oven) is used to carry out the hybridization of up to 64 arrays at one time. The fluidics station performs washing and staining of the probe arrays. It is completely automated and contains four modules, with each module holding one probe array. Each module is controlled independently through Microarray Suite software using preprogrammed fluidics protocols. The scanner is a confocal laser fluorescence scanner which measures fluorescence intensity emitted by the labeled cRNA bound to the probe arrays. The computer workstation with Microarray Suite software controls the fluidics station and the scanner. Microarray Suite software can control up to eight fluidics stations using preprogrammed hybridization, wash, and stain protocols for the probe array. The software also acquires and converts hybridization intensity data into a presence/absence call for each gene using appropriate algorithms. Finally, the software detects changes in gene expression between experiments by comparison analysis and formats the output into .txt files, which can be used with other software programs for further data analysis.

In some embodiments, the treatment is for a cancer selected from the group consisting of colorectal cancer, lung cancer, ovarian cancer, pituitary cancer, pancreatic cancer, mammary fibroadenoma, prostate cancer, head and neck squamous cell carcinoma, soft tissue sarcoma, breast cancer, neuroblastomas, melanoma, breast carcinoma, gastric cancer, colorectal cancer (CRC), epithelial carcinomas, brain cancer, endometrial cancer, testis cancer, cholangiocarcinoma, gallbladder carcinoma, and hepatocellular carcinoma.

Biological samples are described herein, e.g., in the definition of Biological Sample.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, etc. The containers may be formed from a variety of materials such as glass or plastic. The container holds a composition which is by itself or when combined with another composition(s) effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice, such as cancer. Moreover, the article of manufacture may comprise (a) a first container with a composition contained therein, wherein the composition comprises an antibody of the invention; and (b) a second container with a composition contained therein. The article of manufacture in this embodiment of the invention may further comprise a package insert indicating that the first and second antibody compositions can be used to treat a particular condition, e.g. cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The following are examples of the methods and compositions of the invention. It is understood that various other embodiments may be practiced, given the general description provided above.

EXAMPLES

Commercially available reagents referred to in the Examples were used according to manufacturer's instructions unless otherwise indicated.

Example 1

Generation of Anti-Bv8 Antibodies

This example demonstrates the humanization of the murine anti-Bv8 antibodies directed against Bv8. Residue numbers are according to Kabat (Kabat et al., Sequences of proteins of immunological interest, 5th Ed., Public Health Service, National Institutes of Health, Bethesda, Md. (1991)). Single letter amino acid abbreviations are used.

Generation of Hybridoma-Derived Anti-Bv8 Antibodies

Anti-Bv8 antibodies were generated by immunizing mouse or hamster with recombinant human Bv8 extracellular domain polypeptides (PeproTech, Rock Hill, N.J.). Clones 2G9, 2B9, 3F1, derived from mouse hybridoma, comprising the variable light (VL) and variable heavy (VH) sequences set forth in FIGS. 2A, 2B, 3A, 3B, 4A and 4B, were selected. Clone 2D3, derived from hamster hybridoma, comprising the VH and VL sequences set forth in FIGS. 5A and 5B, was also selected.

Cloning of Hybridoma-Derived Anti-Bv8 Antibodies Variable Domains and Generation of Chimeric Antibodies Total RNA was extracted from hybridoma cells producing the mouse anti Bv8 monoclonal antibody 2B9, 3F1, and 2G9, as well as hamster anti Bv8 monoclonal antibody 2D3, respectively, using RNeasy Mini Kit (Catalog 74104; QIAGEN; Valencia, Calif.). The variable light (VL) and variable heavy (VH) domains were amplified using RT-PCR with the following degenerate primers:

```
2B9 Light chain (LC) forward:
                                (SEQ ID NO: 225)
5'GTCAGATATCGTKCTSACMCARTCTCCAGCAATMA3'

2B9 heavy chain (HC) forward:
                                (SEQ ID NO: 226)
'GATCGACGTACGCTCAGGTGACKCTGAARGAGTCWGG3'

3F1 Light chain (LC) forward:
                                (SEQ ID NO: 227)
5'GTACGATATCGTKCTSACCCARTCTCC3'

3F1 heavy chain (HC) forward:
                                (SEQ ID NO: 228)
5'GATCGACGTACGCTCAGGTGACKCTGAARGAGTCWGG3'

2G9 Light chain (LC) forward:
                                (SEQ ID NO: 229)
5' GTACGATATCGTKCTSACCCARTCTCC 3'

2G9 heavy chain (HC) forward:
                                (SEQ ID NO: 230)
'GATCGACGTACGCTGAGGTYCAGCTSCAGCAGTCTGG3'

2D3 Light chain (LC) forward:
                                (SEQ ID NO: 231)
5' GATCGATATCCARATGACNCARACNCC 3'

2D3 heavy chain (HC) forward:
                                (SEQ ID NO: 232)
5' GATCGA CGTACGCTGARGTGCARYTGGTGGARTCTGG3'

Light chain reverse:
                                (SEQ ID NO: 233)
5'GCTGTAGGTGCTGTCTTTGCT3'

Heavy chain reverse:
                                (SEQ ID NO: 234)
5'CTGGWCAGGGMTCCAGAGTTCCA3'
```

The primer sequences as shown according to the following RJB code:

IUB CODES
G Guanine
A Adenine
T Thymine
C Cytosine
R (A or G)
Y (C or T)
M (A or C)
K (G or T)
S (C or G)
W (A or T)
H (A or C or T)
B (C or G or T)
V (A or C or G)
D (A or G or T)
N (A or C or G or T)

The forward primers were specific for the N-terminal amino acid sequence of the VL and VH region. Respectively, the light chain (LC) and heavy chain (HC) reverse primers were designed to anneal to a region in the constant light (CL) and constant heavy domain 1 (CH1), which is highly conserved across species.

Amplified PCR products were subsequently ligated to a TA cloning vector (Invitrogen, Carlsbad, Calif.) and sequenced. The identified VL DNA sequence was then subcloned into pRK mammalian cell expression vector (Carter et al., *Proc. Natl. Acad. Sci. USA*, 89, 4285-4289 (1992)) containing the human kappa constant domain. The VH DNA sequence was inserted into pRK vectors encoding the full-length human γ1 constant domains.

The LC and HC expression vectors were co-transfected into the adenovirus-transformed human embryonic kidney cell line 293 using Fugene transfection reagents (Roche, Mannheim, Germany) Antibody was produced in serum-free media and purified by Protein A chromatography.

Direct Hypervariable Region Grafts onto the Acceptor Human Consensus Framework

The phagemid used for this work is a monovalent Fab-g3 display vector and consists of 2 open reading frames under control of a single phoA promoter. The first open reading frame consists of the stII signal sequence fused to the VL and CL domains of the acceptor light chain and the second consists of the stII signal sequence fused to the VH and CH1 domains of the acceptor heavy chain followed by the minor phage coat protein P3.

Prior to generating CDR-graft variants of anti-Bv8 antibodies, the variable light (VL) and variable heavy (VH) domains of mouse antibodies were sequence aligned with human consensus sequences.

For clones 2B9 and 3F1, human consensus light chain kappa 1 (huKI) and human consensus heavy chain subgroup III (huGIII) were the closest human frameworks, and the hypervariable regions of mouse 2B9 (m2B9) and mouse 3F1 (m3F1) light chain and heavy chain sequences were grafted into huKI and huGIII consensus acceptor frameworks, respectively, to generate direct CDR-graft variants, called h2B9.v1 (FIGS. 6A and 6B) and h3F1.v1 (FIGS. 4A and 4B).

Interestingly, for clone 2G9, the closest human frameworks to mouse 2G9 were human consensus light chain kappa IV (huKIV) and human consensus heavy chain subgroup I (huGI). Therefore, initially, the hypervariable regions of mouse 2G9 (m2G9) light chain and heavy chain were grafted not only into huKI and huGIII, but also huKIV and huGI consensus acceptor frameworks, respectively, to generate four different CDR-graft variants identified as h2G9.K1G1, h2G9.K1G3, h2G9.K4G1 and h2G9.K4G3 (FIGS. 14 and 15). Human VL kappa subgroup IV consensus framework sequence minus Kabat light chain HVR sequences is shown in SEQ ID NO:240. Human VH subgroup I consensus framework sequence minus heavy chain HVR sequences is shown in SEQ ID NO:241. See FIG. 1G. In the VL domain the following regions were grafted to the human consensus acceptor: positions 24-34 in L, 50-56 in L2 and 89-97 in L3. In the VH domain, positions 26-35 in H1, 49-65, 71 and 73 in H2 and 95-102 in H3 were grafted.

Direct CDR-graft variants (h2B9.v1, h3F1.v1, h2G9.K1G1, h2G9.K1G3, h2G9.K4G1, h2G9.K4G3) were generated by Kunkel mutagenesis as both a Fab displayed on phage and an IgG using separate oligonucleotides for each hypervariable region. Correct clones were identified by DNA sequencing.

Selecting and Polishing Humanized 2G9.K4G1

Binding affinities of the four CDR-graft anti-Bv8 antibody variants, h2G9.K1G1, h2G9.K1G3, h2G9.K4G1 and h2G9.K4G3, were measured by Biacore using a BIAcore™-3000 instrument as described herein. In addition, adrenal cortical endothelial cells (ACE) proliferation assay was performed, as described herein, to investigate the Bv8 neutralizing activity of the four variants.

The results of the BIAcore analysis showed that variants h2G9.K1G1 and h2G9.K1G3 had significantly fast off-rate at high concentration analysis compared to h2G9.K4G1 and h2G9.K4G3. Furthermore, the ACE proliferation assay showed that among the four variants, variant h2G9.K4G1 had the best activity as it almost completely blocked the binding of Bv8 to ACE cells. However, the BIAcore analysis and ACE proliferation assay indicated that the binding affinity and neutralizing activity of h2G9.K4G1 anti-Bv8 antibody were still lower than those of the chimeric 2G9 anti-Bv8 antibody. Therefore, anti-Bv8 antibody h2G9.K4G1 was selected for affinity maturation to further improve its binding affinity.

Prior to initiating affinity maturation of anti-Bv8 antibody h2G9.K4G1, the HVR sequences were analysed for potential stability problems involving isomerization, unpaired cysteine and deamidation during the manufacturing process. Potential problems were identified at the following sites: (i) the adjacent residues at positions 28 and 29 of the light chain variable sequence; (ii) position 52a of the heavy chain variable sequence; (iii) position 54 of the heavy chain variable sequence; and (iv) the adjacent residues at positions 95 and 96 of the heavy chain variable sequence.

Variants of anti-Bv8 antibody h2G9.K4G1 with single amino acid substitution at residue positions mentioned above were generated and each variant was displayed as a Fab on the phage. Total of 12 variants with the following single amino acid modification were generated, and their binding affinities were evaluated by the phage competition ELISA: CDR-L1-D28E, D28S, G29A, G29S; CDR-H2-C52aA, C52aS, N54A, N54S; CDR-H3: D95E, D95S, G96A, G96S. The binding affinities of the 12 variants compared to h2G9.K4G1 are shown in FIGS. 14A and 14B. The Figures show that most of the variants retained similar or slightly improved binding affinity. Surprisingly, the variant with D95S substitution in CDR-H3 completely lost the binding at 1 µM of human Bv8. Furthermore, the variant with D95E substitution in CDR-H3 showed a significant binding affinity drop by 100 fold compared to h2G9.K4G1.

A clone identified as h2G9.K4G1.Polish was generated by combining all of the following four amino acid substitutions: CDR-L1-D28S; CDR-H2-C52aS, N54S; CDR-H3: G96S. BIAcore analysis showed a similar binding affinities for chimeric 2G9 Fab and h2G9.K4G1.Polish Fab, and both chimeric 2G9 IgG and h2G9.K4G1.Polish IgG showed complete blocking of Bv8-induced ACE cell proliferation (FIG. 21). Furthermore, the amino acid substitutions at CDR-L1-D28S; CDR-H2-C52aS, N54S; CDR-H3: G96S (anti-Bv8 antibody h2G9.K4G1.Polish) unexpectedly restored the binding affinity close to that of the chimeric 2G9 anti-Bv8 antibody.

Soft Randomization of the Hypervariable Regions

The sequence diversity was introduced into each hypervariable region to further improve affinity for clone h2G9.K4G1.Polish using a soft randomization strategy that maintains a bias towards the murine hypervariable region sequence. This was accomplished using a poisoned oligonucleotide synthesis strategy first described by Gallop et al., *J. Med. Chem.* 37:1233-1251 (1994). For a given position within a hypervariable region to be mutated, the codon encoding the wild-type amino acid is poisoned with a 70-10-10-10 mixture of nucleotides resulting in an average 50 percent mutation rate at each position. Soft randomized oligonucleotides were patterned after the murine hypervariable region sequences and encompassed the same regions defined by the direct hypervariable region grafts.

Generation of Phage Libraries

Randomized oligonucleotide pools designed for each hypervariable region were phosphorylated separately in six 20 µl reactions containing 660 ng of oligonucleotide, 50 mM Tris pH 7.5, 10 mM $MgCl_2$, 1 mM ATP, 20 mM DTT, and 5 U polynucleotide kinase for 1 h at 37° C. The six phosphorylated oligonucleotide pools were then combined with 20 µg of Kunkel template in 50 mM Tris pH 7.5, 10 mM $MgCl_2$ in a final volume of 500 µl resulting in an oligonucleotide to template ratio of 3. The mixture was annealed at 90° C. for 4 min, 50° C. for 5 min and then cooled on ice. Excess, unannealed oligonucleotide was removed with a QIAquick PCR purification kit (Catalog 28106, QIAGEN Inc., Valencia, Calif.) using a modified protocol to prevent excessive denaturation of the annealed DNA. To the 500 µl of annealed mixture, 150 µl of PB was added, and the mixture was split between 2 silica columns. Following a wash of each column with 750 µl of PE and an extra spin to dry the columns, each column was eluted with 110 µl of 10 mM Tris, 1 mM EDTA, pH 8. The annealed and cleaned-up template (220 µl) was then filled in by adding 1 µl 100 mM ATP, 10 µl 25 mM dNTPs (25 mM each of dATP, dCTP, dGTP and dTTP), 15 µl 100 mM DTT, 25 µl 10×TM buffer (0.5 M Tris pH 7.5, 0.1 M $MgCl_2$), 2400 U T4 ligase, and 30 U T7 polymerase for 3 h at room temperature.

The filled in product was analyzed on Tris-Acetate-EDTA/agarose gels (Sidhu et al., *Methods in Enzymology* 328:333-363 (2000)). Three bands are usually visible: the bottom band is correctly filled and ligated product, the middle band is filled but unligated and the top band is strand displaced. The top band is produced by an intrinsic side activity of T7 polymerase and is difficult to avoid (Lechner et al., *J. Biol. Chem.* 258:11174-11184 (1983)); however, this band transforms 30-fold less efficiently than the top band and usually contributes little to the library. The middle band is due to the absence of a 5' phosphate for the final ligation reaction; this band transforms efficiently and unfortunately, gives mainly wild type sequence.

The filled in product was then cleaned-up and electroporated into SS320 cells and propagated in the presence of M13/KO7 helper phage as described by Sidhu et al., *Methods in Enzymology* 328:333-363 (2000). Library sizes ranged from $1-2 \times 10^9$ independent clones. Random clones from the initial libraries were sequenced to assess library quality.

Phage Selection

The human Bv8 (PeproTech) was used as the target for phage selection. Human Bv8 was coated on Maxisorp microtiter plates (Nunc) at 10 µg/ml in PBS for the $1^{st}$ round panning. For the first round of selection, 8 wells of target were used; a single well of target was used for successive rounds of selection. Wells were blocked for 1 h using Super Blocker (Pierce). Phage were harvested from the culture supernatant and suspended in PBS containing 1% BSA and 0.05 Tween 20 (PBST). After binding to the wells for 2 h, unbound phage were removed by extensive washing with PBS containing 0.05% Tween 20 (PBT). Bound phage were eluted by incubating the wells with 50 mM HCl, 0.5 M KCl for 30 min. Phage were propagated and amplified using XL1 blue cells (Strategene) and M13/KO7 helper phage (New England BioLabs) and grown overnight at 37° C. in 2YT, 50 μg/ml carbenacillin for the next round of panning. The titers of phage eluted from a target coated well were compared to titers of phage recovered from a non-target coated well to assess the enrichment.

Beginning at the $2^{nd}$ round sorting, the phage libraries were sorted using a solution sorting method (Lee, C. V., et al. (2004) *J. Mol. Biol.* 340(5): 1073-93), which allow us to increase the stringency of selection to isolate affinity-improved clones. Human Bv8 was biotinylated using Sulfo-NHS-LC-biotin (b-Bv8, Pierce, Rockford, Ill.). Microtiter wells were coated with 10 μg/ml neutravidin in PBS overnight at 4 C and then blocked for 1 h using Super Blocker (Pierce). For the second round of selection, 200 μl phage suspended in PBST buffer were mixed with 5 nM b-Bv8 for 2 hr at room temperature (RT). Phage bound to b-Bv8 were captured on neutravidin coated wells for 15 min at RT and unbound phage were washed away with PBT buffer. Phage were eluted using 100 mM HCl for 30 m, neutralized, and propagated as described above. The next rounds of selection were performed similarly as round 2 selection with the following exceptions: in round 3 and 4, the final b-Bv8 concentration was 0.1 nM, in rounds 5 the final b-Bv8 concentration was 0.05 nM. Beginning round 4 and 5, after phage binding with b-Bv8, 500 and 1000 fold excess of unbiotinylated human Bv8 respectively were added to the mixture for 1-2 hr at RT to compete off fast off-rate binders prior to capture on neutravidin.

Phage Competition ELISA to Determine Phage $IC_{50}$

MAXISORP™ microtiter plates were coated with recombinant human Bv8 (PeproTech) at 2 μg/ml in PBS overnight and then blocked with PBST buffer (0.5% BSA and 0.05% Tween 20 in PBS) for an hour at room temperature (RT). Phage from culture supernatants were incubated with serially diluted human Bv8 in PBST buffer in a tissue-culture microtiter plate for an hour at RT, after which 80 μl of the mixture was transferred to the target-coated wells for 15 minutes to capture unbound phage. The plate was washed with PBT buffer (0.05% Tween 20 in PBS), and HRP-conjugated anti-M13 (Amersham Pharmacia Biotech) was added (1:5000 in PBST buffer) for 40 minutes. The plate was washed with PBT buffer and developed by adding tetramethylbenzidine substrate (Kirkegaard and Perry Laboratories, Gaithersburg, Md.). The absorbance at 450 nm was plotted as a function of target concentration in solution to determine phage $IC_{50}$. This was used as an affinity estimate for the Fab clone displayed on the surface of the phage. FIGS. 14A and 14B depict results from a phage competition assay demonstrating the binding of polished h2G9.K4G1 variants (L1: D28E, D28S, G29A, G29S, H2: C52aA, C52aS, N54A, N54S, H3: D95E, D95S, G96A and G96S) against human Bv8. FIGS. 16 and 17 depict results from a phage competition assay demonstrating the binding of affinity-improved h2G9.K4G1.Polish variants (h2G9.K4G1.v27, v52, v55, v63, v64, v67, v77, v80 from L1/L2 soft-randomized library; h2G9.K4G1.v19, v25, v37, v65, v73, v75, v77. v92 from H1/H2 soft-randomized library) against human Bv8.

Antibody Affinity Determinations by BIAcore

For binding affinity determinations of anti-Bv8 antibodies (Fab or IgG), Surface Plasmon Resonance (SRP) measurement with a BIAcore™-3000 instrument was used. Briefly, CM5 biosensor chip was activated with EDC and NHS reagents according to the supplier's instructions, and human Bv8 (PeproTech) or Cynomologus Monkey (Genentech; PUR21590) was coupled to achieve approximately 150 response units (RU), then following by blocking un-reacted groups with 1M ethanolamine. For kinetics measurements, two-fold serial dilutions of anti-Bv8 Fabs (0.19 nM to 25 nM) or IgGs (0.019 nM to 10 nM) were injected in HBS-P buffer (0.01M HEPES pH 7.4, 0.15M NaCl, 0.005% surfactant P20) at 25° C. with a flow rate of 30 μl/min. Association rates ($k_{on}$) and dissociation rates ($k_{off}$) were calculated using a simple one-to-one Langmuir binding model (BIAcore Evaluation Software version 3.2). The equilibrium dissociation constant ($K_d$) was calculated as the ratio $k_{off}/k_{on}$. See FIGS. 18 to 21. The results show that the humanized anti-Bv8 antibodies, h2G9.K4G1.v19 and h2G9.K4G1.v55, bind to human and cyno Bv8 at least two fold tighter than the chimeric 2G9 anti-Bv8 antibody.

ACE Proliferation Assay

ACE cells were seeded at a density of 5000 cells per well in 6-well plates in growth medium. For inhibition assay, anti-Bv8 antibodies were added at indicated concentrations (μg/mL) first. After 0.5-1 hr, human Bv8 (Peprotech) was then added to a final concentration of 10 nM. After 6 days, cells were dissociated by adding 1 ml of 2× Trypsin (GIBCO) to each well, and duplicated wells were counted using Z2 coulter particle count and size analyzer (Beckman Coulter). See FIGS. 12, 13, 15, 23 and 24. FIG. 23 shows that humanized anti-Bv8 antibodies h2G9K4G1.v19, h2G9K4G1.v52, h2G9K4G1.v55 and h2G9K4G1.v73 showed significant improvement in blocking human Bv8-induced ACE proliferation.

Competition ELISA to Map Bv8 Antibody Epitopes

NUNC™ 96-well Maxisorp immunoplates (NUNC; Roskilde, Denmark) were coated with chimeric 2B9 IgG at 1 μg/mL in PBS overnight and then blocked for an hour at room temperature with PBST buffer (0.5% BSA and 0.05% Tween 20 in PBS). Biotinylation of human Bv8 was prepared using EZ-link Sulfo-NHS-LC-Biotin (Catalog 21335; Pierce; Rockford, Ill.) reagent in a molar ratio of 1:4 (HuBv8: biotin).

To determine the amount of biotinylated human Bv8 in the competition assay, threefold serially diluted biotinylated human Bv8 from 100 nM to 0.04 nM were added to the antibody-coated plates for 15 minutes. Then, the plates were washed with PBT buffer (PBS and 0.05% Tween 20). Bound biotinylated were detected using streptavidin, which were conjugated with horseradish peroxidase (Catalog 21126; Pierce; Rockford, Ill.) and diluted 1:2500 in PBST buffer. After 45 minutes of incubation, the plate was washed and 100 μL of tetramethylbenzidine (R&D Systems) was added to each well for approximately 5 minutes to induce signal revelation. When blue coloration appeared, 100 μL of phosphoric acid at 1 M was added to each well to stop the revelation process. The optical density was read spectrophotometrically at 450 nm.

To map the Bv8 antibody epitopes with chimeric 2B9, threefold serial dilutions of IgGs (chimeric 2B9, chimeric 3F1, chimeric 2D3, chimeric 2G9 and control IgG) were first incubated with 2 nM biotinylated human Bv8, determined by the above binding assay, in PBST buffer for 1-2 hours at room temperature, and then transferring it onto antibody (chimeric 2B9 IgG; 1 μg/mL)-coated plate for 15 min. Then the plate was washed with PBT buffer and the amount of biotinylated human Bv8 bound to chimeric 2B9 IgG on the plate was detected by the protocols as described above.

In the competition assay, chimeric 3F1 and chimeric 2G9 antibodies competed with chimeric 2B9 binding to human Bv8, suggesting that both antibodies have overlapping epitopes with chimeric 2B9. However, chimeric 2D3 only showed partially competed with chimeric 2B9 antibody binding to human Bv8, suggesting that chimeric 2D3 antibody may have distinct epitope(s) from chimeric 2B9 as well as chimeric 3F1 and chimeric 2G9 antibodies (FIG. 11).

Example 2

In Vivo Efficacy Studies

Human HT-55, Colo-205 (colorectal carcinoma), A673 (rhabdomyosarcoma), HPAC (pancreatic carcinoma) and Calu-6 (lung carcinoma) cells were obtained from the American Type Culture Collection (Manassas, Va.). The human colorectal carcinoma HM7 cell line is a derivative of LS174T. The Calu-6, A673, HPAC and HM7 were grown in Ham's F12, low glucose DMEM 1:1. Colo-205 and HT-55 were grown in RPMI 1640 medium. Both media were supplemented with 10% v/v FBS, 1% v/v penicillin/streptomycin (Invitrogen, Carlsbad, Calif.), 2 mM L-glutamine (Invitrogen, Carlsbad, Calif.) and 1 µg/ml FUNGIZONET™ (Invitrogen, Carlsbad, Calif.). Cells were grown at 37° C. in 5% $CO_2$ until confluent, harvested, and resuspended in sterile Matrigel at $15 \times 10^6$ cells per ml. Xenografts were inoculated in 6- to 8-week-old BALB/c Nude mice (Charles River; Hollister, Calif.) by dorsal flank subcutaneous (S.C.) injection of $1.5 \times 10^6$ cells per mouse and allowed to grow. The treatment with anti-Bv8 antibodies, chimeric 2D3, chimeric 3F1, chimeric 2B9 and chimeric 2G9; humanized 2G9 variant 19, humanized 2G9 variant 55 and humanized 2G9.K4G1.Polish, i.p. at the dose of 10 mg/kg twice weekly were initiated 24 h after tumor cell inoculation. As controls, we employed anti-GP-120 Mab 10 mg/kg twice weekly and anti-VEGF Mab G6.31 or B20 5 mg/kg twice weekly (Liang, W. C., et al., *J Biol Chem* 281, 951-961 (2006)). All experiments, transplanted tumors were measured twice weekly along the longest axis and the perpendicular axis by using a caliper. Tumor volumes were calculated using the ellipsoid volume formulas ($0.5 \times L \times W \times W$ and the mean tumor volumes and standard error from 10 mice per group in all of treatments appearanced on the figures. Anti-Bv8 antibodies also have an additive effect in LXFL529 human lung non-small cell carcinoma when used in combination with anti-VEGF antibody. Beige nude mice (n=7-9) were implanted with LXFL529 human lung non-small cell carcinoma cells. Mice were then treated with control anti-Ragweed 1428 and anti-Bv8 mouse antibodies (3F1 and 2B9) within 24 hours after tumor inoculation. Mice were treated with anti-VEGF antibody after the tumors had reached ~400 $mm^3$. The results show that treatment with chimeric and humanized anti-Bv8 antibody resulted in a reduction of tumor growth in various tumors as a single agent and in combination with anti-VEGF antibody. See FIGS. 25 to 37.

Mouse LLC (Lewis lung carcinoma), human H460 (non-small cell lung carcinoma) and HT29 (colorectal carcinoma) cells were obtained from the American Type Culture Collection (Manassas, Va.). The LLC and HM7 cells were cultured in RPMI 1640 media plus 1% L-glutamine with 10% fetal bovine serum (Hyclone; Logan, Utah). Cells were grown at 37° C. in 5% $CO_2$, harvested, centrifuged, washed once with Hanks' balanced salt solution (HBSS), and counted. LLC cells were resuspended in 50% HBSS and 50% Matrigel™ (BD Biosciences; San Jose, Calif.) and HM7 cells were resuspended in HBSS (Invitrogen; Carlsbad, Calif.), both at a concentration of $3.5 \times 10^7$ cells/mL for injection into mice. H460 cells were cultured in RPMI-1640 medium containing 10% fetal bovine serum, 100 units/mL penicillin G, 100 µg/mL streptomycin sulfate, 1 mM sodium pyruvate, 2 mM glutamine, 10 mM HEPES, 0.075% sodium bicarbonate, and 25 µg/mL gentamicin. Cells were cultured in tissue culture flasks in a humidified incubator at 37° C., in an atmosphere of 5% $CO_2$ and 95% air, then harvested, and resuspended in phosphate buffered saline (PBS) at a concentration of $5 \times 10^7$ cells/mL for injection into mice. HT29 cells were originally obtained from ATCC, and resulting xenograft tumors were subsequently maintained as an in vivo line by serially subcutaneous transplantation in athymic nude mice prior to implantation for an experiment. LLC cells were inoculated in 8- to 9-week-old female BALB/c Nude mice (Charles River, Hollister, Calif.) by dorsal flank subcutaneous (S.C.) injection with $3.5 \times 10^6$ cells per mouse and allowed to grow as allografts. HM7 cells were inoculated in 12-week old female athymic nude (nu/nu) mice (Harlan Sprague Dawley, Inc; Frederick, Md.) by hind leg S.C. injection with $3.5 \times 10^6$ cells per mouse, H460 cells were inoculated in 10- to 11-week-old female athymic nude (nu/nu) mice (Harlan Sprague Dawley, Inc; Federick, Md.) by dorsal flank S.C. injection with $1 \times 10^7$ cells per mouse, and HT29 tumor fragments at 1 $mm^3$ were implanted S.C. in the flank of 11- to 12-week old female athymic nude (nu/nu) mice (Harlan Sprague Dawley, Inc; Federick, Md.). Anti-Bv8 antibodies chimeric 2D3, murine 3F1, and murine 2B9 were dosed by i.p. at 10 mg/kg twice per week and humanized anti-Bv8 antibody 2G9, i.p. at 30 mg/kg once weekly. As controls, we administered anti-ragweed MAb, i.p. at 30 or 100 mg/kg twice per week, and anti-VEGF MAb B20-4.1.1, i.p. at 5 mg/kg twice per week. Treatments were initiated at the following length of time after cell inoculation or tumor implantation (HT29): 7 h for LLC, 8 days for HM7, 11 days for H460, and 36 days for HT29. Tumors and body weights were measured, and general clinical observations were performed at a minimum of twice each week for the duration of the study. Tumor volumes were calculated using the ellipsoid volume formula ($0.5 \times L \times W \times W$). To analyze the repeated measurement of tumor volumes from the same animals over time, a mixed-modeling approach was used, and fitted tumor volume data were generated (Pinheiro et al. nlme: linear and nonlinear mixed effects models; 2009; Version R package version 3.1-96). Kaplan-Meier plots are constructed to show the percentage of animals remaining in the study as a function of time. Treatment with murine and humanized anti-Bv8 antibodies resulted in a reduction of tumor growth in various tumors (see FIGS. 38 to 40, and 42) and prolonged survival (see FIGS. 41 and 43) as a single agent and in combination with anti-VEGF antibody.

Example 3

Competitive ELISA to Measure the Ability of Humanized Anti-Bv8 Antibodies to Block Binding of Human Bv8 to Mouse 2G9 Antibody Maxisorp 384 well plates were coated with 1 µg/ml parent mouse 2G9 IgG1 antibody at 25 µl/well in 50 mM sodium carbonate buffer, pH 9.6, at 4° C. overnight. Plates were washed with phosphate buffered saline (PBS) containing 0.05% polysorbate, pH 7.4 and blocked with PBS containing 0.5% BSA, 10 ppm Proclin, pH 7.4, at 80 µL1/well. After one-hour incubation at room temperature, plates were washed. A mixture of serially diluted humanized 2G9 antibodies (0.11 pM-180 nM) in PBS containing 0.5% BSA, 0.05% polysorbate 20, pH 7.4 and biotinylated human Bv8 (final concentration 0.5 ng/ml or 57 pM) were added at 25 µL1/well. After two hour incubation, plates were washed and horseradish peroxidase conjugated streptavidin (GE Healthcare) was added. After a final 30 minute incubation, plates were washed and the substrate 3,3',5,5'-tetramethyl benzidine (Kirkegaard & Perry Laboratories) was added. The reaction was stopped by adding 1 M phosphoric acid and absorbance was read at 450 nm on a Multiskan Ascent reader (Thermo Scientific, Hudson, N.H.). For data analysis, the titration curves were fitted using a four-parameter nonlinear regression curve-fitting program and the $IC_{50}$ concentrations were determined (KaleidaGraph, Synergy Software, Reading, Pa.).

The results show that humanized anti-Bv8 antibodies h2G9.K4G1.v19, h2G9.K4G1.v52, h2G9.K4G1.v55, h2G9.K4G1.v73 and h2G9.K4G1.v19H/v55L have greater ability to block binding of human Bv8 to mouse 2G9 antibody compared to chimeric 2G9 and h2G9.K4G1.Polish anti-Bv8 antibodies. See FIG. 22.

All references cited throughout the disclosure are hereby expressly incorporated by reference in their entirety.

While the present invention has been described with reference to what are considered to be the specific embodiments, it is to be understood that the invention is not limited to such embodiments. To the contrary, the invention is intended to cover various modifications and equivalents included within the spirit and scope of the appended claims.

Throughout the present application, including the claims, the term "comprising" is used as an inclusive, open-ended transition phrase, which does not exclude additional, unrecited elements or method steps.

What is claimed is:

1. An anti-Bv8 antibody comprising a variable domain comprising the following six hypervariable region (HVR) sequences:
(i) HVR-L1 comprising KASQSX$_1$X$_2$YX$_3$X$_4$X$_5$SYMN, wherein X$_1$ is L or V; X$_2$ is D; X$_3$ is S or Y; X$_4$ is G or H; and X$_5$ is D or Y;
(ii) HVR-L2 comprising AASX$_1$X$_2$EX$_3$, wherein X$_1$ is N; X$_2$ is L or R; and X$_3$ is S;
(iii) HVR-L3 comprising QQINEDPFT;
(iv) HVR-H1 comprising GYX$_1$X$_2$X$_3$X$_4$YDMH, wherein X$_1$ is S; X$_2$ is F or L; X$_3$ is T; X$_4$ is D or N;
(v) HVR-H2 comprising YIX$_1$X$_2$YX$_3$GX$_4$TX$_5$YNQKFKG, wherein X$_1$ is H or S; X$_2$ is S; X$_3$ is S; X$_4$ is A or S; X$_5$ is L or T, and
(vi) HVR-H3 comprising DX$_1$NYGEAYAMDY, wherein X$_1$ is S, or an antigen-binding fragment thereof.

2. The anti-Bv8 antibody of claim 1, wherein HVR-L1 comprises an amino acid sequence of SEQ ID NO: 61 or 91, HVR-L2 comprises an amino acid sequence of SEQ ID NO: 62 or 92, HVR-L3 comprises an amino acid sequence of SEQ ID NO: 63 or 93, HVR-H1 comprises an amino acid sequence of SEQ ID NO: 64 or 94, HVR-H2 comprises an amino acid sequence of SEQ ID NO: 65 or 95, and HVR-H3 comprises an amino acid sequence of SEQ ID NO: 66 or 96, or an antigen-binding fragment thereof.

3. The anti-Bv8 antibody of claim 2, wherein the antibody comprises:
(1) an HVR-L1 comprising the amino acid sequence of SEQ ID NO:61;
(2) an HVR-L2 comprising the amino acid sequence of SEQ ID NO:62;
(3) an HVR-L3 comprising the amino acid sequence of SEQ ID NO:63;
(4) an HVR-H1 comprising the amino acid sequence of SEQ ID NO:64;
(5) an HVR-H2 comprising the amino acid sequence of SEQ ID NO:65; and
(6) an HVR-H3 comprising the amino acid sequence of SEQ ID NO:66, or an antigen-binding fragment thereof.

4. The anti-Bv8 antibody of claim 3 comprising a light chain variable domain comprising SEQ ID NO:7 and the heavy chain variable domain comprising SEQ ID NO:8, or an antigen-binding fragment thereof.

5. The anti-Bv8 antibody of claim 2, wherein the antibody comprises:
(1) an HVR-L1 comprising the amino acid sequence of SEQ ID NO:91;
(2) an HVR-L2 comprising the amino acid sequence of SEQ ID NO:92;
(3) an HVR-L3 comprising the amino acid sequence of SEQ ID NO:93;
(4) an HVR-H1 comprising the amino acid sequence of SEQ ID NO:94;
(5) an HVR-H2 comprising the amino acid sequence of SEQ ID NO:95; and
(6) an HVR-H3 comprising the amino acid sequence of SEQ ID NO:96, or an antigen-binding fragment thereof.

6. The anti-Bv8 antibody of claim 5 comprising a light chain variable domain comprising SEQ ID NO: 11 and the heavy chain variable domain comprising SEQ ID NO:12, or an antigen-binding fragment thereof.

* * * * *

UNITED STATES PATENT AND TRADEMARK OFFICE
CERTIFICATE OF CORRECTION

PATENT NO. : 8,771,685 B2  
APPLICATION NO. : 12/975784  
DATED : July 8, 2014  
INVENTOR(S) : Wu et al.

Page 1 of 1

It is certified that error appears in the above-identified patent and that said Letters Patent is hereby corrected as shown below:

Title page, item (73) "Assignee," please replace "F. Hoffmann-La Roche AG, Basel (CH)" with "Genentech, Inc., South San Francisco, CA (US)"

Signed and Sealed this  
Twentieth Day of October, 2015

Michelle K. Lee  
*Director of the United States Patent and Trademark Office*